(12) United States Patent
Lou

(10) Patent No.: US 12,331,026 B2
(45) Date of Patent: Jun. 17, 2025

(54) SULFONAMIDO DERIVATIVES AS CYCLIN-DEPENDENT KINASE 2 INHIBITORS

(71) Applicant: NiKang Therapeutics, Inc., Wilmington, DE (US)

(72) Inventor: Yan Lou, Wilmington, DE (US)

(73) Assignee: NiKang Therapeutics, Inc., Wilmington, DE (US)

( * ) Notice: Subject to any disclaimer, the term of this patent is extended or adjusted under 35 U.S.C. 154(b) by 105 days.

(21) Appl. No.: 18/189,380

(22) Filed: Mar. 24, 2023

(65) Prior Publication Data

US 2023/0303509 A1    Sep. 28, 2023

Related U.S. Application Data

(60) Provisional application No. 63/362,036, filed on Mar. 28, 2022.

(51) Int. Cl.
*C07D 331/04* (2006.01)
*A61P 35/00* (2006.01)

(52) U.S. Cl.
CPC ............ *C07D 331/04* (2013.01); *A61P 35/00* (2018.01)

(58) Field of Classification Search
CPC .. C07D 331/04; C07D 417/04; C07D 417/14; C07D 471/08; C07D 487/08; C07D 491/08; C07D 498/08; A61P 35/00; A61K 31/506
See application file for complete search history.

(56) References Cited

U.S. PATENT DOCUMENTS 7,994,185 B2 *  8/2011  Rheault .............. C07D 413/04
                                                                514/275

FOREIGN PATENT DOCUMENTS

| CR | 20140051 A | 5/2014 |
|---|---|---|
| WO | WO 01/72745 A1 | 10/2001 |
| WO | WO 2009/137391 A2 | 11/2009 |
| WO | WO 2010010154 A1 | 1/2010 |
| WO | WO 2010059610 A1 | 5/2010 |
| WO | WO 2010104899 A1 | 9/2010 |
| WO | WO 2011023773 A1 | 3/2011 |
| WO | WO 2011049274 A1 | 4/2011 |
| WO | WO 2011161216 A1 | 12/2011 |
| WO | WO 2012113774 A1 | 8/2012 |
| WO | WO 2012125981 A2 | 9/2012 |
| WO | WO 2014194127 A1 | 12/2014 |
| WO | WO 20151718733 A1 | 11/2015 |
| WO | WO 2016059548 A1 | 4/2016 |
| WO | WO 2018055097 A1 | 3/2018 |
| WO | WO 2019207087 A1 | 10/2019 |
| WO | WO 2020/124397 A1 | 6/2020 |

OTHER PUBLICATIONS

International Search Report for PCT/US2023/064895, dated Jun. 28, 2023.
"Profiling of Dabrafenib in 4 cell line mix lysate using Kinobeads," Technical University Munich 2017.
Susan Klaeger, et al. "Supplementary Materials for The target landscape of clinical kinase drugs," Dec. 1, 2017, Science 358, eaan4368 (2017) DOI: 10.1126/science.aan4368.
Susan Klaeger, et al. "The target landscape of clinical kinase drugs," Dec. 1, 2017, Science 358, eaan4368 (2017) DOI: 10.1126/science.aan4368.

* cited by examiner

*Primary Examiner* — Joseph K McKane
*Assistant Examiner* — Anna Grace Kuckla
(74) *Attorney, Agent, or Firm* — Finnegan, Henderson, Farabow, Garrett & Dunner, LLP

(57) ABSTRACT

The present disclosure provides certain sulfonamido derivatives that are Cyclin-dependent kinase 2 (CDK2) inhibitors of Formula (I):

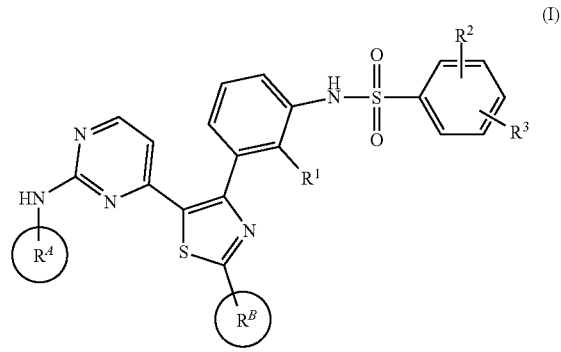

for the treatment of diseases treatable by inhibition of CDK2. Also provided are pharmaceutical compositions containing such compounds and processes for preparing such compounds.

37 Claims, No Drawings

SULFONAMIDO DERIVATIVES AS CYCLIN-DEPENDENT KINASE 2 INHIBITORS

This application claims priority to U.S. Provisional Application No. 63/362,036, filed on Mar. 28, 2022, the contents of which is incorporated herein by reference in its entirety.

FIELD OF THE DISCLOSURE

The present disclosure provides certain sulfonamido derivatives that are Cyclin-dependent kinase 2 (CDK2) inhibitors and are therefore useful for the treatment of diseases treatable by inhibition of CDK2. Also provided are pharmaceutical compositions containing such compounds and processes for preparing such compounds.

BACKGROUND

Cyclin-dependent kinases (CDKs) are cellular kinases that are critical for orchestrating signaling events such as DNA replication and protein synthesis to ensure faithful eukaryotic cell division and proliferation. To achieve activation, the cyclin-dependent kinase catalytic units of CDK often require binding with regulatory subunits known as cyclins. In addition, the activity of CDK is also controlled by its phosphorylation status, as well as by binding of inhibitory proteins.

Of the CDKs identified thus far, at least CDK1/Cyclin B, CDK2/Cyclin E, CDK2/Cyclin A, CDK4/Cyclin D, and CDK6/Cyclin D complexes are known to be important regulators of cell cycle progression; while other CDKs are important in regulating gene transcription, DNA repair, differentiation, and apoptosis (see Morgan, D. O. *Annu. Rev. Cell. Dev. Biol.* (1997) 13: 261-291).

Due to their key roles in regulating cell cycle and other essential cellular processes, increased activity or temporally abnormal activation of CDKs has been shown to result in the development of various types of cancer. CDK2/Cyclin E complex plays an important role in regulation of the G1/S transition, histone biosynthesis and centrosome duplication. Following the initial phosphorylation of retinoblastoma (Rb) by CDK 4/6/cyclin D, CDK2/Cyclin E further hyper-phosphorylates p-RB, releases G1 transcription factor, E2F, to transcribe genes required for S-phase entry. During S-phase, Cyclin E is degraded and CDK2 forms a complex with Cyclin A to promote phosphorylation of substrates that permit DNA replication and inactivation of E2F, for S-phase completion (see Asghar et al. *Nat. Rev. Drug. Discov.* (2015) 14: 130-146). In addition to cyclin bindings, the activity of CDK2 is also tightly regulated through its interaction with negative regulators, such as p21 and p27. In response to mitogenic stimulation, which signals optimal environment for cell cycle, p21 and p27 are phosphorylated and degraded, releasing the break on CDK2/Cyclin activation.

Cyclin E, the regulatory cyclin for CDK2, is frequently overexpressed in cancer, and its overexpression correlates with poor prognosis. For example, Cyclin E amplification or overexpression has been shown to associate with poor outcomes in breast cancer (see Keyomarsi et al., *N Engl J Med*. (2002) 347:1566-75). Cyclin E2 (CCNE2) overexpression is associated with endocrine resistance in breast cancer cells and CDK2 inhibition has been reported to restore sensitivity to tamoxifen or CDK4/6 inhibitors in tamoxifen resistant and CCNE2 overexpressing cells. (see Caldon et al., *Mol Cancer Ther*. (2012) 11:1488-99; and Herrera-Abreu et al., *Cancer Res*. (2016)76:2301-2313). Cyclin E amplification also reportedly contributes to trastuzumab resistance in HER2+ breast cancer. (see Scaltriti et al. *Proc Natl Acad Sci*. (2011) 108:3761-6).

Cyclin E overexpression has also been reported to play a role in basal-like and triple negative breast cancer (TNBC), as well as inflammatory breast cancer (see Elsawaf Z. et al. *Breast Care* (2011) 6:273-278; and Alexander A. et al. *Oncotarget* (2017) 8:14897-14911.) Amplification or overexpression of cyclin E1 (CCNE1) is also frequently found in ovarian, gastric, endometrial, uterus, bladder, esophagus, prostate, lung and other types of cancers (see Nakayama et al. *Cancer* (2010) 116:2621-34; Etemadmoghadam et al. *Clin Cancer Res* (2013) 19: 5960-71; Au-Yeung et al. *Clin. Cancer Res*. (2017) 23:1862-1874; Ayhan et al. *Modern Pathology* (2017) 30: 297-303; Ooi et al. *Hum Pathol*. (2017) 61:58-67; and Noske et al. *Oncotarget* (2017) 8: 14794-14805) and often correlates with poor clinical outcomes.

The turnover of cyclin E1 is regulated by the $SCF^{Fbxw7}$ ubiquitin E3 ligase component FBXW7 and the deubiquitinase USP28, which are frequently dysregulated in cancer. Loss-of-function mutations in FBXW7 or overexpression of USP28 lead to cyclin E overexpression and CDK2 activation (Welcker, M. & Clurman, B. E. 2008 *Nat. Rev. Cancer* 8, 83; Diefenbacher, M. E. et al. (2014) *J. Clin. Invest.* 124, 3407-3418). Alternatively, certain cancer cells express a hyperactive, truncated form of cyclin E (Caruso J A et al. *Cancer Res*. 2018 Oct. 1; 78(19):5481-5491). In addition, cyclin A amplification and overexpression have also been reported in various cancers such as hepatocellular carcinomas (Bayard, Q., et al. *Nat. Commun.* 9, 5235 (2018)), colorectal and breast cancers.

In contrast to the frequent upregulation of Cyclin E, the inhibitory regulators of CDK2, p21 and p27 are often abnormally downregulated in cancers. SKP2, a component of the SKP1-CUL1-F-box (SCF) complex, has also been implicated in tumorigenesis owing to its capacity to degrade p27 (Zhen Cai et al., (2020) *Seminars in Cancer Biology* 67(2):16-33). It is postulated that the loss or decrease of p21/p27 or overexpression of SKP2 lead to high and/or abnormal temporal activation of CDK2, thereby promoting oncogenic growth.

In addition, CDC25A and CDC25B, protein phosphatases responsible for the dephosphorylations that activate the CDK2, are overexpressed in various tumors. These various mechanisms of CDK2 activation have been validated using mouse cancer models.

The retinoblastona (Rb) protein functions as transcription co-repressor and represents the key substrate of CDK4/6 and CDK2 complexes in driving cell division. Consistent with this canonical model, Rb-deficient tumors do not depend on CDK4/6 and are uniformly resistant to CDK4/6 inhibitors. However, an analysis on DepMAP (McFarland et al., 2018; Tsherniak et al., 2017), a database to assess the functional requirements of genes across 717 cancer cell lines using CRISPR technology, discovered that Rb-deficiency and high CDKN2A were associated with higher vulnerability to CDK2 or Cyclin E1 inhibition (Erik S. Knudsen et al. *Cell Reports* Mar. 1, 2022, 38:110448). It was proposed that CDK2/Cyclin E1 drives the phosphorylation of p130 to enable cell-cycle progression in this Rb-deficient CDK2/Cyclin E1-dependent setting.

Furthermore, CDK2/cyclin E phosphorylates oncogenic Myc to oppose ras-induced senescence, highlighting the importance of CDK2 in myc/ras-induced tumorigenesis (Per Hydbring, *PNAS* Jan. 5, 2010, 107 (1) 58-63; Campaner, S., Doni, M., Hydbring, P. et al., *Nat Cell Biol* 12, 54-59

(2010)). Inactivation of CDK2 has been shown to be synthetically lethal to myc over-expressing cancer cells (Jan J. Molenaar, *PNAS* Aug. 4, 2009 106 (31) 12968-12973; Sara Bolin et al., *Oncogene* 37: 2850-2862 (2018)).

Centrosomal protein CP 110 plays an important role in centrosome duplication/separation and requires CDK2 phosphorylation to induce centrosome clustering (reviewed in M Kawakami et al., (2018) *Mol Cancer Ther* 17(4):724-731). Aneuploidy cancer cells are genetically unstable and often have supernumerary centrosomes. If centrosome clustering is blocked, aneuploid cells with supernumerary centrosomes undergo multipolar division, leading to apoptosis of daughter cells, a process called anaphase catastrophe. In addition, CP110 is downregulated in KRAS-mutant lung cancer, enhancing sensitivity of this cancer to CDK2 inhibitors. In models of KRAS-mutant lung cancer, CDK2 inhibition resulted in anaphase catastrophe and apoptosis and reduced growth of lung cancer xenografts. Because aneuploid cells with supernumerary centrosomes occur in many cancers, there might be potential to extend CDK2 inhibitors to other settings beyond KRAS-mutant lung cancer.

CDK2 was also shown to play a role in blocking myeloid differentiation in AML (Meidan Ying et al., *Blood* 2018 Jun. 14; 131(24):2698-2711). Inhibiting CDK2 effectively induced granulocytic differentiation in AML cell lines and arrested tumor growth in AML mice models. Synergetic effect was demonstrated for combining CDK2 inhibition and all-trans-retinoic acid (ATRA) in AML both in vitro and in vivo (Xuejing Shao et al., *Pharmacol Res,* 2020 151: 104545).

Pharmacologic inhibition or genetic deletion of CDK2 has also been shown to preserve hearing function in animal models treated with cisplatin or noise (see Teitz T. et al., *J Exp Med.* 2018 Apr. 2; 215(4):1187-1203). Therefore, in addition to anti-tumor therapies, CDK2 inhibition can also be used as a promising preventive treatment for noise-, cisplatin-, or antibiotic-induced or age-related hearing loss, for which no Food and Drug Administration approved drugs are currently available.

Given the role of CDK2 in human malignancy, there is a need for CDK2 inhibitors for the treatment of cancers and related diseases. The present disclosure fulfills this and related needs.

SUMMARY

In a first aspect, provided is a compound of Formula (I):

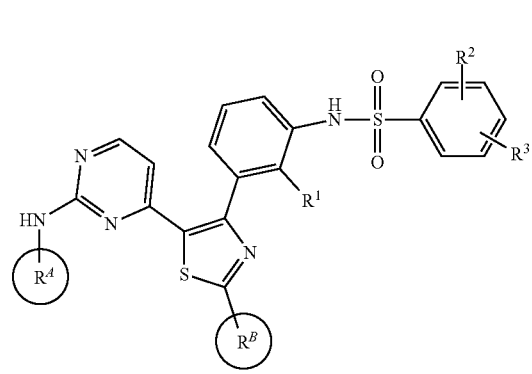

(I)

wherein:
  $R^1$ is hydrogen or halo;
  ring $R^A$ is a ring of formula (i), (ii), (iii), or (iv):

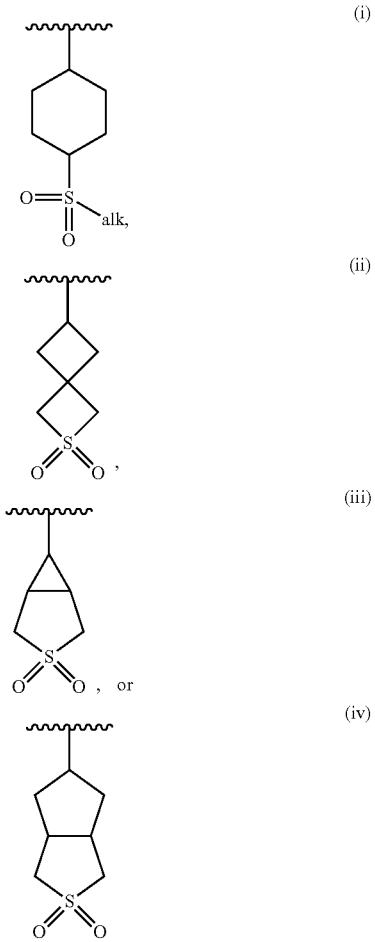

where alk is alkyl and each ring of $R^A$ is substituted with $R^4$ and $R^5$ independently selected from hydrogen, alkyl, and halo;

$R^2$ and $R^3$ are independently selected from hydrogen, alkyl, cycloalkyl, alkoxy, halo, haloalkyl, and haloalkoxy;

ring $R^B$ is cycloalkyl, bridged cycloalkyl, heterocyclyl, or bridged heterocyclyl, wherein:
  (A) cycloalkyl and bridged cycloalkyl of ring $R^B$ are substituted with $R^a$ selected from hydrogen, halo, haloalkyl, and hydroxyalkyl;
  (B) heterocyclyl of ring $R^B$ is substituted with $R^b$, $R^c$, and $R^d$ where $R^b$ and $R^c$ are independently selected from hydrogen, alkyl, alkoxy, hydroxy, cyano, halo, haloalkyl, and haloalkoxy and $R^d$ is hydrogen, alkyl, deuteroalkyl, cycloalkyl (optionally substituted with one or two substituents independently selected from alkyl, halo, hydroxy, and cyano), alkoxy, halo, haloalkyl, haloalkoxy, alkoxycarbonyl, amino, alkylamino, dialkylamino, aryl, aralkyl, heterocyclyl, or heteroaryl; and
  (C) bridged heterocyclyl of ring $R^B$ is substituted with $R^e$, $R^f$, and $R^g$ where $R^e$ and $R^f$ are independently selected from hydrogen, alkyl, alkoxy, hydroxy, cyano, halo, haloalkyl, and haloalkoxy and $R^9$ is hydrogen, alkyl, deuteroalkyl, cycloalkyl (optionally substituted with one or two substituents independently selected from alkyl, halo, hydroxy, or cyano), alkoxy, halo, haloalkyl, haloalkoxy, alkoxycarbonyl, oxo, amino, alkylamino, dialkylamino, aryl, aralkyl, heterocyclyl, or heteroaryl; or a pharmaceutically acceptable salt thereof.

In a second aspect, provided is a pharmaceutical composition comprising a compound of Formula (I) as described in the first aspect (or any of the embodiments 1 to 66 thereof described herein), or a pharmaceutically acceptable salt thereof; and a pharmaceutically acceptable excipient.

In general, compounds of Formula (I) selectively inhibit CDK2 over CDK1. The compounds of Formula (I), generally, also selectively inhibit CDK2 over CDK4 and/or CDK6. As such, in a third aspect, provided is a method of treating a disease treatable by inhibition of CDK2 in a patient, preferably the patient is in need of such treatment, which method comprises administering to the patient, preferably a patient in need of such treatment, a therapeutically effective amount of a compound of Formula (I) as described in the first aspect (or any of the embodiments thereof described herein), or a pharmaceutically acceptable salt thereof; or a pharmaceutical composition thereof as disclosed herein.

In a first embodiment of the third aspect, the disease is cancer. In a second embodiment of the third aspect, the disease is cancer selected from ovarian cancer (e.g., serous carcinomas, clear cell carcinoma, mucinous carcinoma, and/or endometroid carcinoma), endometrial cancer, breast cancer (e.g., hormone receptor-positive breast cancer, and/or triple-negative breast cancer), lung cancer (e.g., adenocarcinoma, small cell lung cancer and/or non-small cell lung carcinomas, parvicellular and non-parvicellular carcinoma, bronchial carcinoma, bronchial adenoma, and/or pleuropulmonary blastoma), skin cancer (e.g. melanoma, squamous cell carcinoma, Kaposi sarcoma, and/or Merkel cell skin cancer), bladder cancer, cervical cancer, colorectal cancer, cancer of the small intestine, colon cancer, rectal cancer, cancer of the anus, gastric cancer (e.g., tubular adenocarcinoma, papillary adenocarcinoma, mucinous adenocarcinoma, signet ring cell carcinoma, and/or adenosquamous carcinoma), head and neck cancer (e.g., cancers of the larynx, hypopharynx, nasopharynx, oropharynx, lips, and/or mouth), liver cancer (e.g., hepatocellular carcinoma, and/or cholangiocellular carcinoma), prostate cancer, testicular cancer, uterine cancer, esophageal cancer, gall bladder cancer, pancreatic cancer (e.g. exocrine pancreatic carcinoma), stomach cancer, thyroid cancer, and parathyroid cancer. In a third embodiment of the third aspect, the disease is cancer that are resistant to CDK4/6 inhibitors through CDK2-mediated mechanisms.

In a fourth aspect, provided is a method of treating noise-, cisplatin-, antibiotic-induced- or age-related hearing loss, which method comprises administering to the patient, preferably a patient in need of such treatment, a therapeutically effective amount of a compound of Formula (I) as described in the first aspect (or any of the embodiments thereof described herein), or a pharmaceutically acceptable salt thereof; or a pharmaceutical composition thereof as disclosed herein. In some embodiments, the amount of hearing loss is reduced when compared to an age-matched control. In some embodiments, the hearing loss is prevented when compared to an age-matched control.

In a fifth aspect, provided is a compound of Formula (I) as described in the first aspect (or any of the embodiments thereof described herein), or a pharmaceutically acceptable salt thereof for use as a medicament. In one embodiment of the fourth aspect, the compound Formula (I) (and any of the embodiments thereof described herein), or a pharmaceutically acceptable salt thereof is useful for the treatment of one or more of diseases disclosed in the third and/or fourth aspects above (including embodiments therein).

In a sixth aspect, provided is the use of a compound of Formula (I) as described in the first aspect (and any of the embodiments thereof disclosed herein), or a pharmaceutically acceptable salt thereof in the manufacture of a medicament for treating a disease in a patient in which the activity of CDK2 contributes to the pathology and/or symptoms of the disease. In an embodiment of the sixth aspect, the disease is one or more of diseases disclosed in the third and/or fourth aspects above (including embodiments therein).

In a seventh aspect, provided is a method of inhibiting CDK2 which method comprises contacting CDK2 with a compound of Formula (I) as described in the first aspect (or any of the embodiments thereof described herein), or a pharmaceutically acceptable salt thereof; or contacting CDK2 with a pharmaceutical composition comprising a compound of Formula (I) (or any of the embodiments thereof described herein), or a pharmaceutically acceptable salt thereof, and a pharmaceutically acceptable excipient. In one embodiment, the CDK2 is contacted with a compound of Formula (I) (or any of the embodiments thereof described herein), or a pharmaceutically acceptable salt thereof, in vitro. In another embodiment, the CDK2 is contacted with a compound of Formula (I) (or any of the embodiments thereof described herein), or a pharmaceutically acceptable salt thereof, in vivo.

In any of the aforementioned aspects involving the treatment of cancer, are further embodiments comprising administering the compound of Formula (I) as described in the first aspect (or any of the embodiments thereof disclosed herein), or a pharmaceutically acceptable salt thereof in combination with at least one additional anticancer agent. When combination therapy is used, the agents can be administered simultaneously or sequentially.

In an eighth aspect, provided is a process of preparing a compound of Formula (I):

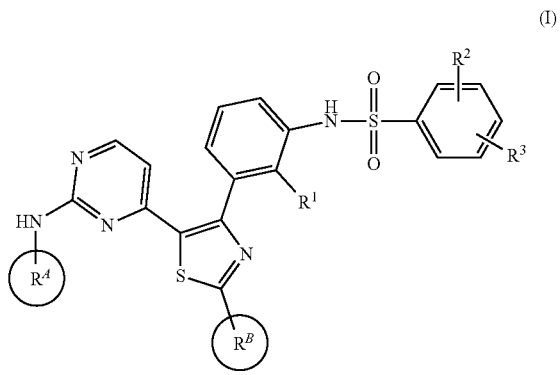

wherein:
(1) when $R^1$, $R^2$, $R^3$, ring $R^A$, and ring $R^B$ are as defined in the first aspect (or any of the embodiments thereof hereinbelow); the process comprises:

(i) reacting a compound of (a):

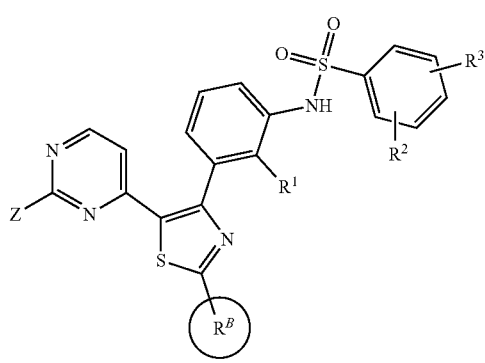

where Z is a leaving group under an $S_NAr$ or metal-catalyzed cross-coupling reaction condition and $R^1$, $R^2$, $R^3$, and ring $R^B$ are as defined in the first aspect (or any of the embodiments thereof hereinbelow) with an amine of formula (b):

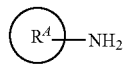

where ring $R^A$ is as defined in the first aspect (or any of the embodiments thereof hereinbelow); or (ii) reacting a compound of (c):

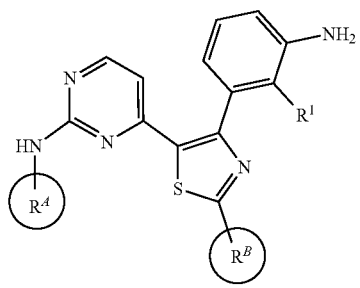

where $R^1$, $R^A$, and ring $R^B$ are as defined in the first aspect (or any of the embodiments thereof hereinbelow) with a sulfonyl compound of formula (d):

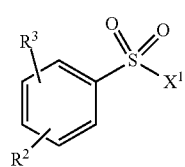

where $X^1$ is a leaving group under nucleophilic substitution reaction conditions and $R^2$ and $R^3$ are as defined in the first aspect (or any one of the embodiments thereof hereinbelow); or (2) when $R^1$, $R^2$, $R^3$, and ring $R^A$ are as defined in the first aspect (or any of the embodiments thereof hereinbelow) and ring $R^B$ is heterocyclylaminyl substituted with $R^b$, $R^c$, and $R^d$ or bridged heterocyclylaminyl substituted with $R^e$, $R^f$, and $R^g$, and the heterocyclylaminyl and bridged heterocyclylaminyl are attached to thiazolyl ring via a ring nitrogen atom, the process comprises reacting a compound of formula (e):

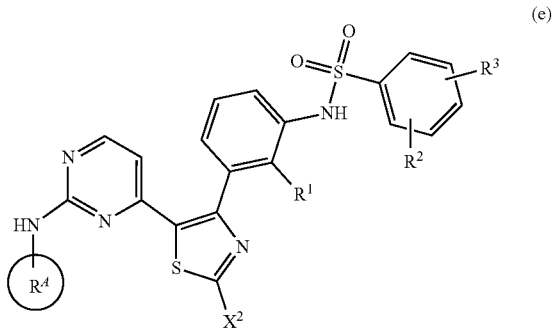

where $X^2$ is a leaving group under an $S_NAr$ or metal-catalyzed cross-coupling reaction condition and $R^1$, $R^2$, $R^3$, and ring $R^A$ are as defined in the first aspect (or any of the embodiments thereof hereinbelow) with an amine compound of formula (f):

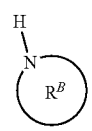

where ring $R^B$ is heterocyclylaminyl substituted with $R^b$, $R^c$, and $R^d$ or bridged heterocyclylaminyl substituted with $R^e$, $R^f$, and $R^g$; and (3) optionally modifying one or more of $R^2$, $R^3$, $R^b$, $R^c$, $R^d$, $R^e$, $R^f$, and $R^g$ to provide a compound of Formula (I);

(4) optionally forming an acid addition salt of the Compound of Formula (I) obtained from Step (1), (2), and/or (3) above; and (5) optionally forming free base of an acid addition salt of Compound of Formula (I) obtained from Step (1), (2), (3), and/or (4).

In an embodiment of the eighth aspect, Z is halo or alkylsulfonyl e.g., methylsulfonyl and $X^1$ and $X^2$ are halo (such as chloro or bromo).

In a ninth aspect, provided is an intermediate of formula:

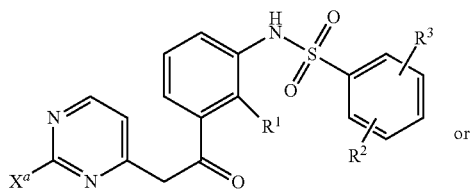

or

-continued

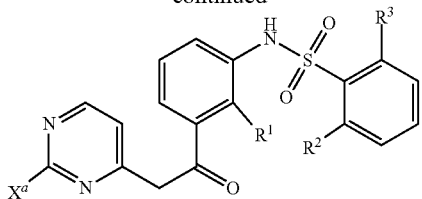

where $X^a$ is a leaving group under $S_NAr$ or metal-catalyzed cross-coupling reaction condition, $R^1$ is hydrogen or halo, and $R^2$ and $R^3$ are independently selected from hydrogen, alkyl, cycloalkyl, alkoxy, halo, haloalkyl, and haloalkoxy (or any of the embodiments thereof disclosed hereinbelow); provided that when one of $R^2$ and $R^3$ is hydrogen or halo, then the other of $R^2$ and $R^3$ is alkyl, cycloalkyl, alkoxy, haloalkyl, and haloalkoxy (or any of the embodiments thereof disclosed hereinbelow). In one embodiment of the ninth aspect, $X^a$ is halo (e.g., chloro, bromo) or alkylsulfonyl (e.g., methylsulfonyl).

In a tenth aspect, provided is an intermediate of formula:

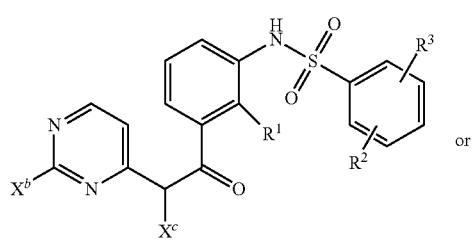

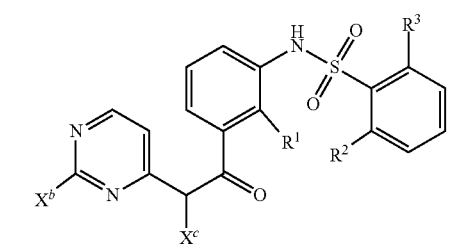

where $X^b$ is a leaving group under a $S_NAr$ or metal catalyzed cross-coupling reaction condition and $X^c$ is a leaving group under nucleophilic addition reaction condition, $R^1$ is hydrogen or halo, and $R^2$ and $R^3$ are independently selected from hydrogen, alkyl, cycloalkyl, alkoxy, halo, haloalkyl, and haloalkoxy (or any of the embodiments thereof disclosed herein below); provided when $R^1$ is halo, then $R^2$ and $R^3$ are not halo simultaneously. In one embodiment of the tenth aspect, $X^b$ and $X^c$ are independently halo (e.g., chloro or bromo). In another embodiment of the tenth aspect, $X^b$ is chloro and $X^c$ is bromo.

In an eleventh aspect, provided is an intermediate of formula:

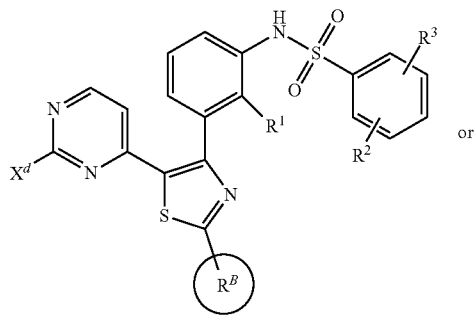

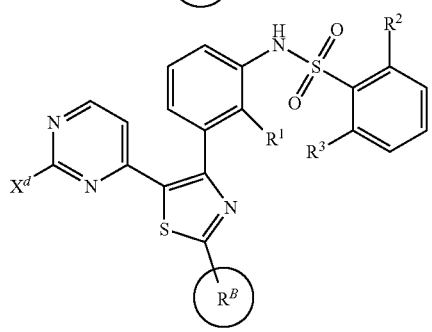

where:
$X^d$ is a leaving group under $S_NAr$ or metal catalyzed coupling conditions;
$R^1$ is hydrogen or halo;
$R^2$ and $R^3$ are independently selected from hydrogen, alkyl, cycloalkyl, alkoxy, halo, haloalkyl, and haloalkoxy;
ring $R^B$ is cycloalkyl, bridged cycloalkyl, heterocyclyl, or bridged heterocyclyl, wherein:
(A) cycloalkyl are substituted with $R^a$ selected from halo, haloalkyl, and hydroxalkyl and bridged cycloalkyl of ring $R^B$ are substituted with $R^a$ selected from hydrogen, halo, haloalkyl, and hydroxalkyl;
(B) heterocyclyl of ring $R^B$ is substituted with $R^b$, $R^c$, and $R^d$ where $R^b$ and $R^c$ are independently selected from hydrogen, alkoxy, hydroxy, cyano, halo, haloalkyl, and haloalkoxy and $R^d$ is hydrogen, alkyl, deuteroalkyl, alkoxy, halo, haloalkyl, haloalkoxy, amino, alkylamino, dialkylamino, aryl, aralkyl, heterocyclyl, or heteroaryl; and
(C) bridged heterocyclyl of ring $R^B$ is substituted with $R^e$, $R^f$, and $R^g$ where $R^e$ and R are independently selected from hydrogen, alkyl, alkoxy, hydroxy, cyano, halo, haloalkyl, and haloalkoxy and $R^g$ is hydrogen, alkyl, deuteroalkyl, cycloalkyl (optionally substituted with one or two substituents independently selected from alkyl, halo, hydroxy, or cyano), alkoxy, halo, haloalkyl, haloalkoxy, alkoxycarbonyl, oxo, amino, alkylamino, dialkylamino, aryl, aralkyl, heterocyclyl, or heteroaryl; (or any one of embodiments of $R^1$, $R^2$, $R^3$, ring $R^A$, and ring $R^B$ disclosed hereinbelow).

In one embodiment of the eleventh aspect, $X^d$ is halo (e.g., chloro or bromo) or alkylsulfonyl (e.g., methylsulfonyl).

In a twelfth aspect, provided is an intermediate of formula:

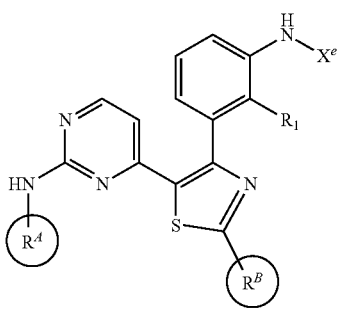

where $X^e$ is H or an amino protecting group and $R^1$, $R^A$, and $R^B$ are as disclosed in the first aspect (or any embodiments thereof disclosed herein below). In one embodiment of the twelfth aspect, $X^e$ is alkylcarbonyl (e.g., acetyl).

In a thirteenth aspect, provided is an intermediate of formula:

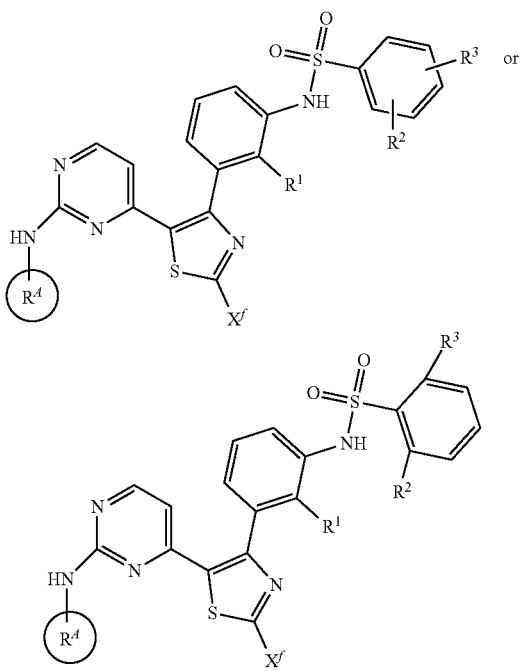

where $X^f$ is amino or halo and $R^1$, $R^2$, $R^3$, and $R^A$ are as disclosed in the first aspect (or any one of embodiments thereof disclosed hereinbelow).

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated; e.g., methylene, ethylene, propylene, 1-methylpropylene, 2-methylpropylene, butylene, pentylene, and the like.

"Alkoxy" means a —OR radical where R is alkyl as defined above, e.g., methoxy, ethoxy, propoxy, or 2-propoxy, n-, iso-, or tert-butoxy, and the like.

"Amino" means a —NH$_2$.

"Alkylamino" means a —NHR where R is alkyl as defined above e.g., methylamino, ethylamino, propylamino, and the like.

"Alkoxycarbonyl" means a —C(O)OR$^z$ radical where R$^z$ is alkyl as defined above, e.g., ethoxycarbonyl, ethoxycarbonyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R$^z$ radical where R$^z$ is aryl as defined above. Examples include, but are not limited to, benzyl, phenethyl, and the like.

"Bridged cycloalkyl" means a saturated monovalent bicyclic or tricyclic hydrocarbon radical having 5 to 10 ring carbon ring atoms in which one or two ring atoms are linked by a (CR$^z$R$^{z1}$)n group (where n is an integer selected from 1 to 3 inclusive and R$^z$ and R$^{z1}$ are independently H or methyl) to a non-adjacent ring atom(s) (also may be referred to herein as "bridging" group). For clarity, when the bridged cycloalkyl is a bicylic ring, it has one bridging group and when the bridged cycloalkyl is a tricylic ring, it has two bridging groups). Examples include, but are not limited to, bicyclo[1.1.1]pentyl, bicyclo[2.1.1]hexyl, bicyclo[2.2.2]octyl, adamantyl, and the like.

"Bridged heterocyclyl" means a saturated monovalent bicyclic radical having 5 to 9 ring carbon ring atoms in which two non-adjacent ring atoms are linked by a (CR$^z$R$^{z1}$)n group where n is 1 to 3 and R$^z$ and R$^{z1}$ are independently H or methyl (also may be referred to herein as "bridging" group) and further wherein one or two ring carbon atoms, including an atom in the bridging group, is replaced by a heteroatom selected from N, O, and S(O)$_n$, where n is an integer selected from 0 to 2 inclusive. When the bridged heterocyclyl group contains at least one nitrogen atom, it is also referred to herein as bridged heterocycylaminyl and is a subset of the bridged heterocyclyl group. Examples include, but are not limited to, 2-azabicyclo[2.2.2]octyl, quinuclidinyl, 7-oxabicyclo[2.2.1]heptyl, and the like.

"Cycloalkyl" means a monocyclic saturated monovalent hydrocarbon radical of three to ten carbon atoms. Examples include, but are not limited to, cyclopropyl, cyclobutyl, cyclopentyl, cyclohexyl, and the like.

"Dialkylamino" means a —NRR' where R and R' are independently alkyl as defined above e.g., dimethylamino, diethylamino, methylpropylamino, and the like.

"Deuteroalkyl" mean alkyl as defined above, which is substituted with one, two, or three deuterium e.g., trideuteromethyl.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present, they are both not on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms and is a monocyclic ring, it is also referred to herein as 5- or 6-membered monocyclic heteroaryl. When the heteroaryl ring contains 9- or 10 ring atoms and is a bicyclic ring, it is also referred to herein as 9- or 10-membered fused bicyclic heteroaryl.

"Heterocyclyl" means a saturated monovalent monocyclic radical of 4 to 8 ring atoms in which one or two ring atoms are heteroatom independently selected from N, O, and $S(O)_n$, where n is an integer from 0 to 2, the remaining ring atoms being C, unless stated otherwise. Additionally, one or two ring carbon atoms in the heterocyclyl ring can optionally be replaced by a —C(=O)— group. More specifically the term heterocyclyl includes, but is not limited to, pyrrolidinyl, piperidinyl, homopiperidinyl, 2-oxopyrrolidinyl, 2-oxopiperidinyl, morpholinyl, piperazinyl, tetrahydropyranyl, thiomorpholinyl, and the like. When the heterocyclyl group contains at least one nitrogen atom, it is also referred to herein as heterocyclylaminyl and is a subset of the heterocyclyl group.

The term "oxo," as used herein, alone or in combination, refers to =(O).

The present disclosure also includes protected derivatives of compounds of Formula (I). For example, when compounds of Formula (I) contain groups such as hydroxy, carboxy, or any group containing a nitrogen atom(s), these groups can be protected with suitable protecting groups. A comprehensive list of suitable protective groups can be found in T. W. Greene, *Protective Groups in Organic Synthesis*, 5$^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes polymorphic forms and deuterated forms of the compound of Formula (I) or a pharmaceutically acceptable salt thereof.

The term "prodrug" refers to a compound that is made more active in vivo. Certain compounds Formula (I) may also exist as prodrugs, as described in *Hydrolysis in Drug and Prodrug Metabolism: Chemistry, Biochemistry, and Enzymology* (see Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, P A, 1985, which is incorporated herein by reference in its entirety.

The compounds of Formula (I) may have asymmetric centers. Compounds of Formula (I) containing an asymmetrically substituted atom may be isolated in optically active or racemic forms. Individual stereoisomers of compounds can be synthesized from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diastereomeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl is substituted, it includes all the positional isomers albeit only a few examples are set forth. Furthermore, all hydrates of a compound of Formula (I) are within the scope of this disclosure.

The compounds of Formula (I) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (I) (and any embodiments thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of Formula (I), including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$ $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass 10%, preferably +5%, the recited value and the range is included.

The phrase "optionally" or "optional" as used herein means that the subsequently described event or circumstance may but need not occur, and that the description includes instances where the event or circumstance occurs and instances in which it does not. For example, the phrase "cycloalkyl optionally substituted with alkyl" is intended to cover cycloalkyl that is not substituted with alkyl and cycloalkyl that is substituted with alkyl.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses.

Preferably, the patient is a human.

"Treating" or "treatment" of a disease includes:
(1) preventing the disease, i.e., causing the clinical symptoms of the disease not to develop in a mammal that may be exposed to or predisposed to the disease but does not yet experience or display symptoms of the disease;
(2) inhibiting the disease, i.e., delaying, arresting (i.e., stabilizing), or reducing the development or severity of the disease or its clinical symptoms; or
(3) relieving the disease, i.e., causing regression of the disease or its clinical symptoms.

In one embodiment, treating or treatment of a disease includes inhibiting the disease, i.e., delaying, arresting or reducing the development or severity of the disease or its clinical symptoms; or relieving the disease, i.e., causing regression of the disease or its clinical symptoms.

A "therapeutically effective amount" means the amount of a compound of the present disclosure or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation to CDK2, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of CDK2 activity compared to its normal activity.

Representative compounds of the disclosure made are disclosed in Table I below:

TABLE I

| Cpd No. | Structure | Name |
|---|---|---|
| 1 | 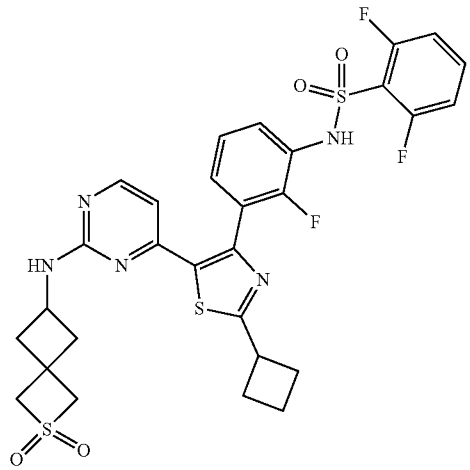 [SMILES: O=S1(=O)CC2(CC(Nc3nccc(-c4sc(C5CCC5)nc4-c4cccc(NS(=O)(=O)c5c(F)cccc5F)c4F)n3)C2)C1] | N-(3-(2-cyclobutyl-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 2 | 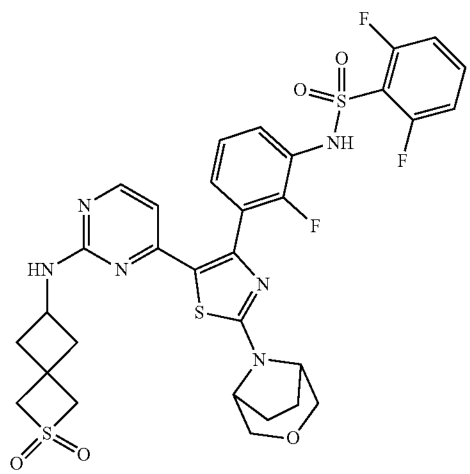 [SMILES: O=S1(=O)CC2(CC(Nc3nccc(-c4sc(N5C6CCC5COC6)nc4-c4cccc(NS(=O)(=O)c5c(F)cccc5F)c4F)n3)C2)C1] | N-(3-(2-(3-oxa-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 3 | 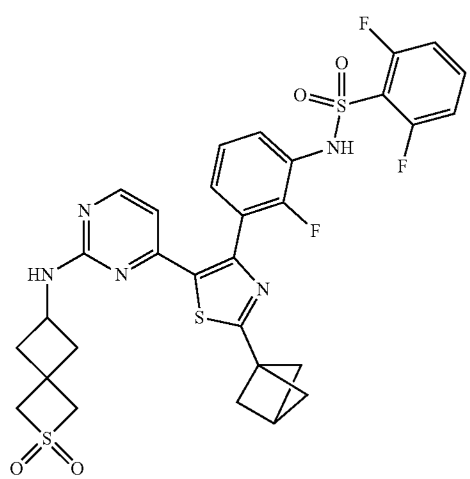 [SMILES: O=S1(=O)CC2(CC(Nc3nccc(-c4sc(C56CC(C5)C6)nc4-c4cccc(NS(=O)(=O)c5c(F)cccc5F)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 4 | 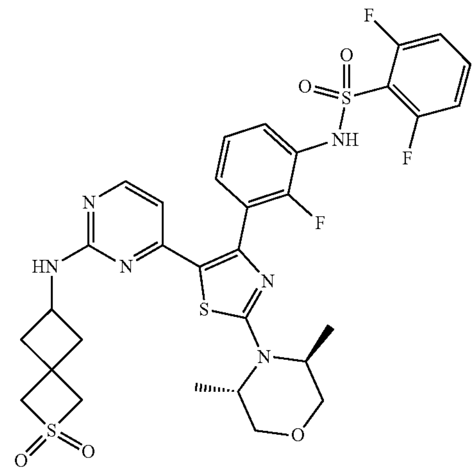 [SMILES: C[C@H]1COC[C@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((3S,5S)-3,5-dimethylmorpholino)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 5 | 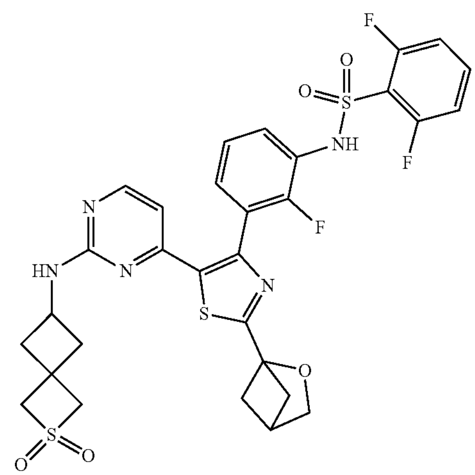 [SMILES: O=S1(=O)CC2(CC(Nc3nccc(-c4sc(C56CC(CO5)C6)nc4-c4cccc(NS(=O)(=O)c5c(F)cccc5F)c4F)n3)C2)C1] | N-(3-(2-(2-oxabicyclo[2.1.1]hexan-1-yl)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 6 | 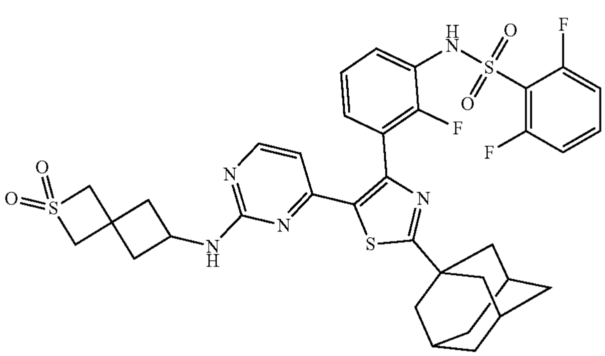 [SMILES: O=S1(=O)CC2(CC(Nc3nccc(-c4sc(C56CC7CC(CC(C7)C5)C6)nc4-c4cccc(NS(=O)(=O)c5c(F)cccc5F)c4F)n3)C2)C1] | N-(3-(2-((3r,5r,7r)-adamantan-1-yl)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 7 | 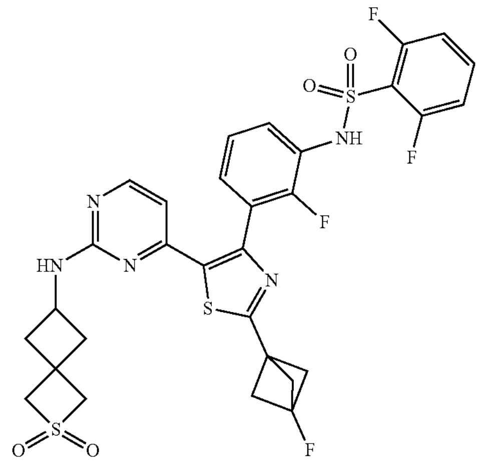 [SMILES: O=S1(=O)CC2(CC(Nc3nccc(-c4sc(C56CC(F)(C5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)pyrimidin-4-yl)-2-(3-fluorobicyclo[1.1.1]pentan-1-yl)thiazol-4-yl)-2-fluorophenyl)-2,6-difluorobenzenesulfonamide |
| 8 | 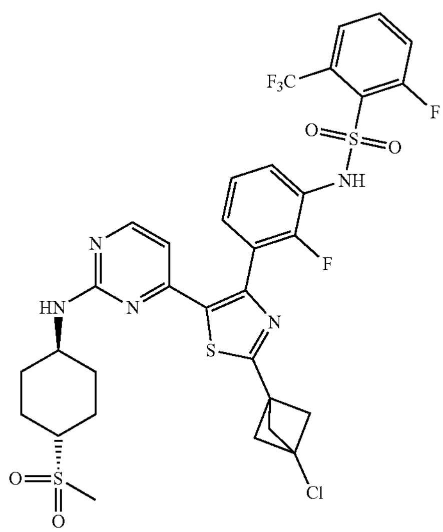 | N-(3-(2-(3-chlorobicyclo[1.1.1]pentan-1-yl)-5-(2-(((1s,4s)-4-(methylsulfonyl)cyclohexyl)amino)pyrimidin-4-yl)thiazol-4-yl)-2-fluorophenyl)-2-fluoro-6-(trifluoromethyl)benzenesulfonamide |
| 9 | 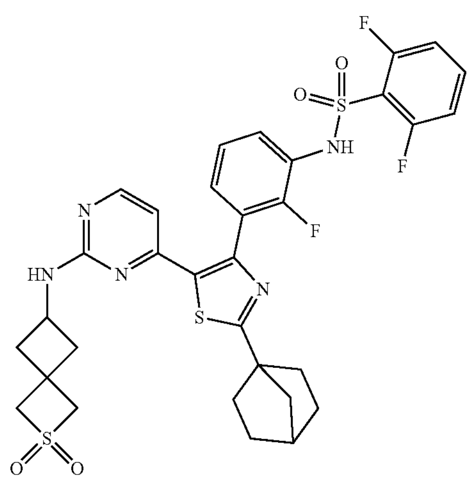 [SMILES: O=S1(=O)CC2(CC(Nc3nccc(-c4sc(C56CCC(CC5)C6)nc4-c4cccc(NS(=O)(=O)c5c(F)cccc5F)c4F)n3)C2)C1] | N-(3-(2-(bicyclo[2.2.1]heptan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
| --- | --- | --- |
| 10 | 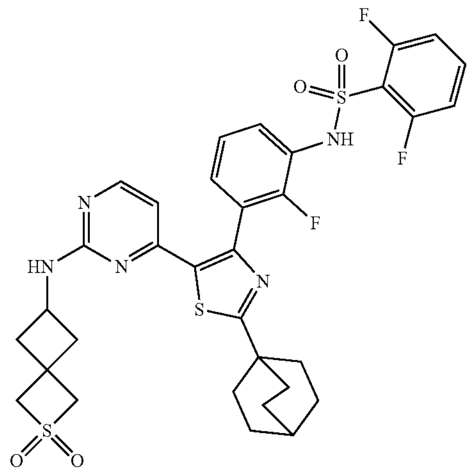 [SMILES: O=S1(=O)CC2(CC(Nc3nccc(-c4sc(C56CCC(CC5)CC6)nc4-c4cccc(NS(=O)(=O)c5c(F)cccc5F)c4F)n3)C2)C1] | N-(3-(2-(bicyclo[2.2.2]octan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 11 | 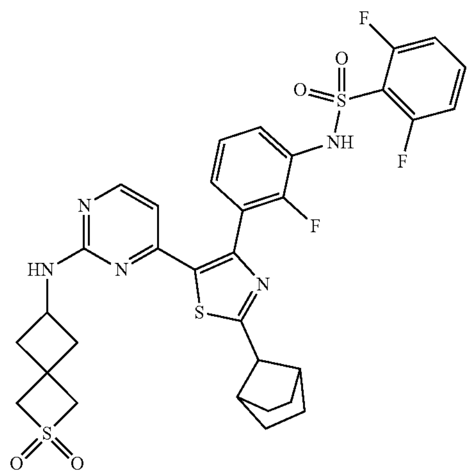 [SMILES: O=S1(=O)CC2(CC(Nc3nccc(-c4sc(C5C6CCC5CC6)nc4-c4cccc(NS(=O)(=O)c5c(F)cccc5F)c4F)n3)C2)C1] | N-(3-(2-(7-azabicyclo[2.2.1]heptan-7-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 12 | 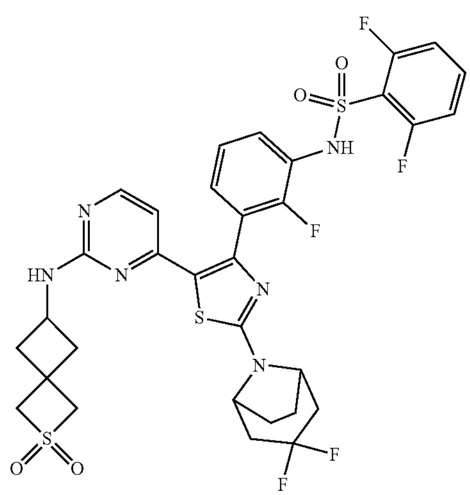 [SMILES: O=S1(=O)CC2(CC(Nc3nccc(-c4sc(N5C6CCC5CC(F)(F)C6)nc4-c4cccc(NS(=O)(=O)c5c(F)cccc5F)c4F)n3)C2)C1] | N-(3-(2-(3,3-difluoro-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 13 | 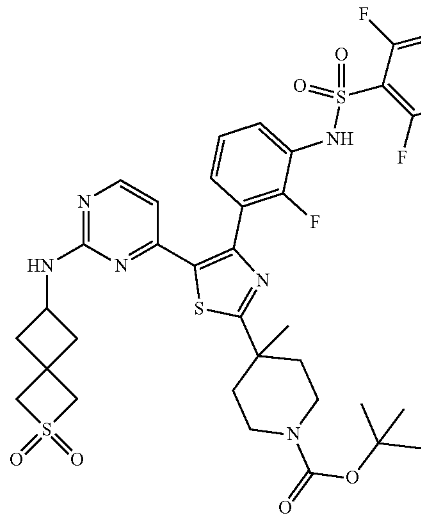 | tert-butyl 4-(4-(3-((2,6-difluorophenyl)sulfonamido)-2-fluorophenyl)-5-(2-((2,2-dioxido-2-thiaspiro[3.3]heptan-6-yl)amino)pyrimidin-4-yl)thiazol-2-yl)-4-methylpiperidine-1-carboxylate |
| 14 | 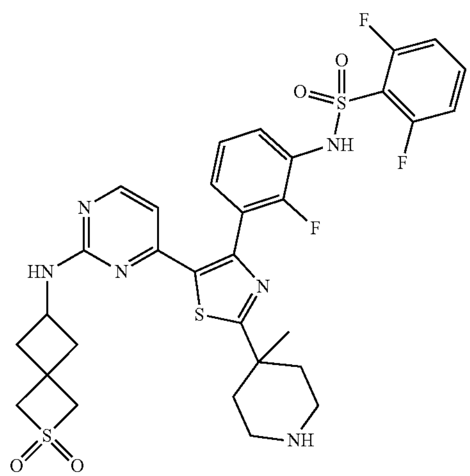 [SMILES: CC1(c2nc(-c3cccc(NS(=O)(=O)c4c(F)cccc4F)c3F)c(-c3ccnc(NC4CC5(C4)CS(=O)(=O)C5)n3)s2)CCNCC1] | N-(3-(5-(2-((2,2-dioxido-2-thiaspiro[3.3]heptan-6-yl)amino)pyrimidin-4-yl)-2-(4-methylpiperidin-4-yl)thiazol-4-yl)-2-fluorophenyl)-2,6-difluorobenzenesulfonamide |
| 15 | 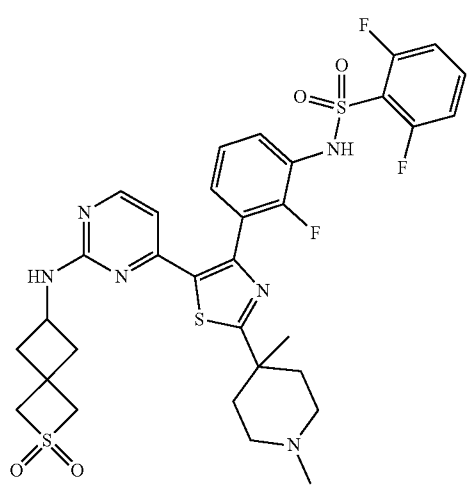 [SMILES: CN1CCC(C)(c2nc(-c3cccc(NS(=O)(=O)c4c(F)cccc4F)c3F)c(-c3ccnc(NC4CC5(C4)CS(=O)(=O)C5)n3)s2)CC1] | N-(3-(2-(1,4-dimethylpiperidin-4-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 16 | 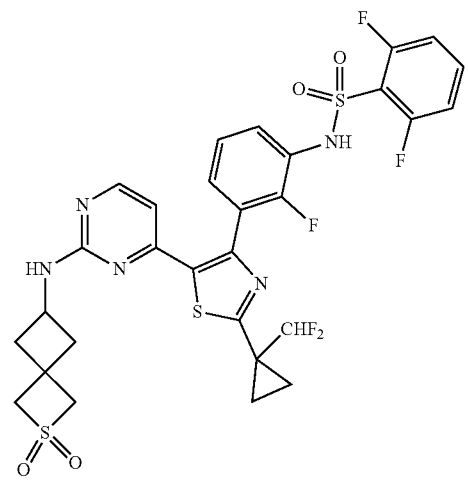 [SMILES: O=S1(=O)CC2(CC(Nc3nccc(-c4sc(C5(C(F)F)CC5)nc4-c4cccc(NS(=O)(=O)c5c(F)cccc5F)c4F)n3)C2)C1] | N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 17 | 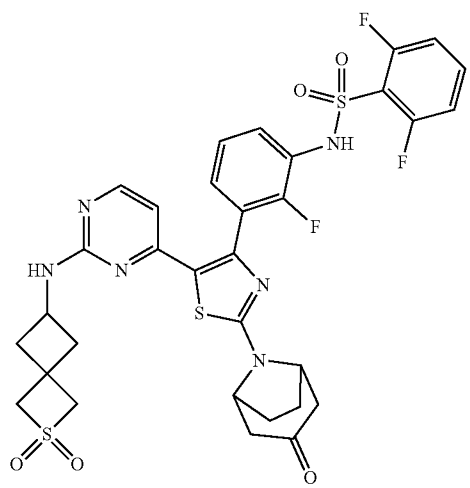 [SMILES: O=C1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)pyrimidin-4-yl)-2-(3-oxo-8-azabicyclo[3.2.1]octan-8-yl)thiazol-4-yl)-2-fluorophenyl)-2,6-difluorobenzenesulfonamide |
| 18 | 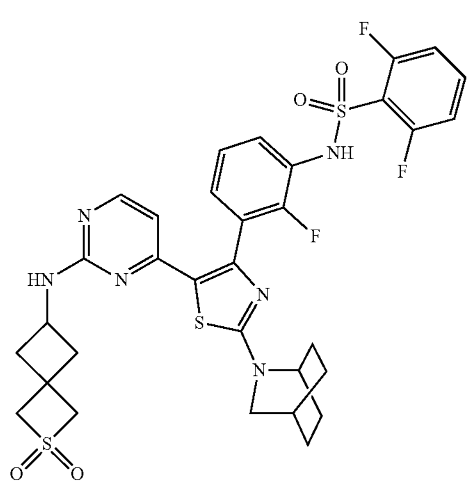 [SMILES: O=S1(=O)CC2(CC(Nc3nccc(-c4sc(N5CC6CCC5CC6)nc4-c4cccc(NS(=O)(=O)c5c(F)cccc5F)c4F)n3)C2)C1] | N-(3-(2-(2-azabicyclo[2.2.2]octan-2-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
| --- | --- | --- |
| 19 | 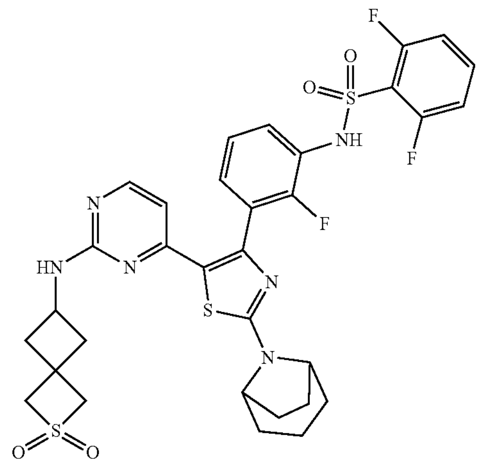 [SMILES: O=S1(=O)CC2(CC(Nc3nccc(-c4sc(N5C6CCCC5CC6)nc4-c4cccc(NS(=O)(=O)c5c(F)cccc5F)c4F)n3)C2)C1] | N-(3-(2-(8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 20 | 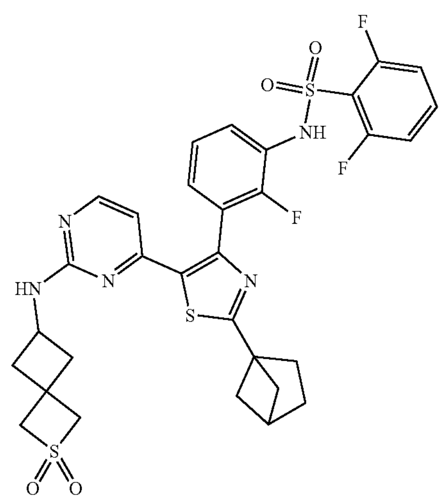 [SMILES: O=S1(=O)CC2(CC(Nc3nccc(-c4sc(C56CCC(C5)C6)nc4-c4cccc(NS(=O)(=O)c5c(F)cccc5F)c4F)n3)C2)C1] | N-(3-(2-(bicyclo[2.1.1]hexan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 21 | 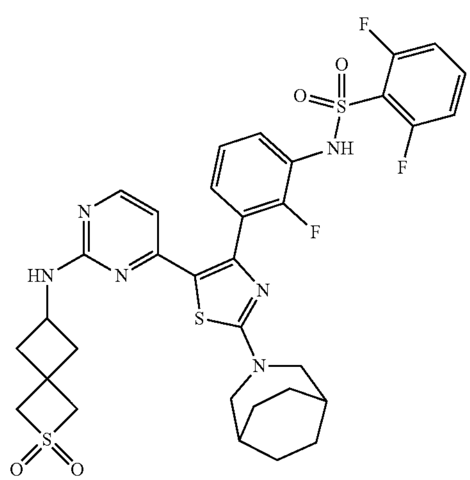 [SMILES: O=S1(=O)CC2(CC(Nc3nccc(-c4sc(N5CC6CCC(CC6)C5)nc4-c4cccc(NS(=O)(=O)c5c(F)cccc5F)c4F)n3)C2)C1] | N-(3-(2-(3-azabicyclo[3.2.2]nonan-3-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 22 | 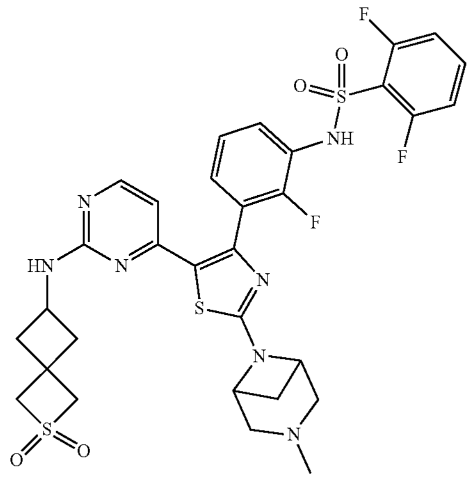 [SMILES: CN1CC2CC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)pyrimidin-4-yl)-2-(3-methyl-3,6-diazabicyclo[3.1.1]heptan-6-yl)thiazol-4-yl)-2-fluorophenyl)-2,6-difluorobenzenesulfonamide |
| 23 | 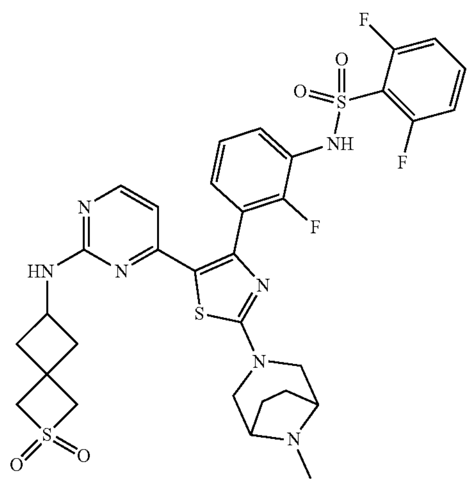 [SMILES: CN1C2CCC1CN(c1nc(-c3cccc(NS(=O)(=O)c4c(F)cccc4F)c3F)c(-c3ccnc(NC4CC5(C4)CS(=O)(=O)C5)n3)s1)C2] | N-(3-(5-(2-((2,2-dioxido-2-thiaspiro[3.3]heptan-6-yl)amino)pyrimidin-4-yl)-2-(8-methyl-3,8-diazabicyclo[3.2.1]octan-3-yl)thiazol-4-yl)-2-fluorophenyl)-2,6-difluorobenzenesulfonamide |
| 24 | 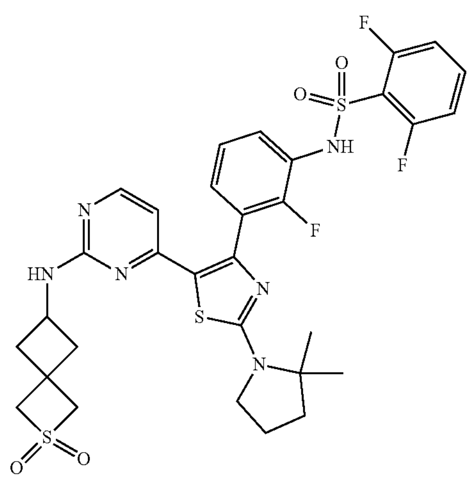 [SMILES: CC1(C)CCCN1c1nc(-c2cccc(NS(=O)(=O)c3c(F)cccc3F)c2F)c(-c2ccnc(NC3CC4(C3)CS(=O)(=O)C4)n2)s1] | N-(3-(2-(2,2-dimethylpyrrolidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 25 | 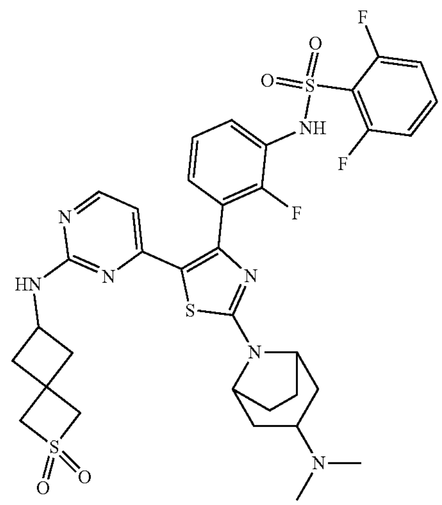 [SMILES: CN(C)C1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(2-(3-(dimethylamino)-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 26 | 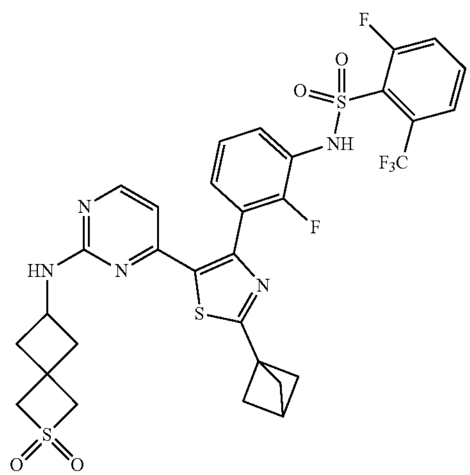 [SMILES: O=S1(=O)CC2(CC(Nc3nccc(-c4sc(C56CC(C5)C6)nc4-c4cccc(NS(=O)(=O)c5c(F)cccc5C(F)(F)F)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 27 | 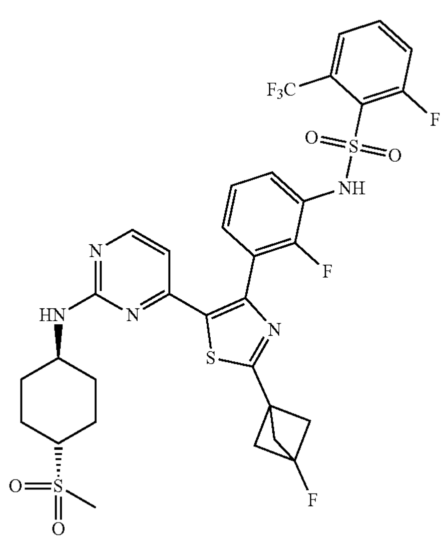 | 2-fluoro-N-(2-fluoro-3-(2-(3-fluorobicyclo[1.1.1]pentan-1-yl)-5-(2-(((1s,4s)-4-(methylsulfonyl)cyclohexyl)amino)pyrimidin-4-yl)thiazol-4-yl)phenyl)-6-(trifluoromethyl)benzenesulfonamide |

TABLE I-continued

| Cpd No. | Structure | Name |
|---|---|---|
| 28 | 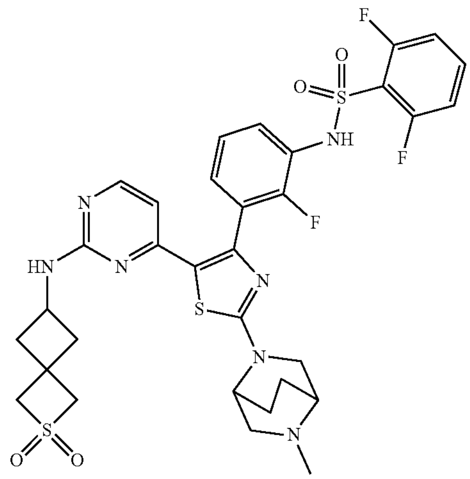 [SMILES: CN1CC2CCC1CN2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)pyrimidin-4-yl)-2-(5-methyl-2,5-diazabicyclo[2.2.2]octan-2-yl)thiazol-4-yl)-2-fluorophenyl)-2,6-difluorobenzenesulfonamide |
| 29 | 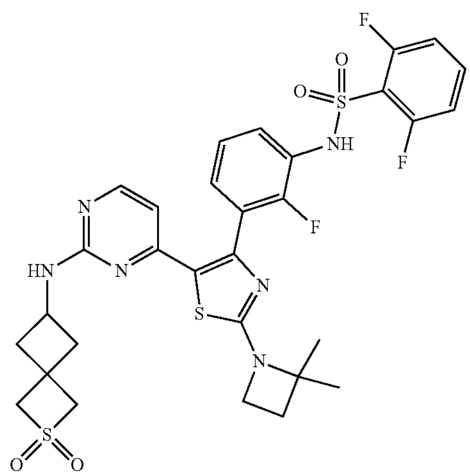 [SMILES: CC1(C)CCN1c1nc(-c2cccc(NS(=O)(=O)c3c(F)cccc3F)c2F)c(-c2ccnc(NC3CC4(C3)CS(=O)(=O)C4)n2)s1] | N-(3-(2-(2,2-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 30 | 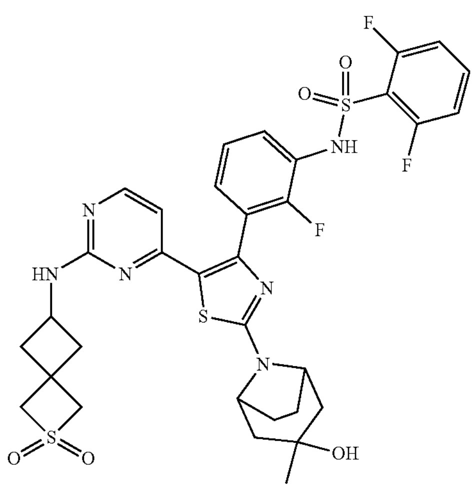 [SMILES: CC1(O)CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)pyrimidin-4-yl)-2-(3-hydroxy-3-methyl-8-azabicyclo[3.2.1]octan-8-yl)thiazol-4-yl)-2-fluorophenyl)-2,6-difluorobenzenesulfonamide |

TABLE I-continued

| Cpd No. | Structure | Name |
|---|---|---|
| 31 | 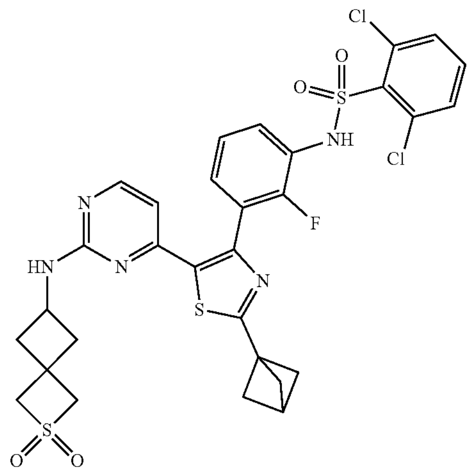 [SMILES: O=S1(=O)CC2(CC(Nc3nccc(-c4sc(C56CC(C5)C6)nc4-c4cccc(NS(=O)(=O)c5c(Cl)cccc5Cl)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-dichlorobenzenesulfonamide |
| 32 | 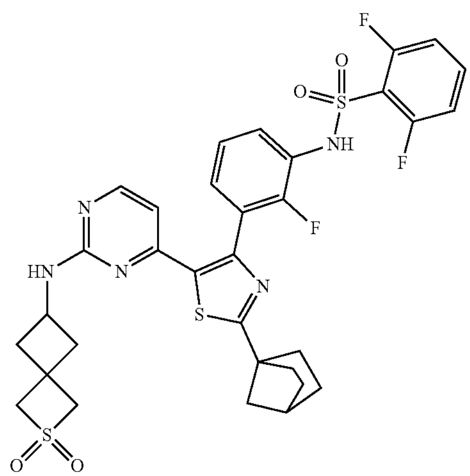 [SMILES: O=S1(=O)CC2(CC(Nc3nccc(-c4sc(C56CCC(CC5)C6)nc4-c4cccc(NS(=O)(=O)c5c(F)cccc5F)c4F)n3)C2)C1] | N-(3-(2-(bicyclo[2.2.1]heptan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 33 | 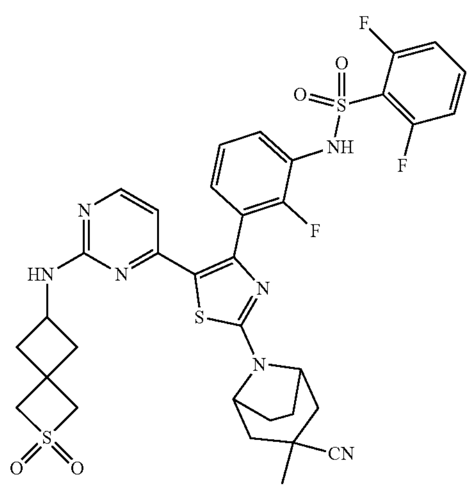 [SMILES: CC1(C#N)CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(2-(3-cyano-3-methyl-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 34 | 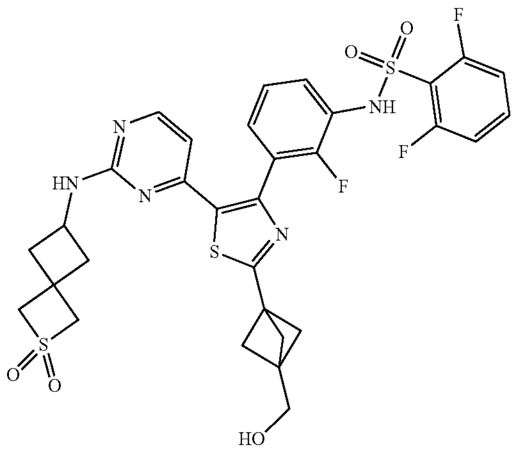 [SMILES: O=S1(=O)CC2(CC(Nc3nccc(-c4sc(C56CC(CO)(C5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)pyrimidin-4-yl)-2-(3-(hydroxymethyl)bicyclo[1.1.1]pentan-1-yl)thiazol-4-yl)-2-fluorophenyl)-2,6-difluorobenzenesulfonamide |
| 35 | 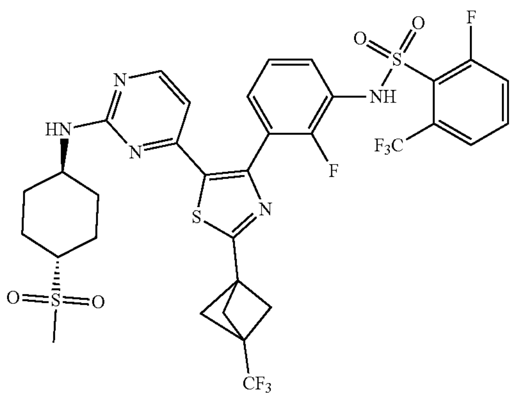 [SMILES: CS(=O)(=O)[C@H]1CC[C@H](Nc2nccc(-c3sc(C45CC(C(F)(F)F)(C4)C5)nc3-c3cccc(NS(=O)(=O)c4c(F)cccc4C(F)(F)F)c3F)n2)CC1] | 2-fluoro-N-(2-fluoro-3-(5-(2-(((1r,4r)-4-(methylsulfonyl)-cyclohexyl)amino)pyrimidin-4-yl)-2-(3-(trifluoromethyl)-bicyclo[1.1.1]pentan-1-yl)thiazol-4-yl)phenyl)-6-(trifluoromethyl)-benzenesulfonamide |
| 36 | 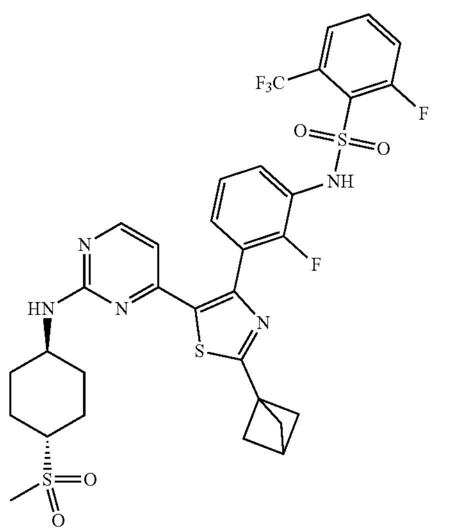 [SMILES: CS(=O)(=O)[C@H]1CC[C@H](Nc2nccc(-c3sc(C45CC(C4)C5)nc3-c3cccc(NS(=O)(=O)c4c(F)cccc4C(F)(F)F)c3F)n2)CC1] | N-(3-(2-(bicyclo[1.1.1]pentan-1-yl)-5-(2-(((1r,4r)-4-(methylsulfonyl)cyclohexyl)amino)pyrimidin-4-yl)thiazol-4-yl)-2-fluorophenyl)-2-fluoro-6-(trifluoromethyl)benzenesulfonamide |

TABLE I-continued
| Cpd No. | Structure | Name |
|---|---|---|
| 37 | 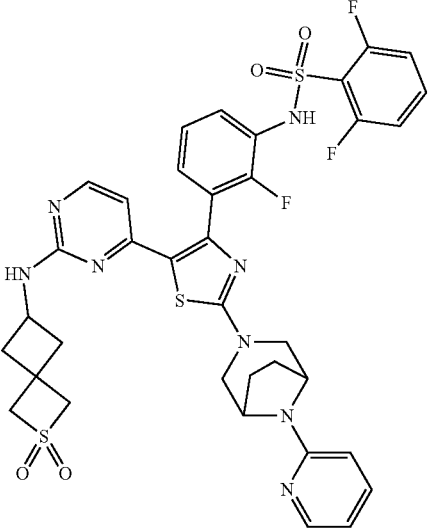 [SMILES: O=S1(=O)CC2(CC(Nc3nccc(-c4sc(N5CC6CCC(C5)N6c5ccccn5)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(8-(pyridin-2-yl)-3,8-diazabicyclo[3.2.1]octan-3-yl)thiazol-4-yl)-2-fluorophenyl)-2,6-difluorobenzenesulfonamide |
| 38 | 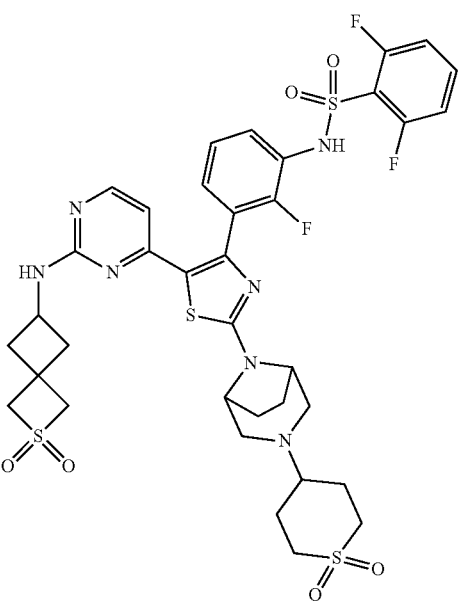 [SMILES: O=S1(=O)CCC(N2CC3CCC(C2)N3c2nc(-c3cccc(NS(=O)(=O)c4c(F)cccc4F)c3F)c(-c3ccnc(NC4CC5(C4)CS(=O)(=O)C5)n3)s2)CC1] | N-(3-(5-(2-((2,2-dioxido-2-thiaspiro[3.3]heptan-6-yl)amino)-pyrimidin-4-yl)-2-(3-(1,1-dioxidotetrahydro-2H-thiopyran-4-yl)-3,8-diazabicyclo[3.2.1]octan-8-yl)thiazol-4-yl)-2-fluorophenyl)-2,6-difluorobenzenesulfonamide |

TABLE I-continued

| Cpd No. | Structure | Name |
|---|---|---|
| 39 | 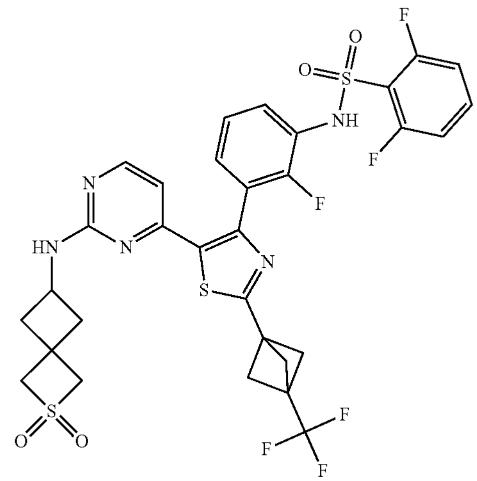 [SMILES: O=S1(=O)CC2(CC(Nc3nccc(-c4sc(C56CC(C(F)(F)F)(C5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(3-(trifluoromethyl)bicyclo[1.1.1]pentan-1-yl)thiazol-4-yl)-2-fluorophenyl)-2,6-difluorobenzenesulfonamide |
| 40 | 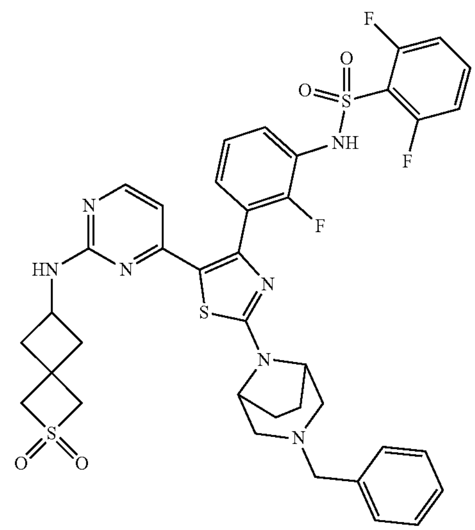 [SMILES: O=S1(=O)CC2(CC(Nc3nccc(-c4sc(N5C6CCC5CN(Cc5ccccc5)C6)nc4-c4cccc(NS(=O)(=O)c5c(F)cccc5F)c4F)n3)C2)C1] | N-(3-(2-(3-benzyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 41 | 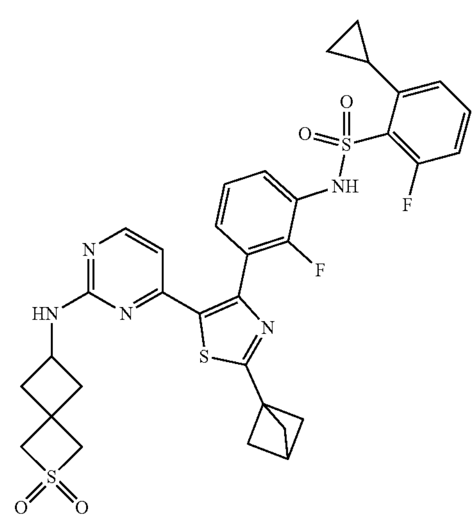 [SMILES: O=S1(=O)CC2(CC(Nc3nccc(-c4sc(C56CC(C5)C6)nc4-c4cccc(NS(=O)(=O)c5c(F)cccc5C5CC5)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-cyclopropyl-6-fluorobenzenesulfonamide |

TABLE I-continued
| Cpd No. | Structure | Name |
|---|---|---|
| 42 | 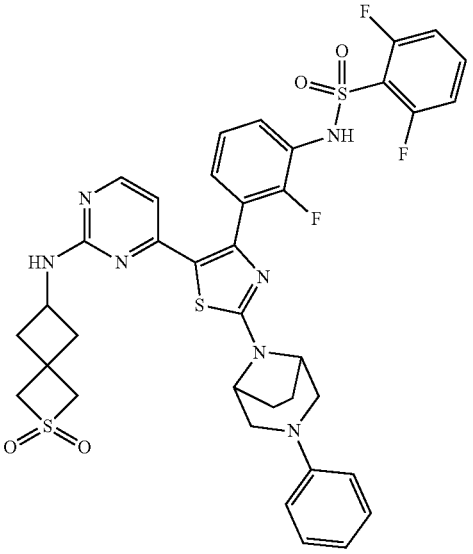 [SMILES: O=S1(=O)CC2(CC(Nc3nccc(-c4sc(N5C6CCC5CN(c5ccccc5)C6)nc4-c4cccc(NS(=O)(=O)c5c(F)cccc5F)c4F)n3)C2)C1] | N-(3-(5-(2-(((2,2-dioxido-2-thiaspiro[3.3]heptan-6-yl)amino)-pyrimidin-4-yl)-2-(3-phenyl-3,8-diazabicyclo[3.2.1]octan-8-yl)thiazol-4-yl)-2-fluorophenyl)-2,6-difluorobenzenesulfonamide |
| 43 | 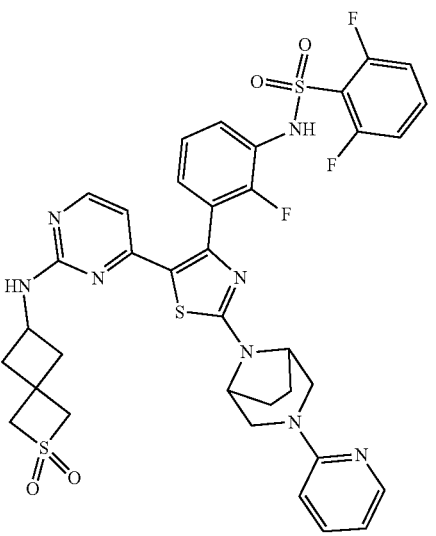 [SMILES: O=S1(=O)CC2(CC(Nc3nccc(-c4sc(N5C6CCC5CN(c5ccccn5)C6)nc4-c4cccc(NS(=O)(=O)c5c(F)cccc5F)c4F)n3)C2)C1] | N-(3-(5-(2-(((2,2-dioxido-2-thiaspiro[3.3]heptan-6-yl)amino)-pyrimidin-4-yl)-2-(3-(pyridin-2-yl)-3,8-diazabicyclo[3.2.1]octan-8-yl)thiazol-4-yl)-2-fluorophenyl)-2,6-difluorobenzenesulfonamide |

TABLE I-continued
| Cpd No. | Structure | Name |
|---|---|---|
| 44 | 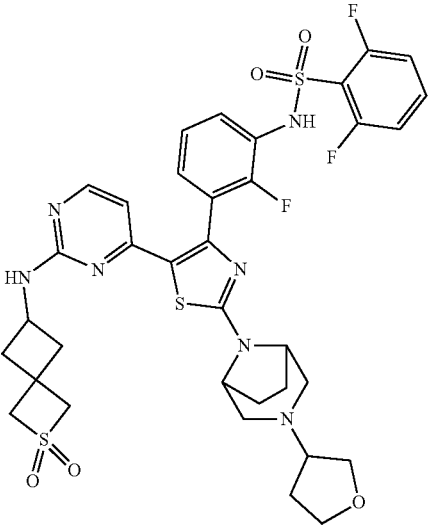 [SMILES: O=S1(=O)CC2(CC(Nc3nccc(-c4sc(N5C6CCC5CN(C5CCOC5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(3-(tetrahydrofuran-3-yl)-3,8-diazabicyclo-[3.2.1]octan-8-yl)thiazol-4-yl)-2-fluorophenyl)-2,6-difluoro-benzenesulfonamide |
| 45 | 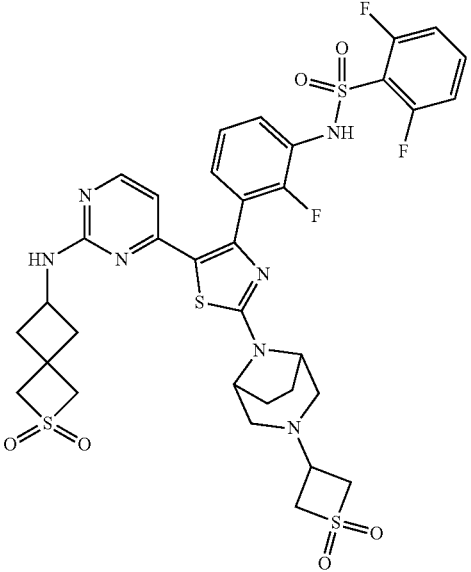 [SMILES: O=S1(=O)CC(N2CC3CCC(C2)N3c2nc(-c3cccc(NS(=O)(=O)c4c(F)cccc4F)c3F)c(-c3ccnc(NC4CC5(C4)CS(=O)(=O)C5)n3)s2)C1] | N-(3-(5-(2-((2,2-dioxido-2-thiaspiro[3.3]heptan-6-yl)amino)-pyrimidin-4-yl)-2-(3-(1,1-dioxidothietan-3-yl)-3,8-diazabicyclo[3.2.1]octan-8-yl)thiazol-4-yl)-2-fluorophenyl)-2,6-difluorobenzenesulfonamide |

TABLE I-continued

| Cpd No. | Structure | Name |
|---|---|---|
| 46 | 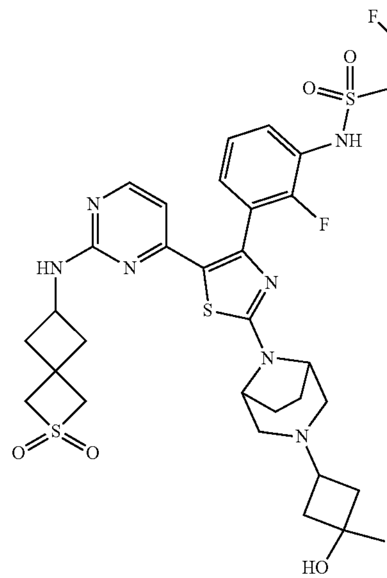 | N-(3-(5-(2-((2,2-dioxido-2-thiaspiro[3.3]heptan-6-yl)amino)-pyrimidin-4-yl)-2-(3-(3-hydroxy-3-methylcyclobutyl)-3,8-diazabicyclo[3.2.1]octan-8-yl)thiazol-4-yl)-2-fluorophenyl)-2,6-difluorobenzenesulfonamide |
| 47 | 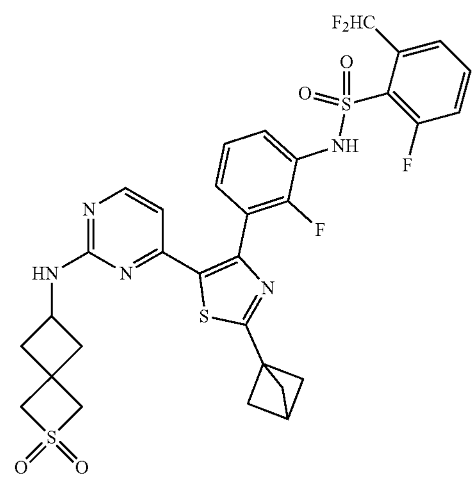 [SMILES: O=S1(=O)CC2(CC(Nc3nccc(-c4sc(C56CC(C5)C6)nc4-c4cccc(NS(=O)(=O)c5c(F)cccc5C(F)F)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-(difluoromethyl)-6-fluorobenzenesulfonamide |
| 48 | 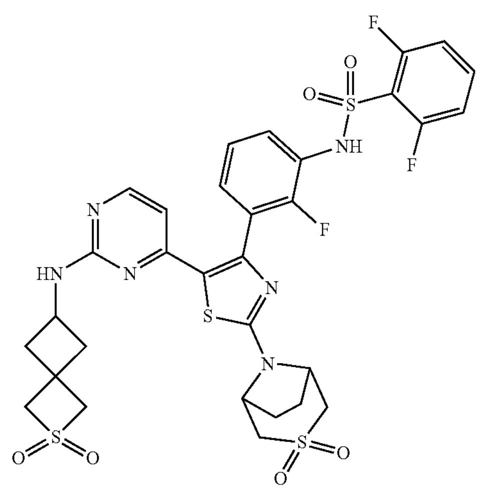 [SMILES: O=S1(=O)CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-(3,3-dioxido-3-thia-8-azabicyclo[3.2.1]octan-8-yl)thiazol-4-yl)-2-fluorophenyl)-2,6-difluorobenzenesulfonamide |

TABLE I-continued
| Cpd No. | Structure | Name |
|---|---|---|
| 49 | 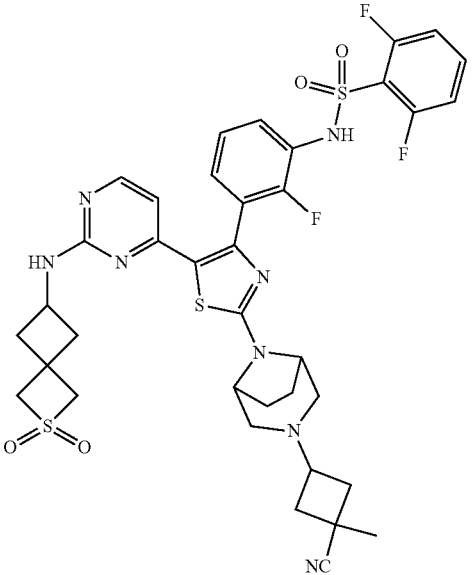 [SMILES: CC1(C#N)CC(N2CC3CCC(C2)N3c2nc(-c3cccc(NS(=O)(=O)c4c(F)cccc4F)c3F)c(-c3ccnc(NC4CC5(C4)CS(=O)(=O)C5)n3)s2)C1] | N-(3-(2-(3-(3-cyano-3-methylcyclobutyl)-3,8-diazabicyclo-[3.2.1]octan-8-yl)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 50 | 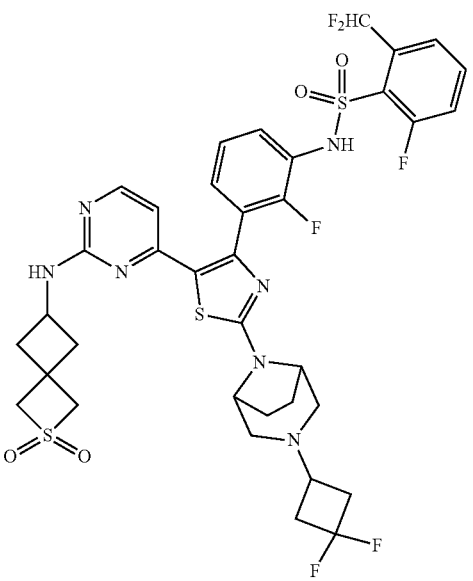 [SMILES: O=S1(=O)CC2(CC(Nc3nccc(-c4sc(N5C6CCC5CN(C5CC(F)(F)C5)C6)nc4-c4cccc(NS(=O)(=O)c5c(F)cccc5C(F)F)c4F)n3)C2)C1] | N-(3-(2-(3-(3,3-difluorocyclobutyl)-3,8-diazabicyclo[3.2.1]octan-8-yl)-5-(2-(((2,2-dioxido-2-thiaspiro[3.3]heptan-6-yl)amino)pyrimidin-4-yl)thiazol-4-yl)-2-fluorophenyl)-2-(difluoromethyl)-6-fluorobenzenesulfonamide |

TABLE I-continued

| Cpd No. | Structure | Name |
|---|---|---|
| 51 | 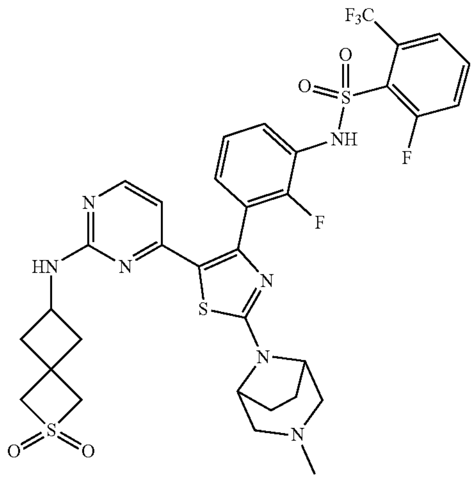 [SMILES: CN1CC2CCC(C1)N2c1nc(-c2cccc(NS(=O)(=O)c3c(F)cccc3C(F)(F)F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-fluoro-6-(trifluoromethyl)-benzenesulfonamide |
| 52 | 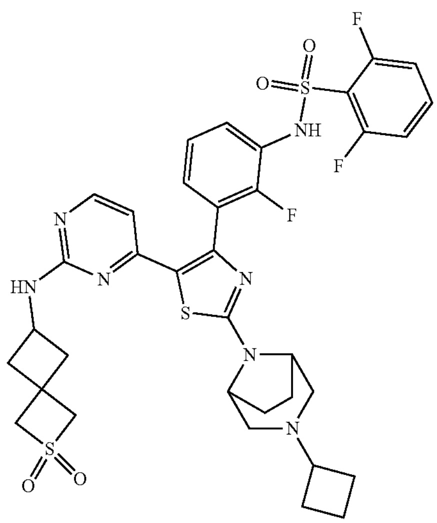 [SMILES: O=S1(=O)CC2(CC(Nc3nccc(-c4sc(N5C6CCC5CN(C5CCC5)C6)nc4-c4cccc(NS(=O)(=O)c5c(F)cccc5F)c4F)n3)C2)C1] | N-(3-(2-(3-cyclobutyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 53 | 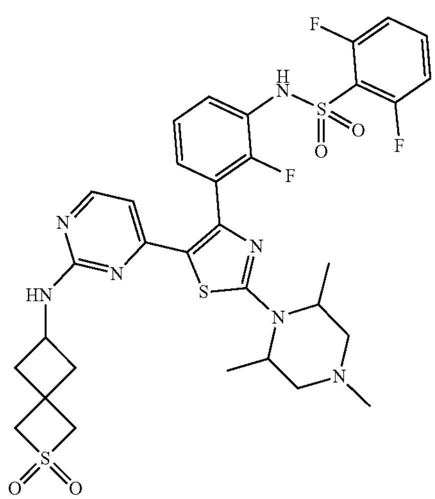 [SMILES: CC1CN(C)CC(C)N1c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-(2,4,6-trimethylpiperazin-1-yl)thiazol-4-yl)-2-fluorophenyl)-2,6-difluorobenzenesulfonamide |

TABLE I-continued

| Cpd No. | Structure | Name |
|---|---|---|
| 54 | 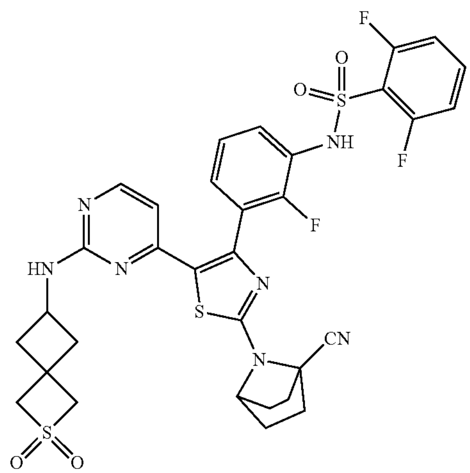 [SMILES: N#CC12CCC(CC1)N2c1nc(-c2cccc(NS(=O)(=O)c3c(F)cccc3F)c2F)c(-c2ccnc(NC3CC4(C3)CS(=O)(=O)C4)n2)s1] | N-(3-(2-(1-cyano-7-azabicyclo[2.2.1]heptan-7-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 55 | 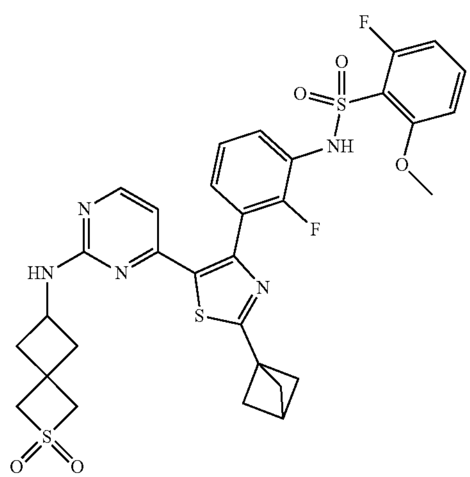 [SMILES: COc1cccc(F)c1S(=O)(=O)Nc1cccc(-c2nc(C34CC(C3)C4)sc2-c2ccnc(NC3CC4(C3)CS(=O)(=O)C4)n2)c1F] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-methoxybenzenesulfonamide |
| 56 | 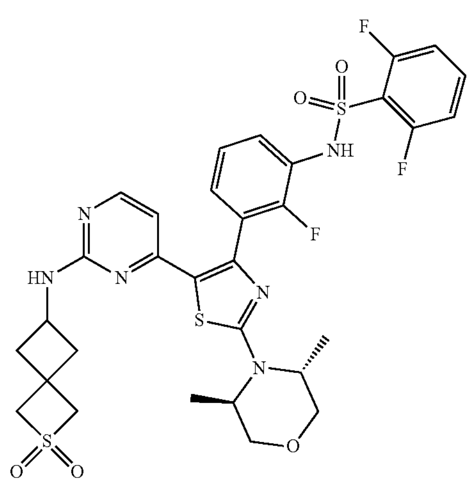 [SMILES: C[C@@H]1COC[C@@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((3R,5R)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 57 | 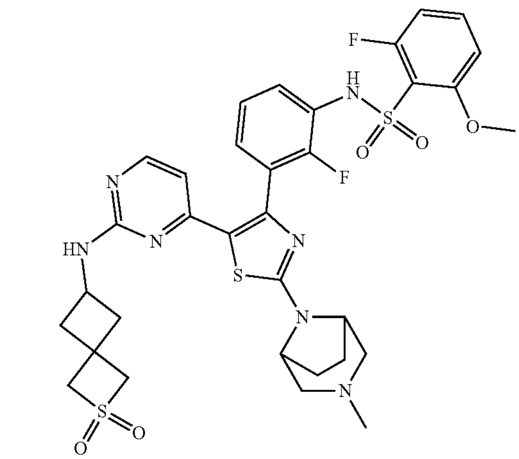 [SMILES: COc1cccc(F)c1S(=O)(=O)Nc1cccc(-c2nc(N3C4CCC3CN(C)C4)sc2-c2ccnc(NC3CC4(C3)CS(=O)(=O)C4)n2)c1F] | N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-fluoro-6-methoxybenzenesulfonamide |
| 58 | 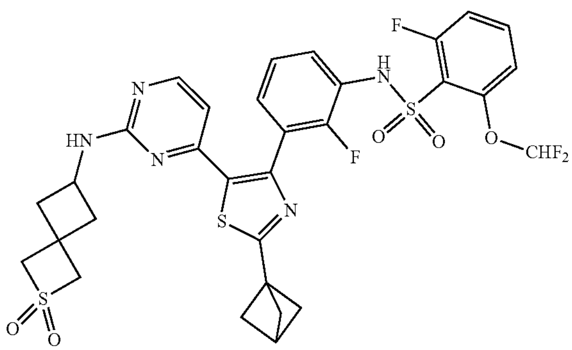 [SMILES: O=S1(=O)CC2(CC(Nc3nccc(-c4sc(C56CC(C5)C6)nc4-c4cccc(NS(=O)(=O)c5c(F)cccc5OC(F)F)c4F)n3)C2)C1] | N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-(difluoromethoxy)-6-fluorobenzenesulfonamide |
| 59 | 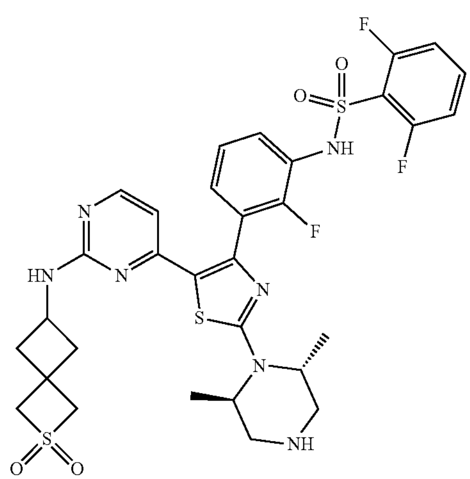 [SMILES: C[C@@H]1CNC[C@@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((2R,6R)-2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 60 | 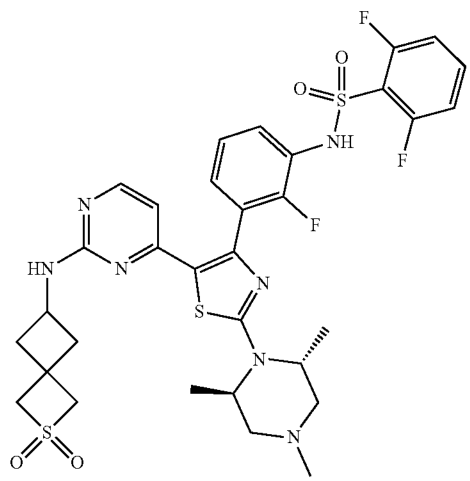 [SMILES: C[C@@H]1CN(C)C[C@@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-((2R,6R)-2,4,6-trimethylpiperazin-1-yl)thiazol-4-yl)-2-fluorophenyl)-2,6-difluorobenzenesulfonamide |
| 61 | 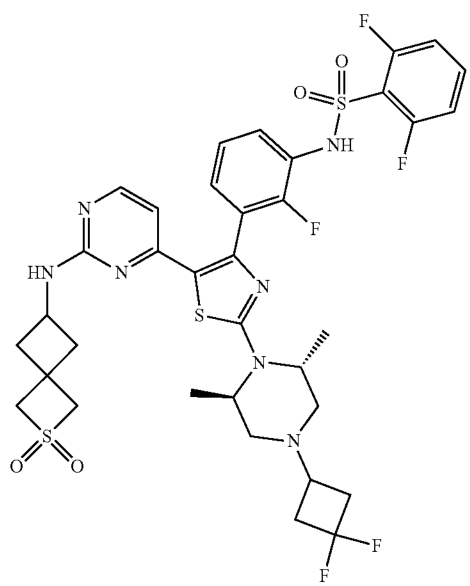 [SMILES: C[C@@H]1CN(C2CC(F)(F)C2)C[C@@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((2R,6R)-4-(3,3-difluorocyclobutyl)-2,6-dimethylpiperazin-1-yl)-5-(2-((2,2-dioxido-2-thiaspiro[3.3]heptan-6-yl)amino)-pyrimidin-4-yl)thiazol-4-yl)-2-fluorophenyl)-2,6-difluoro-benzenesulfonamide |
| 62 | 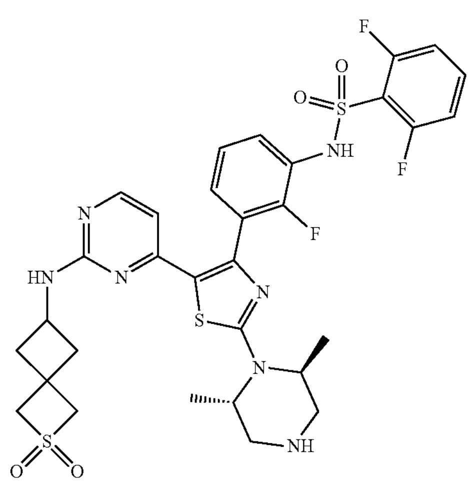 [SMILES: C[C@H]1CNC[C@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((2S,6S)-2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 63 | 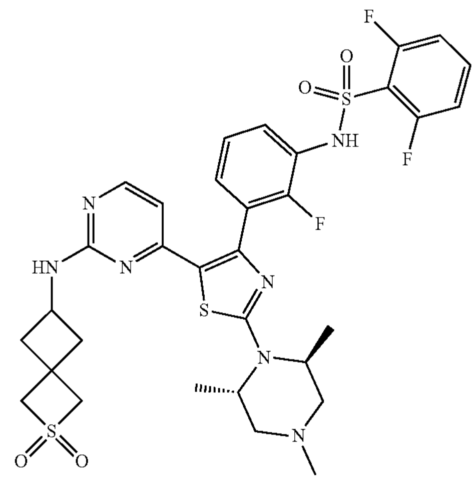 [SMILES: C[C@H]1CN(C)C[C@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-((2S,6S)-2,4,6-trimethylpiperazin-1-yl)thiazol-4-yl)-2-fluorophenyl)-2,6-difluorobenzenesulfonamide |
| 64 | 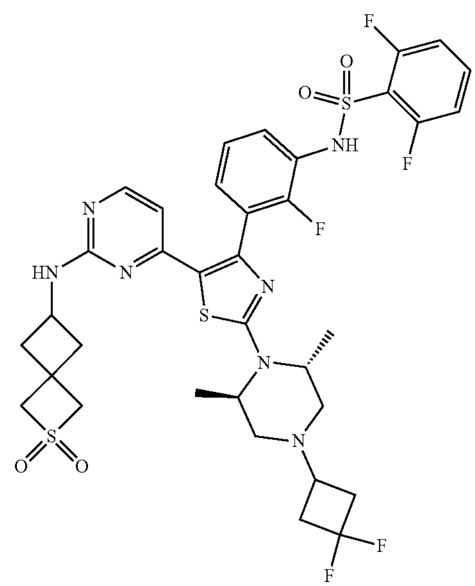 [SMILES: C[C@@H]1CN(C2CC(F)(F)C2)C[C@@H](C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-((2S,6S)-4-(3,3-difluorocyclobutyl)-2,6-dimethylpiperazin-1-yl)-5-(2-((2,2-dioxido-2-thiaspiro[3.3]heptan-6-yl)amino)-pyrimidin-4-yl)thiazol-4-yl)-2-fluorophenyl)-2,6-difluoro-benzenesulfonamide |
| 65 | 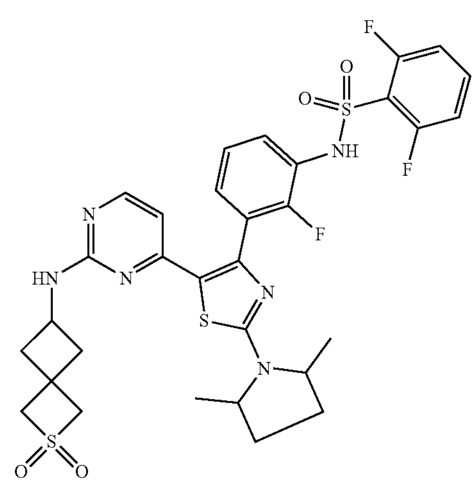 [SMILES: CC1CCC(C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-(2,5-dimethylpyrrolidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 66 | 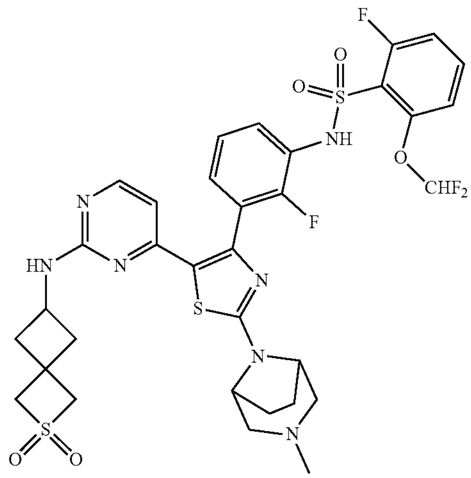 [SMILES: CN1CC2CCC(C1)N2c1nc(-c2cccc(NS(=O)(=O)c3c(F)cccc3OC(F)F)c2F)c(-c2ccnc(NC3CC4(C3)CS(=O)(=O)C4)n2)s1] | 2-(difluoromethoxy)-N-(3-(5-(2-((2,2-dioxido-2-thiaspiro[3.3]-heptan-6-yl)amino)pyrimidin-4-yl)-2-(3-methyl-3,8-diazabicyclo[3.2.1]octan-8-yl)thiazol-4-yl)-2-fluorophenyl)-6-fluorobenzenesulfonamide |
| 67 | 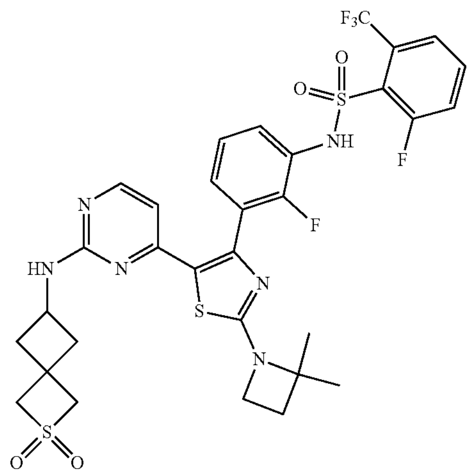 [SMILES: CC1(C)CCN1c1nc(-c2cccc(NS(=O)(=O)c3c(F)cccc3C(F)(F)F)c2F)c(-c2ccnc(NC3CC4(C3)CS(=O)(=O)C4)n2)s1] | N-(3-(2-(2,2-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 68 | 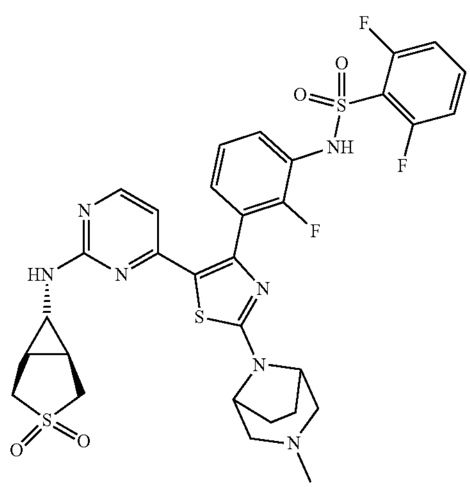 | N-(3-(5-(2-(((1S,5S)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2,6-difluorobenzenesulfonamide |

TABLE I-continued

| Cpd No. | Structure | Name |
|---|---|---|
| 69 | 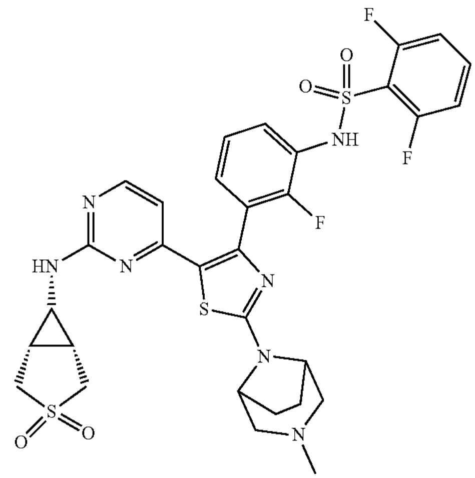 | N-(3-(5-(2-(((1R,5S,6s)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2,6-difluorobenzenesulfonamide |
| 70 | 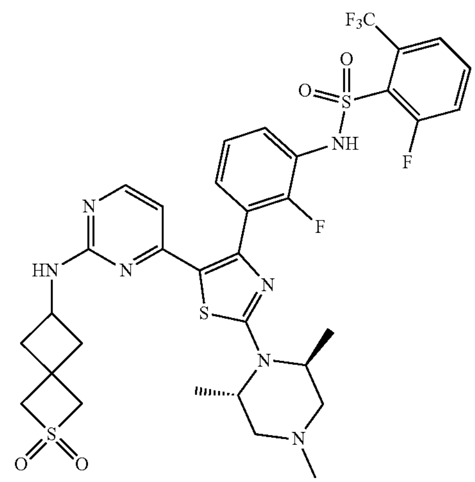 [SMILES: C[C@H]1CN(C)C[C@H](C)N1c1nc(-c2cccc(NS(=O)(=O)c3c(F)cccc3C(F)(F)F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide |
| 71 | 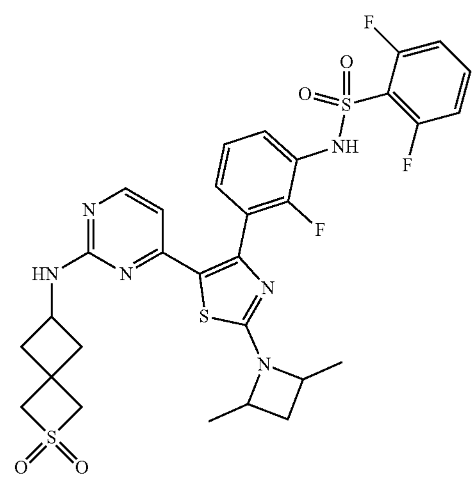 [SMILES: CC1CC(C)N1c1nc(-c2cccc(NS(=O)(=O)c3c(F)cccc3F)c2F)c(-c2ccnc(NC3CC4(C3)CS(=O)(=O)C4)n2)s1] | N-(3-(2-(2,4-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 72 | 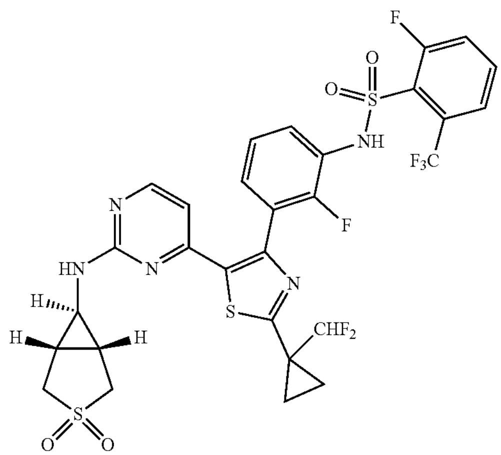 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3C(F)(F)F)c2F)n1] | N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 73 | 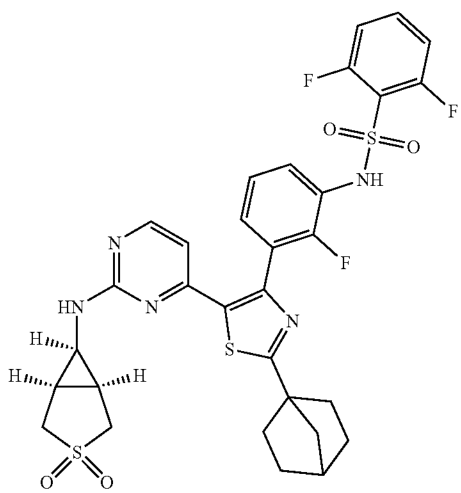 [SMILES: O=S1(=O)C[C@@H]2[C@H](C1)[C@@H]2Nc1nccc(-c2sc(C34CCC(CC3)C4)nc2-c2cccc(NS(=O)(=O)c3c(F)cccc3F)c2F)n1] | N-(3-(2-(bicyclo[2.2.1]heptan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 74 | 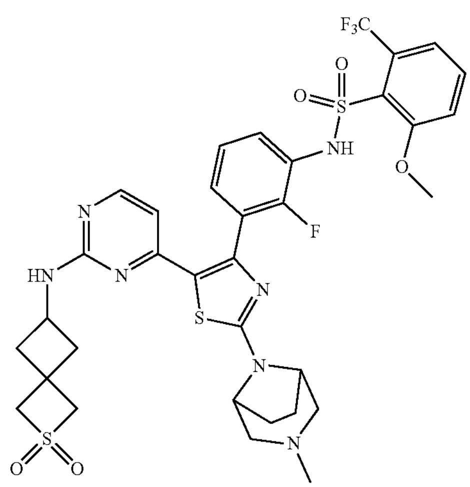 | N-(3-(5-(2-(((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-methoxy-6-(trifluoromethyl)benzenesulfonamide |

TABLE I-continued

| Cpd No. | Structure | Name |
|---|---|---|
| 75 | 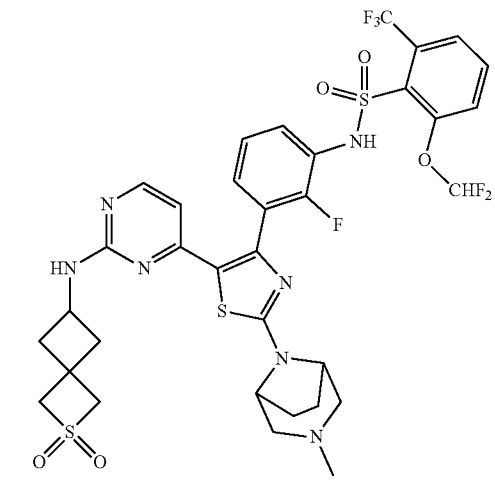 | 2-(difluoromethoxy)-N-(3-(5-(2-((2,2-dioxido-2-thiaspiro[3.3]heptan-6-yl)amino)pyrimidin-4-yl)-2-(3-methyl-3,8-diazabicyclo[3.2.1]octan-8-yl)thiazol-4-yl)-2-fluorophenyl)-6-(trifluoromethyl)benzenesulfonamide |
| 76 | 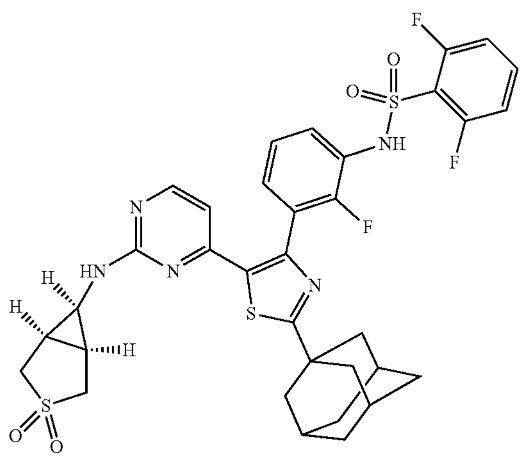 [SMILES: O=S1(=O)C[C@@H]2[C@H](C1)[C@@H]2Nc1nccc(-c2sc(C34CC5CC(CC(C5)C3)C4)nc2-c2cccc(NS(=O)(=O)c3c(F)cccc3F)c2F)n1] | N-(3-(2-((3R,5R,7R)-adamantan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 77 | 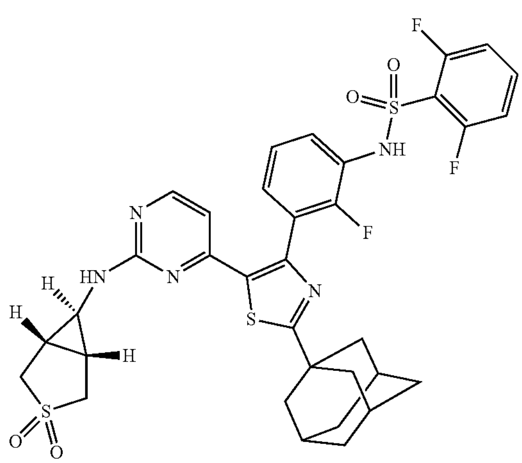 [SMILES: O=S1(=O)C[C@@H]2[C@H](C1)[C@H]2Nc1nccc(-c2sc(C34CC5CC(CC(C5)C3)C4)nc2-c2cccc(NS(=O)(=O)c3c(F)cccc3F)c2F)n1] | N-(3-(2-((3R,5R,7R)-adamantan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 78 | 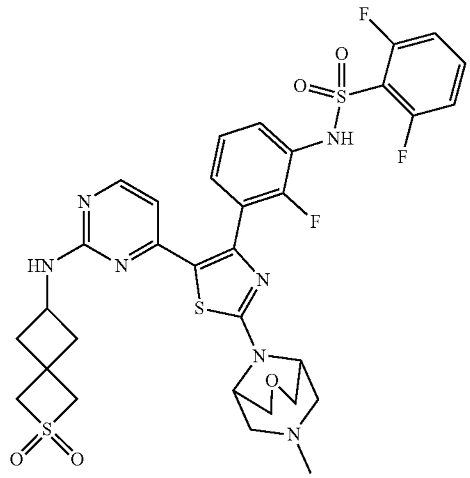 [SMILES: CN1CC2COCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-(7-methyl-3-oxa-7,9-diazabicyclo[3.3.1]nonan-9-yl)thiazol-4-yl)-2-fluorophenyl)-2,6-difluorobenzenesulfonamide |
| 79 | 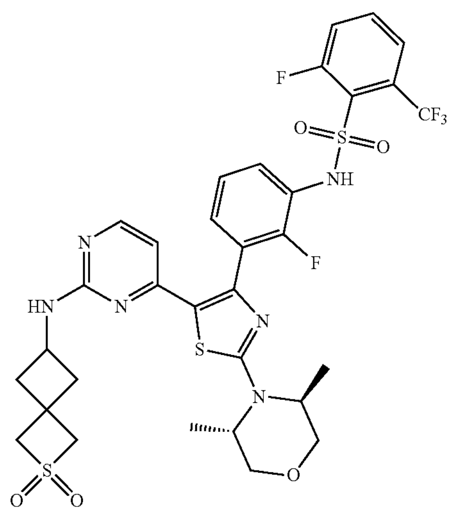 [SMILES: C[C@H]1COC[C@H](C)N1c1nc(-c2cccc(NS(=O)(=O)c3c(F)cccc3C(F)(F)F)c2F)c(-c2ccnc(NC3CC4(C3)CS(=O)(=O)C4)n2)s1] | N-(3-(2-((3S,5S)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 80 | 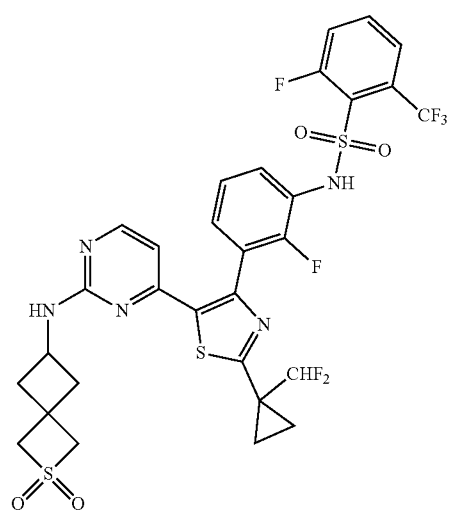 [SMILES: O=S1(=O)CC2(CC(Nc3nccc(-c4sc(C5(C(F)F)CC5)nc4-c4cccc(NS(=O)(=O)c5c(F)cccc5C(F)(F)F)c4F)n3)C2)C1] | N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 81 | 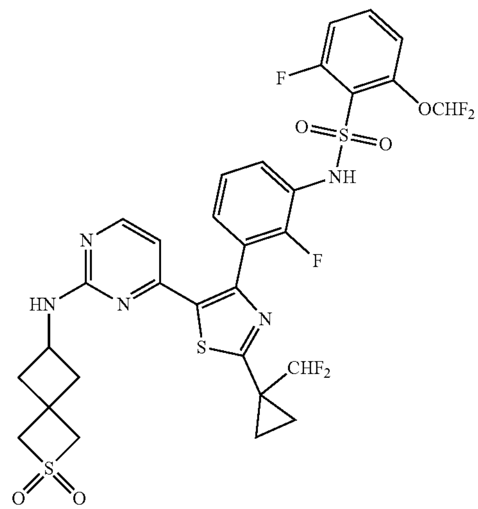 [SMILES: O=S1(=O)CC2(CC(Nc3nccc(-c4sc(C5(C(F)F)CC5)nc4-c4cccc(NS(=O)(=O)c5c(F)cccc5OC(F)F)c4F)n3)C2)C1] | 2-(difluoromethoxy)-N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-6-fluorobenzenesulfonamide |
| 82 | 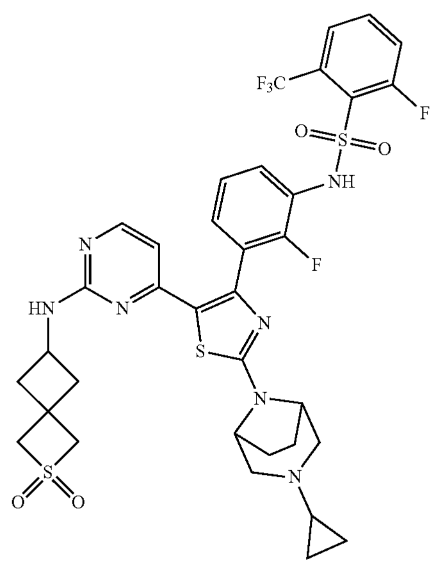 [SMILES: O=S1(=O)CC2(CC(Nc3nccc(-c4sc(N5C6CCC5CN(C5CC5)C6)nc4-c4cccc(NS(=O)(=O)c5c(F)cccc5C(F)(F)F)c4F)n3)C2)C1] | N-(3-(2-(3-cyclopropyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 83 | 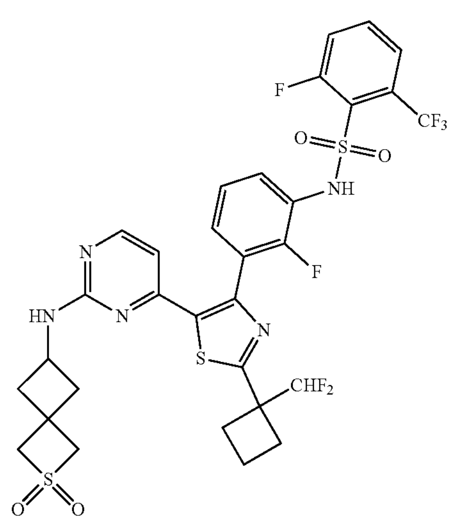 [SMILES: O=S1(=O)CC2(CC(Nc3nccc(-c4sc(C5(C(F)F)CCC5)nc4-c4cccc(NS(=O)(=O)c5c(F)cccc5C(F)(F)F)c4F)n3)C2)C1] | N-(3-(2-(1-(difluoromethyl)cyclobutyl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 84 | 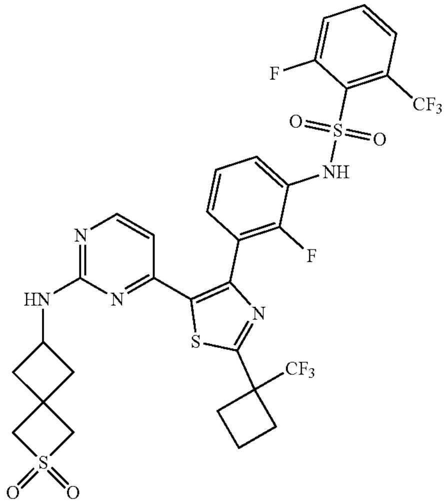 [SMILES: O=S1(=O)CC2(CC(Nc3nccc(-c4sc(C5(C(F)(F)F)CCC5)nc4-c4cccc(NS(=O)(=O)c5c(F)cccc5C(F)(F)F)c4F)n3)C2)C1] | N-(3-(5-(2-((2,2-dioxido-2-thiaspiro[3.3]heptan-6-yl)amino)-pyrimidin-4-yl)-2-(1-(trifluoromethyl)cyclobutyl)thiazol-4-yl)-2-fluorophenyl)-2-fluoro-6-(trifluoromethyl)benzenesulfonamide |
| 85 | 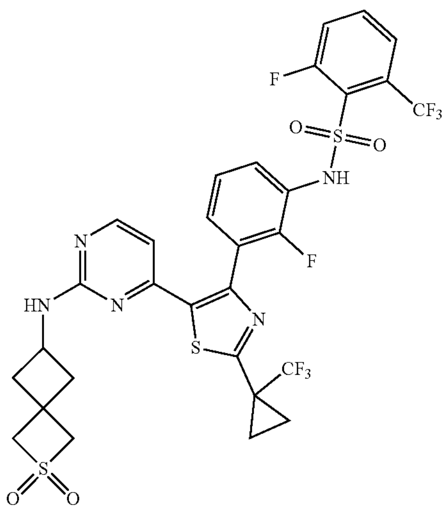 [SMILES: O=S1(=O)CC2(CC(Nc3nccc(-c4sc(C5(C(F)(F)F)CC5)nc4-c4cccc(NS(=O)(=O)c5c(F)cccc5C(F)(F)F)c4F)n3)C2)C1] | N-(3-(5-(2-((2,2-dioxido-2-thiaspiro[3.3]heptan-6-yl)amino)-pyrimidin-4-yl)-2-(1-(trifluoromethyl)cyclopropyl)thiazol-4-yl)-2-fluorophenyl)-2-fluoro-6-(trifluoromethyl)benzenesulfonamide |
| 86 | 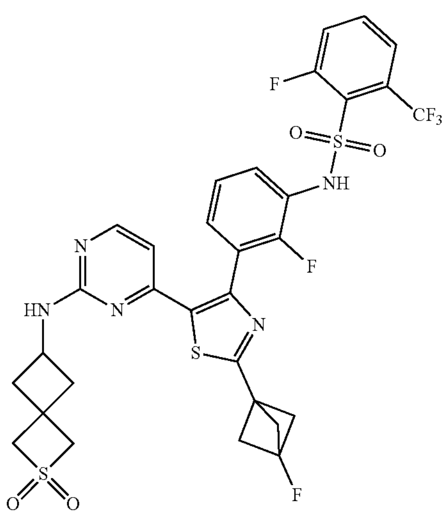 [SMILES: O=S1(=O)CC2(CC(Nc3nccc(-c4sc(C56CC(F)(C5)C6)nc4-c4cccc(NS(=O)(=O)c5c(F)cccc5C(F)(F)F)c4F)n3)C2)C1] | N-(3-(5-(2-((2,2-dioxido-2-thiaspiro[3.3]heptan-6-yl)amino)-pyrimidin-4-yl)-2-(3-fluorobicyclo[1.1.1]pentan-1-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 87 | 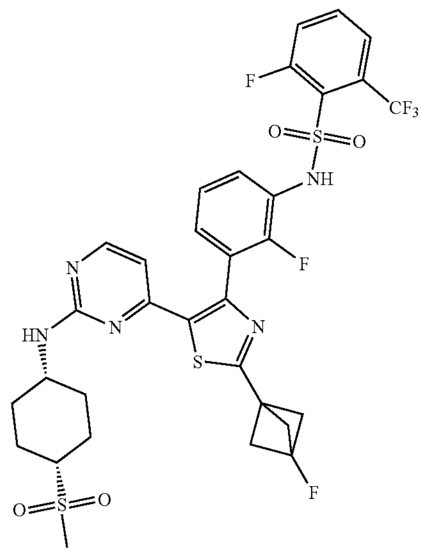 [SMILES: CS(=O)(=O)[C@H]1CC[C@@H](Nc2nccc(-c3sc(C45CC(F)(C4)C5)nc3-c3cccc(NS(=O)(=O)c4c(F)cccc4C(F)(F)F)c3F)n2)CC1] | 2-fluoro-N-(2-fluoro-3-(2-(3-fluorobicyclo[1.1.1]pentan-1-yl)-5-(2-(((1s,4s)-4-(methylsulfonyl)cyclohexyl)-amino)pyrimidin-4-yl)thiazol-4-yl)phenyl)-6-(trifluoromethyl)benzenesulfonamide |
| 88 | 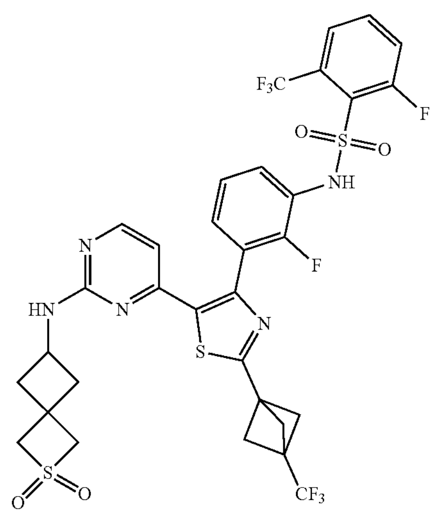 [SMILES: O=S1(=O)CC2(CC(Nc3nccc(-c4sc(C56CC(C(F)(F)F)(C5)C6)nc4-c4cccc(NS(=O)(=O)c5c(F)cccc5C(F)(F)F)c4F)n3)C2)C1] | N-(3-(5-(2-((2,2-dioxido-2-thiaspiro[3.3]heptan-6-yl)amino)-pyrimidin-4-yl)-2-(3-(trifluoromethyl)bicyclo[1.1.1]pentan-1-yl)thiazol-4-yl)-2-fluorophenyl)-2-fluoro-6-(trifluoromethyl)-benzenesulfonamide |
| 89 | 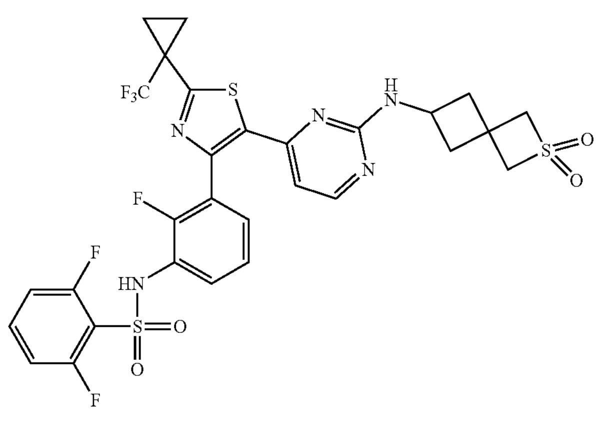 [SMILES: O=S1(=O)CC2(CC(Nc3nccc(-c4sc(C5(C(F)(F)F)CC5)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(1-(trifluoromethyl)cyclopropyl)thiazol-4-yl)-2-fluorophenyl)-2,6-difluorobenzenesulfonamide |

TABLE I-continued

| Cpd No. | Structure | Name |
|---|---|---|
| 91 | 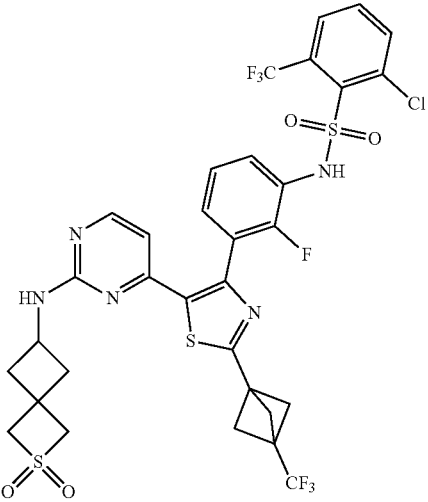 [SMILES: O=S1(=O)CC2(CC(Nc3nccc(-c4sc(C56CC(C(F)(F)F)(C5)C6)nc4-c4cccc(NS(=O)(=O)c5c(Cl)cccc5C(F)(F)F)c4F)n3)C2)C1] | 2-chloro-N-(3-(5-(2-(((2,2-dioxido-2-thiaspiro[3.3]heptan-6-yl)amino)pyrimidin-4-yl)-2-(3-(trifluoromethyl)bicyclo-[1.1.1]pentan-1-yl)thiazol-4-yl)-2-fluorophenyl)-6-(trifluoromethyl)benzenesulfonamide |
| 92 | 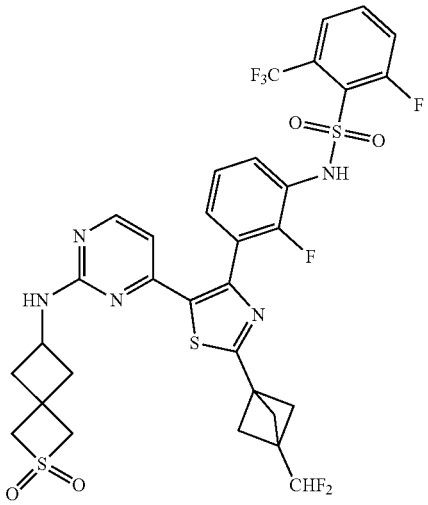 [SMILES: O=S1(=O)CC2(CC(Nc3nccc(-c4sc(C56CC(C(F)F)(C5)C6)nc4-c4cccc(NS(=O)(=O)c5c(F)cccc5C(F)(F)F)c4F)n3)C2)C1] | N-(3-(2-(3-(difluoromethyl)bicyclo[1.1.1]pentan-1-yl)-5-(2-(((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 93 | 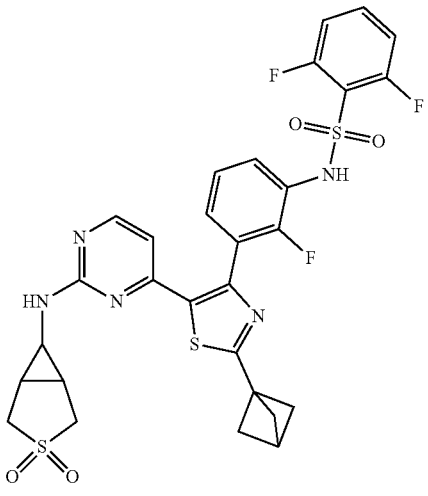 [SMILES: O=S1(=O)CC2C(C1)C2Nc1nccc(-c2sc(C34CC(C3)C4)nc2-c2cccc(NS(=O)(=O)c3c(F)cccc3F)c2F)n1] | N-(3-(2-(bicyclo[1.1.1]pentan-1-yl)-5-(2-((3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 94 | 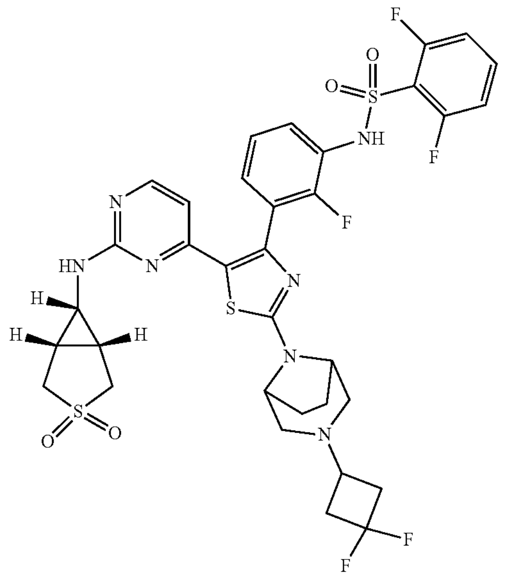 [SMILES: O=S1(=O)C[C@@H]2[C@H](C1)[C@@H]2Nc1nccc(-c2sc(N3C4CCC3CN(C3CC(F)(F)C3)C4)nc2-c2cccc(NS(=O)(=O)c3c(F)cccc3F)c2F)n1] | N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 95 | 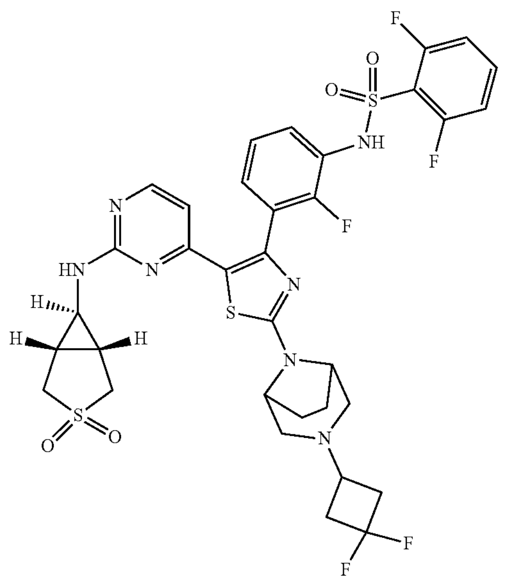 [SMILES: O=S1(=O)C[C@@H]2[C@H](C1)[C@H]2Nc1nccc(-c2sc(N3C4CCC3CN(C3CC(F)(F)C3)C4)nc2-c2cccc(NS(=O)(=O)c3c(F)cccc3F)c2F)n1] | N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 96 | 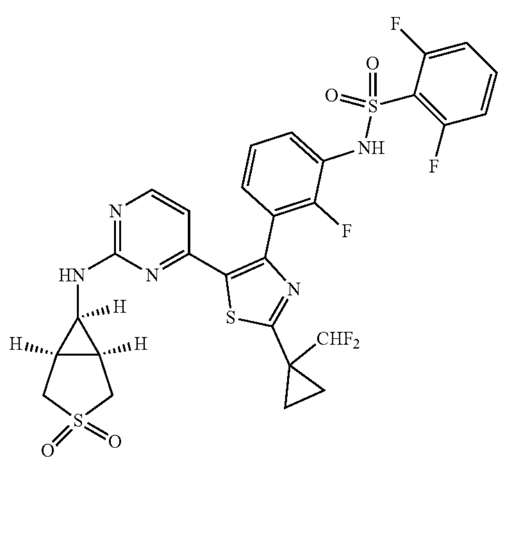 [SMILES: O=S1(=O)C[C@@H]2[C@H](C1)[C@@H]2Nc1nccc(-c2sc(C3(C(F)F)CC3)nc2-c2cccc(NS(=O)(=O)c3c(F)cccc3F)c2F)n1] | N-(3-(2-(1-(difluoromethyl)cyclopropyl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 97 | 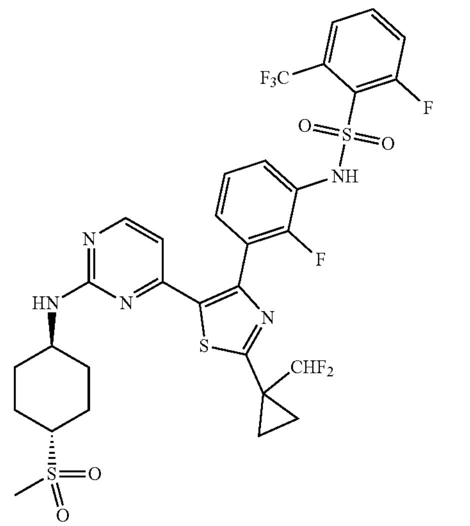 [SMILES: CS(=O)(=O)[C@H]1CC[C@H](Nc2nccc(-c3sc(C4(C(F)F)CC4)nc3-c3cccc(NS(=O)(=O)c4c(F)cccc4C(F)(F)F)c3F)n2)CC1] | N-(3-(2-(1-(difluoromethyl)cyclopropyl)-5-(2-(((1r,4r)-4-(methylsulfonyl)cyclohexyl)amino)pyrimidin-4-yl)thiazol-4-yl)-2-fluorophenyl)-2-fluoro-6-(trifluoromethyl)benzenesulfonamide |
| 98 | 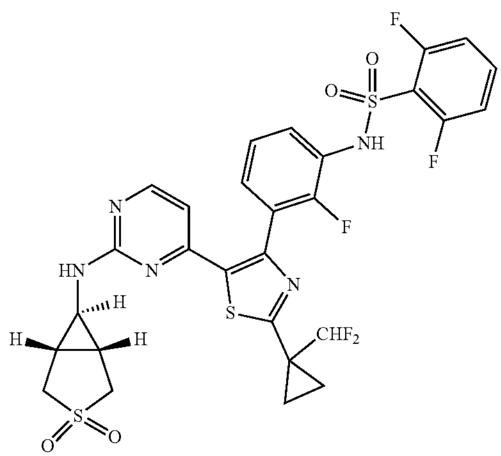 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3F)c2F)n1] | N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 99 | 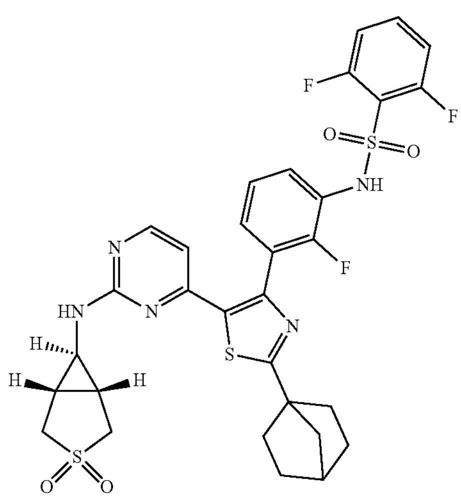 [SMILES: O=S1(=O)C[C@@H]2[C@H](C1)[C@H]2Nc1nccc(-c2sc(C34CCC(CC3)C4)nc2-c2cccc(NS(=O)(=O)c3c(F)cccc3F)c2F)n1] | N-(3-(2-(bicyclo[2.2.1]heptan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 100 | 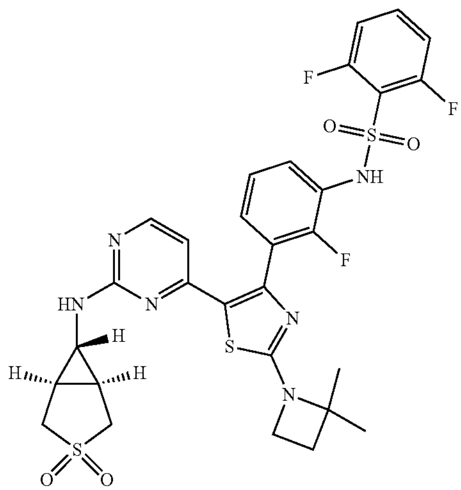 [SMILES: CC1(C)CCN1c1nc(-c2cccc(NS(=O)(=O)c3c(F)cccc3F)c2F)c(-c2ccnc(N[C@H]3[C@@H]4CS(=O)(=O)C[C@@H]43)n2)s1] | N-(3-(2-(2,2-dimethylazetidin-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 101 | 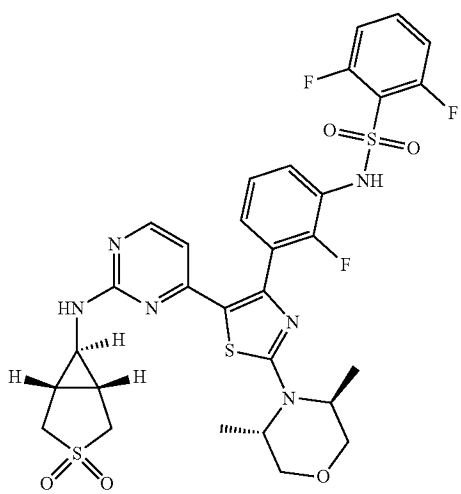 [SMILES: C[C@H]1COC[C@H](C)N1c1nc(-c2cccc(NS(=O)(=O)c3c(F)cccc3F)c2F)c(-c2ccnc(N[C@H]3[C@@H]4CS(=O)(=O)C[C@@H]43)n2)s1] | N-(3-(2-((3S,5S)-3,5-dimethylmorpholino)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 102 | 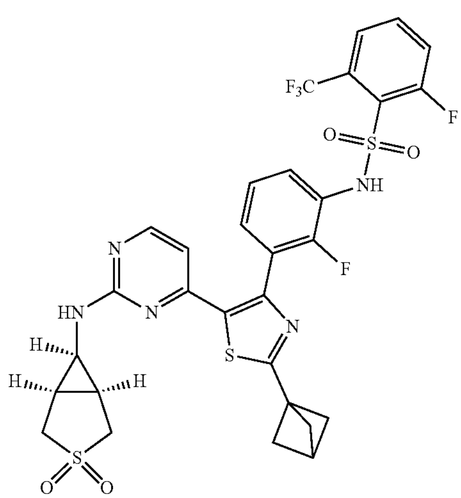 [SMILES: O=S1(=O)C[C@@H]2[C@H](C1)[C@@H]2Nc1nccc(-c2sc(C34CC(C3)C4)nc2-c2cccc(NS(=O)(=O)c3c(F)cccc3C(F)(F)F)c2F)n1] | N-(3-(2-(bicyclo[1.1.1]pentan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 103 | 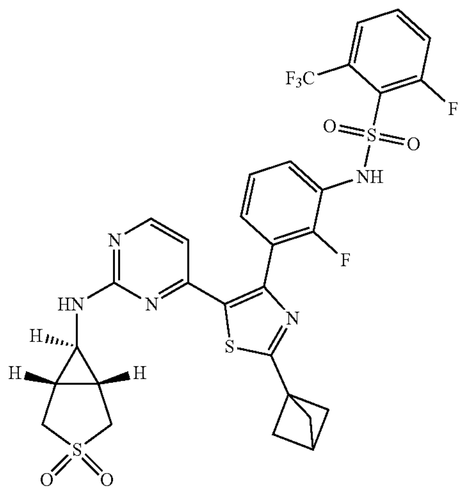 [SMILES: O=S1(=O)C[C@@H]2[C@H](C1)[C@H]2Nc1nccc(-c2sc(C34CC(C3)C4)nc2-c2cccc(NS(=O)(=O)c3c(F)cccc3C(F)(F)F)c2F)n1] | N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 104 | 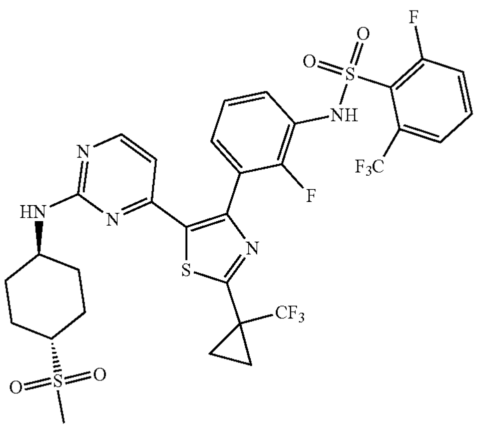 [SMILES: CS(=O)(=O)[C@H]1CC[C@H](Nc2nccc(-c3sc(C4(C(F)(F)F)CC4)nc3-c3cccc(NS(=O)(=O)c4c(F)cccc4C(F)(F)F)c3F)n2)CC1] | 2-fluoro-N-(2-fluoro-3-(5-(2-(((1r,4r)-4-(methylsulfonyl)cyclohexyl)amino)pyrimidin-4-yl)-2-(1-(trifluoromethyl)cyclopropyl)thiazol-4-yl)phenyl)-6-(trifluoromethyl)benzenesulfonamide |
| 105 | 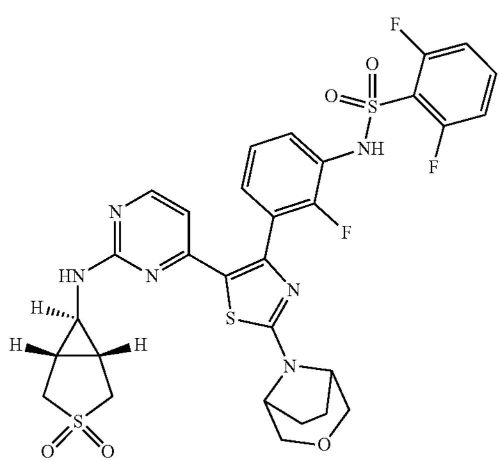 [SMILES: O=S1(=O)C[C@@H]2[C@H](C1)[C@H]2Nc1nccc(-c2sc(N3C4CCC3COC4)nc2-c2cccc(NS(=O)(=O)c3c(F)cccc3F)c2F)n1] | N-(3-(2-(3-oxa-8-azabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued
| Cpd No. | Structure | Name |
|---|---|---|
| 106 | 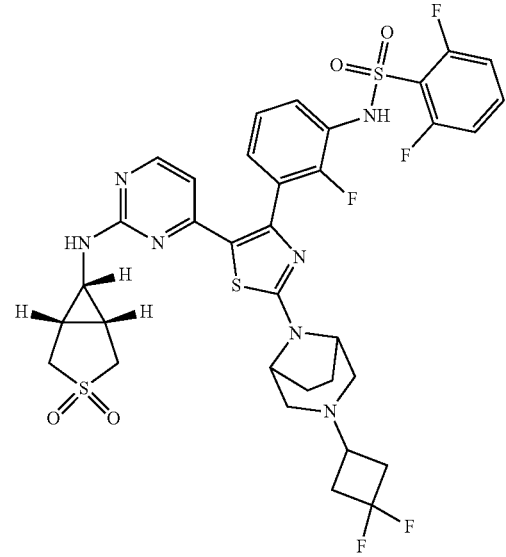 [SMILES: O=S1(=O)C[C@@H]2[C@H](C1)[C@@H]2Nc1nccc(-c2sc(N3C4CCC3CN(C3CC(F)(F)C3)C4)nc2-c2cccc(NS(=O)(=O)c3c(F)cccc3F)c2F)n1] | N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 107 | 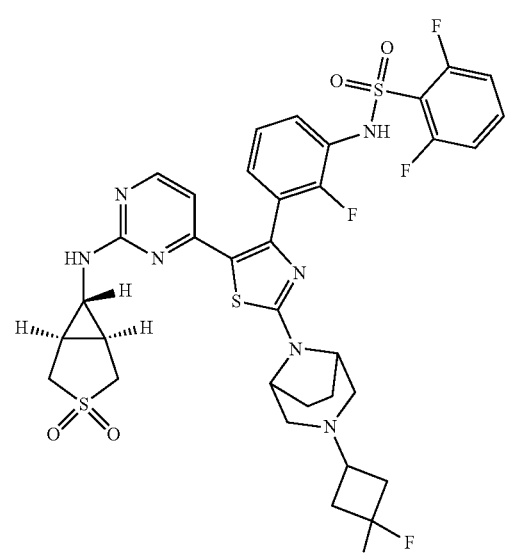 | N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 108 | 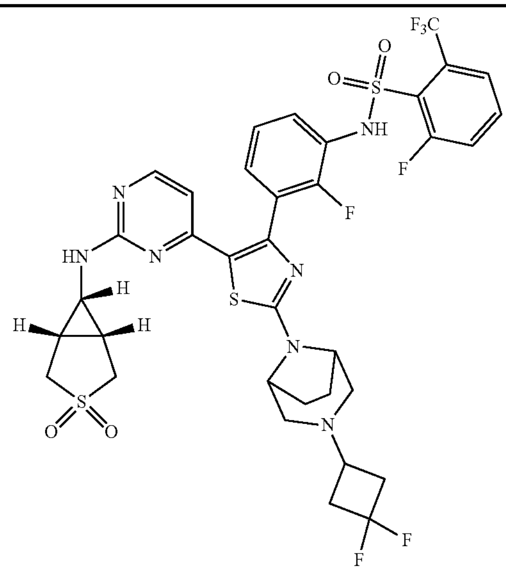 | N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 109 | 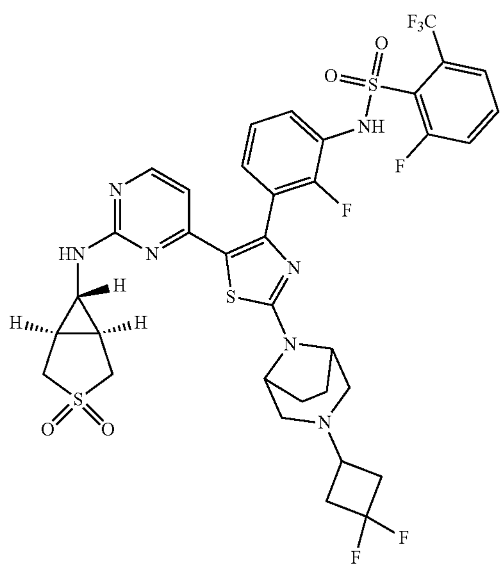 [SMILES: O=S1(=O)C[C@@H]2[C@H](C1)[C@H]2Nc1nccc(-c2sc(N3C4CCC3CN(C3CC(F)(F)C3)C4)nc2-c2cccc(NS(=O)(=O)c3c(F)cccc3C(F)(F)F)c2F)n1] | N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 110 | 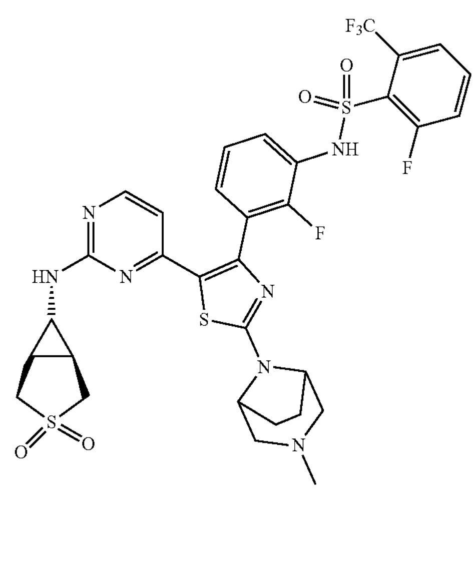 | N-(3-(5-(2-(((1S,5S)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 111 | 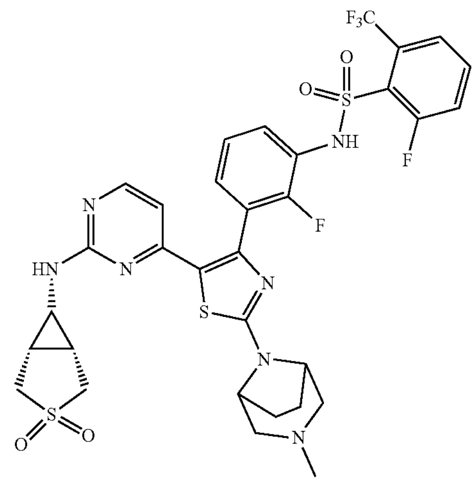 | N-(3-(5-(2-(((1R,5S,6s)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2-fluoro-6-(trifluoromethyl)benzenesulfonamide |
| 112 | 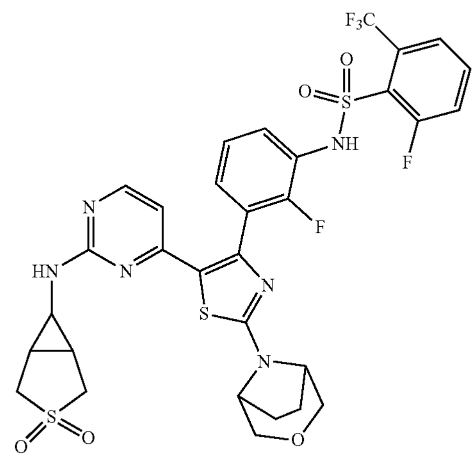 [SMILES: O=S1(=O)CC2C(C1)C2Nc1nccc(-c2sc(N3C4CCC3COC4)nc2-c2cccc(NS(=O)(=O)c3c(F)cccc3C(F)(F)F)c2F)n1] | N-(3-(2-(3-oxa-8-azabicyclo[3.2.1]octan-8-yl)-5-(2-((3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 113 | 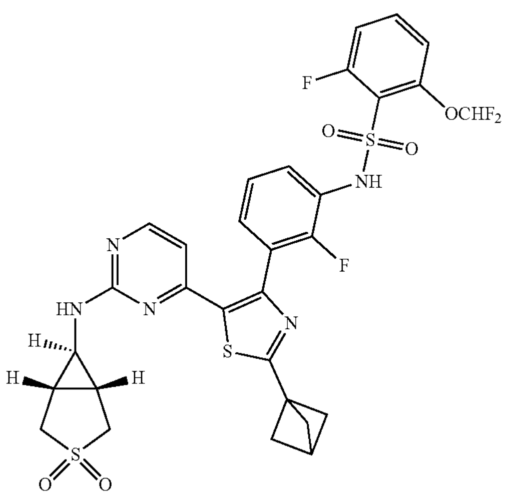 [SMILES: O=S1(=O)C[C@@H]2[C@H](C1)[C@H]2Nc1nccc(-c2sc(C34CC(C3)C4)nc2-c2cccc(NS(=O)(=O)c3c(F)cccc3OC(F)F)c2F)n1] | N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-fluorobenzenesulfonamide |

TABLE I-continued

| Cpd No. | Structure | Name |
|---|---|---|
| 114 | 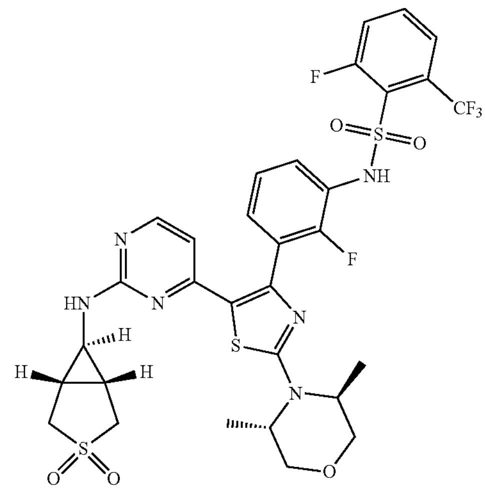 [SMILES: C[C@H]1COC[C@H](C)N1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1] | N-(3-(2-((3S,5S)-3,5-dimethylmorpholino)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 115 | 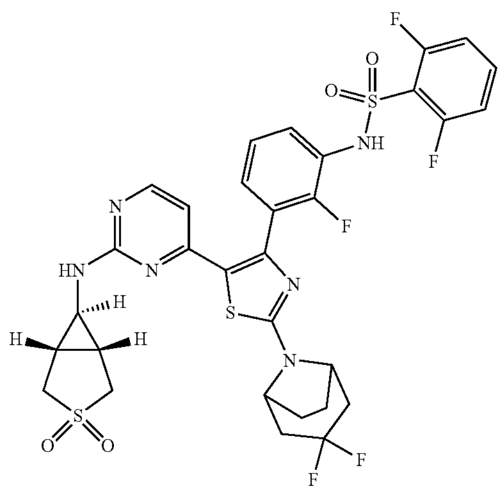 [SMILES: O=S1(=O)C[C@@H]2[C@H](C1)[C@H]2Nc1nccc(-c2sc(N3C4CCC3CC(F)(F)C4)nc2-c2cccc(NS(=O)(=O)c3c(F)cccc3F)c2F)n1] | N-(3-(2-(3,3-difluoro-8-azabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |
| 116 | 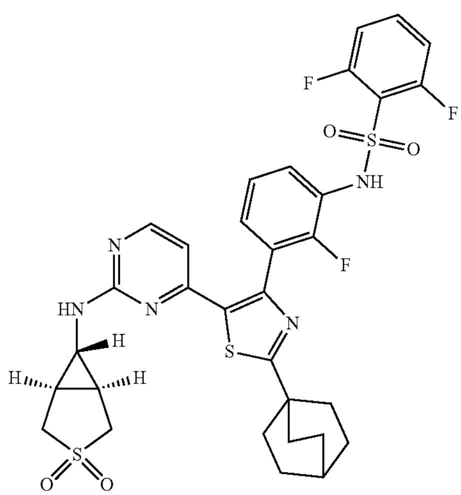 [SMILES: O=S1(=O)C[C@@H]2[C@H](C1)[C@H]2Nc1nccc(-c2sc(C34CCC(CC3)CC4)nc2-c2cccc(NS(=O)(=O)c3c(F)cccc3F)c2F)n1] | N-(3-(2-(bicyclo[2.2.2]octan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 117 | 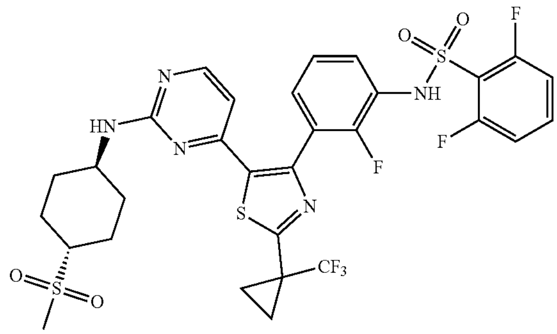 [SMILES: CS(=O)(=O)[C@H]1CC[C@H](Nc2nccc(-c3sc(C4(C(F)(F)F)CC4)nc3-c3cccc(NS(=O)(=O)c4c(F)cccc4F)c3F)n2)CC1] | 2,6-difluoro-N-(2-fluoro-3-(5-(2-(((1s,4s)-4-(methylsulfonyl)-cyclohexyl)amino)pyrimidin-4-yl)-2-(1-(trifluoromethyl)-cyclopropyl)thiazol-4-yl)phenyl)benzenesulfonamide |
| 118 | 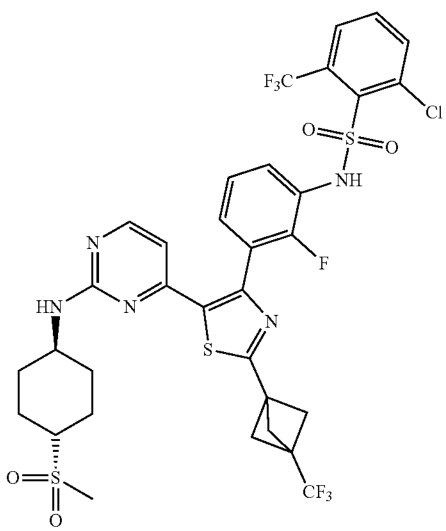 | 2-chloro-N-(2-fluoro-3-(5-(2-(((1s,4s)-4-(methylsulfonyl)-cyclohexyl)amino)pyrimidin-4-yl)-2-(3-(trifluoromethyl)bicyclo-[1.1.1]pentan-1-yl)thiazol-4-yl)phenyl)-6-(trifluoromethyl)-benzenesulfonamide |
| 119 | 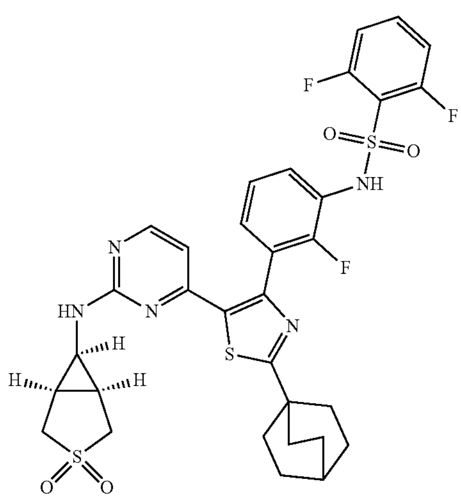 [SMILES: O=S1(=O)C[C@@H]2[C@H](C1)[C@@H]2Nc1nccc(-c2sc(C34CCC(CC3)CC4)nc2-c2cccc(NS(=O)(=O)c3c(F)cccc3F)c2F)n1] | N-(3-(2-(bicyclo[2.2.2]octan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 120 | 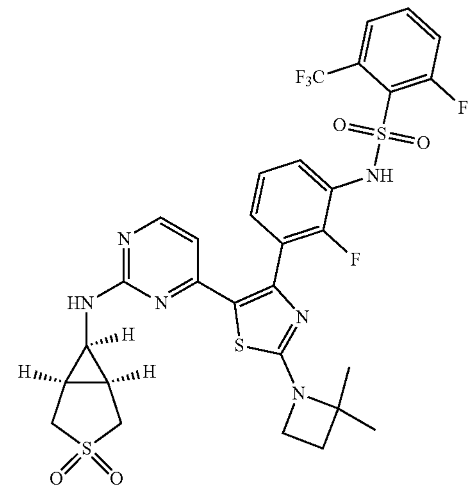 [SMILES: CC1(C)CCN1c1nc(-c2cccc(NS(=O)(=O)c3c(F)cccc3C(F)(F)F)c2F)c(-c2ccnc(N[C@@H]3[C@@H]4CS(=O)(=O)C[C@@H]43)n2)s1] | N-(3-(2-(2,2-dimethylazetidin-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 121 | 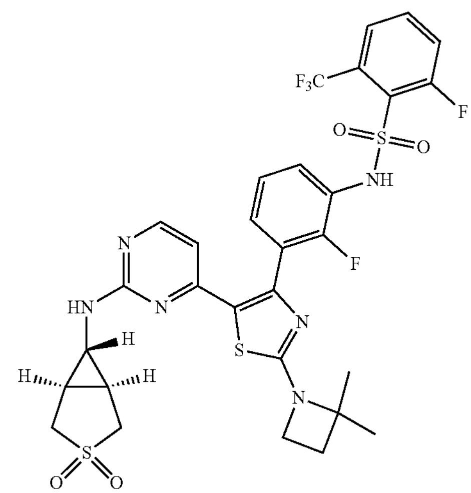 [SMILES: CC1(C)CCN1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1] | N-(3-(2-(2,2-dimethylazetidin-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide |
| 122 | 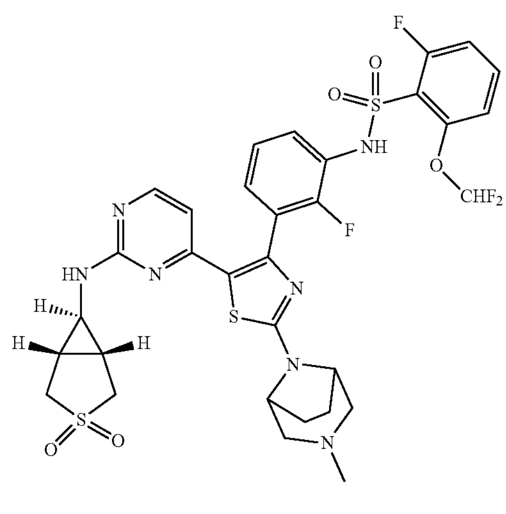 [SMILES: CN1CC2CCC(C1)N2c1nc(-c2cccc(NS(=O)(=O)c3c(F)cccc3OC(F)F)c2F)c(-c2ccnc(N[C@H]3[C@@H]4CS(=O)(=O)C[C@@H]43)n2)s1] | 2-(difluoromethoxy)-N-(3-(5-(2-(((1R,5S,6r)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-6-fluorobenzenesulfonamide |

TABLE I-continued

| Cpd No. | Structure | Name |
|---|---|---|
| 123 | 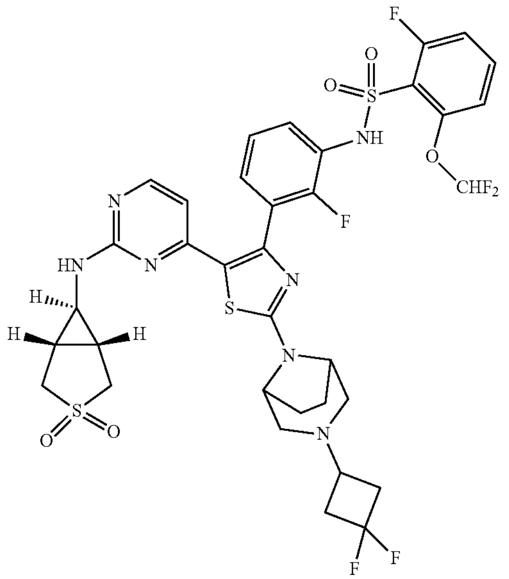 [SMILES: O=S1(=O)C[C@@H]2[C@H](C1)[C@H]2Nc1nccc(-c2sc(N3C4CCC3CN(C3CC(F)(F)C3)C4)nc2-c2cccc(NS(=O)(=O)c3c(F)cccc3OC(F)F)c2F)n1] | N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-fluorobenzenesulfonamide |
| 124 | 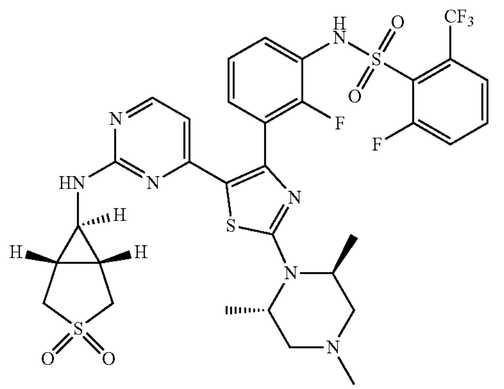 [SMILES: C[C@H]1CN(C)C[C@H](C)N1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1] | N-(3-(5-(2-(((1R,5S,6r)-3,3-dioxido-3-thiabicyclo[3.1.0]hexan-6-yl)amino)pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide |
| 125 | 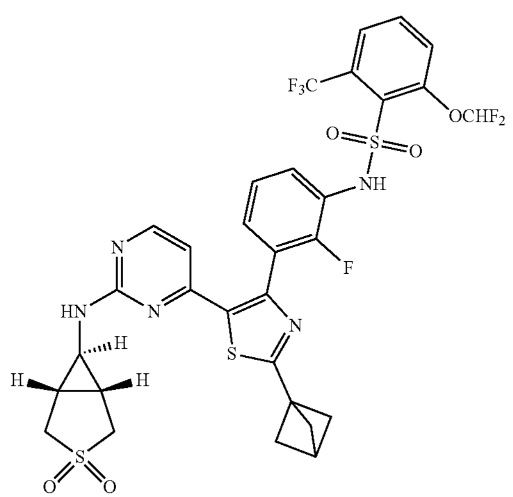 [SMILES: O=S1(=O)C[C@@H]2[C@H](C1)[C@H]2Nc1nccc(-c2sc(C34CC(C3)C4)nc2-c2cccc(NS(=O)(=O)c3c(OC(F)F)cccc3C(F)(F)F)c2F)n1] | N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-(trifluoromethyl)-benzenesulfonamide |

| Cpd No. | Structure | Name |
|---|---|---|
| 126 | 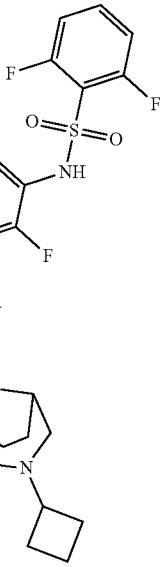 | N-(3-(2-(3-cyclobutyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2,6-difluorobenzenesulfonamide |
| 127 | 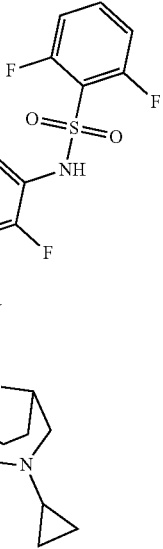 | N-(3-(2-(3-cyclopropyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2,6-difluorobenzene-sulfonamide |
| 128 | 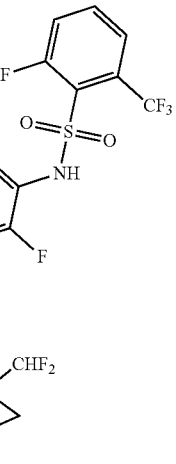 | N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)-benzenesulfonamide |

TABLE I-continued
| Cpd No. | Structure | Name |
|---|---|---|
| 129 | 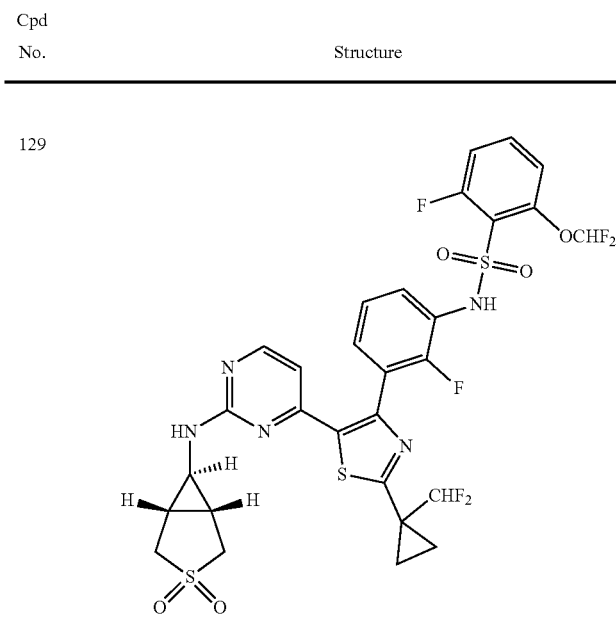 | 2-(difluoromethoxy)-N-(3-(2-(1-(difluoromethyl)cyclopropyl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-6-fluorobenzene-sulfonamide |
| 130 | 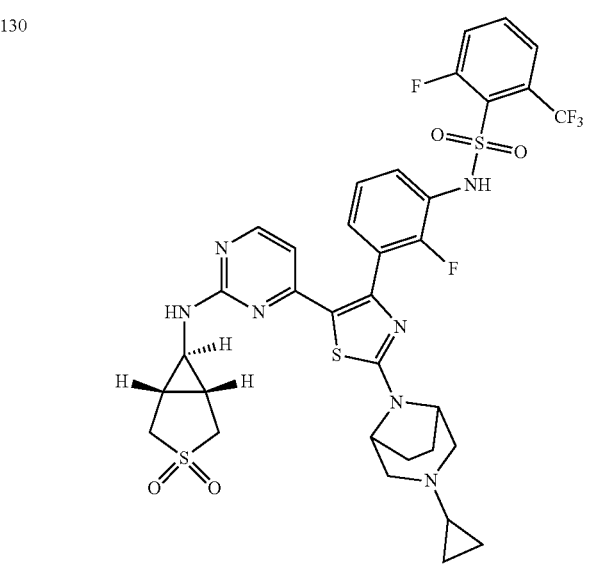 | N-(3-(2-(3-cyclopropyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 131 | 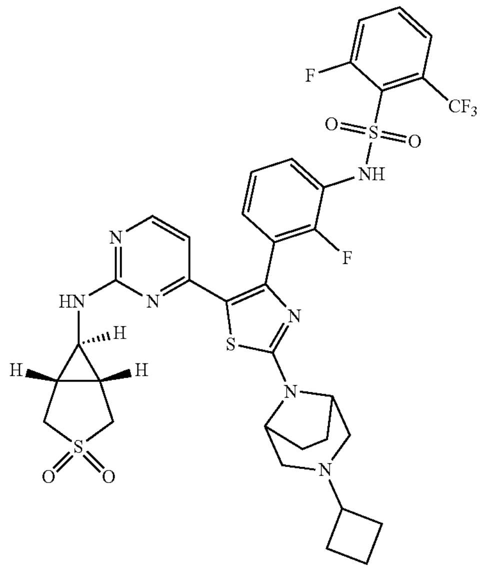 [SMILES: O=S1(=O)C[C@@H]2[C@H](C1)[C@H]2Nc1nccc(-c2sc(N3C4CCC3CN(C3CCC3)C4)nc2-c2cccc(NS(=O)(=O)c3c(F)cccc3C(F)(F)F)c2F)n1] | N-(3-(2-(3-cyclobutyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2-fluoro-6-(trifluoromethyl)benzenesulfonamide |
| 132 | 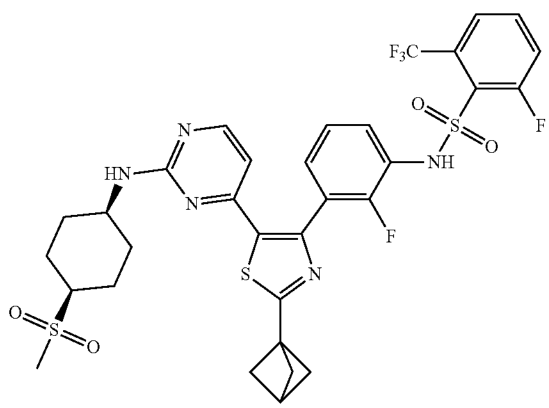 [SMILES: CS(=O)(=O)[C@H]1CC[C@@H](Nc2nccc(-c3sc(C45CC(C4)C5)nc3-c3cccc(NS(=O)(=O)c4c(F)cccc4C(F)(F)F)c3F)n2)CC1] | N-(3-(2-(bicyclo[1.1.1]pentan-1-yl)-5-(2-(((1s,4s)-4-(methylsulfonyl)cyclohexyl)amino)pyrimidin-4-yl)thiazol-4-yl)-2-fluorophenyl)-2-fluoro-6-(trifluoromethyl)benzenesulfonamide |
| 133 | 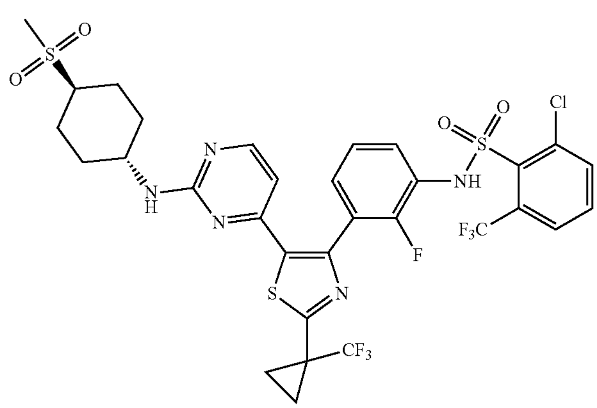 [SMILES: CS(=O)(=O)[C@H]1CC[C@H](Nc2nccc(-c3sc(C4(C(F)(F)F)CC4)nc3-c3cccc(NS(=O)(=O)c4c(Cl)cccc4C(F)(F)F)c3F)n2)CC1] | 2-chloro-N-(2-fluoro-3-(5-(2-(((1r,4r)-4-(methylsulfonyl)-cyclohexyl)amino)pyrimidin-4-yl)-2-(1-(trifluoromethyl)-cyclopropyl)thiazol-4-yl)phenyl)-6-(trifluoromethyl)benzene-sulfonamide |

TABLE I-continued

| Cpd No. | Structure | Name |
|---|---|---|
| 134 | 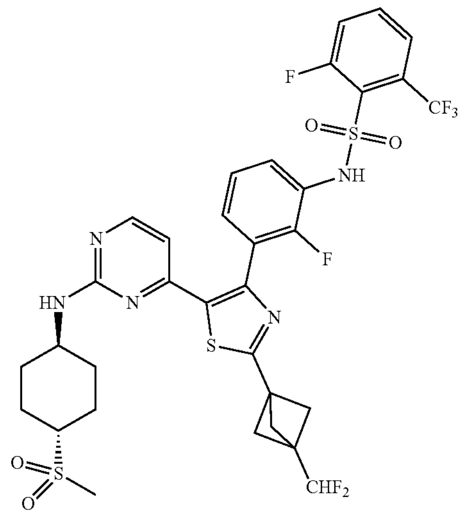 [SMILES: CS(=O)(=O)[C@H]1CC[C@H](Nc2nccc(-c3sc(C45CC(C(F)F)(C4)C5)nc3-c3cccc(NS(=O)(=O)c4c(F)cccc4C(F)(F)F)c3F)n2)CC1] | N-(3-(2-(3-(difluoromethyl)bicyclo[1.1.1]pentan-1-yl)-5-(2-(((1r,4r)-4-(methylsulfonyl)cyclohexyl)amino)pyrimidin-4-yl)thiazol-4-yl)-2-fluorophenyl)-2-fluoro-6-(trifluoromethyl)benzenesulfonamide |
| 135 | 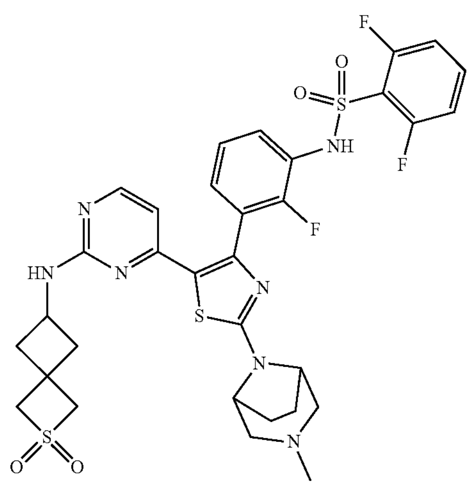 [SMILES: CN1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2,6-difluorobenzenesulfonamide |
| 136 | 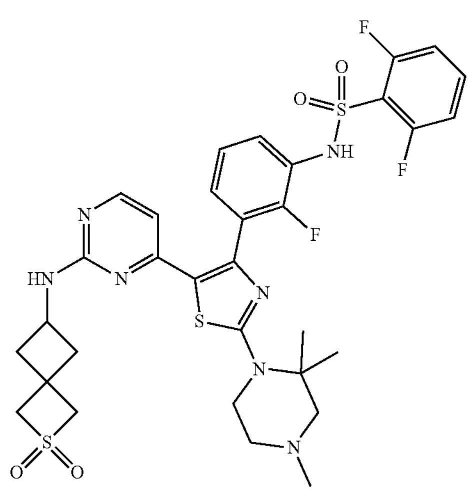 [SMILES: CN1CCN(c2nc(-c3cccc(NS(=O)(=O)c4c(F)cccc4F)c3F)c(-c3ccnc(NC4CC5(C4)CS(=O)(=O)C5)n3)s2)C(C)(C)C1] | N-(3-(5-(2-((2,2-dioxido-2-thiaspiro[3.3]heptan-6-yl)amino)-pyrimidin-4-yl)-2-(2,2,4-trimethylpiperazin-1-yl)thiazol-4-yl)-2-fluorophenyl)-2,6-difluorobenzenesulfonamide |

TABLE I-continued

| Cpd No. | Structure | Name |
|---|---|---|
| 137 | 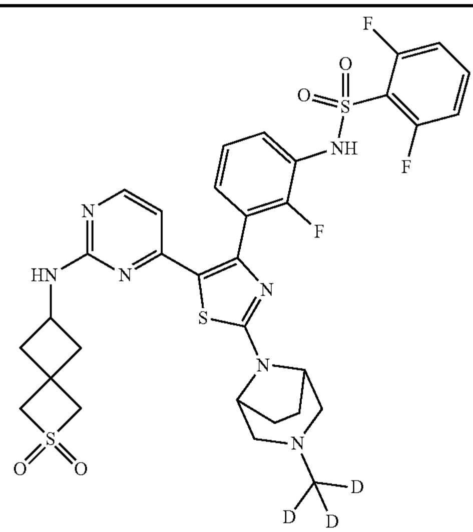 | N-(3-(5-(2-((2,2-dioxido-2-thiaspiro[3.3]heptan-6-yl)amino)-pyrimidin-4-yl)-2-(3-(methyl-d3)-3,8-diazabicyclo[3.2.1]octan-8-yl)thiazol-4-yl)-2-fluorophenyl)-2,6-difluorobenzenesulfonamide |
| 138 | 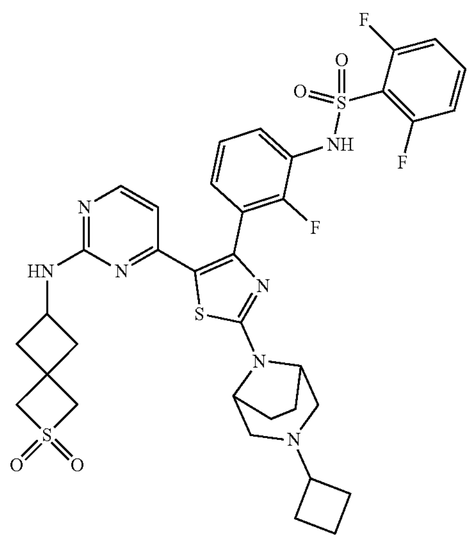 [SMILES: O=S1(=O)CC2(CC(Nc3nccc(-c4sc(N5C6CCC5CN(C5CCC5)C6)nc4-c4cccc(NS(=O)(=O)c5c(F)cccc5F)c4F)n3)C2)C1] | N-(3-(2-(3-cyclopropyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 139 | 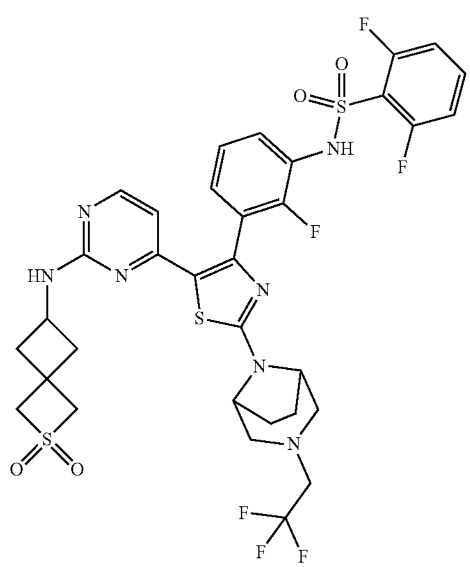 [SMILES: O=S1(=O)CC2(CC(Nc3nccc(-c4sc(N5C6CCC5CN(CC(F)(F)F)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(3-(2,2,2-trifluoroethyl)-3,8-diazabicyclo-[3.2.1]octan-8-yl)thiazol-4-yl)-2-fluorophenyl)-2,6-difluoro-benzenesulfonamide |

TABLE I-continued

| Cpd No. | Structure | Name |
|---|---|---|
| 140 | 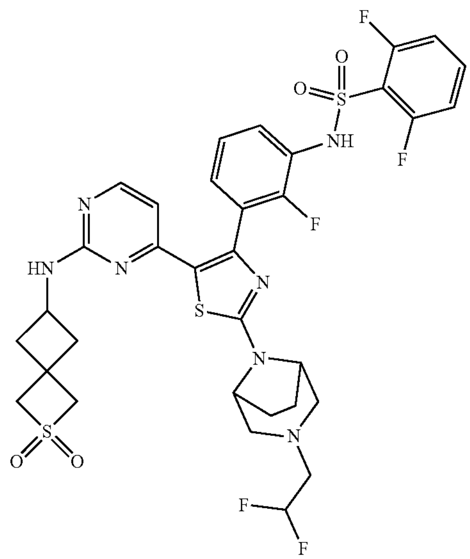 [SMILES: O=S1(=O)CC2(CC(Nc3nccc(-c4sc(N5C6CCC5CN(CC(F)F)C6)nc4-c4cccc(NS(=O)(=O)c5c(F)cccc5F)c4F)n3)C2)C1] | N-(3-(2-(3-(2,2-difluoroethyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 141 | 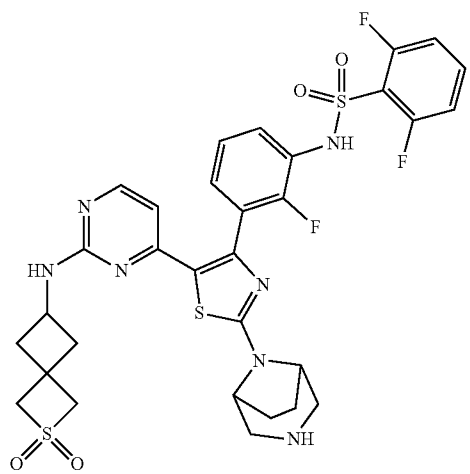 [SMILES: O=S1(=O)CC2(CC(Nc3nccc(-c4sc(N5C6CCC5CNC6)nc4-c4cccc(NS(=O)(=O)c5c(F)cccc5F)c4F)n3)C2)C1] | N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 142 | 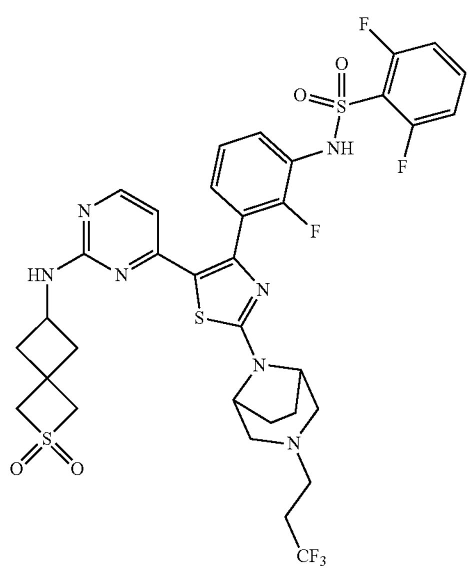 [SMILES: O=S1(=O)CC2(CC(Nc3nccc(-c4sc(N5C6CCC5CN(CCC(F)(F)F)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(3-(3,3,3-trifluoropropyl)-3,8-diazabicyclo-[3.2.1]octan-8-yl)thiazol-4-yl)-2-fluorophenyl)-2,6-difluorobenzenesulfonamide |

TABLE I-continued
| Cpd No. | Structure | Name |
|---|---|---|
| 143 | 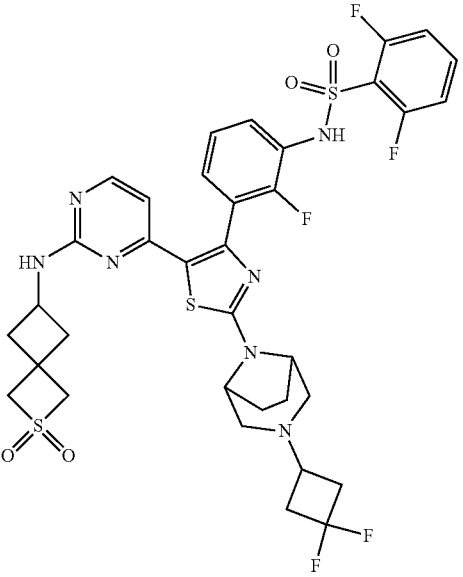 [SMILES: O=S1(=O)CC2(CC(Nc3nccc(-c4sc(N5C6CCC5CN(C5CC(F)(F)C5)C6)nc4-c4cccc(NS(=O)(=O)c5c(F)cccc5F)c4F)n3)C2)C1] | N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide |
| 144 | 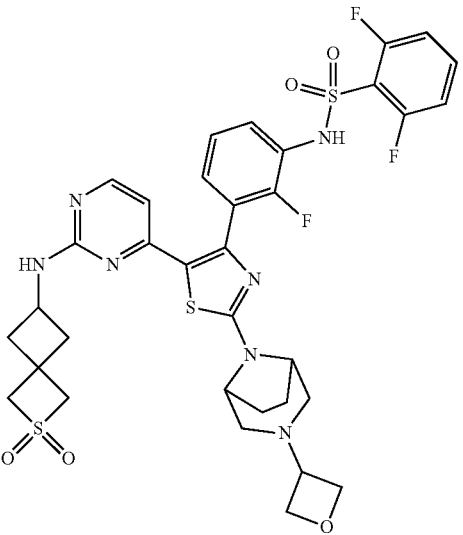 [SMILES: O=S1(=O)CC2(CC(Nc3nccc(-c4sc(N5C6CCC5CN(C5COC5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)-pyrimidin-4-yl)-2-(3-(oxetan-3-yl)-3,8-diazabicyclo[3.2.1]octan-8-yl)thiazol-4-yl)-2-fluorophenyl)-2,6-difluorobenzenesulfonamide |

TABLE I-continued
| Cpd No. | Structure | Name |
|---|---|---|
| 146 | 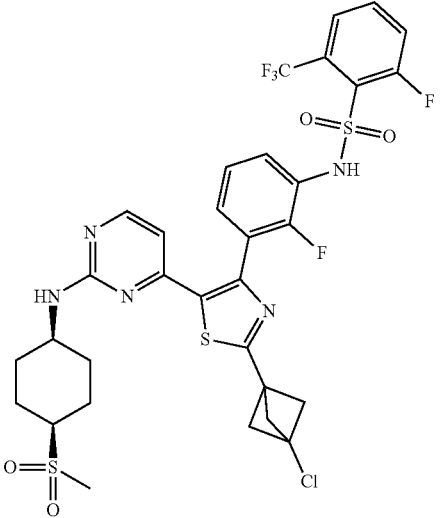 [SMILES: CS(=O)(=O)[C@H]1CC[C@@H](Nc2nccc(-c3sc(C45CC(Cl)(C4)C5)nc3-c3cccc(NS(=O)(=O)c4c(F)cccc4C(F)(F)F)c3F)n2)CC1] | N-(3-(2-(3-chlorobicyclo[1.1.1]pentan-1-yl)-5-(2-(((1s,4s)-4-(methylsulfonyl)cyclohexyl)amino)pyrimidin-4-yl)thiazol-4-yl)-2-fluorophenyl)-2-fluoro-6-(trifluoromethyl)benzenesulfonamide |
| 147 | 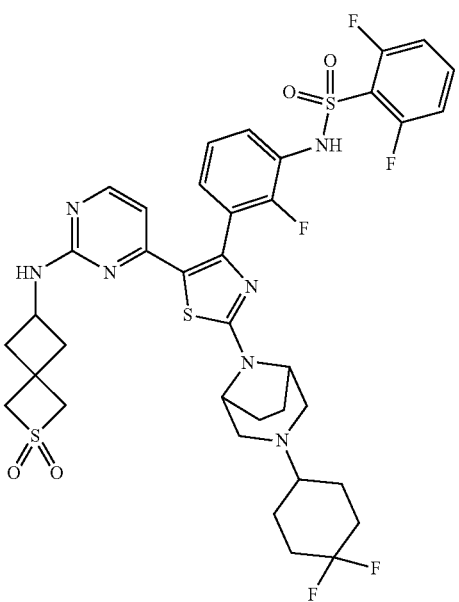 [SMILES: O=S1(=O)CC2(CC(Nc3nccc(-c4sc(N5C6CCC5CN(C5CCC(F)(F)CC5)C6)nc4-c4cccc(NS(=O)(=O)c5c(F)cccc5F)c4F)n3)C2)C1] | N-(3-(2-(3-(4,4-difluorocyclohexyl)-3,8-diazabicyclo[3.2.1]octan-8-yl)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide |

TABLE I-continued
| Cpd No. | Structure | Name |
|---|---|---|
| 148 | 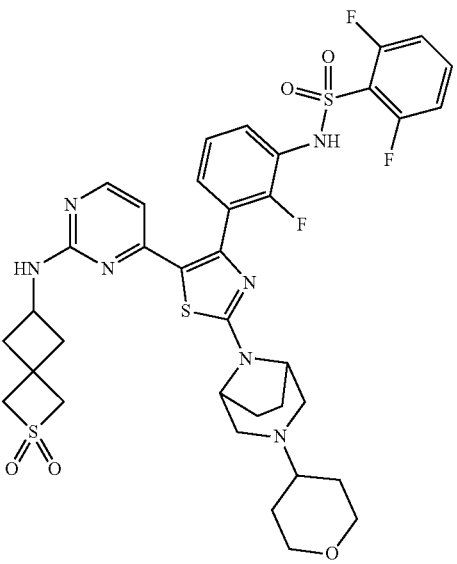 [SMILES: O=S1(=O)CC2(CC(Nc3nccc(-c4sc(N5C6CCC5CN(C5CCOCC5)C6)nc4-c4cccc(NS(=O)(=O)c5c(F)cccc5F)c4F)n3)C2)C1] | N-(3-(5-(2-((2,2-dioxido-2-thiaspiro[3.3]heptan-6-yl)amino)pyrimidin-4-yl)-2-(3-(tetrahydro-2H-pyran-4-yl)-3,8-diazabicyclo[3.2.1]octan-8-yl)thiazol-4-yl)-2-fluorophenyl)-2,6-difluorobenzenesulfonamide |
| 149 | 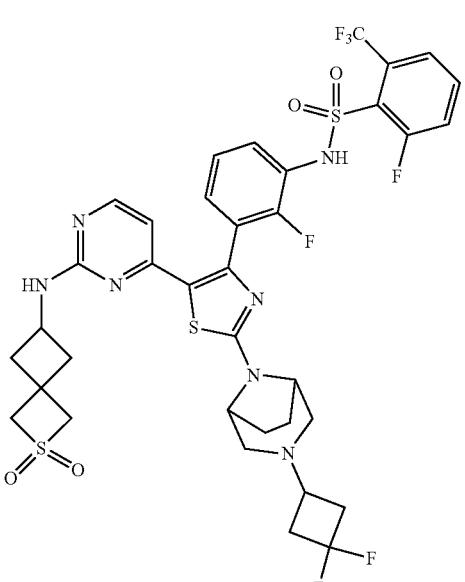 | N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |

TABLE I-continued

| Cpd No. | Structure | Name |
|---|---|---|
| 150 | 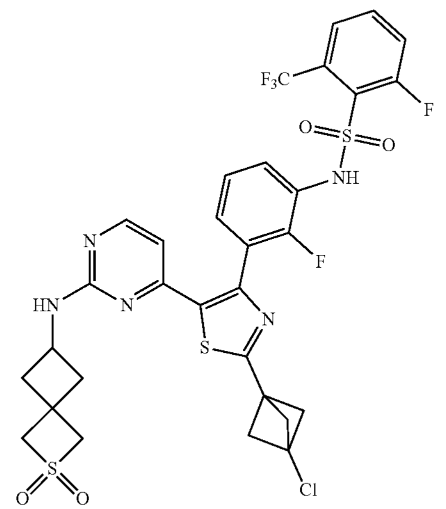 [SMILES: O=S1(=O)CC2(CC(Nc3nccc(-c4sc(C56CC(Cl)(C5)C6)nc4-c4cccc(NS(=O)(=O)c5c(F)cccc5C(F)(F)F)c4F)n3)C2)C1] | N-(3-(2-(3-chlorobicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 151 | 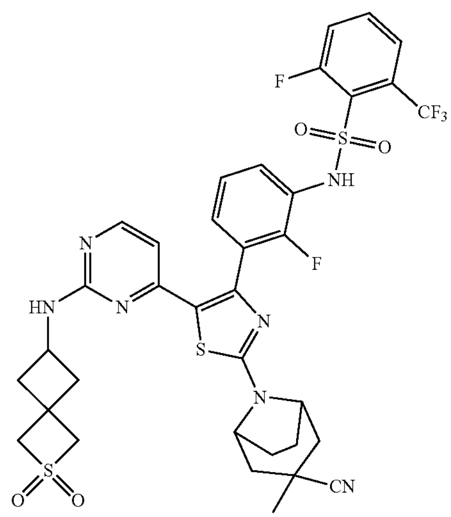 [SMILES: CC1(C#N)CC2CCC(C1)N2c1nc(-c2cccc(NS(=O)(=O)c3c(F)cccc3C(F)(F)F)c2F)c(-c2ccnc(NC3CC4(C3)CS(=O)(=O)C4)n2)s1] | N-(3-(2-(3-cyano-3-methyl-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide |
| 152 | 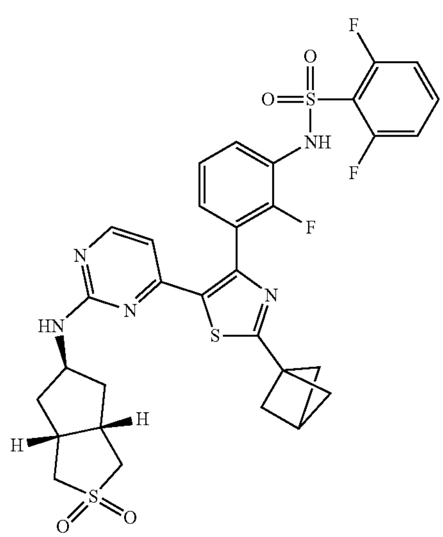 [SMILES: O=S1(=O)C[C@H]2C[C@H](Nc3nccc(-c4sc(C56CC(C5)C6)nc4-c4cccc(NS(=O)(=O)c5c(F)cccc5F)c4F)n3)C[C@H]2C1] | N-(3-(2-(bicyclo[1.1.1]pentan-1-yl)-5-(2-(((3aR,5s,6aS)-2,2-dioxidohexahydro-1H-cyclopenta[c]thiophen-5-yl)amino)pyrimidin-4-yl)thiazol-4-yl)-2-fluorophenyl)-2,6-difluorobenzenesulfonamide |

TABLE I-continued

| Cpd No. | Structure | Name |
|---|---|---|
| 153 | 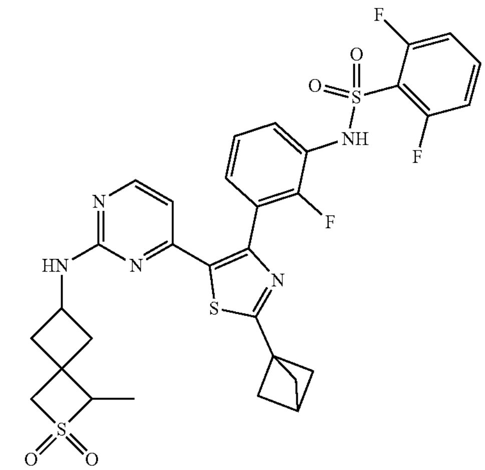 [SMILES: CC1C2(CC(Nc3nccc(-c4sc(C56CC(C5)C6)nc4-c4cccc(NS(=O)(=O)c5c(F)cccc5F)c4F)n3)C2)CS1(=O)=O] | N-(3-(2-(bicyclo[1.1.1]pentan-1-yl)-5-(2-((1-methyl-2,2-dioxido-2-thiaspiro[3.3]heptan-6-yl)amino)pyrimidin-4-yl)thiazol-4-yl)-2-fluorophenyl)-2,6-difluorobenzenesulfonamide |
| 154 | 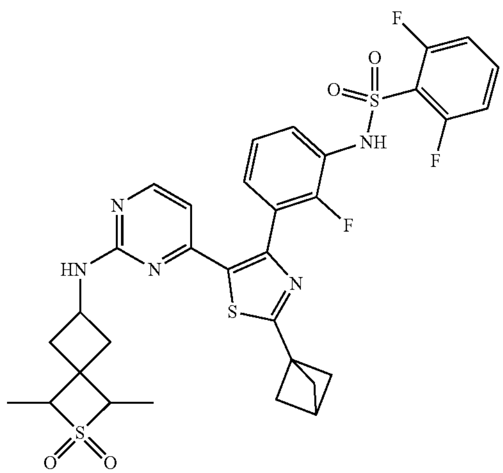 [SMILES: CC1C2(CC(Nc3nccc(-c4sc(C56CC(C5)C6)nc4-c4cccc(NS(=O)(=O)c5c(F)cccc5F)c4F)n3)C2)C(C)S1(=O)=O] | N-(3-(2-(bicyclo[1.1.1]pentan-1-yl)-5-(2-((1,3-dimethyl-2,2-dioxido-2-thiaspiro[3.3]heptan-6-yl)amino)pyrimidin-4-yl)thiazol-4-yl)-2-fluorophenyl)-2,6-difluorobenzenesulfonamide |
| 155 | 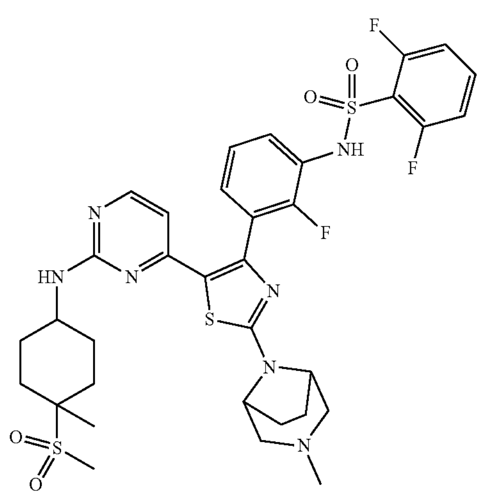 [SMILES: CN1CC2CCC(C1)N2c1nc(-c2cccc(NS(=O)(=O)c3c(F)cccc3F)c2F)c(-c2ccnc(NC3CCC(C)(S(C)(=O)=O)CC3)n2)s1] | 2,6-difluoro-N-(2-fluoro-3-(5-(2-((4-methyl-4-(methylsulfonyl)-cyclohexyl)amino)pyrimidin-4-yl)-2-(3-methyl-3,8-diaza-bicyclo[3.2.1]octan-8-yl)thiazol-4-yl)phenyl)benzenesulfonamide |

Embodiments

In further embodiments 1-66 below, the present disclosure includes:

1. In embodiment 1, the compound of Formula (I), or a pharmaceutically acceptable salt thereof, is as provided in the first aspect of the Summary above.

2. In embodiment 2, the compound of Formula (I), or a pharmaceutically acceptable salt thereof, of embodiment 1, is wherein ring $R^B$ is cycloalkyl or bridged cycloalkyl wherein cycloalkyl and bridged cycloalkyl are substituted with $R^a$.

3. In embodiment 3, the compound of Formula (I), or a pharmaceutically acceptable salt thereof, of embodiment 1 or 2, is wherein ring $R^B$ is cycloalkyl substituted with $R^a$.

4. In embodiment 4, the compound of Formula (I), or a pharmaceutically acceptable salt thereof, of embodiment 1 or 2 is wherein ring $R^B$ is bridged cycloalkyl substituted with $R^a$.

5. In embodiment 5, the compound of Formula (I), or a pharmaceutically acceptable salt thereof, of embodiment 1, is wherein ring $R^B$ is heterocyclyl or bridged heterocyclyl wherein heterocyclyl is substituted with $R^b$, $R^c$, and $R^d$ and bridged heterocyclyl is substituted with $R^e$, $R^f$, and $R^g$.

6. In embodiment 6, the compound of Formula (I), or a pharmaceutically acceptable salt thereof, of embodiment 1 or 5, is wherein ring $R^B$ is heterocyclyl substituted with $R^b$, $R^c$, and $R^d$.

7. In embodiment 7, the compound of Formula (I), or a pharmaceutically acceptable salt thereof, of embodiment 1 or 5, is wherein ring $R^B$ is bridged heterocyclyl substituted with $R^e$, $R^f$, and $R^g$.

8. In embodiment 8, the compound of Formula (I), or a pharmaceutically acceptable salt thereof, of embodiment 1, is wherein cycloalkyl and bridged cycloalkyl of ring $R^B$ are selected from:

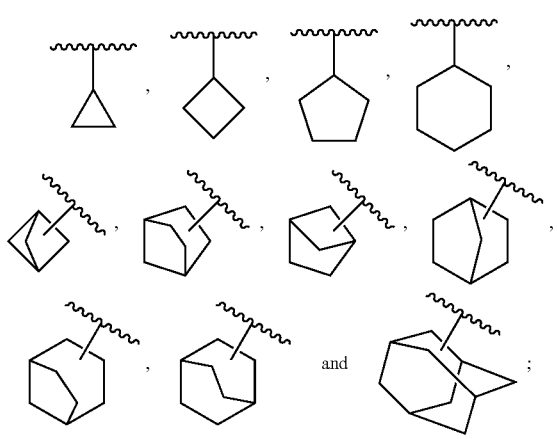

and heterocyclyl and bridged heterocyclyl of ring $R^B$ are selected from:

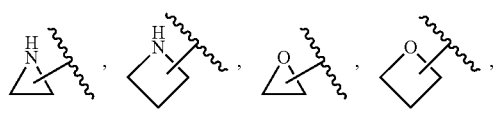

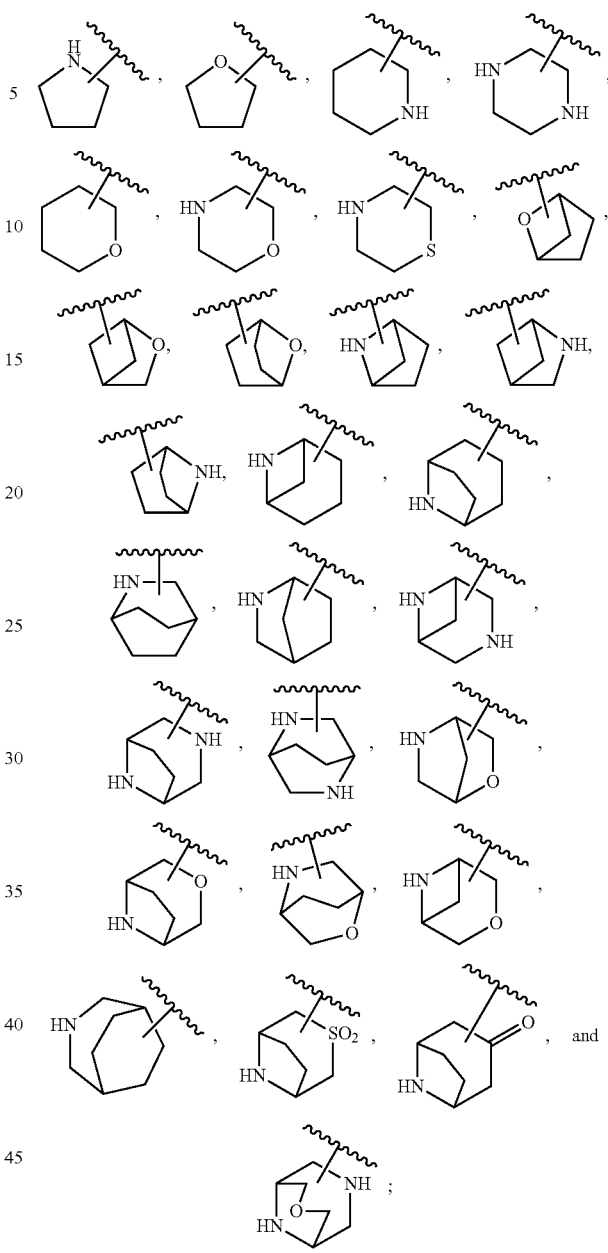

wherein each cycloalkyl and bridged cycloalkyl is substituted with $R^a$; each heterocyclyl is substituted with $R^b$, $R^c$, and $R^d$, and each bridged heterocyclyl is substituted with $R^e$, $R^f$, and $R^g$.

9. In embodiment 9, the compound of Formula (I), or a pharmaceutically acceptable salt thereof, of embodiment 1 or 8, is wherein cycloalkyl and bridged cycloalkyl of ring $R^B$ are selected from:

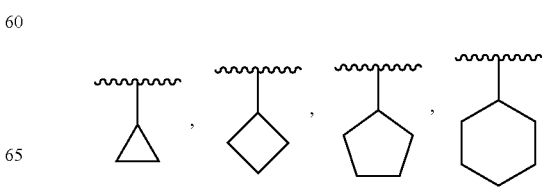

-continued

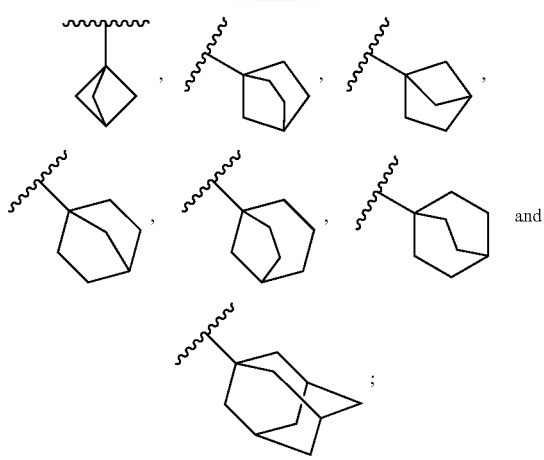

and heterocyclyl and bridged heterocyclyl of ring $R^B$ are selected from:

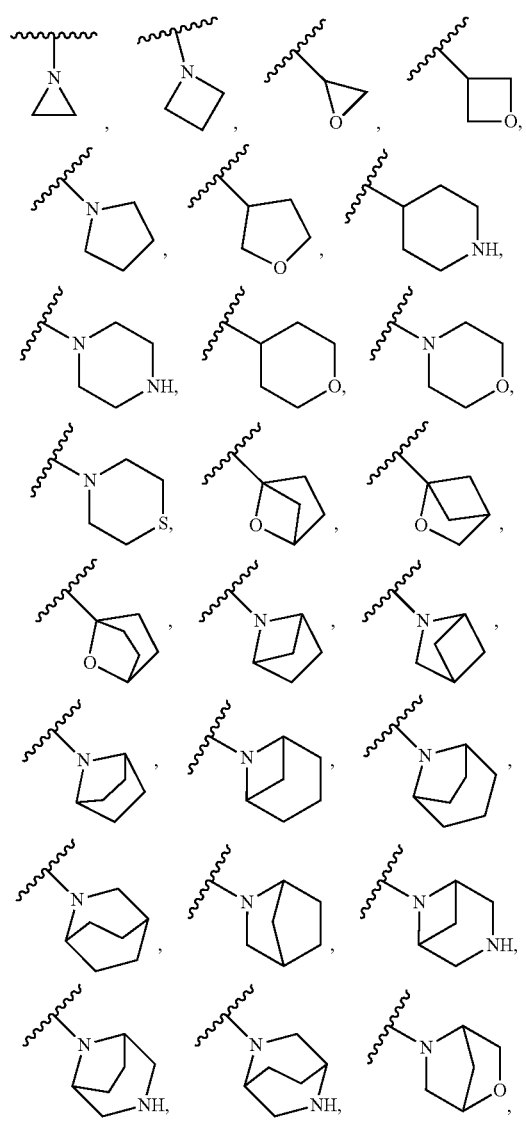

-continued

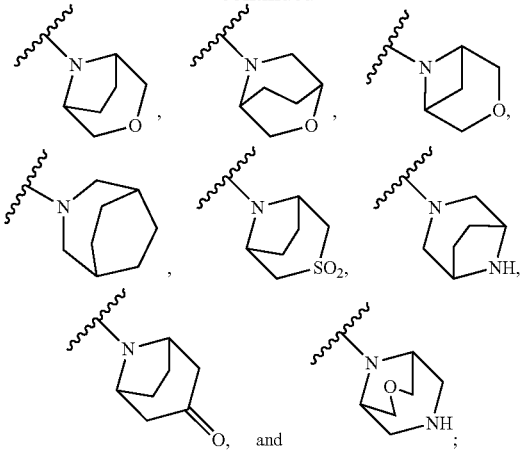

wherein each cycloalkyl and bridged cycloalkyl is substituted with $R^a$; each heterocyclyl ring is substituted with $R^b$, $R^c$, and $R^d$, and each bridged heterocyclyl is substituted with $R^e$, $R^f$, and $R^g$.

10. In embodiment 10, the compound of Formula (I), or a pharmaceutically acceptable salt thereof, of embodiment 1 or 2, is wherein the cycloalkyl and bridged cycloalkyl of ring $R^B$ are selected from:

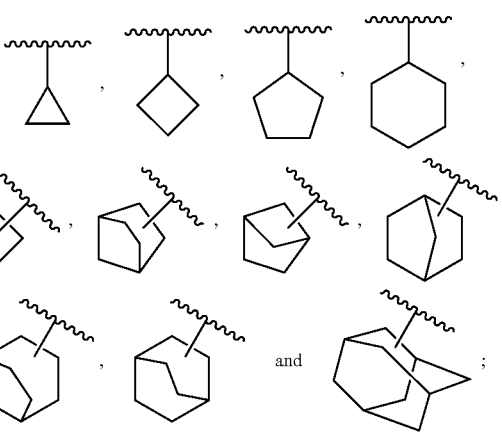

wherein each cycloalkyl and bridged cycloalkyl is substituted with $R^a$.

11. In embodiment 11, the compound of Formula (I), or a pharmaceutically acceptable salt thereof, of embodiment 1, 2, or 10, is wherein the cycloalkyl and bridged cycloalkyl of ring $R^B$ are selected from:

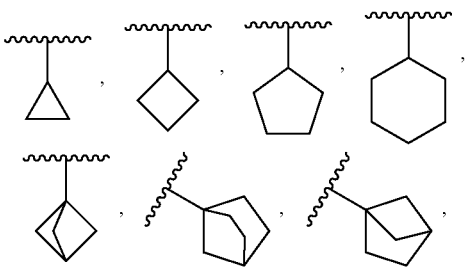

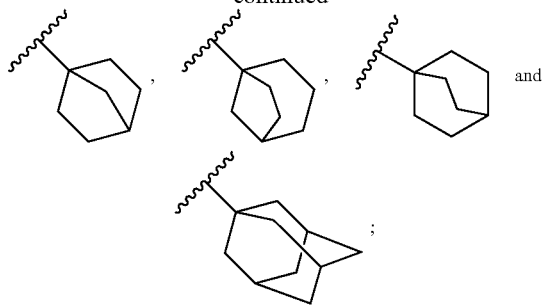

wherein each cycloalkyl and bridged cycloalkyl is substituted with R$^a$.

12. In embodiment 12, the compound of Formula (I), or a pharmaceutically acceptable salt thereof, of embodiment 1 or 5, is wherein the heterocyclyl and bridged heterocyclyl of ring R$^B$ are selected from:

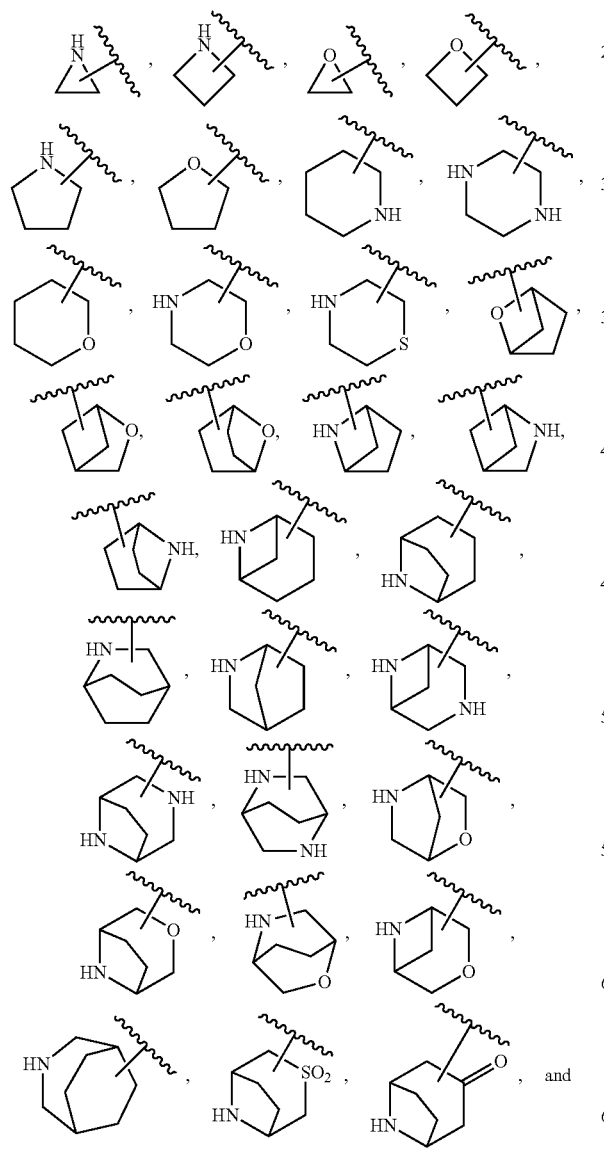

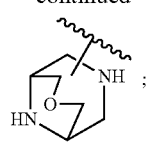

wherein each heterocyclyl is substituted with R$^b$, R$^c$, and R$^d$ and each bridged heterocyclyl is substituted with R$^e$, R$^f$, and R$^g$.

13. In embodiment 13, the compound of Formula (I), or a pharmaceutically acceptable salt thereof, of embodiment 1 or 5, is wherein the heterocyclyl and bridged heterocyclyl of ring R$^B$ are selected from:

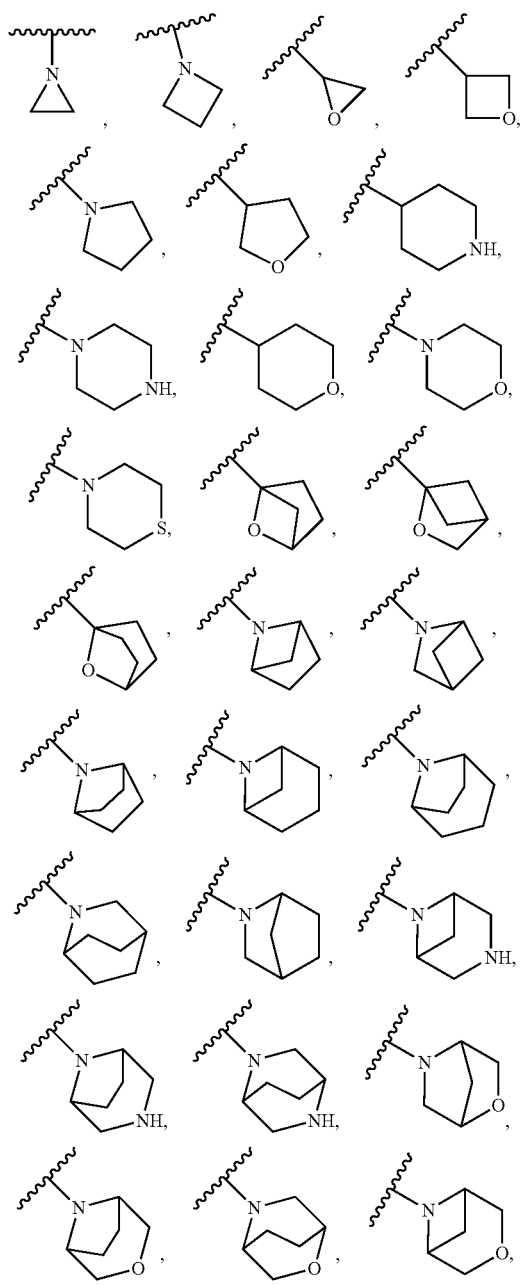

-continued

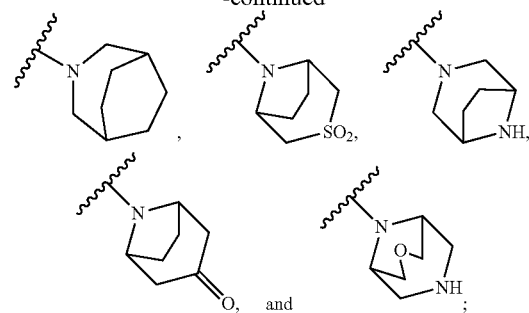

wherein each heterocyclyl is substituted with $R^b$, $R^c$, and $R^d$ and each bridged heterocyclyl is substituted with $R^e$, $R^f$, and $R^g$.

14. In embodiment 14, the compound of Formula (I), or a pharmaceutically acceptable salt thereof, of embodiment 1, 2, or 3, is wherein the cycloalkyl of ring $R^B$ is selected from:

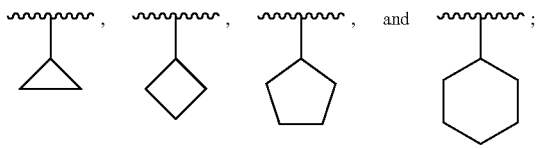

wherein each cycloalkyl is substituted with $R^a$.

15. In embodiment 15, the compound of Formula (I), or a pharmaceutically acceptable salt thereof, of any one of embodiments 1 to 3, 8 to 11, and 14, is wherein the cycloalkyl of ring $R^B$ is selected from:

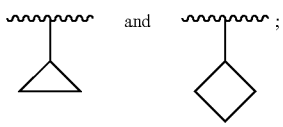

wherein each cycloalkyl is substituted with $R^a$.

16. In embodiment 16, the compound of Formula (I), or a pharmaceutically acceptable salt thereof, of embodiment 1, 2, or 4, is wherein the bridged cycloalkyl of ring $R^B$ is selected from:

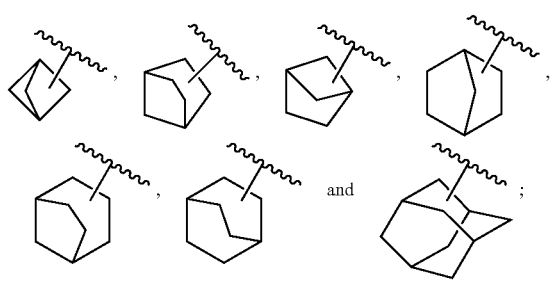

wherein each bridged cycloalkyl is substituted with $R^a$.

17. In embodiment 17, the compound of Formula (I), or a pharmaceutically acceptable salt thereof, of any one of embodiments 1, 2, 4, 8 to 11, and 16, is wherein the bridged cycloalkyl of ring $R^B$ is selected from:

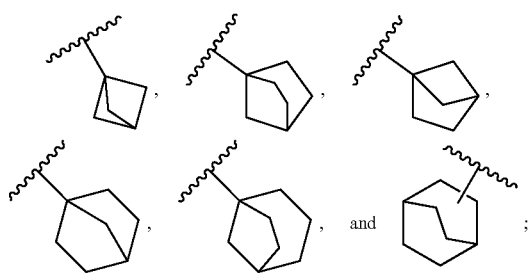

wherein each bridged cycloalkyl is substituted with $R^a$.

18. In embodiment 18, the compound of Formula (I), or a pharmaceutically acceptable salt thereof, of any one of embodiments 1, 2, 4, 8 to 11, 16, and 17, is wherein the bridged cycloalkyl of ring $R^B$ is:

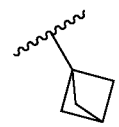 [SMILES: *C12CC(C1)C2]

and is substituted with R.

19. In embodiment 19, the compound of Formula (I), or a pharmaceutically acceptable salt thereof, of embodiment 1, 5, or 6, is wherein the heterocyclyl of ring $R^B$ is selected from:

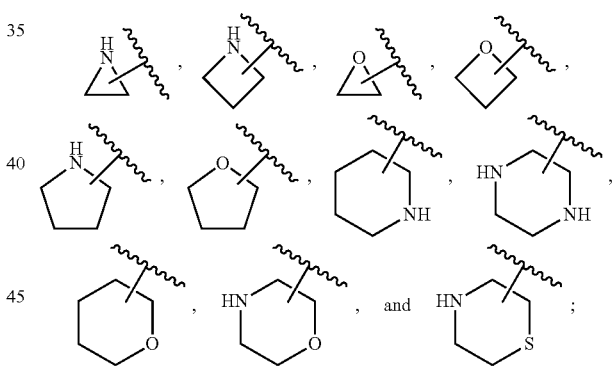

wherein each heterocyclyl is substituted with $R^b$, $R^c$, and $R^d$.

20. In embodiment 20, the compound of Formula (I), or a pharmaceutically acceptable salt thereof, of embodiment 1, 5, or 6, is wherein the heterocyclyl of ring $R^B$ is selected from:

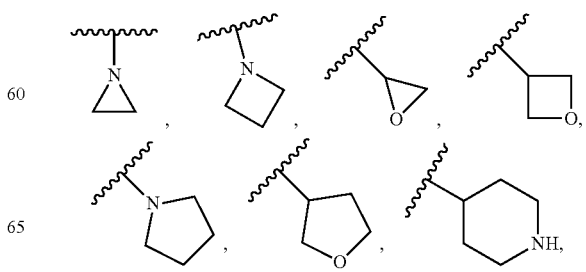

-continued

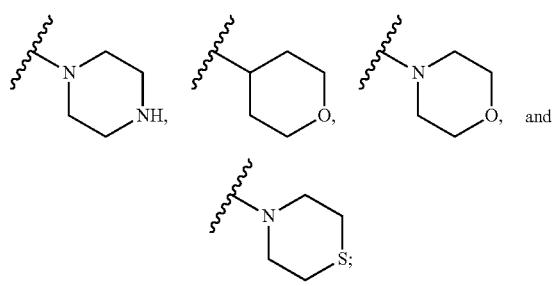

wherein each heterocyclyl is substituted with $R^b$, $R^c$, and $R^d$.

21. In embodiment 21, the compound of Formula (I), or a pharmaceutically acceptable salt thereof, of embodiment 1, 5, 6, 8, 9, 12, 19, or 20, is wherein the heterocyclyl of ring $R^B$ is selected from:

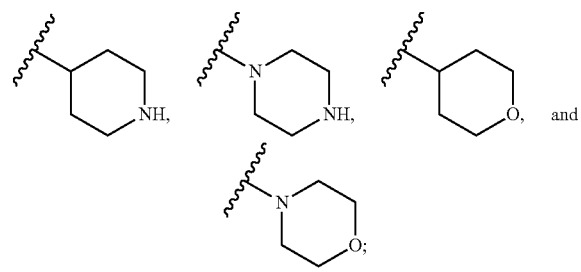

wherein each heterocyclyl is substituted with $R^b$, $R^c$, and $R^d$.

22. In embodiment 22, the compound of Formula (I), or a pharmaceutically acceptable salt thereof, of embodiment 1, 5, or 7, is wherein the bridged heterocyclyl of ring $R^B$ is selected from:

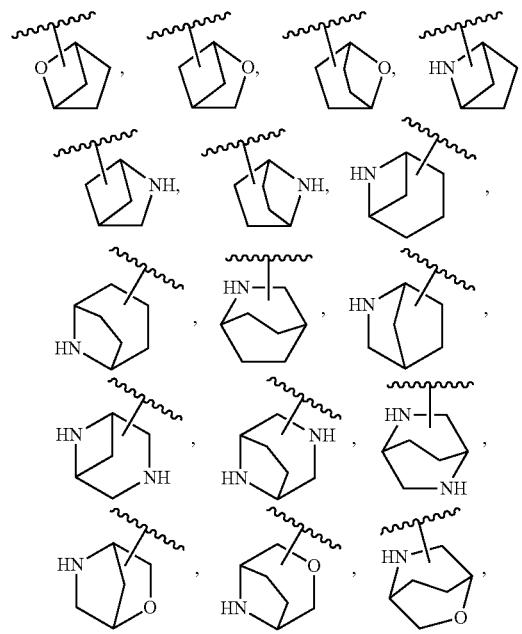

-continued

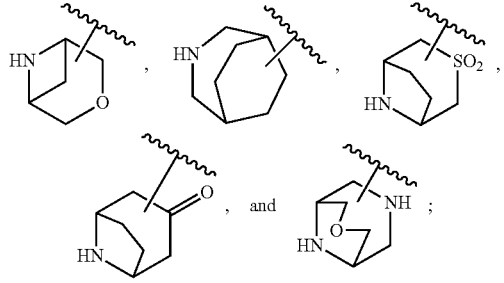

wherein each bridged heterocyclyl is substituted with $R^e$, $R^f$, and $R^g$.

23 In embodiment 23, the compound of Formula (I), or a pharmaceutically acceptable salt thereof, of embodiment 1, 5, 7, or 22, is wherein the bridged heterocyclyl of ring $R^B$ is selected from:

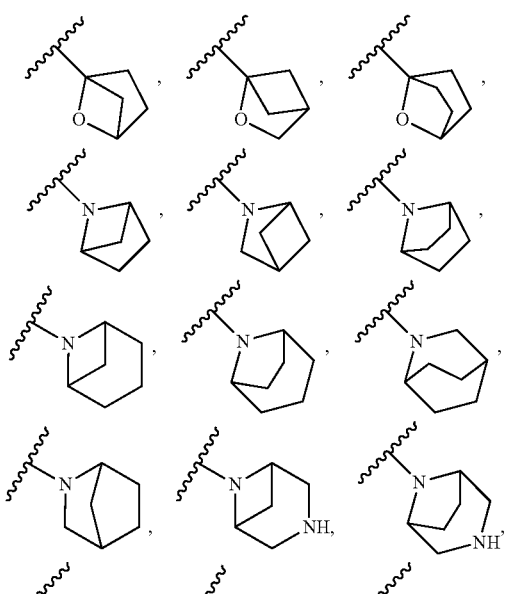

wherein each bridged heterocyclyl is substituted with $R^e$, $R^f$, and $R^g$.

24. In embodiment 24, the compound of Formula (I), or a pharmaceutically acceptable salt thereof, of embodiment 1, 5, 7, 8, 9, 12, or 23, is wherein the bridged heterocyclyl of ring $R^B$ is selected from:

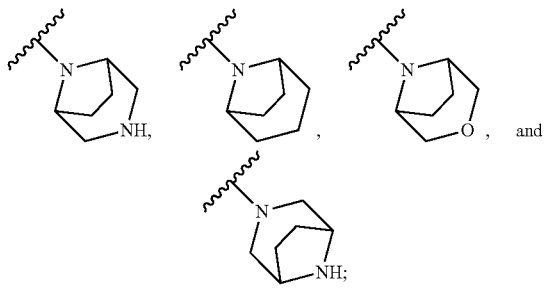

wherein each bridged heterocyclyl is substituted with $R^e$, $R^f$, and $R^g$.

25. In embodiment 25, the compound of Formula (I), or a pharmaceutically acceptable salt thereof, of any one of embodiments 1 to 4, 8 to 11, and 14-18, is wherein $R^a$ is hydrogen, chloro, fluoro, difluoromethyl, trifluoromethyl, or hydroxymethyl.

26. In embodiment 26, the compound of Formula (I), or a pharmaceutically acceptable salt thereof, of any one of embodiments 1 to 4, 8 to 11, 14-18, and 25, is wherein $R^a$ is hydrogen.

27. In embodiment 27, the compound of Formula (I), or a pharmaceutically acceptable salt thereof, of any one of embodiments 1 to 4, 8 to 11, 14-18, and 25, is wherein $R^a$ is fluoro or chloro.

28. In embodiment 28, the compound of Formula (I), or a pharmaceutically acceptable salt thereof, of any one of embodiments 1 to 4, 8 to 11, 14-18, and 25, is wherein $R^a$ is difluoromethyl, or trifluoromethyl.

29. In embodiment 29, the compound of Formula (I), or a pharmaceutically acceptable salt thereof, of any one of embodiments 1 to 4, 8 to 11, 14-18, and 25, is wherein $R^a$ is hydrogen, chloro, fluoro, difluoromethyl, or trifluoromethyl.

30. In embodiment 30, the compound of Formula (I), or a pharmaceutically acceptable salt thereof, of any one of embodiments 1 to 4, 8 to 11, and 14-18, is wherein $R^a$ is hydrogen or haloalkyl.

31. In embodiment 31, the compound of Formula (I), or a pharmaceutically acceptable salt thereof, of any one of embodiments 1 to 4, 8 to 11, and 14-18, is wherein $R^a$ is hydrogen or halo.

32. In embodiment 32, the compound of Formula (I), or a pharmaceutically acceptable salt thereof, of any one of embodiments 1 to 4, 8 to 11, and 14-18, is wherein $R^a$ is halo or haloalkyl.

33. In embodiment 33, the compound of Formula (I), or a pharmaceutically acceptable salt thereof, of any one of embodiments 1 to 4, 8 to 11, 14 to 18, and 25 to 32, is wherein ring $R^B$ is bicyclo[1.1.1]pentan-1-yl, 3-fluorobicyclo[1.1.1]pentan-1-yl, 3-chlorobicyclo[1.1.1]pentan-1-yl, 3-(hydroxymethyl)bicyclo[1.1.1]pentan-1-yl, 3-(trifluoromethyl)bicyclo[1.1.1]pentan-1-yl, 3-(difluoromethyl)bicyclo[1.1.1]pentan-1-yl, cyclobutyl, cyclopropyl, 1-(difluoromethyl)cyclobutyl, 1-(trifluoromethyl)cyclobutyl, 1-(difluoromethyl)cyclopropyl, or 1-(trifluoromethyl)cyclopropyl.

34. In embodiment 34, the compound of Formula (I), or a pharmaceutically acceptable salt thereof, of any one of embodiments 1, 2, 4, 8 to 11, 16-18, and 25 to 33, is wherein ring $R^B$ is bicyclo[1.1.1]pentan-1-yl, 3-fluorobicyclo[1.1.1]pentan-1-yl, 3-chlorobicyclo[1.1.1]pentan-1-yl, 3-(hydroxymethyl)bicyclo[1.1.1]pentan-1-yl, 3-(trifluoromethyl)bicyclo[1.1.1]pentan-1-yl, or 3-(difluoromethyl)bicyclo[1.1.1]pentan-1-yl.

35. In embodiment 35, the compound of Formula (I), or a pharmaceutically acceptable salt thereof, of any one of embodiments 1, 2, 3, 8 to 11, 14, 15, and 25, 26, 28 to 30, 32, and 33, is wherein ring $R^B$ is cyclobutyl, cyclopropyl, 1-(difluoromethyl)-cyclobutyl, 1-(trifluoromethyl)cyclobutyl, 1-(difluoromethyl)-cyclopropyl, or 1-(trifluoromethyl)-cyclopropyl.

36. In embodiment 36, the compound of Formula (I), or a pharmaceutically acceptable salt thereof, of any one of embodiments 1, 3, 8 to 11, 14, 15, 25, 26, 28 to 30, 32, 33, and 34, is wherein ring $R^B$ is 1-(difluoromethyl)cyclobutyl, 1-(trifluoromethyl)cyclobutyl, 1-(difluoromethyl)-cyclopropyl, or 1-(trifluoromethyl)cyclopropyl.

37. In embodiment 37, the compound of Formula (I), or a pharmaceutically acceptable salt thereof, of any one of embodiments 1, 5 to 9, 12, 13, and 19-24, is wherein $R^b$ and $R^c$ are independently selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^d$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl; and $R^e$ and $R^f$ are independently selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^g$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl.

38. In embodiment 38, the compound of Formula (I), or a pharmaceutically acceptable salt thereof, of any one of embodiments 1, 5 to 9, 12, 13, 19-24, and 37, is wherein $R^b$ is hydrogen, $R^c$ is selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^d$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl; and $R^e$ is hydrogen, R is selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^9$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl.

39. In embodiment 39, the compound of Formula (I), or a pharmaceutically acceptable salt thereof, of any one of embodiments 1, 5 to 9, 12, 13, 19-24, and 38, is wherein $R^b$ and $R^c$ are hydrogen and $R^d$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl; and
  $R^e$ and $R^f$ are hydrogen and $R^g$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl.

40. In embodiment 40, the compound of Formula (I), or a pharmaceutically acceptable salt thereof, of any one of embodiments 1, 5 to 9, 12, 13, 19-24, and 37 to 39, is wherein (i) heterocyclyl of ring $R^B$ is 3,5-dimethylmorpholino, 4-methyltetrahydro-2H-pyran-4-yl, 2,2,4-trimethylpiperazin-1-yl, 4-methylpiperidin-4-yl, 1,4-dimethylpiperidin-4-yl, 3-oxo-8-azabicyclo[3.2.1]octan-8-yl, 2,2-dimethylpyrrolidin-1-yl, 2,2-dimethylazetidin-1-yl, 2,4-dimethylazetidin-1-yl, 2,4,6-trimethylpiperazin-1-yl, 2,6-dimethylpiperazin-1-yl, or 2,5-dimethylpyrrolidin-1-yl; and
  (ii) bridged heterocyclyl of ring $R^B$ is 2-oxabicyclo[2.1.1]hexan-1-yl, 7-azabicyclo[2.2.1]heptan-7-yl, 3-oxa-8-azabicyclo[3.2.1]octan-8-yl, 3-methyl-3,8-diazabicyclo[3.2.1]octan-8-yl, 3,3-difluoro-8-azabicyclo[3.2.1]octan-8-yl, 3-(methyl-d3)-3,8-diazabicyclo[3.2.1]octan-8-yl, 3-cyclopropyl-3,8-diazabicyclo[3.2.1]octan-8-yl, 3-(2,2,2-trifluoroethyl)-3,8-diazabicyclo[3.2.1]octan-8-yl, 3-(2,2-difluoroethyl)-3,8-diazabicyclo[3.2.1]octan-8-yl, 3,8-diazabicyclo[3.2.1]octan-8-yl, 2-azabicyclo[2.2.2]octan-2-yl, 8-azabicyclo[3.2.1]octan-8-yl, 3-(3,3,3-trifluoropropyl)-3,8-diazabicyclo[3.2.1]octan-8-yl, 3-azabicyclo[3.2.2]nonan-3-yl, 3-methyl-3,6-diazabicyclo[3.1.1]heptan-6-yl, 8-methyl-3,8-diazabicyclo[3.2.1]octan-3-yl, 3-(dimethylamino)-8-azabicyclo[3.2.1]octan-8-yl, 3-(3,3-difluorocyclobutyl)-3,8-diazabicyclo[3.2.1]octan-8-yl, 3-(oxetan-3-yl)-3,8-diazabicyclo[3.2.1]octan-8-yl, 5-methyl-2,5-diazabicyclo[2.2.2]octan-2-yl, 3-hydroxy-3-methyl-8-azabicyclo[3.2.1]octan-8-yl, 3-cyano-3-methyl-8-azabicyclo[3.2.1]octan-8-yl, 3-(4,4-difluorocyclohexyl)-3,8-diazabicyclo[3.2.1]octan-8-yl, 3-(tetrahydro-2H-pyran-4-yl)-3,8-diazabicyclo[3.2.1]octan-8-yl, 8-(pyridin-2-yl)-3,8-diazabicyclo[3.2.1]octan-3-yl, 3-(1,1-dioxidotetrahydro-2H-thiopyran-4-yl)-3,8-diazabicyclo[3.2.1]octan-8-yl, 3-benzyl-3,8-diazabicyclo[3.2.1]octan-8-yl, 3-phenyl-3,8-diazabicyclo[3.2.1]octan-8-yl, 3-(pyridin-2-yl)-3,8-diazabicyclo[3.2.1]octan-8-yl, 3-(tetrahydrofuran-3-yl)-3,8-diazabicyclo[3.2.1]octan-8-yl, 3-(1,1-dioxidothietan-3-yl)-3,8-diazabicyclo[3.2.1]octan-8-yl, 3-(3-hydroxy-3-methylcyclobutyl)-3,8-diazabicyclo[3.2.1]octan-8-yl, 3,3-dioxido-3-thia-8-azabicyclo[3.2.1]octan-8-yl, 3-(3-cyano-3-methylcyclobutyl)-3,8-diazabicyclo[3.2.1]octan-8-yl, 3-cyclobutyl-3,8-diazabicyclo[3.2.1]octan-8-yl, 2-(1-cyano-7-azabicyclo[2.2.1]heptan-7-yl, 4-(3,3-difluorocyclobutyl)-2,6-dimethylpiperazin-1-yl, 7-methyl-3-oxa-7,9-diazabicyclo[3.3.1]nonan-9-yl, or 3-cyclopropyl-3,8-diazabicyclo[3.2.1]octan-8-yl.

41. In embodiment 41, the compound of Formula (I), or a pharmaceutically acceptable salt thereof, of any one of embodiments 1, 5 to 9, 12, 13, 19-24, and 37 to 40, is wherein bridged heterocyclyl of ring $R^B$ is 3-(3,3-difluorocyclobutyl)-3,8-diazabicyclo[3.2.1]octan-8-yl.

42. In embodiment 42, the compound of Formula (I), or a pharmaceutically acceptable salt thereof, of any one of embodiments 1, 5 to 9, 12, 13, 19-24, and 37 to 40, is wherein bridged heterocyclyl of ring $R^B$ is 3-methyl-3,8-diazabicyclo[3.2.1]octan-8-yl.

43. In embodiment 43, the compound of Formula (I), or a pharmaceutically acceptable salt thereof, of any one of embodiments 1 to 42, is wherein ring $R^A$ is a ring of formula (i) or (ii):

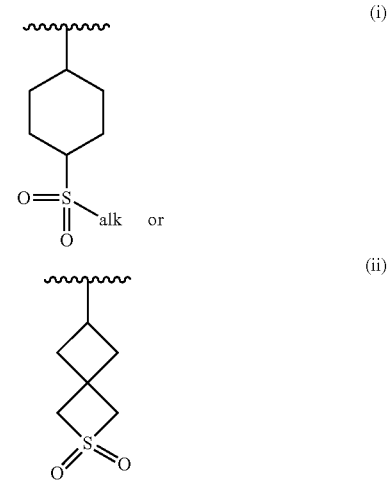

where alk is alkyl and each ring $R^A$ is substituted with $R^4$ and $R^5$.

44. In embodiment 44, the compound of Formula (I), or a pharmaceutically acceptable salt thereof, of any one of embodiments 1 to 43, is wherein ring $R^A$ is a ring of formula (i):

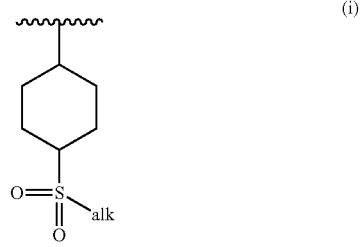

where alk is alkyl and the ring of formula (i) is substituted with $R^4$ and $R^5$.

45. In embodiment 45, the compound of Formula (I), or a pharmaceutically acceptable salt thereof, of any one of embodiments 1 to 44, is wherein ring $R^A$ is a ring of formula (i):

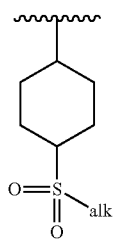

(i)

where alk is alkyl, $R^4$ is hydrogen, and $R^5$ is fluoro or methyl which is attached at carbon that is meta to the carbon of ring (i) that is substituted with —$SO_2$alk.

46. In embodiment 46, the compound of Formula (I), or a pharmaceutically acceptable salt thereof, of any one of embodiments 1 to 44, is wherein ring $R^A$ is a ring of formula (i):

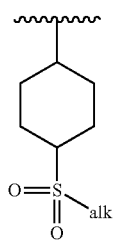

(i)

where alk is alkyl and $R^4$ and $R^5$ are hydrogen.

47. In embodiment 46, the compound of Formula (I), or a pharmaceutically acceptable salt thereof, of any one of embodiments 1 to 44 and 46, is wherein ring $R^A$ is a ring of formula:

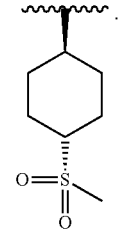

48. In embodiment 48, the compound of Formula (I), or a pharmaceutically acceptable salt thereof, of any one of embodiments 1 to 43, is wherein ring $R^A$ is a ring of formula (ii):

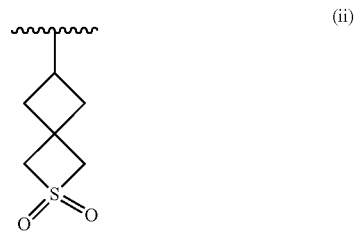 [SMILES: *C1CC2(C1)CS(=O)(=O)C2]

(ii)

where the ring of formula (ii) is substituted with R and $R^5$.

49. In embodiment 49, the compound of Formula (I), or a pharmaceutically acceptable salt thereof, of any one of embodiments 1 to 43 and 48, is wherein ring $R^A$ is a ring of formula:

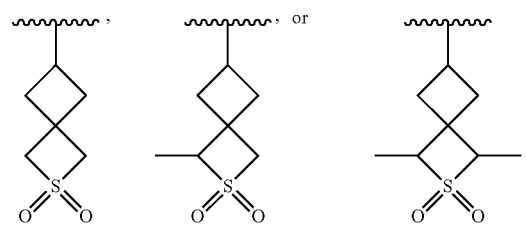

50. In embodiment 50, the compound of Formula (I), or a pharmaceutically acceptable salt thereof, of any one of embodiments 1 to 42, is wherein ring $R^A$ is a ring of formula (iii) or (iv):

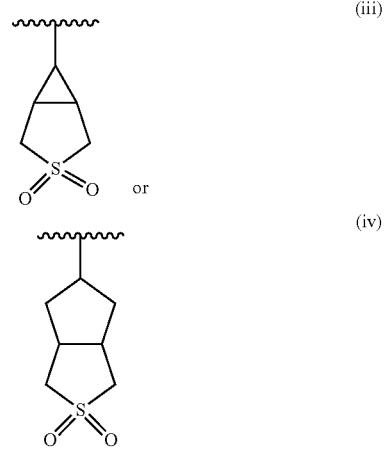

where each ring is substituted with $R^4$ and $R^5$.

51. In embodiment 51, the compound of Formula (I), or a pharmaceutically acceptable salt thereof, of any one of embodiments 1 to 42 and 50, is wherein ring $R^A$ is a ring of formula:

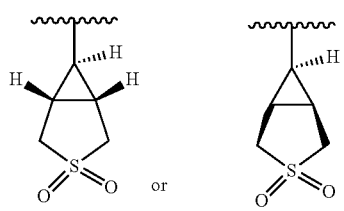

52. In embodiment 52, the compound of Formula (I), or a pharmaceutically acceptable salt thereof, of any one of embodiments 1 to 42, is wherein ring $R^A$ is a ring of formula:

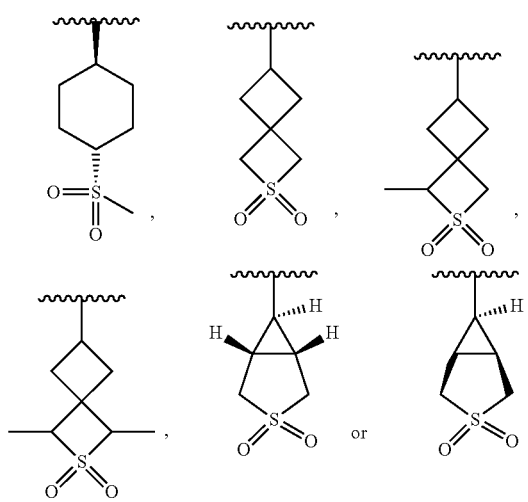

53. In embodiment 53, the compound of Formula (I), or a pharmaceutically acceptable salt thereof, of any one of embodiments 1 to 52, is wherein

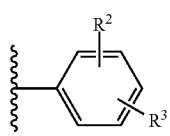
(a)

is

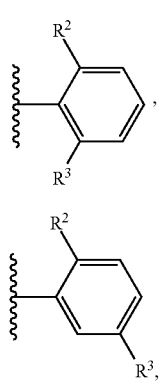
(a1)

(a2)

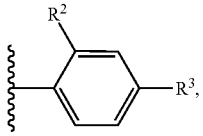
(a3)

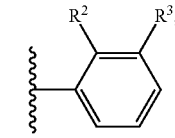
(a4)

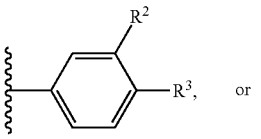
(a5)

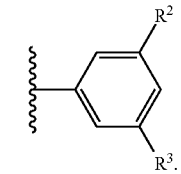
(a6)

54. In embodiment 54, the compound of Formula (I), or a pharmaceutically acceptable salt thereof, of any one of embodiments 1 to 53, is wherein

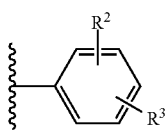
(a)

is (a1):

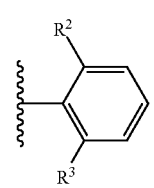
(a1)

55. In embodiment 55, the compound of Formula (I), or a pharmaceutically acceptable salt thereof, of any one of embodiments 1 to 54, is wherein $R^2$ and $R^3$ are independently selected from hydrogen, fluoro, chloro, methyl, ethyl, propyl, cyclopropyl, cyclobutyl, methoxy, ethoxy, propoxy, difluoromethyl, trifluoromethyl, difluoroethyl, trifluoroethyl, difluoromethoxy, and trifluoromethoxy.

56. In embodiment 56, the compound of Formula (I), or a pharmaceutically acceptable salt thereof, of any one of embodiments 1 to 55, is wherein $R^2$ and $R^3$ are independently selected from fluoro, chloro, cyclopropyl, methoxy, difluoromethyl, trifluoromethyl, difluoromethoxy, and trifluoromethoxy.

57. In embodiment 57, the compound of Formula (I), or a pharmaceutically acceptable salt thereof, of any one of embodiments 1 to 54, is wherein $R^2$ is halo, cycloalkyl, or haloalkyl and $R^3$ is halo, alkoxy, or haloalkoxy.

58. In embodiment 58, the compound of Formula (I), or a pharmaceutically acceptable salt thereof, of any one of embodiments 1 to 56, is wherein $R^2$ is fluoro, chloro, cyclopropyl, difluoromethyl, or trifluoromethyl and $R^3$ is fluoro, chloro, methoxy, or difluoromethoxy.

59. In embodiment 59, the compound of Formula (I), or a pharmaceutically acceptable salt thereof, of any one of embodiments 1 to 52, is wherein

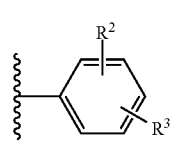

(a)

is 2,6-difluorophenyl, 2-fluoro-6-trifluoromethylphenyl, 2-chloro-6-trifluoromethyl-phenyl, 2-difluoromethoxy-6-fluoro-phenyl, 2-difluoromethoxy-6-trifluoromethylphenyl, 2-methoxy-6-trifluoromethylphenyl, 2-fluoro-6-methoxyphenyl, 2-difluoromethyl-6-fluoro-phenyl, 2-cyclopropyl-6-fluorophenyl, or 2,6-dichlorophenyl.

60. In embodiment 60, the compound of Formula (I), or a pharmaceutically acceptable salt thereof, of any one of embodiments 1 to 52, is wherein

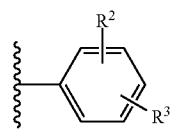

(a)

is 2,6-difluorophenyl or 2-fluoro-6-trifluoromethylphenyl.

61. In embodiment 61, the compound of Formula (I), or a pharmaceutically acceptable salt thereof, of any one of embodiments 1 to 52, is wherein

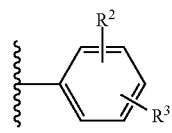

(a)

is 2,6-difluorophenyl.

62. In embodiment 62, the compound of Formula (I), or a pharmaceutically acceptable salt thereof, of any one of embodiments 1 to 52, is wherein

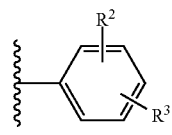

(a)

is 2-fluoro-6-trifluoromethylphenyl.

63. In embodiment 63, the compound of Formula (I), or a pharmaceutically acceptable salt thereof, of any one of embodiments 1 to 62, is wherein $R^1$ is halo.

64. In embodiment 64, the compound of Formula (I), or a pharmaceutically acceptable salt thereof, of any one of embodiments 1 to 62, is wherein $R^1$ is fluoro or chloro.

65. In embodiment 65, the compound of Formula (I), or a pharmaceutically acceptable salt thereof, of any one of embodiments 1 to 62, is wherein $R^1$ is fluoro.

66. In embodiment 66, the compound of Formula (I), or a pharmaceutically acceptable salt thereof, of any one of embodiments 1 to 62, is wherein $R^1$ is hydrogen. It is understood that the embodiments and subembodiments set forth above include all combination of embodiments and subembodiments listed therein.

General Synthetic Scheme

Compounds Formula (I) can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds Formula (I) can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where $R^1$, $R^2$, $R^3$, $R^A$, $R^B$, are defined in the Summary or any of the embodiments thereof disclosed herein above can be prepared as illustrated and described in Scheme 1 below.

Scheme 1

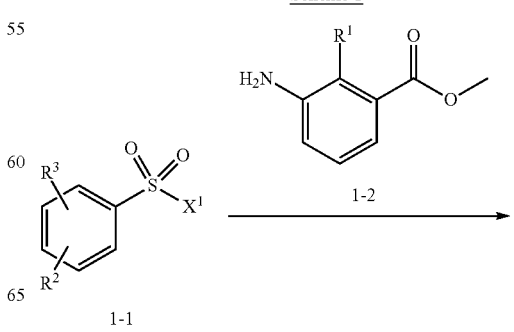

1-1   1-2

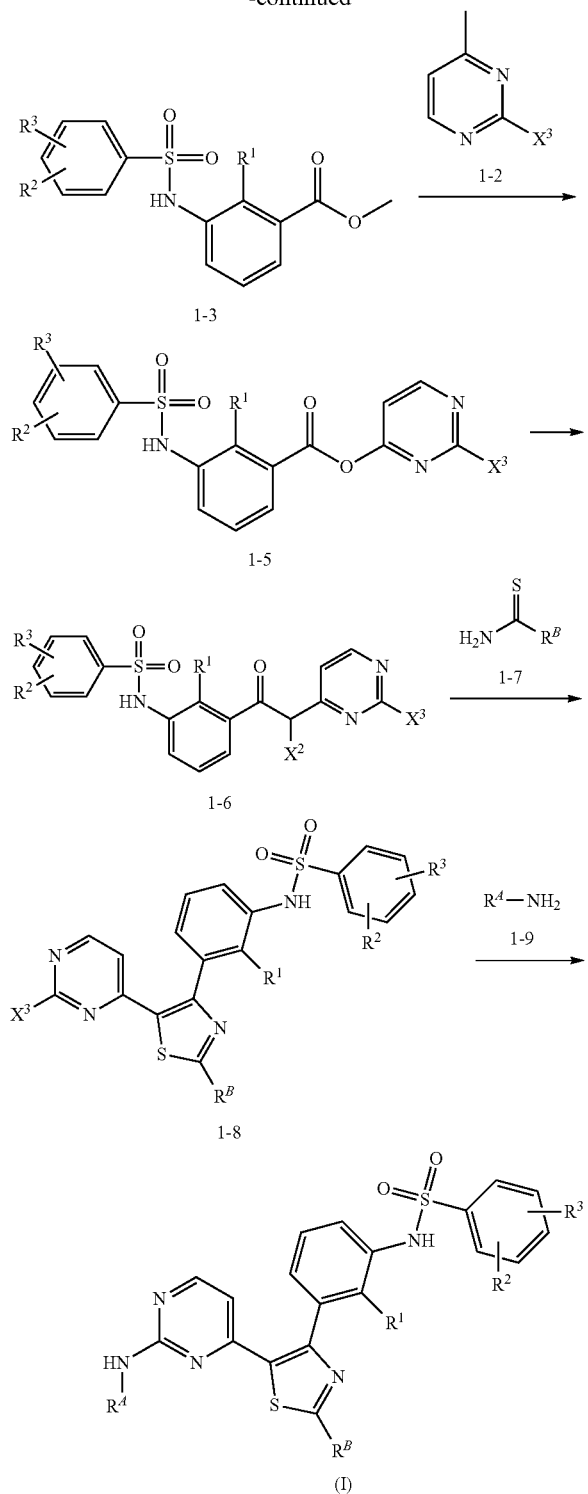

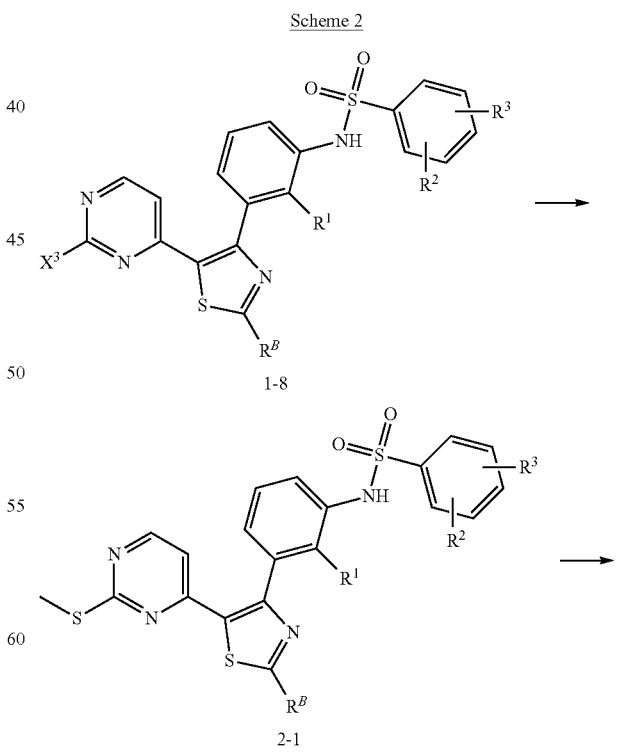

pound of formula 1-4, where $X^3$ is halogen, such as chlorine, bromine, in the presence of a base, such as LiHMDS, under conditions known in the art provides a sulfonamide compound of formula 1-5.

Halogenation of compound 1-5 with a suitable halogenation reagent, such as NBS, under conditions known in the art, followed by cyclization of the resulting compound 1-6 with a thioamide of formula 1-7 where $R^B$ is as defined in the Summary (or any of the embodiments thereof herein above), provides a compound of formula 1-8. The reaction can be carried out in a suitable organic solvent, such as DMA, DMF, at elevated temperature, or alternatively the reaction can be carried out in the presence of suitable reagents, such as TFAA, $NaHCO_3$ under conditions known in the art.

Treatment of a compound of formula 1-8 with an amine of formula 1-9 where $R^A$ is as defined in the Summary (or any of the embodiments thereof herein above), provides a compound of Formula (I). The reaction can be carried out in an organic solvent under basic conditions, such as in the presence of DIPEA, CsF, $K_2CO_3$, in DMSO or under Buchwald-type cross-coupling conditions. Typically, Buchwald-type cross-coupling conditions include a Pd catalyst, a ligand, and a base, for example a combination of Pd-RuPhos G2, and $Cs_2CO_3$. Compound of formula 1-1, 1-2, 1-4, 1-7, and 1-9 are either commercially available or they can be prepared by methods known in the art and/or in Synthetic Examples below.

Alternatively, compounds of Formula (I) where $R^1$, $R^2$, $R^3$, $R^A$, $R^B$, are defined in the Summary (or any of the embodiments thereof herein above), can be prepared as illustrated and described in Scheme 2 below.

Scheme 2

Treatment of a benzenesulfonyl compound of formula 1-1 where $R^2$ and $R^3$ are as described in the Summary (or any of the embodiments thereof herein above), and $X^1$ is halogen with an aniline for formula 1-2 where $R^1$ is as described in the Summary (or any of the embodiments thereof herein above), in the presence of suitable base, such as DIPEA, pyridine, gives a sulfonamido compound of formula 1-3. Reaction between compound 1-3 and a pyrimidine com-

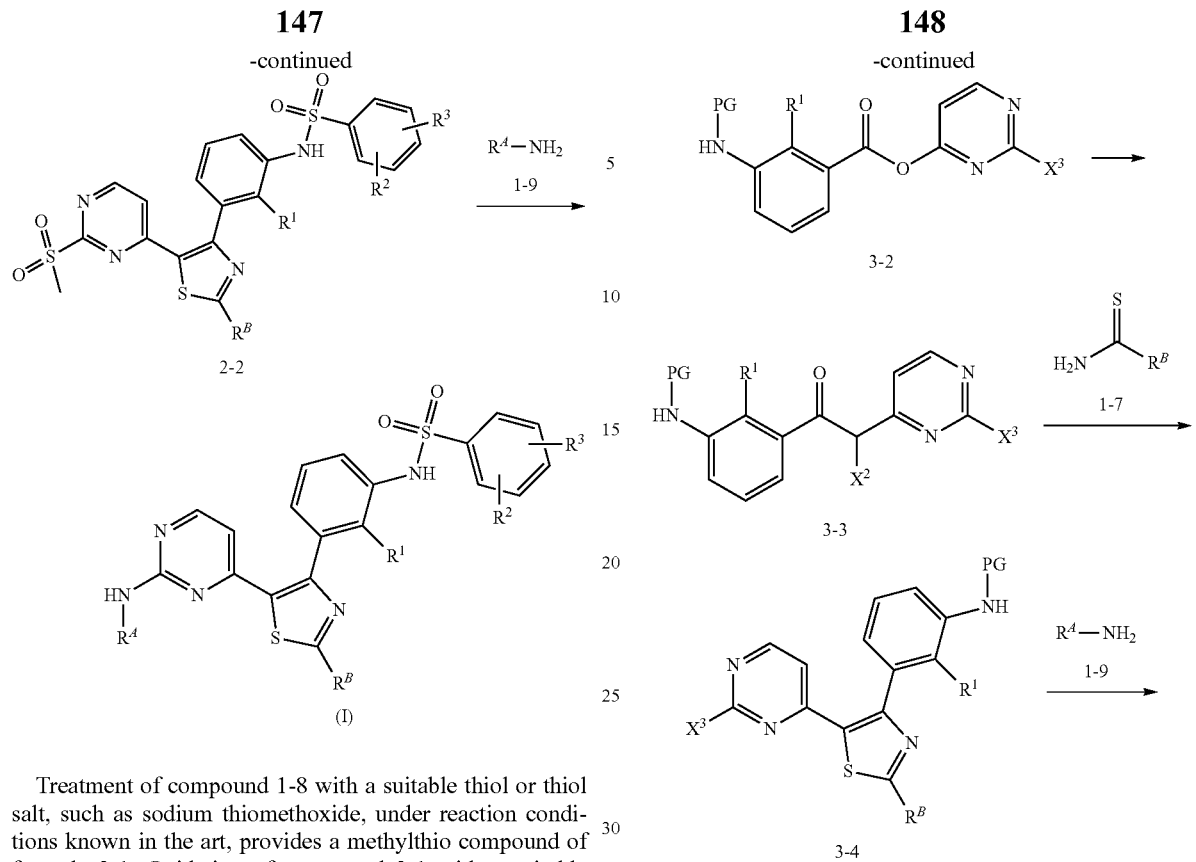

Treatment of compound 1-8 with a suitable thiol or thiol salt, such as sodium thiomethoxide, under reaction conditions known in the art, provides a methylthio compound of formula 2-1. Oxidation of compound 2-1 with a suitable oxidant such as Oxone, mCPBA, provides a methylsulfonyl compound of formula 2-2. Treatment of compound 2-2 with an amine of formula 1-9 where $R^A$ is as defined in the Summary (or any of the embodiments thereof herein above), provides a compound of Formula (I). The reaction can be carried out in an organic solvent under basic conditions, such as in the presence of DIPEA, $K_2CO_3$, in a suitable solvent such as DMF, DMSO.

Compounds of Formula (I) where $R^1$, $R^2$, $R^3$, $R^A$, $R^B$, are defined in the Summary (or any of the embodiments thereof herein above), can also be prepared as illustrated and described in Scheme 3 below.

Scheme 3

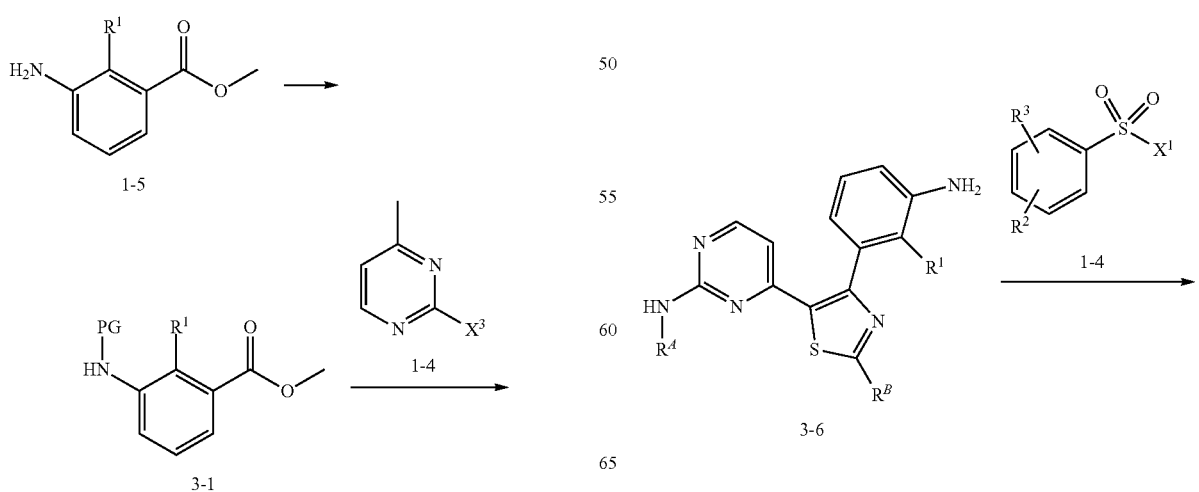

149

-continued

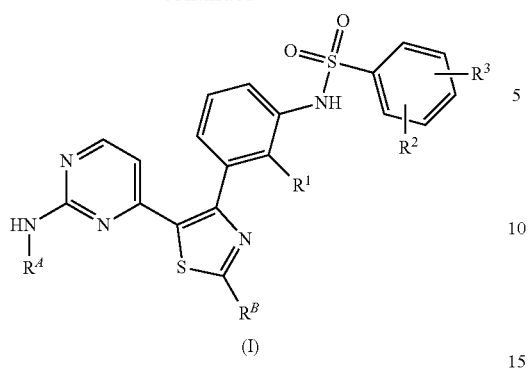

(I)

Protection of the amino group in compounds 1-5 with a suitable nitrogen protecting group (PG), such as acetyl, under conditions well known in the art provides a compound of formula 3-1 which is converted to a compound of formula 3-5 by proceeding analogously as described in Scheme 1 above. Removal of the amino protecting group PG in 3-5 by treatment of 3-5 with suitable reagents, such as NaOH, HCl, under conditions well known in the art, provides compound of formula 3-6 which is converted to a compound of Formula (I) as described in Scheme 1 above.

Compounds of Formula (I) where $R^1$, $R^2$, $R^3$, $R^4$, are defined in the Summary (or any of the embodiments thereof herein above) and $R^B$ is a heterocyclyl or bridged heterocyclyl substituted as defined in the Summary (or any of the embodiments thereof above) and is attached via a nitrogen ring atom, can also be prepared as illustrated and described in Scheme 4 below.

Scheme 4

150

-continued

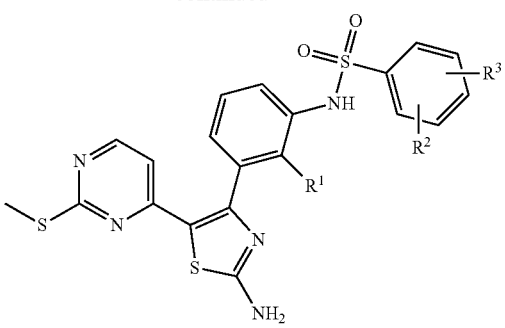

4-3

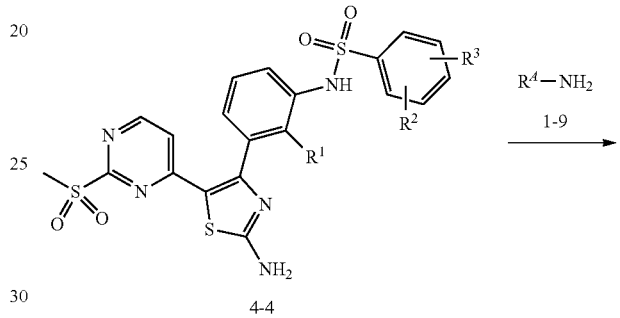

4-4

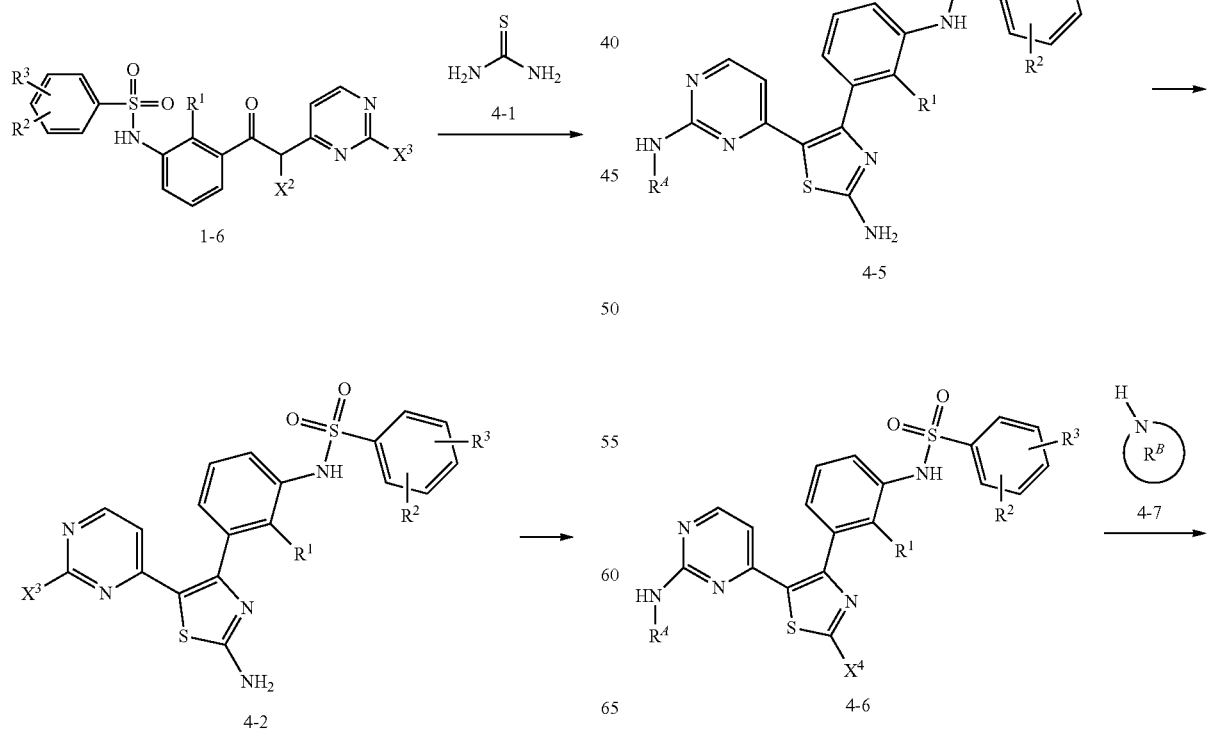

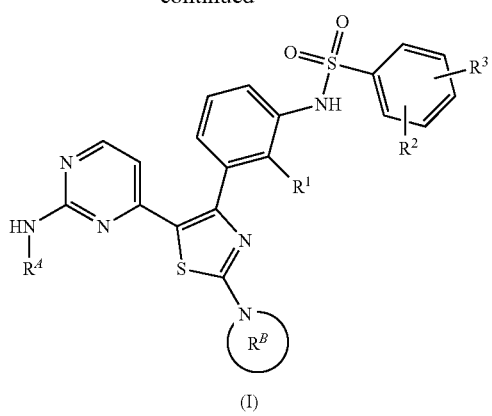

(I)

[$R^B$ = heterocyclyl or briged heterocyclyl]

Cyclization of a compound of formula 1-6 with thiourea 4-1 under conditions analogous as described in Scheme 1 above, provides a compound of formula 4-2 which is converted to a compound of formula 4-5 as described in Scheme 2 above. Compound 4-5 is converted to a compound of formula 4-6 where $X^4$ is a halogen such as chlorine or bromine under conditions known in the art. For example, compound 4-6 where $X^4$ is bromo can be prepared by treatment of compound 4-5 with tert-butyl nitrite and $CuBr_2$. Treatment of a compound of formula 4-6 with an amine of formula 4-7 where $R^B$ corresponds to heterocyclyl or bridged heterocyclyl as defined in compounds of Formula (I) in the Summary provides a compound of Formula (I) where $R^B$ is heterocyclyl or bridged heterocyclyl as defined in the Summary. The reaction can be carried out in an organic solvent under basic conditions, such as in the presence of DIPEA, $K_2CO_3$, in DMSO at elevated temperatures.

Compounds of Formula (I) can be converted to other compound of Formula (I) by methods well known in the art. For example, compound of Formula (I) where $R^B$ is, for example, piperazin-1-yl substituted at the $2^{nd}$ nitrogen ring atom of the piperazin-1-yl ring with $R^d$ (as defined in the Summary) can be as shown below.

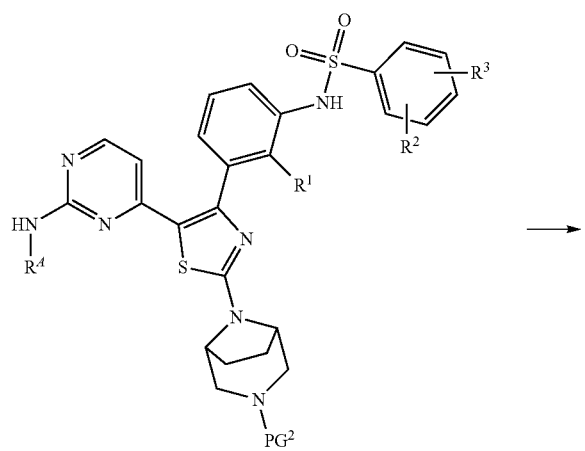

1

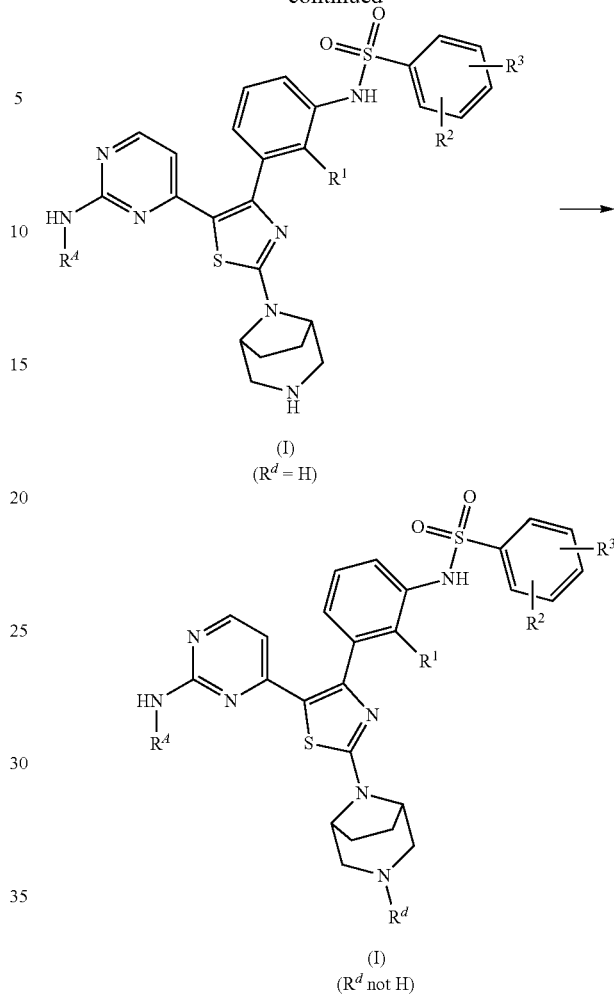

(I)
($R^d$ = H)

(I)
($R^d$ not H)

Removal of protecting group, $PG^2$ such as tert-butyloxycarbonyl, of compound 1 (prepared as described in Scheme 4 above) provides a compound of Formula (I) where $R^d$ is hydrogen, which can then be converted to compounds of Formula (I) where $R^d$ is other than hydrogen by methods well known. For example, a compound of formula (I) where $R^d$ is hydrogen can be reacted with alkyl or cycloalkyl ketones under reduction amination conditions to give corresponding compounds of Formula (I) where $R^d$ is alkyl or cycloalkyl.

Utility

Increasing evidence suggests that over-activated CDK2 leads to abnormal cell cycle regulation and proliferation in cancer cells. The kinase activity of CDK2/Cyclin E or CDK2/Cyclin A complex is elevated via several mechanisms in human cancers. Cyclin E has been found to be frequently amplified, for example, in uterine cancer, ovarian cancer, stomach cancer, and breast cancer. In some cancer types, loss-of-function mutations in FBXW7 or overexpression of USP28, which control the turnover of cyclin E, leads to cyclin E overexpression and CDK2 activation. Alternatively, certain cancer cells express a hyperactive, truncated form of cyclin E or cyclin A. In addition, cyclin A amplification and overexpression have also been reported in various cancers such as hepatocellular carcinomas, colorectal and breast cancers. In some tumors, catalytic activity of CDK2 is increased following loss of the expression or alteration of the location of the endogenous CDK2 inhibitor p27 or p21, or overexpression of SKP2, a negative regulator of p27. In addition, CDC25A and CDC25B, protein phosphatases responsible for the dephosphorylations that activate the CDK2, are overexpressed in various tumors. These various mechanisms of CDK2 activation have been validated using cancer cells or mouse cancer models.

Furthermore, CDK2/cyclin E phosphorylates oncogenic Myc to oppose ras-induced senescence, highlighting the importance of CDK2 in myc/ras-induced tumorigenesis. Inactivation of CDK2 has been shown to be synthetically lethal to myc over-expressing cancer cells. In aneuploid cancer cells, for example KRAS-mutant lung cancer, CDK2 inhibition resulted in anaphase catastrophe and apoptosis. Moreover, inhibiting CDK2 effectively induced granulocytic differentiation in AML cell lines and arrested tumor growth in AML mice models.

CDK2 activation as a result of cyclin E amplification or overexpression has also been identified as a key primary or acquired resistance pathway to tumors treated by CDK4/6 inhibitors or trastuzumab. Accordingly, compounds of Formula (I) can be used in combination with CDK4/6 inhibitors for the treatment of cancers that become refractory to CDK4/6 inhibitors.

Thus, compounds Formula (I) as described in the first aspect (or any of the embodiments thereof herein above) or a pharmaceutically acceptable salt thereof, may be useful for treating tumors characterized by one or more of: overexpression of CDK2, hyperphosphorylation of CDK2 (Thr160), amplification/overexpression of cyclin E or cyclin A, $R^B$-deficiency, loss-of-function of mutation in FBXW7 or overexpression of USP28, expression of truncated cyclin E or cyclin A, dysregulation of p21 or p27 or overexpression of SKP2, amplification/overexpression of CDC25A or/and CDC25B, depletion of AMBRA1, hyperactive MYC/RAS, Aneuploid cancers, CDK4 and/or CDK6 inhibitor refractory cancers.

In some embodiments, the cancer is ovarian cancer, endometrial cancer, breast cancer (e.g., triple negative breast cancer), lung cancer (e.g., adenocarcinoma, small cell lung cancer and/or non-small cell lung carcinomas, parvicellular and/or non-parvicellular carcinoma, bronchial carcinoma, bronchial adenoma, and/or pleuropulmonary blastoma), skin cancer (e.g. melanoma, squamous cell carcinoma, Kaposi sarcoma, and/or Merkel cell skin cancer), bladder cancer, cervical cancer, colorectal cancer, cancer of the small intestine, colon cancer, rectal cancer, cancer of the anus, gastric cancer, head and neck cancer (e.g., cancers of the larynx, hypopharynx, nasopharynx, oropharynx, lips, and/or mouth), liver cancer (e.g., hepatocellular carcinoma, and/or cholangiocellular carcinoma), prostate cancer, testicular cancer, uterine cancer, esophageal cancer, gall bladder cancer, pancreatic cancer (e.g. exocrine pancreatic carcinoma), stomach cancer, thyroid cancer, brain cancer, fallopian tube cancer, peritoneal cancer, AML, and/or parathyroid cancer. In some embodiments, the cancer is ovarian cancer. In some such embodiments, the ovarian cancer is characterized by amplification or overexpression of CCNE1 and/or CCNE2.

In other embodiments, the cancer is breast cancer, including, e.g., ER-positive/HR-positive breast cancer, HER2-negative breast cancer; ER-positive/HR-positive breast cancer, HER2-positive breast cancer; triple negative breast cancer (TNBC); or inflammatory breast cancer. In some embodiments, the breast cancer is endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification or overexpression of CCNE1, CCNE2, and/or CCNA2.

In addition, compounds of Formula (I) as described in the first aspect (or any of the embodiments thereof herein above) can also be useful in treating Ewing sarcoma, osteosarcoma, rhabdomyosarcoma, neuroblastoma, medulloblastoma and AL in pediatric patients.

Besides cancer, CDK2 upregulation is also implicated in autoimmume diseases e.g., rheumatoid arthritis ($R^A$), systemic lupus erythematosus (SLE), primary Sjogren's syndrome (pSS), multiple sclerosis (MS), Crohn's disease (CD), gout, uveitis, pemphigus vulgaris, and sepsis. As such compounds of Formula (I) as described in the Summary as described in the first aspect (or any of the embodiments thereof herein above) are useful in treating above autoimmune diseases.

Testing

The CDK2 inhibitory activity of the compounds of Formula (I) can be tested using the in vitro assay described in Biological Example 1 below.

Pharmaceutical Compositions

In general, the compounds Formula (I) (unless stated otherwise, reference to compound/compounds of Formula (I) herein includes any embodiments thereof described herein above or a pharmaceutically acceptable salt thereof) will be administered in a therapeutically effective amount by any of the accepted modes of administration for agents that serve similar utilities. Therapeutically effective amounts of compounds Formula (I) may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound Formula (I), i.e., the active ingredient, will depend upon numerous factors such as the severity of the disease to be treated, the age and relative health of the patient, the potency of the compound being utilized, the route and form of administration, and other factors.

In general, compounds Formula (I) will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of Formula (I) in combination with at least one pharmaceutically acceptable excipient. Acceptable excipients are generally non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds of Formula (I) may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds of Formula (I) may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds of Formula (I) may also be formulated in rectal compositions such as suppositories or retention enemas, e.g., containing conventional suppository bases such as cocoa butter, polyethylene glycol, or other glycerides.

Certain compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds of Formula (I) may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds of Formula (I) may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound of Formula (I) in a formulation can vary within the full range employed by those skilled in the art. Typically, the formulation will contain, on a weight percent (wt. %) basis, from about 0.01-99.99 wt. % of a compound of Formula (I) based on the total formulation, with the balance being one or more suitable pharmaceutical excipients. For example, the compound is present at a level of about 1-80 wt. %.

Combinations and Combination Therapies

The compounds of Formula (I) may be used in combination with one or more other drugs in the treatment of diseases or conditions for which compounds of Formula (I) or the other drugs may have utility. Such other drug(s) may be administered, by a route and in an amount commonly used therefore, contemporaneously or sequentially with a compound of Formula (I). When a compound of Formula (I) is used contemporaneously with one or more other drugs, a pharmaceutical composition in unit dosage form containing such other drugs and the compound of Formula (I) is preferred. However, the combination therapy may also include therapies in which the compound of Formula (I) and one or more other drugs are administered on different overlapping schedules. It is also contemplated that when used in combination with one or more other active ingredients, the compounds of Formula (I) and the other active ingredients may be used in lower doses than when each is used singly.

Accordingly, the pharmaceutical compositions of the present disclosure also include those that contain one or more other drugs, in addition to a compound of Formula (I).

The above combinations include combinations of a compound of Formula (I) not only with one other drug, but also with two or more other active drugs. Likewise, a compound of Formula (I) may be used in combination with other drugs that are used in the prevention, treatment, control, amelioration, or reduction of risk of the diseases or conditions for which a compound of Formula (I) is useful. Such other drugs may be administered, by a route and in an amount commonly used therefore, contemporaneously or sequentially with a compound of Formula (I). When a compound of Formula (I) is used contemporaneously with one or more other drugs, a pharmaceutical composition containing such other drugs in addition to the compound of Formula (I) can be used. Accordingly, the pharmaceutical compositions of the present disclosure also include those that also contain one or more other active ingredients, in addition to a compound of Formula (I). The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of Formula (I) in any combination with one or more other anti-cancer agents including but not limited to: MAP kinase pathway (RAS/RAF/MEK/ERK) inhibitors including but not limited to: Vemurafanib (PLX4032), Dabrafenib, Encorafenib (LGX818), TQ-B3233, XL-518 (Cas No. 1029872-29-4, available from ACC Corp); trametinib, selumetinib (AZD6244), TQ-B3234, PD184352, PD325901, TAK-733, pimasertinib, binimetinib, refametinib, cobimetinib (GDC-0973), AZD8330, BVD-523, LTT462, Ulixertinib, AMG510, ARS853, and any RAS inhibitors disclosed in patents WO2016049565, WO2016164675, WO2016168540, WO2017015562, WO2017058728, WO2017058768, WO2017058792, WO2017058805, WO2017058807, WO2017058902, WO2017058915, WO2017070256, WO2017087528, WO2017100546, WO2017172979, WO2017201161, WO2018064510, WO2018068017, WO2018119183;

CSF1R inhibitors (PLX3397, LY3022855, etc.) and CSF1R antibodies (IMC-054, RG7155);

TGF beta receptor kinase inhibitor such as LY2157299;

BTK inhibitor such as ibrutinib; BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358); AT9283 (CAS 1133385-83-7); Saracatinib (AZD0530); and N-[2-[(1S,4R)-6-[[4-(cyclobutylamino)-5-(trifluoromethyl)-2-pyrimidinyl]amino]-1, 2,3,4-tetrahydronaphthalen-1, 4-imin-9-yl]-2-oxoethyl]-acetamide (PF-03814735, CAS 942487-16-3);

ALK inhibitors: PF-2341066 (XALKOPJ®; crizotinib); 5-chloro-N4-(2-(isopropylsulfonyl)phenyl)-N2-(2-methoxy-4-(4-(4-methylpiper azin-1-yl)piperidin-1-yl) phenyl)pyrimidine-2,4-diamine; GSK1838705 A; CH5424802; Ceritinib (ZYKADIA); TQ-B3139, TQ-B3101 PI3K inhibitors: 4-[2-(1H-indazol-4-yl)-6-[[4-(methylsulfonyl)-piperazin-1-yl]methyl]thieno[3, 2-d]pyrimidin-4-yl]morpholine (also known as GDC 0941 and described in PCT Publication Nos. WO 09/036082 and WO 09/055730), 2-methyl-2-[4-[3-methyl-2-oxo-8-(quinolin-3-yl)-2,3-dihydroimidazo[4, 5-c]quinolin-1-yl]phenyl]propio-nitrile (also known as BEZ 235 or NVP-BEZ 235, and described in PCT Publication No. WO 06/122806);

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-fluoro-2-methyl-1H-indol-5-yloxy)-5-methylpyrrolo[2,1-f][1,2, 4]triazin-6-yloxy)propan-2-yl)-2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®); AL-2846 MET inhibitor such as foretinib, carbozantinib, or crizotinib;

FLT3 inhibitors-sunitinib malate (sold under the tradename Sutent® by Pfizer); PKC412 (midostaurin); tanutinib, sorafenib, lestaurtinib, KW-2449, quizartinib (AC220) and crenolanib;

Epidermal growth factor receptor (EGFR) inhibitors: Gefitnib (sold under the tradename Iressa®), N-[4-[(3-chloro-4-fluorophenyl)amino]-7-[[(3S)-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

HER dimerization inhibitors: Pertuzumab (sold under the trademark Omnitarg®, by Genentech);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT-869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R3S,4R,5R)-2-(2-amino-6-methoxy-purin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc); Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

MCl-1 inhibitors: MIK665, S64315, AMG 397, and AZD5991;

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®));

mTOR inhibitors: Temsirolimus (sold under the tradename Torisel® by Pfizer), ridaforolimus (formally known as deferolimus, (1R,2R,4S)-4-[(2R)-2-[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0 4' 9]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Proteasome inhibitor such as carfilzomib, MLN9708, delanzomib, or bortezomib;

BET inhibitors such as INCB054329, OTX015, and CPI-0610;

LSD1 inhibitors such as GSK2979552, and INCB059872;

HIF-2α inhibitors such as PT2977 and PT2385;

Osteoclastic bone resorption inhibitors: 1-hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®);

Biologic response modifiers: bacillus calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also known as MK-0822, N-(1-cyanocyclopropyl)-4-fluoro-N2-{(1 S)-2,2,2-trifluoro-1-[4'-(methylsulfonyl)biphenyl-4-yl] ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989), NVP-HSP990, AUY922, AT13387, STA-9090, Debio 0932, KW-2478, XL888, CNF2024, TAS-116;

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

CDK (CDK1, CDK2, CDK3, CDK5, CDK7, CDK8, CDK9, CDK11/12, or CDK16) inhibitors including but not limited to Alvocidib (pan-CDK inhibitor, also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

CDK4/6 inhibitors including but not limited to pabociclib, ribociclib, abemaciclib, and Trilaciclib;

CDK9 inhibtiors including but not limited to AZD 4573, P276-00, AT7519M, TP-1287;

CDK2/4/6 inhibitor such as PF-06873600;

Cell division cycle 25A (CDC25A) inhibitors such as 2-(2-mercaptoethanol)-3-methyl-1,4-naphthoquinone, 1-([1,1'-biphenyl]-4-yl)-3,4-bis((2-hydroxyethyl)thio-1H-pyrrole-2,5-dione (PM-20), 2-(2,5-difluorophenyl)-6-((3-(methyl(3-((2-methyl-4,7-dioxo-4,7-dihydrobenzo[d]-thiazol-5-yl)amino)propyl)amino)propyl)amino)benzo[d]oxazole-4,7-dione (IRC 083864), or 2-methoxyestadiol, or a pharmaceutically acceptable salt thereof;

SHP-2 inhibitor such as TNO155;

MDM2/MDMX, MDM2/p53 and/or MDMX/p53 modulators;

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7,10-dimethoxy-9-oxo-5,20-epoxytax-11-ene-2a,4,13a-triyl-4-acetate-2-benzoate-13-[(2R,3S)-3-{[(tert-butoxy)carbonyl]-amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}-oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573); HPC vaccines: Cervarix® sold by GlaxoSmithKline, Gardasil® sold by Merck; Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®); Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®); Estrogen receptor down-regulators: Fulvestrant (sold under the tradename Faslodex®);

Anti-estrogens: tamoxifen (sold under the tradename Novaldex®); Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®); Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®);

One or more immune checkpoint inhibitors CD27, CD28, CD40, CD122, CD96, CD73, CD39, CD47, OX40, GITR, CSF1R, JAK, PI3K delta, PI3K gamma, TAM kinase, arginase, CD137 (also known as 4-1BB), ICOS, A2AR, A2BR, HIF-2a, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of Formula (I) can also be used to increase or enhance an immune response, including increasing the immune response to an antigen; to improve immunization, including increasing vaccine efficacy; and to increase inflammation. In some embodiments, the compounds of Formula (I) can be sued to enhance the immune response to vaccines including, but not limited, *Listeria* vaccines, oncolytic viral vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation.

A compound of Formula (I) can also be used in combination with the following adjunct therapies: anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

SYNTHETIC EXAMPLES

The following preparations of intermediates and compounds of Formula (I) are given to enable those skilled in the art to more clearly understand and to practice the present disclosure. They should not be considered as limiting the scope of the disclosure, but merely as being illustrative and representative thereof.

Intermediate 1

Synthesis of (3aR,5s,6aS)-5-aminohexahydro-1H-cyclopenta[c]thiophene 2,2-dioxide

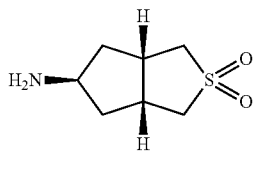 [SMILES: N[C@H]1C[C@@H]2CS(=O)(=O)C[C@@H]2C1]

Step 1: Dimethyl 4-oxocyclopentane-1,2-dicarboxylate

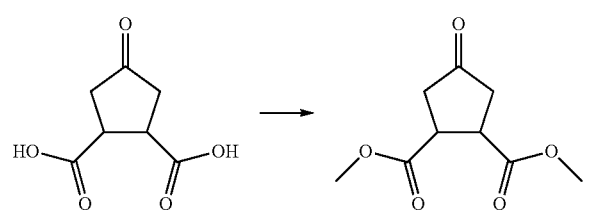

SOCl$_2$ (7.14 g, 60.00 mmol, 2.00 eq) was added dropwise at room temperature to a solution of 4-oxocyclopentane-1,2-dicarboxylic acid (5.16 g, 30.00 mmol, 1.00 eq) in MeOH (100.0 mL). The mixture was heated to 70° C. for 16 h and then concentrated. The residue was dissolved in EtOAc, washed with H$_2$O and brine. The organic layer was dried over Na$_2$SO$_4$, filtered and concentrated to obtain the title compound as colorless oil.

Step 2: Dimethyl 1,4-dioxaspiro[4.4]nonane-7,8-dicarboxylate

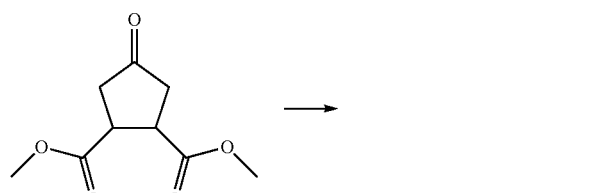

A solution of dimethyl 4-oxocyclopentane-1,2-dicarboxylate (4.70 g, 23.50 mmol, 1.00 eq), ethane-1,2-diol (1.75 g, 28.20 mmol, 1.20 eq) and TsOH H$_2$O (200 mg, cat.) in toluene (100.0 mL) was heated to 140° C. for 16 h with Dean-Stark apparatus. Then the mixture was concentrated and purified with silica gel column chromatography (PE/EtOAc=5:1) to obtain the title compound as colorless oil.

Step 3: 1,4-Dioxaspiro[4.4]nonane-7,8-diyl dimethanol

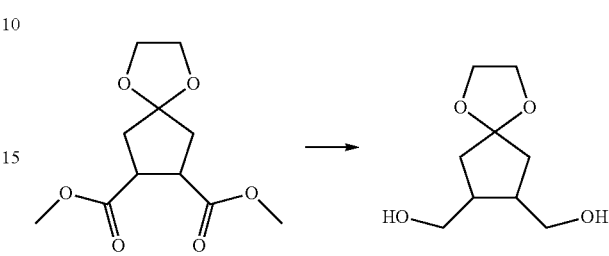

A solution of LiAlH$_4$ (690 mg, 18.20 mmol, 1.20 eq) in THF (20.0 mL) was cooled to 0° C., dimethyl 1,4-dioxaspiro[4.4]nonane-7,8-dicarboxylate (3.70 g, 15.20 mmol, 1.00 eq) in THF (30.0 mL) was added dropwise at 0° C. The mixture was allowed to stir at 0° C. for 1 hour before it was quenched with H$_2$O. The mixture was filtered, and the filter cake was washed with MeOH. The filtrate was combined and concentrated to obtain the title compound as yellow oil.

Step 4: 1,4-Dioxaspiro[4.4]nonane-7,8-diylbis(methylene) Dimethanesulfonate

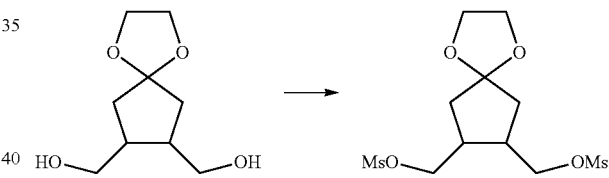

TEA (8.06 g, 79.80 mmol, 6.00 eq) was added to a solution of 1,4-dioxaspiro[4.4]nonane-7,8-diyldimethanol (2.50 g, 13.30 mmol, 1.00 eq) in DCM (30 mL), followed by addition of MsCl (4.55 g, 39.90 mmol, 3.00 eq) dropwise at room temperature. The mixture was stirred at room temperature for 5 h before it was poured onto ice. The mixture was extracted with DCM. The organic layer was combined and concentrated to obtain the title compound as yellow oil.

Step 5: (3aR,6aS)-tetrahydro-1H,3H-spiro[cyclopenta[c]thiophene-5,2'-[1,3]dioxolane]

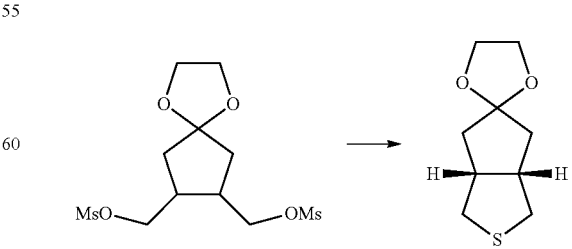

Na$_2$S (907 mg, 11.60 mmol, 1.00 eq) was added to a solution of 1,4-dioxaspiro-[4.4]nonane-7,8-diylbis(methylene) dimethanesulfonate (4.00 g, 11.60 mmol, 1.00 eq) in EtOH (30.0 mL) at room temperature. The mixture was heated to 60° C. for 16 h under $N_2$ atmosphere before it was poured into water. The mixture was extracted with EtOAc. The organic layers were combined, washed with brine, dried over $Na_2SO_4$, concentrated and purified with silica gel column chromatography (PE/EtOAc=10:1) to obtain the title compound as white solid.

Step 6: (3aR,6aS)-tetrahydro-1H-cyclopenta[c]thiophen-5(3H)-one

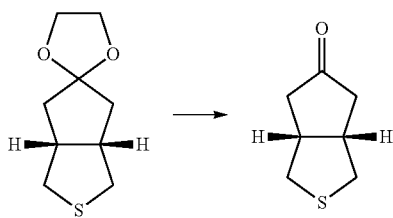 [SMILES: C1COC2(C[C@H]3CSC[C@H]3C2)O1 ; O=C1C[C@H]2CSC[C@H]2C1]

2 M HCl aq. solution (5.0 mL) was added to a mixture of (3aR,6aS)-tetrahydro-1H,3H-spiro[cyclopenta[c]thiophene-5,2'-[1,3]dioxolane] (750 mg, 4.03 mmol, 1.00 eq) in acetone (5.0 mL). The mixture was stirred at room temperature for 16 h, diluted with $H_2O$. The mixture was extracted with EtOAc and the organic layers were combined, washed with sat. $NaHCO_3$ aq. solution and brine, dried with $Na_2SO_4$, filtered and concentrated. The residue was purified with silica gel column chromatography (PE/EtOAc=10:1) to obtain the title compound as yellow solid.

Step 7: (3aR,5r,6aS)-hexahydro-1H-cyclopenta[c]thiophen-5-ol

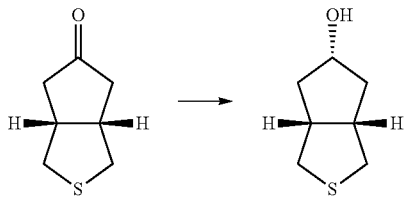 [SMILES: O=C1C[C@H]2CSC[C@H]2C1 ; O[C@H]1C[C@H]2CSC[C@H]2C1]

A solution of (3aR,6aS)-tetrahydro-1H-cyclopenta[c]thiophen-5(3H)-one (400 mg, 2.81 mmol, 1.00 eq) in MeOH (10.0 mL) was added $NaBH_4$ (321 mg, 8.45 mmol, 3.00 eq) portion-wise. The mixture was stirred at room temperature for 3 h, diluted with $H_2O$, extracted with EtOAc. The organic layer was combined, washed with brine, dried with $Na_2SO_4$, filtered and concentrated to obtain the title compound as yellow oil.

Step 8: (3aR,5r,6aS)-hexahydro-1H-cyclopenta[c]thiophen-5-yl Methanesulfonate

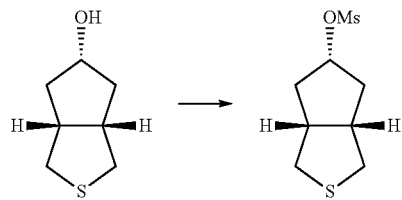 [SMILES: O[C@H]1C[C@H]2CSC[C@H]2C1 ; CS(=O)(=O)O[C@H]1C[C@H]2CSC[C@H]2C1]

TEA (840 mg, 8.33 mmol, 3.00 eq) was added to a solution of (3aR,5r,6aS)-hexahydro-1H-cyclopenta[c]thiophen-5-ol (400 mg, 2.78 mmol, 1.00 eq) in DCM (10.0 mL) followed by addition of MsCl (380 mg, 3.33 mmol, 1.20 eq) dropwise at room temperature. The mixture was stirred 3 h before it was poured into water (10.0 mL), and the mixture was extracted with DCM. The organic layers were combined, washed with brine, dried with $Na_2SO_4$, filtered, and concentrated to obtain the title compound as yellow oil.

Step 9: (3aR,5s,6aS)-hexahydro-1H-cyclopenta[c]thiophen-5-amine

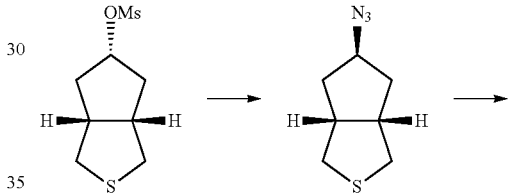

$NaN_3$ (350 mg, 5.40 mmol, 2.00 eq) was added to a solution of (3aR,5r,6aS)-hexahydro-1H-cyclopenta[c]thiophen-5-yl methanesulfonate (600 mg, 2.70 mmol, 1.00 eq) in DMF (6 mL). The mixture was heated to 60° C. 16 h under $N_2$ atmosphere, then it was diluted with EtOAc and $H_2O$. The organic layers were combined, concentrated. The residue was diluted with $NH_3$ in MeOH (7 M, 10 mL), followed by addition of Pd/C (10%, 120 mg, 0.2 W/W). The mixture was stirred at room temperature 16 h under $H_2$ atmosphere before it was filtered and concentrated. The residue was purified by silica gel column chromatography (DCM/MeOH=10:1) to obtain the title compound tas yellow oil.

Step 10: tert-Butyl ((3aR,5s,6aS)-2,2-dioxidohexahydro-1H-cyclopenta[c]thiophen-5-yl)-carbamate

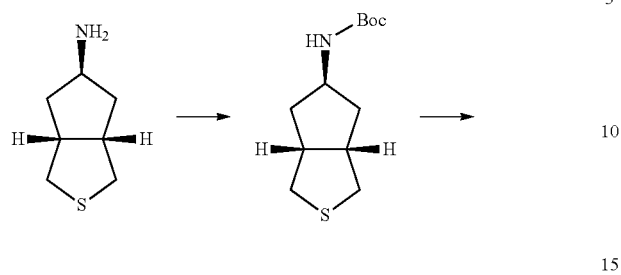

(Boc)$_2$O (685 mg, 3.15 mmol, 1.50 eq) was added to a solution of (3aR,5s,6aS)-hexahydro-1H-cyclopenta[c]thiophen-5-amine (300 mg, 2.10 mmol, 1.00 eq) in THF (10.0 mL) dropwise. The mixture was stirred at room temperature 2 h before it was diluted with H$_2$O and extracted with EtOAc. The organic layers were combined, washed with brine, and concentrated under reduced pressure. The residue was dissolved in THF/H$_2$O (4:1, 10 mL), followed by addition of oxone (2.58 g, 4.20 mmol, 2.00 eq). The mixture was stirred at room temperature 16 h before it was diluted with H$_2$O and extracted with EtOAc. The organic layers were combined, concentrated and purified by silica gel column chromatography (PE/EtOAc=10:1) to obtain the title compound as yellow solid.

Step 11: (3aR,5s,6aS)-5-aminohexahydro-1H-cyclopenta[c]thiophene 2,2-dioxide

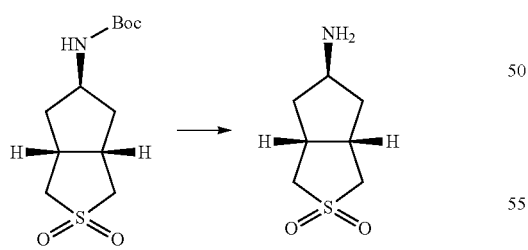

HCl in MeOH (4 M, 5.0 mL) was added to tert-butyl ((3aR,5s,6aS)-2,2-dioxidohexahydro-1H-cyclopenta[c]thiophen-5-yl)carbamate (450 mg, 1.64 mmol, 1.00 eq) at room temperature. After stirring for 3 h, the mixture was concentrated. The residue was suspended in DCM, followed by addition of aq. NaHCO$_3$. The mixture was stirred at room temperature 1 h, then it was filtered. The layers were separated, and the organic layer was concentrated to obtain the title compound.

Intermediate 2

Synthesis of (1R,5S,6s)-6-amino-3-thiabicyclo[3.1.0]hexane 3,3-dioxide

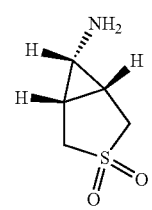

Step 1: Ethyl (1R,5S,6r)-3-thiabicyclo[3.1.0]hexane-6-carboxylate 3,3-dioxide and Ethyl (1R,5S,6s)-3-thiabicyclo[3.1.0]hexane-6-carboxylate 3,3-dioxide

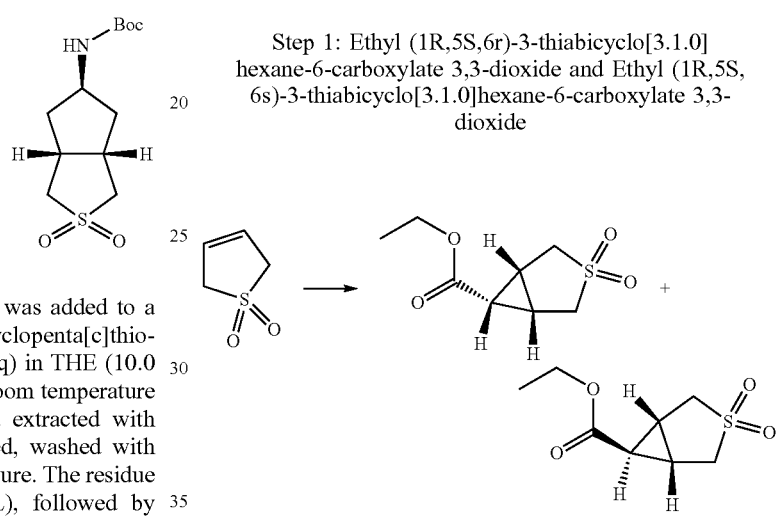

Diazoacetic acid ethyl ester (7.20 g, 63.48 mmol, 1.5 eq) in DCM (50.0 mL) was added slowly via syringe pump over 5 h to a stirred solution of 2,5-dihydro-thiophene 1,1-dioxide (5.00 g, 42.32 mmol, 1.00 eq) and Rhodium(II) acetate (281 mg, 1.27 mmol, 0.03 eq) in DCM (80.0 mL) under N$_2$ at rt. The mixture was concentrated and the residue was purified by column chromatography on silica gel (PE:EA=5:1) to separate the title compounds.

Step 2: (1R,5S,6r)-3-thiabicyclo[3.1.0]hexane-6-carboxylic Acid 3,3-dioxide

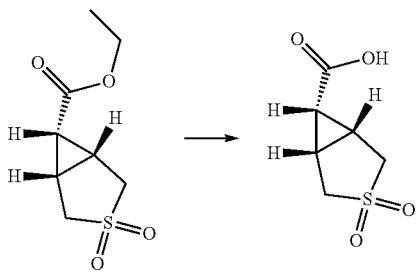

A solution of LiOH·H$_2$O (740 mg, 17.63 mmol, 3.00 eq) in H$_2$O (6.0 mL) was added to a mixture of ethyl (1R,5S, 6r)-3-thiabicyclo[3.1.0]hexane-6-carboxylate 3,3-dioxide (1.2 g, 5.88 mmol, 1.00 eq) in EtOH (12.0 mL). This mixture was stirred at rt. 3 h. pH of the mixture was adjusted to 2~3 with 1N HCl, and the mixture was extracted with DCM. The combined organic layers were concentrated to give the crude product as a pale-yellow solid.

Step 3: Benzyl ((1R,5S,6s)-3,3-dioxido-3-thiabicyclo[3.1.0]hexan-6-yl)carbamate

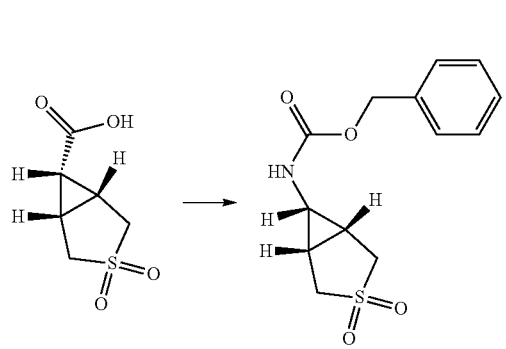 [SMILES: O=C(O)[C@@H]1[C@@H]2CS(=O)(=O)C[C@@H]21 ; O=C(N[C@@H]1[C@@H]2CS(=O)(=O)C[C@@H]21)OCc1ccccc1]

A mixture of (1R,5S,6r)-3-thiabicyclo[3.1.0]hexane-6-carboxylic acid 3,3-dioxide (500 mg, 2.84 mmol, 1.00 eq) in toluene (15.0 mL) was added TEA (459 mg, 4.54 mmol, 1.60 eq) and DPPA (937 mg, 3.41 mmol, 1.20 eq. This mixture was stirred at rt. under $N_2$ for 2 h and then benzyl alcohol (614 mg, 5.68 mmol, 2.00 eq) was added dropwise. This mixture was stirred at 100° C. under $N_2$ overnight before it was concentrated and purified by column chromatography on silica gel (PE:EA=2:1) to give the title compound as a white solid.

Step 4: (1R,5S,6s)-6-amino-3-thiabicyclo[3.1.0]hexane 3,3-dioxide

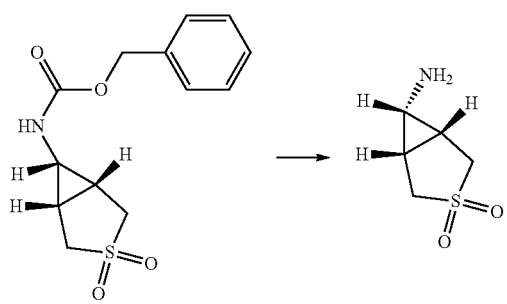 [SMILES: O=C(N[C@@H]1[C@@H]2CS(=O)(=O)C[C@@H]21)OCc1ccccc1 ; N[C@H]1[C@H]2CS(=O)(=O)C[C@@H]12]

A mixture of benzyl ((1R,5S,6s)-3,3-dioxido-3-thiabicyclo[3.1.0]hexan-6-yl)carbamate (500 mg, 0.36 mmol, 1.00 eq) in MeOH (5.0 mL) was added Pd/C (50 mg). This mixture was stirred at rt. under $H_2$ for 5 h. The mixture was filtered, concentrated to give the title compound as a white solid.

Intermediate 3

Synthesis of (1R,5S,6r)-6-amino-3-thiabicyclo[3.1.0]hexane 3,3-dioxide

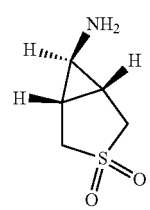

The title compound was prepared by proceeding analogously as described for Intermediate 2 with ethyl (1R,5S,6s)-3-thiabicyclo[3.1.0]hexane-6-carboxylate 3,3-dioxide replacing ethyl (1R,5S,6r)-3-thiabicyclo[3.1.0]hexane-6-carboxylate 3,3-dioxide in Step 2-4.

Intermediate 4

Synthesis of (1s,4s)-4-(methylsulfonyl)cyclohexan-1-amine Trifluoroacetate

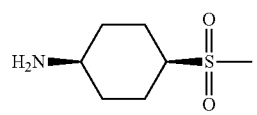

Step 1: (1r,4r)-4-((tert-Butoxycarbonyl)amino)cyclohexyl Methanesulfonate

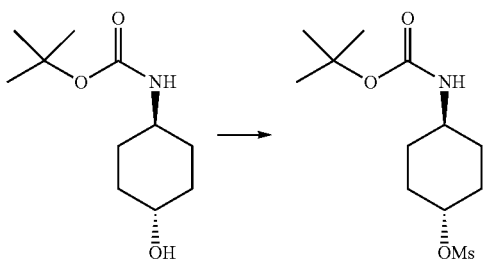 [SMILES: CC(C)(C)OC(=O)N[C@H]1CC[C@H](O)CC1 ; CC(C)(C)OC(=O)N[C@H]1CC[C@H](OS(C)(=O)=O)CC1]

TEA (4.20 g, 41.79 mmol, 3.00 eq.) was added to a mixture of tert-butyl ((1r,4r)-4-hydroxycyclohexyl)carbamate (3.00 g, 13.93 mmol, 1.00 eq.) in DCM (30.0 mL), followed by addition of MsCl (2.40 g, 20.90 mmol, 1.50 eq.) slowly at 0° C. This mixture was stirred at 0° C. under $N_2$ 1 h and then it was warmed to rt. and stirred under $N_2$ 2 h. The mixture was diluted with $H_2O$ and it was extracted with DCM. The combined organic layers were washed with brine, dried over $Na_2SO_4$, concentrated. The residue was purified by column chromatography on silica gel (PE:EA=5:1) to give the title compound as a white solid.

Step 2: Tert-Butyl ((1s,4s)-4-(methylthio)cyclohexyl)carbamate

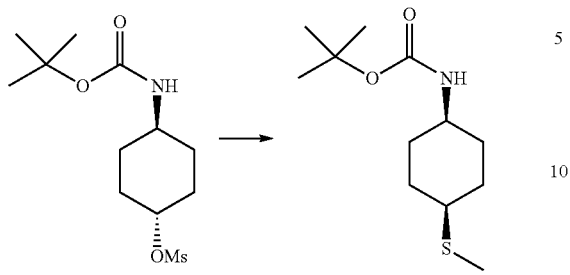

CH₃SNa (1.10 g, 15.68 mmol, 2.00 eq.) was added to a mixture of (1r,4r)-4-((tert-butoxycarbonyl)amino)cyclohexyl methanesulfonate (2.30 g, 7.84 mmol, 1.00 eq.) in DMF (23.0 mL). This mixture was stirred at rt overnight and then diluted with H₂O, and extracted with EtOAc. The combined organic layers were washed with brine, dried over Na₂SO₄, concentrated. The residue was purified by silica gel column chromatography (PE:EA=10:1) to give the title compound as a white solid.

Step 3: tert-Butyl ((1s,4s)-4-(methylsulfonyl)cyclohexyl)carbamate

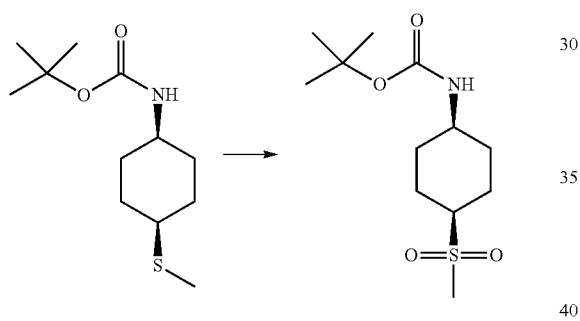

A mixture of tert-butyl ((1s,4s)-4-(methylthio)cyclohexyl)carbamate (202 mg, 0.82 mmol, 1.00 eq.) in THF/MeOH/H₂O (2:2:1, 4.0 mL) was added oxone (504 mg, 1.64 mmol, 2.00 eq.) This mixture was stirred at r.t. under N₂ overnight. H₂O was added and the mixture was extracted with EtOAc, washed with brine, dried over Na₂SO₄, concentrated to give the crude product as a pale-yellow solid.

Step 4: (1s,4s)-4-(Methylsulfonyl)cyclohexan-1-amine Trifluoroacetate

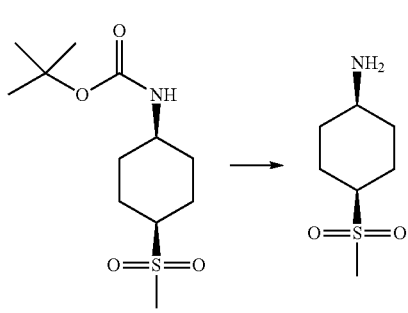 [SMILES: CC(C)(C)OC(=O)N[C@H]1CC[C@@H](S(C)(=O)=O)CC1 ; CS(=O)(=O)[C@H]1CC[C@@H](N)CC1]

TFA (0.5 mL) was added to a mixture of tert-butyl ((1s,4s)-4-(methylsulfonyl)-cyclohexyl)carbamate (100 mg, 0.36 mmol, 1.00 eq) in DCM (2.0 mL). This mixture was stirred at rt for 2 h before it was concentrated to give the crude title compound as a yellow oil.

Intermediate 5

Synthesis of (1r,4r)-4-(methylsulfonyl)cyclohexan-1-amine Trifluoroacetate

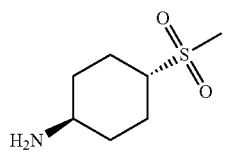

The title compound was prepared by proceeding analogously as described for Intermediate 4 with tert-butyl ((1s,4s)-4-hydroxycyclohexyl)carbamate replacing tert-butyl ((1r,4r)-4-hydroxycyclohexyl) carbamate in Step 1.

Intermediate 6

Synthesis of 6-amino-2-thiaspiro[3.3]heptane 2,2-dioxide

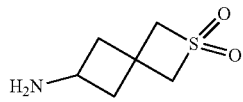

Step 1: Diisopropyl 3-oxocyclobutane-1,1-dicarboxylate

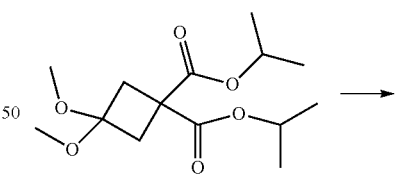

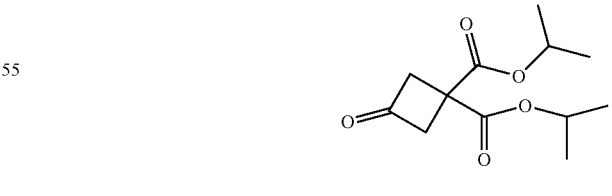

To a mixture of diisopropyl 3,3-dimethoxycyclobutane-1,1-dicarboxylate (40.00 g, 139.00 mmol) in acetone (100.0 ml) was added 2N HCl aq. (100.0 mL) and the mixture was stirred at rt overnight. The reaction mixture was diluted with EA, washed with water, sat. NaHCO₃ aq., brine. The organic layer was dried over Na₂SO₄, concentrated to give crude product as a yellow liquid.

Step 2: Diisopropyl 3-hydroxycyclobutane-1,1-dicarboxylate

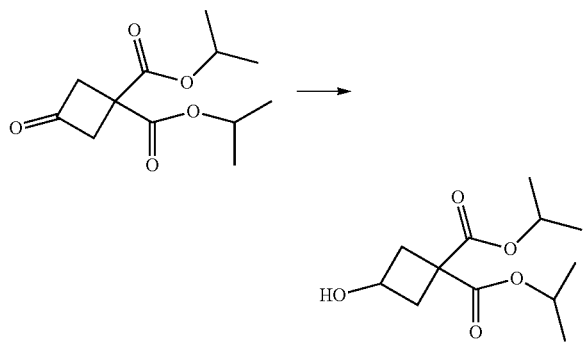

NaBH₄ (15.70 g, 416.10 mmol, 3.00 eq) was added to a mixture of diisopropyl 3-oxocyclobutane-1,1-dicarboxylate (33.60 g, 138.70 mmol, 1.00 eq) in IPA (300.0 ml) and the mixture was stirred at r.t. overnight. The mixture was diluted with water and extracted with EtOAc, and the combined organic layers were washed with water, brine, dried over Na₂SO₄, concentrated to give the crude product as a yellow oil.

Step 3: Diisopropyl 3-((methylsulfonyl)oxy)cyclobutane-1,1-dicarboxylate

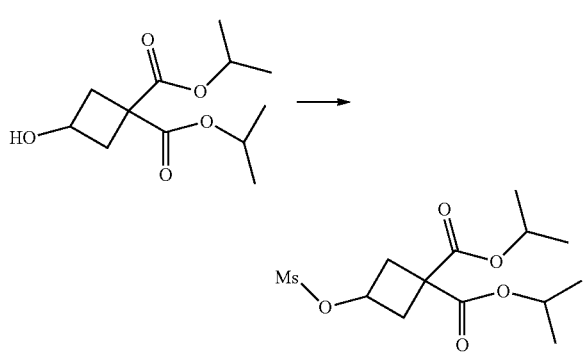

To a mixture of diisopropyl 3-hydroxycyclobutane-1,1-dicarboxylate (28.0 g, 115.0 mmol, 1.00 eq) in DCM (300.0 ml) was added TEA (34.80 g, 344.0 mmol, 3.0 eq), followed by addition of MsCl (15.8 g, 138.0 mmol, 1.2 eq) and the mixture was stirred at rt 3 h. The reaction mixture was diluted with water and extracted with DCM. The combined organic layers were washed with brine, dried over Na₂SO₄, concentrated to give crude product as a yellow oil.

Step 4: Diisopropyl 3-azidocyclobutane-1,1-dicarboxylate

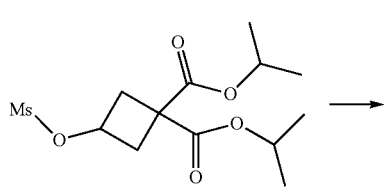

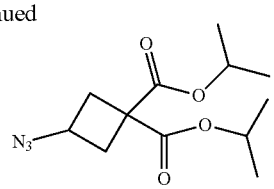

NaN₃ (14.90 g, 229.00 mmol, 2.00 eq) was added to a mixture of diisopropyl 3-((methylsulfonyl)oxy)cyclobutane-1,1-dicarboxylate (36.95 g, 115.0 mmol, 1.00 eq) in DMF (200.0 ml), and the mixture was stirred at 90° C. overnight under N₂. The mixture was diluted with water, extracted with EtOAc, and the combined organic layers were washed with water, brine, dried over Na₂SO₄, concentrated and purified by silica gel column chromatography (PE:EA=20:1) to give the title compound as a yellow liquid.

Step 5: Diisopropyl 3-aminocyclobutane-1,1-dicarboxylate

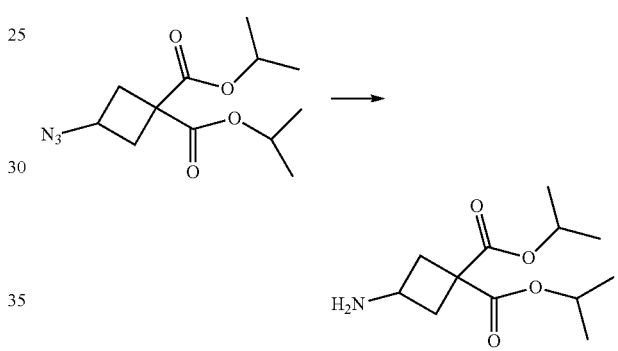

10% Pd/C (3.00 g) was added to a mixture of diisopropyl 3-azidocyclobutane-1,1-dicarboxylate (15.00 g, 55.70 mmol, 1.00 eq) in IPA/NH₃ (150.0 mL), and the mixture was allowed to stir at r.t. overnight under H₂. The mixture was filtered and the filtrate was concentrated and purified by silica gel column chromatography (PE:EA=1:1 to DCM:MeOH=20:1) to give the title compound as a yellow oil.

Step 6: Diisopropyl 3-((tert-butoxycarbonyl)amino)cyclobutane-1,1-dicarboxylate

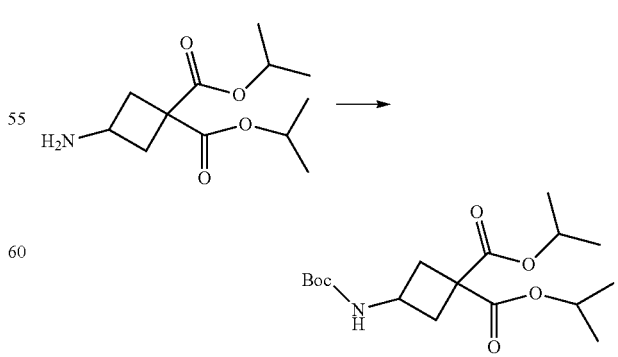

Boc₂O (10.8 g, 49.4 mmol, 1.20 eq) was added to a mixture of diisopropyl 3-aminocyclobutane-1,1-dicarboxylate (10.0 g, 41.10 mmol, 1.00 eq) in DCM (100.0 ml) and the mixture was stirred at r.t. overnight. The reaction mixture was washed with 1N HCl aq., brine, and the organic layer was dried over Na$_2$SO$_4$, concentrated to give crude product as a yellow liquid.

Step 7: tert-Butyl (3,3-bis(hydroxymethyl)cyclobutyl)carbamate

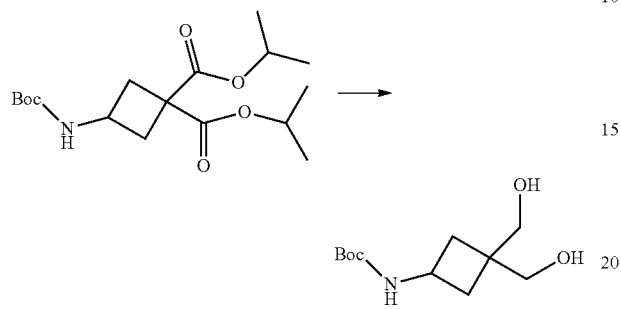

Diisopropyl 3-((tert-butoxycarbonyl)amino)cyclobutane-1,1-dicarboxylate (14.00 g, 40.80 mmol, 1.00 eq) in THF (50.0 mL) was added to LiAlH$_4$ (1.70 g, 44.90 mmol, 1.10 eq) in THF (150.0 ml) dropwise at 0° C. The resulting mixture was warmed to rt and stir for 3 h and then T quenched by water. After stirring for 30 min., the mixture was filtered and the organic layer was concentrated to give crude product as a yellow oil.

Step 8: (3-((tert-Butoxycarbonyl)amino)cyclobutane-1,1-diyl)bis(methylene) Dimethanesulfonate

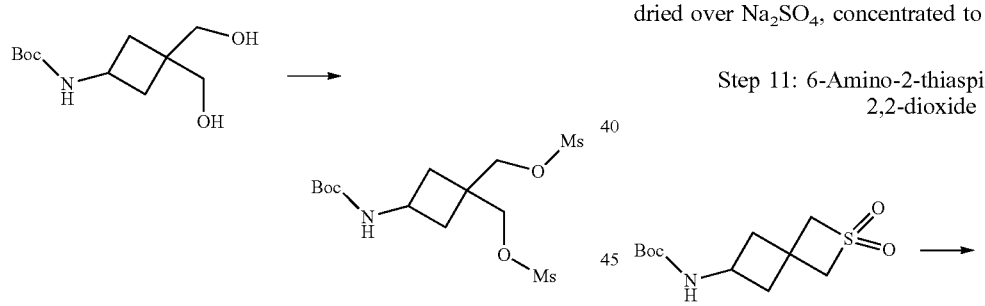

To a mixture of tert-butyl (3,3-bis(hydroxymethyl)cyclobutyl)carbamate (9.40 g, 40.60 mmol, 1.00 eq) and TEA (24.7 g, 243.8 mmol, 6.0 eq) in DCM (120.0 ml) was added MsCl (14.0 g, 121.9 mmol, 3.00 eq) and the mixture was stirred at rt for 3 h. The mixture was poured into ice cold water and extracted with DCM. The combined organic layers were washed with brine, dried over Na$_2$SO$_4$, concentrated to give crude product as a yellow oil.

Step 9: Tert-Butyl 2-thiaspiro[3.3]heptan-6-ylcarbamate

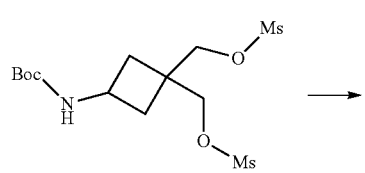

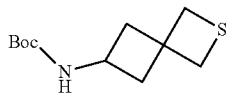

Na$_2$S (3.20 g, 40.50 mmol, 1.00 eq) was added to a mixture of (3-((tert-butoxycarbonyl)-amino)cyclobutane-1,1-diyl)bis(methylene) dimethanesulfonate (15.70 g, 40.50 mmol, 1.00 eq) in EtOH (100.0 ml) and it was stirred at 60° C. overnight under N$_2$. The reaction mixture was poured into ice cold water and extracted with EtOAc. The combined organic layers were washed with brine, dried over Na$_2$SO$_4$, concentrated and purified by column chromatography on silica gel (PE:EA=10:1) to give the title compound as a yellow solid.

Step 10: Tert-Butyl (2,2-dioxido-2-thiaspiro[3.3]heptan-6-yl)carbamate

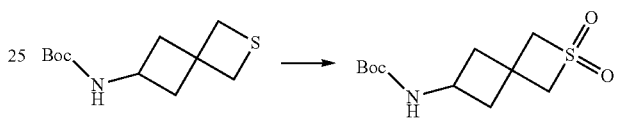

Oxone (22.50 g, 36.70 mmol, 3.00 eq) was added to a mixture of tert-butyl 2-thiaspiro[3.3]heptan-6-ylcarbamate (2.80 g, 12.20 mmol, 1.00 eq) in MeOH:THF:H$_2$O=2:2:1 (100.0 mL) and the mixture was stirred at r.t. overnight. The mixture was diluted with H$_2$O and extracted with EtOAc. The combined organic layers were washed with water, brine, dried over Na$_2$SO$_4$, concentrated to give crude product.

Step 11: 6-Amino-2-thiaspiro[3.3]heptane 2,2-dioxide

To a mixture of tert-butyl (2,2-dioxido-2-thiaspiro[3.3]heptan-6-yl)carbamate (3.19 g, 12.20 mmol, 1.00 eq) in MeOH (2.0 ml) was added MeOH/HCl (10.0 mL) and the mixture was stirred at r.t. for 2 h. The reaction mixture was concentrated and purified by column chromatography on silica gel (PE:EA=1:1 to DCM:MeOH=10:1) to give the title compound.

Intermediate 7

Synthesis of 6-amino-1-methyl-2-thiaspiro[3.3]heptane 2,2-dioxide and 6-amino-1,3-dimethyl-2-thiaspiro[3.3]heptane 2,2-dioxide

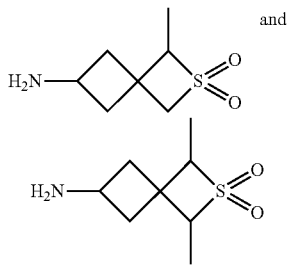

Step 1: 6-(Dibenzylamino)-2-thiaspiro[3.3]heptane 2,2-dioxide

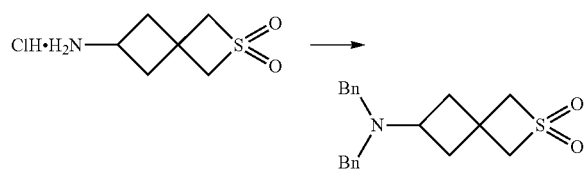

To a solution of 6-amino-2-thiaspiro[3.3]heptane 2,2-dioxide (1.00 g, 5.08 mmol, 1.00 eq.) in MeCN (10.0 mL) was added (bromomethyl)benzene (1.71 g, 10.15 mmol, 2.00 eq.) and $K_2CO_3$ (3.50 g, 25.40 mmol, 5.00 eq.) and the mixture was stirred at rt overnight. The mixture was extracted with DCM and the organic layer was concentrated to give the title compound as white solid.

Step 2: 6-(Dibenzylamino)-1-methyl-2-thiaspiro[3.3]heptane 2,2-dioxide and 6-(dibenzyl-amino)-1,3-dimethyl-2-thiaspiro[3.3]heptane 2,2-dioxide

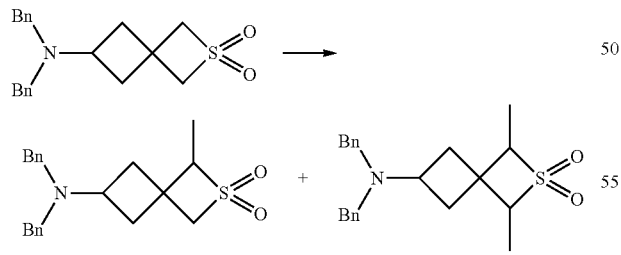

n-BuLi (1.4 mL, 3.53 mmol, 1.50 eq.) was added to a solution of 6-(dibenzylamino)-2-thiaspiro[3.3]heptane 2,2-dioxide (800 mg, 2.35 mmol, 1.00 eq.) in THF (5.0 mL) at −78° C. and the mixture was stirred for 0.5 h. MeI (1.67 g, 11.7 mmol, 5.00 eq.) was added and the mixture was allowed to warm to rt and stirred for 1 h. The mixture was diluted with $NH_4Cl$ aq. and extracted with DCM. The combined organic layers were washed with brine, dried over $Na_2SO_4$, concentrated, and purified by silica gel column chromatography eluting PE/EtOAc (5:1) to give the title compound.

Step 3: 6-Amino-1-methyl-2-thiaspiro[3.3]heptane 2,2-dioxide and 6-amino-1,3-dimethyl-2-thiaspiro[3.3]heptane 2,2-dioxide

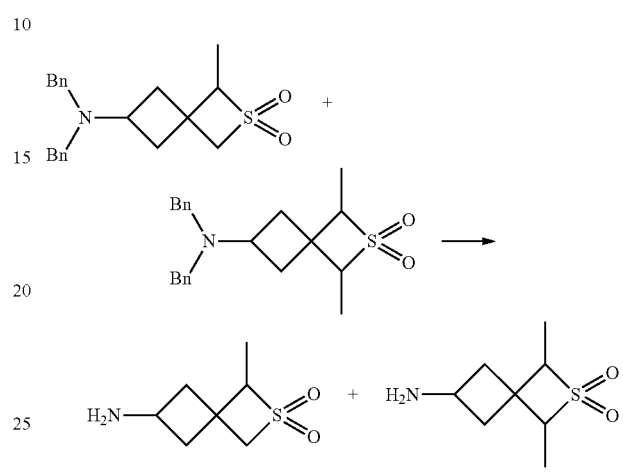

A mixture of 6-(dibenzylamino)-1-methyl-2-thiaspiro[3.3]heptane 2,2-dioxide and 6-(dibenzylamino)-1,3-dimethyl-2-thiaspiro[3.3]heptane 2,2-dioxide (800 mg) was dissolved in MeOH (30.0 mL) and Pd/C (80 mg) was added. The mixture was stirred at rt under $H_2$ atmosphere overnight, filtrated and concentrated to give a mixture of the title compounds.

Intermediate 8

Synthesis of N-(3-(2-bromo-2-(2-chloropyrimidin-4-yl)acetyl)-2-fluorophenyl)-2-fluoro-6-(trifluoromethyl)benzenesulfonamide

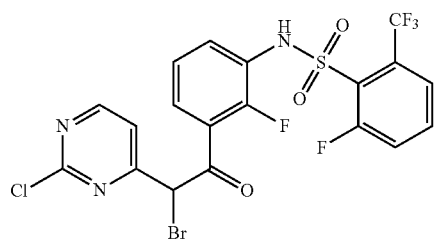 [SMILES: O=C(c1cccc(NS(=O)(=O)c2c(F)cccc2C(F)(F)F)c1F)C(Br)c1ccnc(Cl)n1]

Step 1: Methyl 3-amino-2-fluorobenzoate

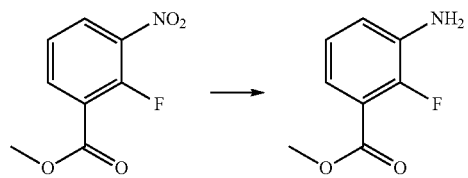

A mixture of methyl 2-fluoro-3-nitrobenzoate (20.0 g, 100.0 mmol, 1.00 eq.) and Pd/C (2.00 g, 10%) in MeOH (200.0 mL) was stirred at 40° C. under H₂ (50 Psi) overnight. The mixture was filtered and concentrated to give the crude product as a brown oil.

Step 2:
Benzyl(2-fluoro-6-(trifluoromethyl)phenyl)sulfane

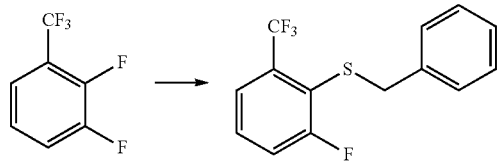 [SMILES: Fc1cccc(C(F)(F)F)c1F ; Fc1cccc(C(F)(F)F)c1SCc1ccccc1]

A solution of phenylmethanethiol (21.45 g, 173.00 mmol, 1.05 eq.) in DMF (20.0 mL) was added to a mixture of 1,2-difluoro-3-(trifluoromethyl)benzene (30.00 g, 165.00 mmol, 1.00 eq.) in DMF (100.0 mL) and K₂CO₃ (34.16 g, 247.50 mmol, 1.50 eq.) dropwise via syringe pump at 0° C. over 3 h and then at 50° C. under N₂ for 3 h. The mixture was diluted with water and extracted with EtOAc. The organic layer was washed with brine, dried over Na₂SO₄, filtered and concentrated. The residue was purified by column chromatography on silica gel (PE) to give the title compound as a colorless oil.

Step 3:
2-Fluoro-6-(trifluoromethyl)benzene-1-sulfonyl Chloride

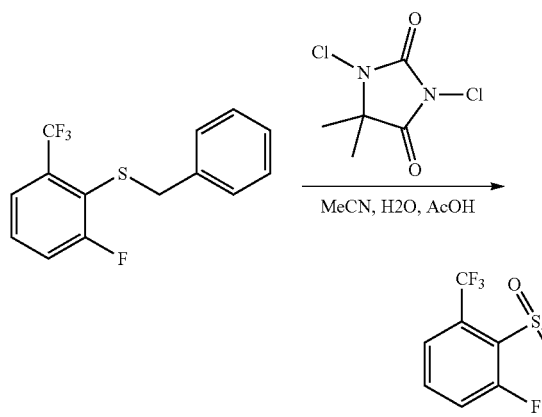

1,3-Dichloro-5,5-dimethylimidazolidine-2,4-dione (13.80 g, 70.00 mmol, 2.00 eq.) was added to a solution of benzyl(2-fluoro-6-(trifluoromethyl)phenyl)sulfane (10.00 g, 35.00 mmol, 1.00 eq.) in MeCN (200.0 mL)/H₂O (30.0 mL)/AcOH (90.0 mL) slowly at 0° C. under N₂ and the mixture was allowed to stir for 3 h. The solution was poured into EtOAc and the organic layer was washed with water, brine, dried over Na₂SO₄, filtered and concentrated. The residue was purified by column chromatography on silica gel (PE/EA=100:1) to give the title compound as a yellow oil.

Step 4: Methyl 2-fluoro-3-(2-fluoro-6-(trifluoromethyl)phenylsulfonamido)benzoate

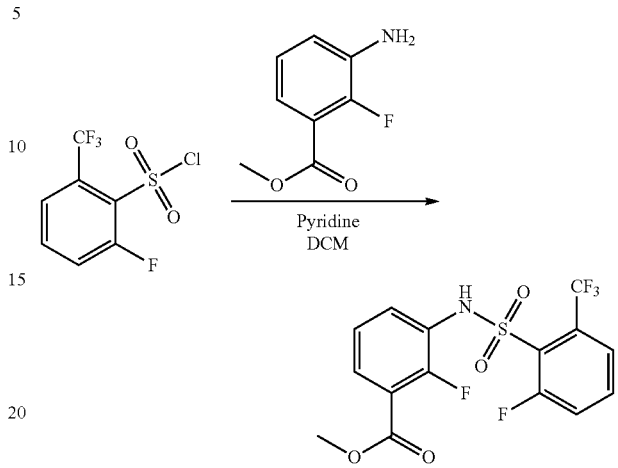

Methyl 3-amino-2-fluorobenzoate (12.80 g, 76.00 mmol, 1.00 eq.) was added to a solution of 2-fluoro-6-(trifluoromethyl)benzene-1-sulfonyl chloride (30.00 g, 114.00 mmol, 1.50 eq.) and pyridine (30.00 g, 380.00 mmol, 5.00 eq.) in DCM (300.0 mL). The solution was stirred at r.t overnight before it was poured into H₂O and extracted with DCM. The combined organic layers were washed with brine, dried over Na₂SO₄, filtered and concentrated. The residue was purified by column chromatography on silica gel (PE/EA=6:1) to give the title compound as a yellow solid.

Step 5: N-(3-(2-(2-Chloropyrimidin-4-yl)acetyl)-2-fluorophenyl)-2-fluoro-6-(trifluoromethyl)-benzenesulfonamide

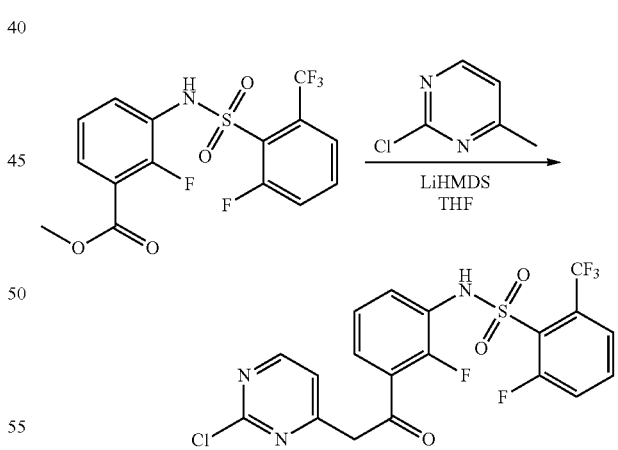

LiHMDS (1M in THF, 182.30 mL, 182.30 mmol, 3.00 eq.) was added to a solution of methyl 2-fluoro-3-(2-fluoro-6-(trifluoromethyl)phenylsulfonamido)benzoate (24.00 g, 60.76 mmol, 1.00 eq.) in THF (250.0 mL) dropwise at 0° C. under N₂ and it was stirred at 0° C. for 1 h. A solution of 2-chloro-4-methylpyrimidine (11.72 g, 91.14 mmol, 1.50 eq) in THF (120.0 mL) was added to the mixture dropwise at 0° C. and the mixture was stirred for 1 h. The solution was poured into ice-water and adjust pH with 0.5 N HCl to pH=5, then the mixture was extracted with EtOAc. The combined organic layers were washed with brine, dried over Na₂SO₄, filter and concentrated. The residue was purified by column chromatography on silica gel (PE/EA=3:1) to give the title product as a yellow solid.

Step 6: N-(3-(2-Bromo-2-(2-chloropyrimidin-4-yl)acetyl)-2-fluorophenyl)-2-fluoro-6-(trifluoromethyl)benzenesulfonamide

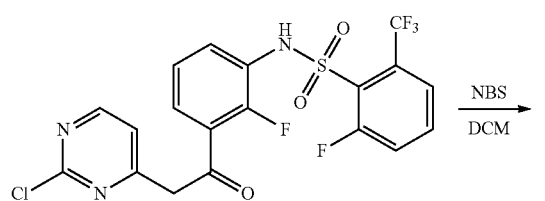

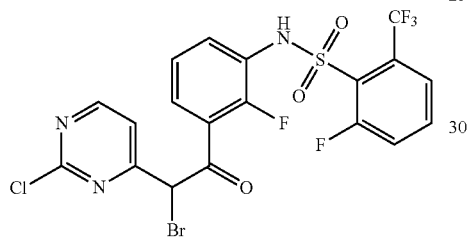

NBS (9.28 g, 52.14 mmol, 1.00 eq.) was added to a solution of N-(3-(2-(2-chloropyrimidin-4-yl)acetyl)-2-fluorophenyl)-2-fluoro-6-(trifluoromethyl)benzene-sulfonamide (25.60 g, 52.14 mmol, 1.00 eq.) in DCM (400.0 mL) in portion at 0° C. and the mixture was stirred at rt overnight. The mixture was concentrated, and the residue was purified by column chromatography on silica gel (PE/EA=3:1) to give the title compound as a yellow solid.

Intermediate 9

Synthesis of N-(3-(2-bromo-2-(2-chloropyrimidin-4-yl)acetyl)-2-fluorophenyl)-2,6-difluorobenzenesulfonamide

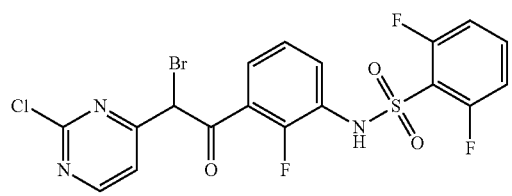 [SMILES: O=C(c1cccc(NS(=O)(=O)c2c(F)cccc2F)c1F)C(Br)c1ccnc(Cl)n1]

The title compound was prepared with 2,6-difluorobenzenesulfonyl chloride replacing 2-fluoro-6-(trifluoromethyl)benzene-1-sulfonyl chloride proceeding analogously as described in Intermediate 8 Step 4.

Intermediate 10

Synthesis of N-(3-(2-bromo-2-(2-chloropyrimidin-4-yl)acetyl)-2-fluorophenyl)acetamide

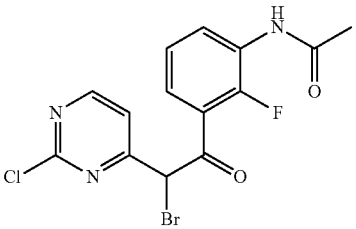 [SMILES: CC(=O)Nc1cccc(C(=O)C(Br)c2ccnc(Cl)n2)c1F]

Step 1: Methyl 3-acetamido-2-fluorobenzoate

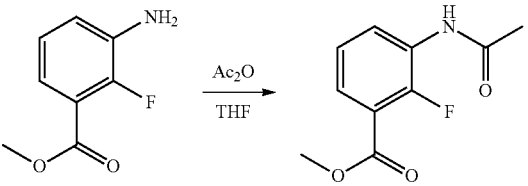

Ac₂O (23.10 g, 0.23 mol, 1.50 eq) was added to a solution of methyl 3-amino-2-fluorobenzoate (25.50 g, 0.15 mol, 1.00 eq) in THF (250.0 mL) and the mixture was stirred at rt overnight under N₂. The mixture was concentrated and purified by column chromatography on silica gel (PE: EA=5:1 to 3:1) to give the title compound as a pink solid.

Step 2: N-(3-(2-(2-Chloropyrimidin-4-yl)acetyl)-2-fluorophenyl)acetamide

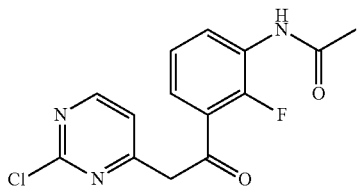

LiHMDS (427.0 mL, 0.43 mol, 3.00 eq) in THF was added to a solution of methyl 3-acetamido-2-fluorobenzoate (30.0 g, 0.14 mol, 1.00 eq) in THF (300.0 mL) at 0° C. under N₂, followed by addition of 2-chloro-4-methylpyrimidine (23.70 g, 0.18 mol, 1.30 eq) in THF (100.0 mL) dropwise at 0° C. The mixture was stirred at r.t. for 2 hours before it was quenched by NH₄Cl aq. The mixture was extracted with EtOAc, and the combined organic layers were dried over Na₂SO₄, concentrated and purified by column chromatography on silica gel (PE:EA=2:1) to 1:1) to give the title compound as a pink solid.

Step 3: N-(3-(2-Bromo-2-(2-chloropyrimidin-4-yl)acetyl)-2-fluorophenyl)acetamide

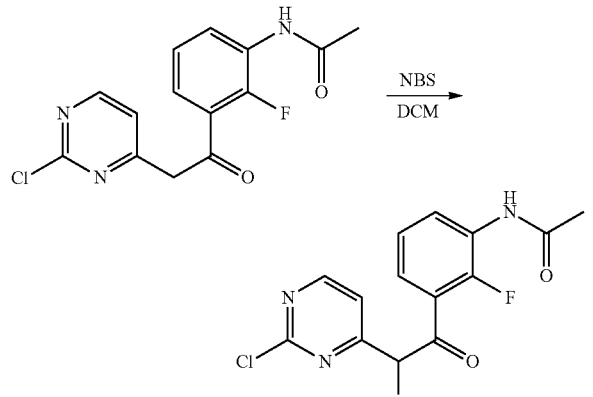

NBS (19.70 g, 0.11 mmol, 1.00 eq) was added to a solution of N-(3-(2-(2-chloropyrimidin-4-yl)acetyl)-2-fluorophenyl)acetamide (34.0 g, 0.11 mol, 1.00 eq) in DCM (350.0 mL) portion-wise and the mixture was stirred at r.t. overnight. The mixture was washed with water, and the organic layer was dried over Na₂SO₄, concentrated and purified by column chromatography on silica gel (PE:EA=5:1) to get the title compound as a yellow oil.

Intermediate 11

Synthesis of 2-(difluoromethoxy)-6-(trifluoromethyl)benzenesulfonyl Chloride

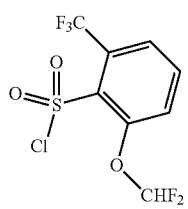 [SMILES: O=S(=O)(Cl)c1c(OC(F)F)cccc1C(F)(F)F]

Step 1: 2-Bromo-1-(difluoromethoxy)-3-(trifluoromethyl)benzene

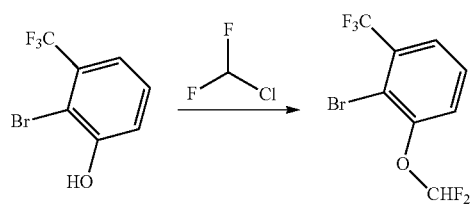

Chlorodifluoromethane was bubbled into a solution of 2-bromo-3-(trifluoromethyl)phenol (10.00 g, 41.49 mmol, 1.00 eq.) and K₂CO₃ (17.18 g, 124.48 mmol, 3.00 eq.) in DMF (100.0 mL). It was sealed and the mixture was stirred at 70° C. overnight. The mixture was diluted with DCM, washed with NaHCO₃ aq., and brine. The organic layer was dried over Na₂SO₄, concentrated and purified by column chromatography on silica gel (PE/EA=20:1) to give the title compound as yellow oil.

Step 2: Benzyl(2-(difluoromethoxy)-6-(trifluoromethyl)phenyl)sulfane

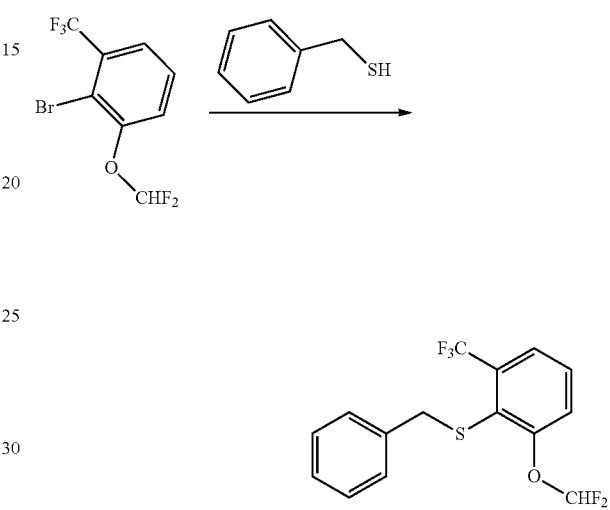

A mixture of 2-bromo-1-(difluoromethoxy)-3-(trifluoromethyl)benzene (1.20 g, 4.12 mmol, 1.00 eq.), phenylmethanethiol (1.02 g, 8.24 mmol, 2.00 eq.), Pd₂(dba)₃ (375 mg, 0.41 mmol, 0.10 eq.), XantPhos (237 mg, 0.41 mmol, 0.10 eq.) and Cs₂CO₃ (4.03 g, 12.36 mmol, 3.00 eq.) in 1,4-dioxane (20.0 mL) was stirred at 100° C. under N₂ overnight. The mixture was concentrated and purified by column chromatography on silica gel (PE/EA=20:1) to give the title compound as yellow solid.

Step 3: 2-(Difluoromethoxy)-6-(trifluoromethyl)benzenesulfonyl Chloride

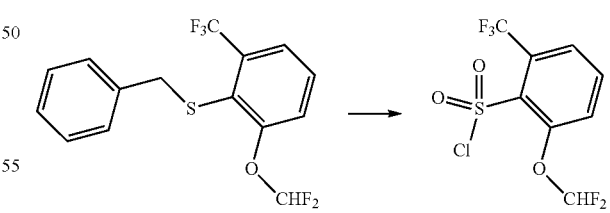

1,3-Dichloro-5,5-dimethylhydantoin (177 mg, 0.90 mmol, 2.00 eq.) was added to a solution of benzyl(2-(difluoromethoxy)-6-(trifluoromethyl)phenyl)sulfane (150 mg, 0.45 mmol, 1.00 eq.) in H₂O/ACN/AcOH (1.0 mL/7.5 mL/3.0 mL) at 0° C. and the mixture was stirred for 3 h. The mixture was diluted with DCM, and the organic layer was washed with NaHCO₃ aq. and brine. The organic layer was dried over Na₂SO₄, concentrated to give the title compound as yellow oil.

Intermediate 12

Synthesis of 2-(difluoromethoxy)-6-fluorobenzene-1-sulfonyl Chloride

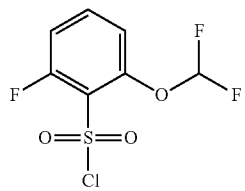 [SMILES: O=S(=O)(Cl)c1c(F)cccc1OC(F)F]

The title intermediate was synthesized with 2-bromo-3-fluorophenol replacing 2-bromo-3-(trifluoromethyl)phenol proceeding analogously as described in Intermediate 11 Step 1.

Intermediate 13

Synthesis of 3-hydroxy-3-methylcyclobutan-1-one

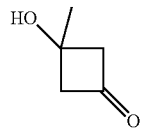

Step 1: 3-(Benzyloxy)-1-methylcyclobutanol

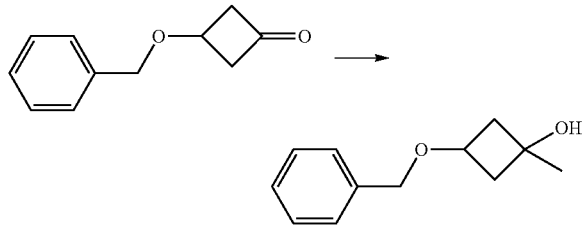

Methylmagnesium bromide (47.0 mL, 141.88 mmol, 10.00 eq. 3M) was added to a solution of 3-(benzyloxy)cyclobutanone (2.50 g, 14.19 mmol, 1.00 eq.) in THF (20.0 mL) dropwise at −78° C. then it was allowed to warm to rt and stir for 2 h. The reaction mixture was quenched with NH$_4$Cl aq. and extracted with EtOAc. The combined organic layers were washed with brine, dried over Na$_2$SO$_4$, concentrated and purified by silica gel chromatography (DCM:MeOH=20:1) to give title compound as a yellow oil.

Step 2: 1-Methylcyclobutane-1,3-diol

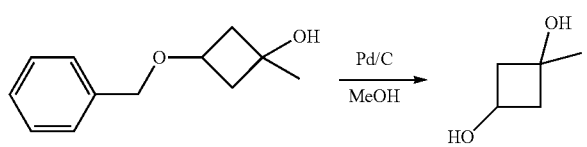

To a stirred solution of 3-(benzyloxy)-1-methylcyclobutanol (1.20 g, 6.25 mmol, 1.00 eq.) in MeOH (20.0 mL) was added Pd/C (1.00 g), and the resulting mixture was stirred at rt under H$_2$ (50 psi) overnight. The reaction mixture was filtered, and the filtrate was concentrated to give the title compound as a yellow oil.

Step 3: 3-Hydroxy-3-methylcyclobutanone

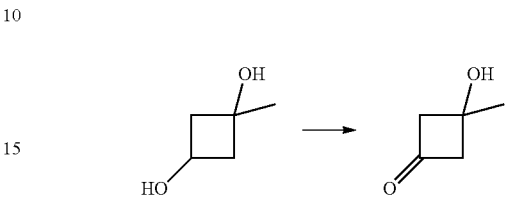

Dess-Martin (3.60 g, 8.69 mmol, 1.10 eq.) was added to a solution of 1-methyl-cyclobutane-1,3-diol (800 mg, 7.90 mmol, 1.00 eq.) in DCM/THF (17.0:2.5 mL) and the mixture was stirred at rt overnight. The reaction mixture was filtered, and the filtrate was concentrated and purified by flash chromatography (EA/PE (20%-40%)) to give the title compound.

Intermediate 14

Synthesis of 3-(((tert-butyldiphenylsilyl)oxy)methyl)bicyclo[1.1.1]pentane-1-carboxylic Acid

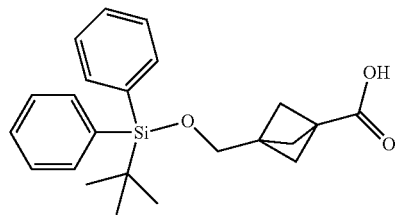 [SMILES: CC(C)(C)[Si](OCC12CC(C(=O)O)(C1)C2)(c1ccccc1)c1ccccc1]

Step 1: Methyl 3-(hydroxymethyl)bicyclo[1.1.1]pentane-1-carboxylate

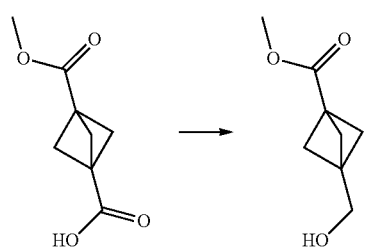

To a stirred solution of 3-(methoxycarbonyl)bicyclo[1.1.1]pentane-1-carboxylic acid (10.00 g, 76.33 mmol, 1.00 eq.) in THF (100.0 mL) was added BH$_3$ (7.80 g, 91.60 mmol, 1.20 eq.) at 0° C. under N$_2$. The resulting mixture was stirred at 0° C. 16 h. The reaction mixture was concentrated to give the title compound

Step 2: Methyl 3-(((tert-butyldiphenylsilyl)oxy)methyl)bicyclo[1.1.1]pentane-1-carboxylate

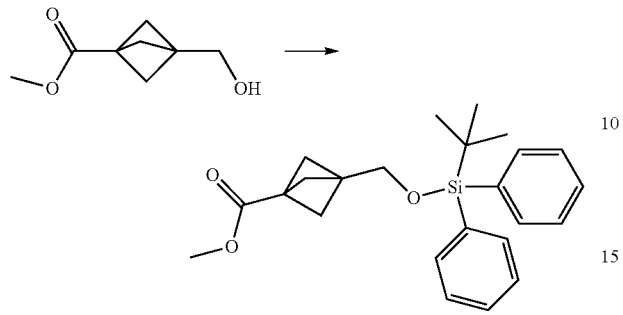

TBDPSCl (15.78 g, 57.60 mmol, 1.50 eq.) and 1H-imidazole (15.25 g, 76.80 mmol, 2.00 eq.) were added to a solution of methyl 3-(hydroxymethyl)bicyclo[1.1.1]pentane-1-carboxylate (6.00 g, 38.40 mmol, 1.00 eq.) in DMF (10.0 mL) at 0° C. The resulting mixture was stirred under $N_2$ at rt 16 h. The reaction mixture was concentrated and purified by silica gel chromatography (EA:PE=1:5) to give the title compound as a white solid.

Step 3: 3-(((tert-Butyldiphenylsilyl)oxy)methyl)bicyclo[1.1.1]pentane-1-carboxylic Acid

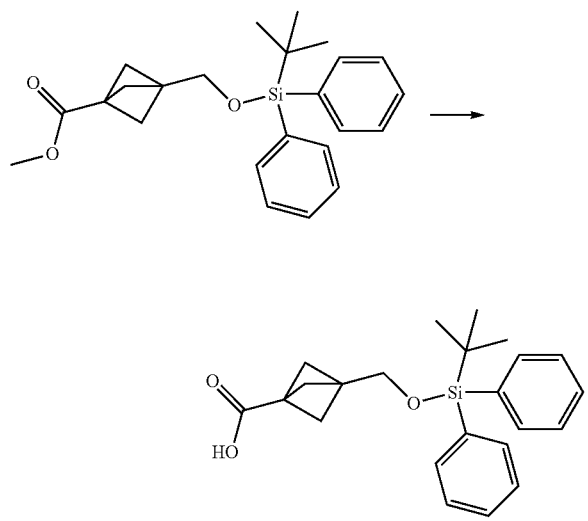

NaOH (1.98 g, 49.60 mmol, 4.00 eq.) was added to a stirred solution of methyl 3-(((tert-butyldiphenylsilyl)oxy)methyl)bicyclo[1.1.1]pentane-1-carboxylate (4.90 g, 12.40 mmol, 1.00 eq.) in MeOH (50.0 mL) at room temperature. The resulting mixture was stirred at 60° C. for 16 h. The reaction mixture pH was adjusted to pH=6 and extracted with DCM. The combined organic layers were concentrated to give title compound as a white solid.

Intermediate 15

Synthesis of bicyclo[1.1.1]pentane-1-carboxylic Acid

Step 1: Tricyclo[1.1.1.01,3]pentane

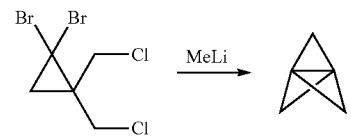 [SMILES: "MeLi" ; ClCC1(CCl)CC1(Br)Br ; C1C23CC12C3]

MeLi (1.6 M in diethyl ether, 126.3 mL, 202.14 mmol, 2.40 eq.) was added to a mixture of 1,1-dibromo-2,2-bis(chloromethyl)cyclopropane (25.0 g, 84.23 mmol, 1.00 eq.) in diethyl ether (40.0 mL) dropwise at −78° C. This mixture was stirred at −78° C. for 15 min and then it was warmed to −5° C. and stirred for 2 h. This reaction mixture was warmed to 40° C., and the title compound was obtained as a solution of diethyl ether by vacuum distillation.

Step 2: Bicyclo[1.1.1]pentan-1-yl(phenyl)sulfane

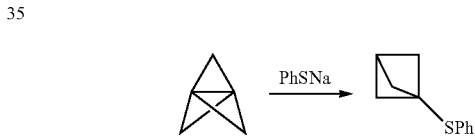

A mixture of sodium benzenethiolate (11.1 g, 84.23 mmol, 1.00 eq.) in $H_2O$ (60.0 mL) was adjusted pH=2-3 with 3M HCl, extracted with METE (100.0 mL). A solution of benzenethiol in MBTE was added to a solution of tricyclo[1.1.1.01,3]pentane (5.70 g, 84.23 mmol, 1.00 eq.) in diethyl ether and the mixture was stirred at r.t. under $N_2$ for 1 h. The mixture was poured into 1 M NaOH, extracted with MBTE, washed with brine, dried over $Na_2SO_4$, concentrated. The residue was purified by column chromatography on silica gel (PE:EA=20:1) to give title compound as a colorless oil.

Step 3: Bicyclo[1.1.1]pentane-1-carboxylic Acid

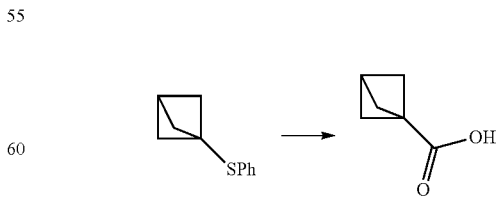

n-BuLi (2.5 M in hexanes, 0.2 mL, 0.57 mmol, 0.10 eq.) was added to a mixture of 4,4'-di-tert-butylbiphenyl (3.00 g, 1.35 mmol, 2.00 eq.) and 1,10-phenanthroline (102 mg, 0.57 mmol, 0.10 eq.) in THE (10.0 mL) at −78° C. The mixture was stirred at −78° C. for 30 min, and then at −50° C. for 30 min. A solution of bicyclo[1.1.1]pentan-1-yl(phenyl)sulfane (1.00 g, 5.67 mmol, 1.00 eq.) in THF (5.0 mL) was added to the mixture. Dry $CO_2$ was bubbled into the solution and the mixture was slowly warmed to r.t. before it was quenched with sat. $Na_2CO_3$. The mixture was extracted with MBTE and the organic layers were washed with sat. $Na_2CO_3$. The aqueous layer was adjusted with pH=1-2 with 2N HCl aq. and extracted with DCM/MeOH. The combined organic layers were concentrated, purified by column chromatography on silica gel (DCM/MeOH=50:1) to give the title compound as a brown oil.

Intermediate 16

Synthesis of 1-(difluoromethyl)cyclopropanecarboxylic Acid

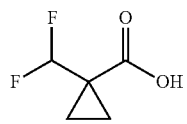

Step 1: Ethyl 1-formylcyclopropanecarboxylate

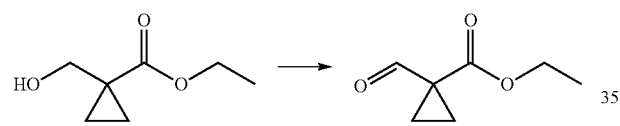

Dess-Martin reagent (110.0 g, 0.26 mol, 1.50 eq.) was added to a stirred mixture of ethyl 1-(hydroxymethyl)cyclopropanecarboxylate (25.00 g, 0.17 mol, 1.00 eq.) in DCM (500.0 mL) and the mixture was stirred at r.t. overnight under $N_2$. The mixture was concentrated and purified by column chromatography on silica gel (PE:EA=20:1) to give the title compound as a pale yellow oil.

Step 2: Ethyl 1-(difluoromethyl)cyclopropanecarboxylate

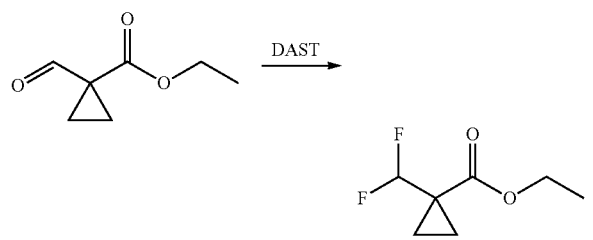

To a stirred mixture of ethyl 1-formylcyclopropanecarboxylate (18.00 g, 0.13 mol, 1.00 eq.) in DCM (350.0 mL) was added DAST (41.00 g, 0.25 mol, 2.00 eq.) at 0° C. and the mixture was stirred at r.t. overnight under $N_2$. The reaction mixture was diluted with water, and extracted with EtOAc, the combined organic layers were washed with water, brine, dried over $Na_2SO_4$, concentrated and purified by column chromatography on silica gel (PE:EA=10:1) to the give title compound as a pale yellow oil.

Step 3: 1-(Difluoromethyl)cyclopropanecarboxylic Acid

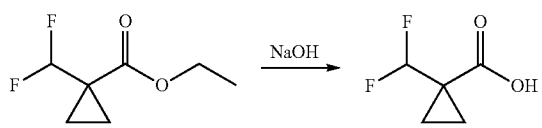

To a stirred mixture of ethyl 1-(difluoromethyl)cyclopropanecarboxylate (16.00 g, 97.56 mmol, 1.00 eq.) in MeOH (150.0 mL) and water (75.0 mL) was added NaOH (7.80 g, 195.12 mmol, 2.00 eq.) and the mixture was stirred at r.t. overnight. The mixture was diluted with water, and adjust pH to 1 by addition of 3N HCl aq. The mixture was extracted with EtOAc, and the combined organic layers were washed with water, brine, dried over $Na_2SO_4$, concentrated to give the title compound as a pale yellow oil.

Intermediate 17

Synthesis of 1-(difluoromethyl)cyclobutanecarboxylic Acid

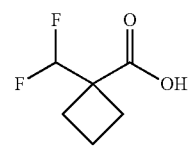

The title compound was prepared by proceeding analogously as described in Intermediate 16, Step 1 using ethyl 1-(hydroxymethyl)cyclobutanecarboxylate instead of ethyl 1-(hydroxymethyl)cyclopropanecarboxylate.

Intermediate 18

Synthesis of 3-chlorobicyclo[1.1.1]pentane-1-carboxylic Acid

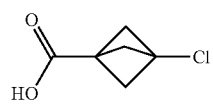

Step 1: Methyl 3-chlorobicyclo[1.1.1]pentane-1-carboxylate

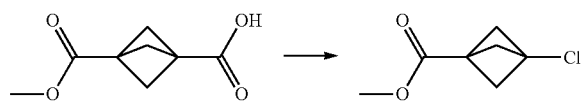

A solution of 3-(methoxycarbonyl)bicyclo[1.1.1]pentane-1-carboxylic acid (500 mg, 2.94 mmol, 1.00 eq.) in $Et_2O$ (12.0 mL) at 0° C. was treated with DMF (21 mg, 0.29 mmol, 0.10 eq.) and oxalyl chloride (821 mg, 6.47 mmol, 2.20 eq.) and the mixture was warmed to r.t. After 70 min, the solvent was removed, and the crude product was dissolved in CCl$_4$ (4.0 mL) in flask A. To a separate flask B was added sodium 2-thioxopyridin-1(2H)-olate (533 mg, 3.53 mmol, 1.20 eq.), and CCl$_4$ (15.0 mL) and the mixture was heated to reflux. Then the solution of crude acid chloride in CCl$_4$ of flask A was added dropwise to flask B over 15 mins under irradiation using a halogen work lamp. After 90 min, the reaction was cooled to r.t. The reaction was diluted with 1M HCl. The mixture was extracted with DCM. The combined organic layers were washed with sat. NaHCO$_3$, dried over Na$_2$SO$_4$, concentrated to give the title compound as a pale yellow oil.

Step 2: 3-Chlorobicyclo[1.1.1]pentane-1-carboxylic Acid

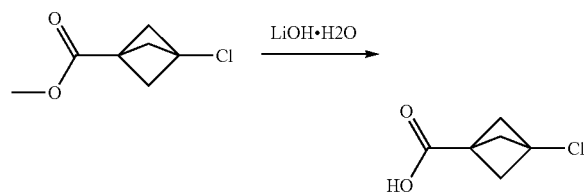

A mixture of methyl 3-chlorobicyclo[1.1.1]pentane-1-carboxylate (472 mg, 2.94 mmol, 1.00 eq.) in THF/H$_2$O (8.0 mL/2.0 mL) was added LiOH·H$_2$O (617 mg, 14.70 mmol, 5.00 eq.). This mixture was stirred at r.t. overnight. The mixture was concentrated and diluted with H$_2$O and adjusted pH=2-3 with 3N HCl. The mixture was extracted with DCM, and the combined organic layers were dried over Na$_2$SO$_4$, concentrated to give the title compound as a pale yellow solid.

Intermediate 19

Synthesis of 1-methyl-3-oxocyclobutane-1-carbonitrile

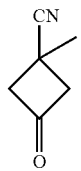

Step 1: 3,3-Dimethoxycyclobutanecarbonitrile

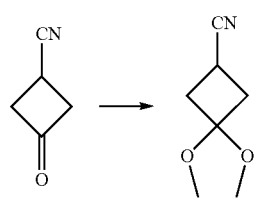

To a stirred solution of 3-oxocyclobutanecarbonitrile (1.50 g, 15.79 mmol, 1.00 eq.) in MeOH (15.0 mL) was added CH(OCH$_3$)$_3$ (14.0 mL) and TsOH (150 mg, 0.79 mmol, 0.05 eq.), and the resulting mixture was then stirred at 65° C. overnight. The mixture was concentrated and the residue was diluted with water and extracted with EtOAc. The combined organic layer was washed with brine, dried over Na$_2$SO$_4$, concentrated to give the title compound as a colorless oil.

Step 2: 3,3-Dimethoxy-1-methylcyclobutanecarbonitrile


To a stirred solution of 3,3-dimethoxycyclobutanecarbonitrile (1.00 g, 7.09 mmol, 1.00 eq.) in THF (5.0 mL) was added LDA (8.5 mL, 21.27 mmol, 3.00 eq. 2.5M) slowly at −78° C., and the mixture was stirred at −78° C. for 1 h. CH$_3$I (2.01 g, 14.18 mmol, 2.00 eq.) was added slowly at −78° C. and the mixture was stirred for 1 h before it was warmed to r.t. After 2 h, the reaction mixture was quenched with NH$_4$Cl aq. and extracted with EtOAc. The combined organic layer was washed with brine, dried over Na$_2$SO$_4$, concentrated and purified by column chromatography on silica gel (PE:EA=5:1) to give the title compound as a yellow oil.

Step 3: 1-Methyl-3-oxocyclobutanecarbonitrile

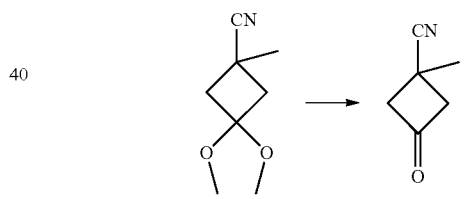

To a stirred solution of 3,3-dimethoxy-1-methylcyclobutanecarbonitrile (100 mg, 0.64 mmol, 1.00 eq.) in acetone/water (1.0:1.0 mL) was added TsOH (122 mg, 0.64 mmol, 1.00 eq.), and the resulting mixture was stirred at 65° C. for 2 h. The reaction mixture was extracted with EtOAc, the combined organic layer was washed with brine, dried over Na$_2$SO$_4$, concentrated to give the title compound as a yellow oil.

Intermediate 20

Synthesis of (1R,5S)-3-thia-8-azabicyclo[3.2.1]octane 3,3-dioxide

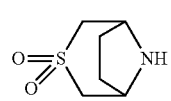

Step 1: Diethyl 1-benzylpyrrolidine-2,5-dicarboxylate

Step 3: tert-Butyl 2,5-bis(hydroxymethyl)pyrrolidine-1-carboxylate

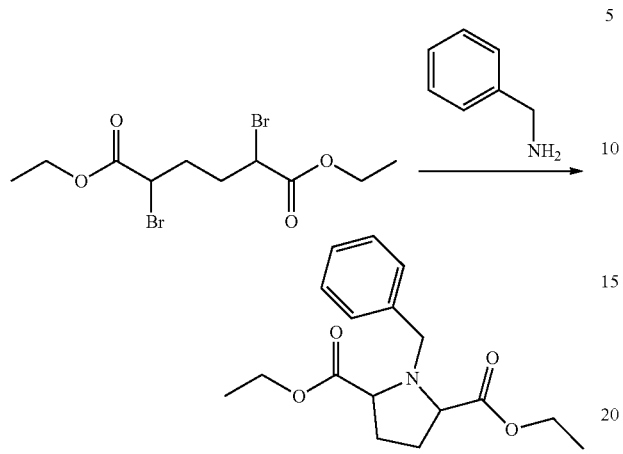

A mixture of diethyl 2,5-dibromohexanedioate (25.00 g, 69.44 mmol, 1.00 eq.), phenylmethanamine (7.40 g, 69.44 mmol, 1.00 eq.) and $K_2CO_3$ (28.70 g, 208.33 mmol, 3.00 eq.) in toluene/$H_2O$ (250.0 mL/25.0 mL) was stirred at reflux overnight. The mixture was concentrated, diluted with EtOAc, and the organic layer was washed with water and brine, dried over $Na_2SO_4$, concentrated. The residue was purified by column chromatography on silica gel (PE/EA=8:1) to give the product as a yellow oil.

A mixture of (1-benzylpyrrolidine-2,5-diyl)dimethanol (1.00 g, 4.52 mmol, 1.00 eq.), $Boc_2O$ (1.97 g, 9.05 mmol, 2.00 eq.) and Pd/C (10%, 200 mg, 20% wt) in MeOH (20.0 mL) was stirred at 50° C. under $H_2$ overnight. The mixture was filtered and the filtrate was concentrated and purified by column chromatography on silica gel (PE/EA=3:1) to give crude title compound as colorless oil.

Step 2: (1-Benzylpyrrolidine-2,5-diyl)dimethanol

Step 4: tert-Butyl 2,5-bis((tosyloxy)methyl)pyrrolidine-1-carboxylate

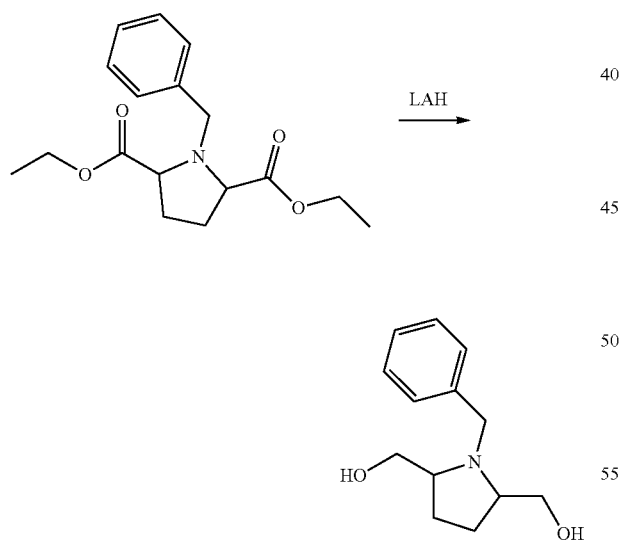

To a solution of diethyl 1-benzylpyrrolidine-2,5-dicarboxylate (11.00 g, 36.06 mmol, 1.00 eq.) in THF (150.0 mL) was added LAH (5.50 g, 144.24 mmol, 4.00 eq.) portionwise at 0° C. The mixture was stirred at rt for 3 h. The mixture was quenched with $Na_2SO_4 \cdot 10H_2O$, filtered and the filtrate was concentrated and the residue was purified by column chromatography on silica gel (PE/EA=3:1) to give the product as yellow oil.

TsCl (3.70 g, 19.48 mmol, 5.00 eq.) in DCM (10.0 mL) was added to a solution of tert-butyl 2,5-bis(hydroxymethyl)pyrrolidine-1-carboxylate (900 mg, 3.90 mmol, 1.00 eq.) and pyridine (3.10 g, 38.96 mmol, 10.00 eq) in DCM (20.0 mL) dropwise at 0° C. The mixture was stirred at RT overnight, then concentrated and purified by column chromatography on silica gel (PE/EA=5:1) to give the title compound as a white solid.

Step 5: tert-Butyl (1R,5S)-3-thia-8-azabicyclo[3.2.1]octane-8-carboxylate

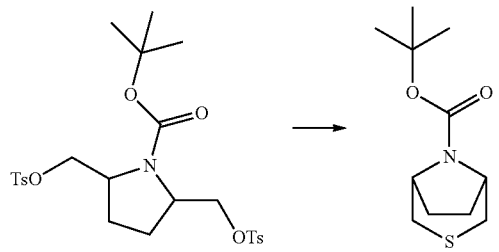 [SMILES: Cc1ccc(S(=O)(=O)OCC2CCC(COS(=O)(=O)c3ccc(C)cc3)N2C(=O)OC(C)(C)C)cc1 ; CC(C)(C)OC(=O)N1C2CCC1CSC2]

To a solution of tert-butyl 2,5-bis((tosyloxy)methyl)pyrrolidine-1-carboxylate (2.00 g, 3.71 mmol, 1.00 eq.) in EtOH (20.0 mL) was added Na$_2$S (60%, 482 mg, 3.71 mmol, 1.00 eq.) in water (4.0 mL). The mixture was stirred at 90° C. overnight and then concentrated, diluted with water, and extracted with EtOAc. The combined organic layers were dried over Na$_2$SO$_4$ concentrated and purified by column chromatography on silica gel (PE/EA=10:1) to give the title compound as white solid.

Step 6: tert-Butyl (1R,5S)-3-thia-8-azabicyclo[3.2.1]octane-8-carboxylate 3,3-dioxide

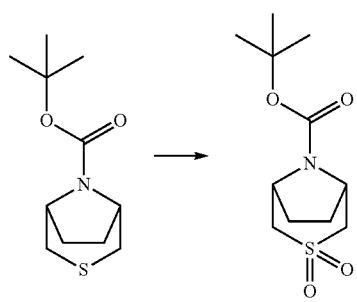 [SMILES: CC(C)(C)OC(=O)N1C2CCC1CSC2 ; CC(C)(C)OC(=O)N1C2CCC1CS(=O)(=O)C2]

A mixture of tert-butyl (1R,5S)-3-thia-8-azabicyclo[3.2.1]octane-8-carboxylate (200 mg, 0.87 mmol, 1.00 eq.) and oxone (1.07 g, 1.75 mmol, 2.00 eq.) in THF/H$_2$O (8.0 mL/2.0 mL) was stirred at rt overnight. The mixture was diluted with water, extracted with EtOAc, and the combined organic layers were washed with brine, dried over Na$_2$SO$_4$ and concentrated to give the title compound as yellow solid.

Step 7: (1R,5S)-3-Thia-8-azabicyclo[3.2.1]octane 3,3-dioxide

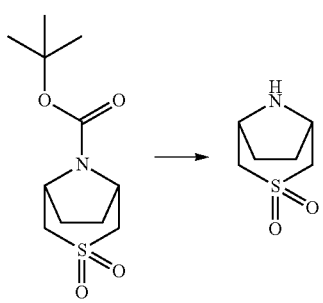 [SMILES: CC(C)(C)OC(=O)N1C2CCC1CS(=O)(=O)C2 ; O=S1(=O)CC2CCC(C1)N2]

A mixture of tert-butyl (1R,5S)-3-thia-8-azabicyclo[3.2.1]octane-8-carboxylate 3,3-dioxide (150 mg, 0.58 mmol, 1.00 eq.) in TFA/DCM (0.5 mL/2.0 mL) was stirred at rt 2 h. The mixture was concentrated to give the title compound as yellow oil.

Intermediate 21

Synthesis of (1R,5S)-3-methyl-8-azabicyclo[3.2.1]octane-3-carbonitrile

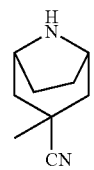

Step 1: tert-Butyl (1R,5S)-3-cyano-3-methyl-8-azabicyclo[3.2.1]octane-8-carboxylate

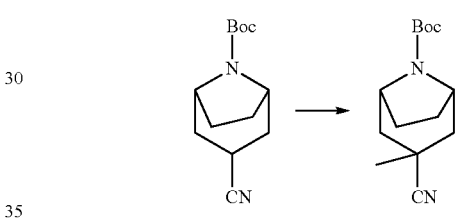

LDA (1.0 M in THF, 3.2 mL, 3.20 mmol, 3.02 eq.) was added to a solution of tert-butyl (1R,5S)-3-cyano-8-azabicyclo[3.2.1]octane-8-carboxylate (250 mg, 1.06 mmol, 1.00 eq.) in THF (5.0 mL) at −78° C. under N$_2$ dropwise and the mixture was stirred for 2 h. CH$_3$I (226 mg, 1.59 mmol, 1.50 eq.) in THF (1.0 mL) was added. The mixture was stirred at rt overnight before it was diluted with NH$_4$Cl aq. The mixture was extracted with EtOAc, and the combined organic layers were dried over Na$_2$SO$_4$, concentrated and purified by column chromatography on silica gel (PE/EA=3:1) to give the title compound as brown solid.

Step 2: (1R,5S)-3-Methyl-8-azabicyclo[3.2.1]octane-3-carbonitrile

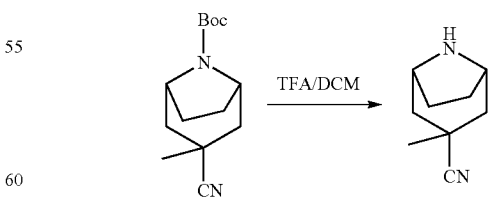

A mixture of tert-butyl (1R,5S)-3-cyano-3-methyl-8-azabicyclo[3.2.1]octane-8-carboxylate (60 mg, 0.24 mmol, 1.00 eq.) in TFA/DCM (0.5 mL/2.0 mL) was stirred at rt for 2 h. The mixture was concentrated to give the title compound as yellow oil.

Intermediate 22

Synthesis of 3-(2,2,2-trifluoroethyl)-3,8-diazabicyclo[3.2.1]octane

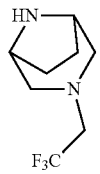

Step 1: Tert-Butyl 3-(2,2,2-trifluoroethyl)-3,8-diazabicyclo[3.2.1]octane-8-carboxylate

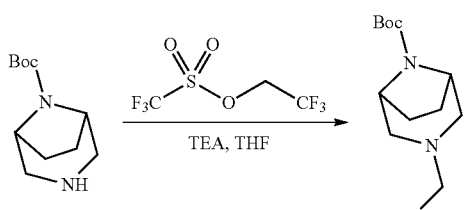

2,2,2-Trifluoroethyl trifluoromethanesulfonate (7.87 g, 33.92 mmol, 1.2 eq) was added to a solution of tert-butyl 3,8-diazabicyclo[3.2.1]octane-8-carboxylate (6.00 g, 28.26 mmol, 1.00 eq) in THF (60.0 mL) and TEA (5.72 g, 56.52 mmol, 2.00 eq) and the mixture was stirred at r.t. overnight under $N_2$. The mixture was concentrated and purified by flash column chromatography (EA:PE=0 to 100%) to give the title compound as a yellow oil.

Step 2: 3-(2,2,2-Trifluoroethyl)-3,8-diazabicyclo[3.2.1]octane

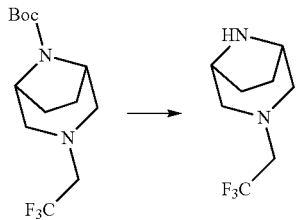

To a solution of tert-butyl 3-(2,2,2-trifluoroethyl)-3,8-diazabicyclo[3.2.1]octane-8-carboxylate (7.00 g, 23.78 mmol, 1.00 eq) in EtOAc (30.0 mL) was added EtOAc/HCl (30.0 mL, 2M) and the mixture was stirred at r.t. for 2 hours under $N_2$. The mixture was concentrated to give the title compound as a yellow solid.

Intermediate 23

Synthesis of 3-(2,2-difluoroethyl)-3,8-diazabicyclo[3.2.1]octane

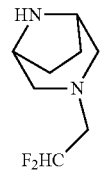

The title compound was prepared by proceeding analogously as described in Intermediate 22 Step, using 2,2-difluoroethyl trifluoromethanesulfonate instead of 2,2,2-trifluoroethyl trifluoromethanesulfonate.

Intermediate 24

Synthesis of 3-(3,3,3-trifluoropropyl)-3,8-diazabicyclo[3.2.1]octane

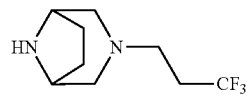

Step 1: Tert-Butyl 3-(3,3,3-trifluoropropyl)-3,8-diazabicyclo[3.2.1]octane-8-carboxylate

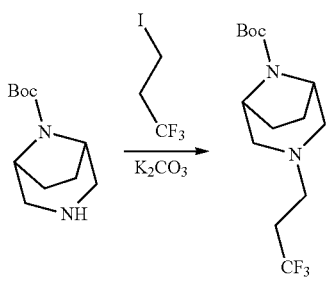

1,1,1-Trifluoro-3-iodopropane (317 mg, 1.41 mmol, 1.50 eq) was added to a solution of tert-butyl 3,8-diazabicyclo[3.2.1]octane-8-carboxylate (200 mg, 0.94 mmol, 1.00 eq) in DMF (5.0 mL) and $K_2CO_3$ (260 mg, 1.89 mmol, 2.00 eq) and the mixture was stirred at r.t. overnight and then further stir at 40° C. for 20 h. The mixture was poured in water, extracted with EtOAc. The combined organic layers were washed with water, brine, dried over $Na_2SO_4$, concentrated and purified by flash column chromatography (EA:PE=0 to 100%) to give the title compound as a yellow oil.

Step 2: 3-(3,3,3-Trifluoropropyl)-3,8-diazabicyclo[3.2.1]octane

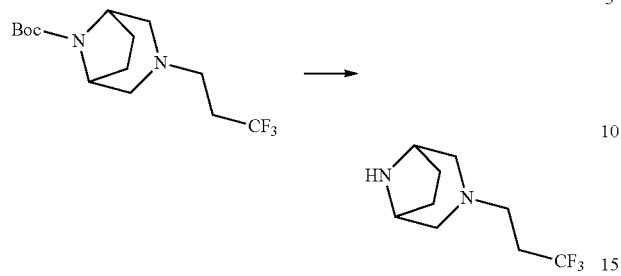

To a solution of tert-butyl 3-(3,3,3-trifluoropropyl)-3,8-diazabicyclo[3.2.1]octane-8-carboxylate (210 mg, 0.68 mmol, 1.0 eq) in EtOAc (1 mL) was added EtOAc/HCl (2M, 1 mL) and the mixture was stirred at r.t. for 2 h. The mixture was concentrated to give the title compound as a yellow solid.

Intermediate 25

Synthesis of 3-benzyl-3,8-diazabicyclo[3.2.1]octane

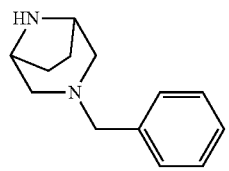 [SMILES: c1ccc(CN2CC3CCC(C2)N3)cc1]

The title compound was prepared by proceeding analogously as described in Intermediate 24, Step 1, using (bromomethyl)benzene instead of 1,1,1-trifluoro-3-iodopropane.

Intermediate 26

Synthesis of 3-cyclopropyl-3,8-diazabicyclo[3.2.1]octane

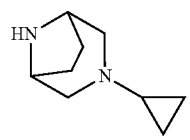 [SMILES: C1CC2CN(C3CC3)CC1N2]

Step 1: Tert-Butyl 3-cyclopropyl-3,8-diazabicyclo[3.2.1]octane-8-carboxylate

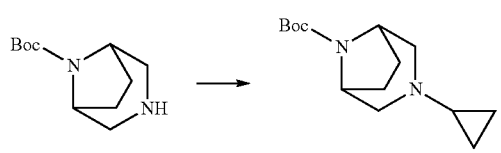 [SMILES: CC(C)(C)OC(=O)N1C2CCC1CNC2 ; CC(C)(C)OC(=O)N1C2CCC1CN(C1CC1)C2]

To a solution of tert-butyl 3,8-diazabicyclo[3.2.1]octane-8-carboxylate (500 mg, 2.36 mmol, 1.00 eq) in MeOH:THF=1:1 (10.0 mL) was added (1-ethoxycyclopropoxy)trimethylsilane (821 mg, 4.71 mmol, 2.00 eq), NaBH$_3$CN (223 mg, 3.54 mmol, 1.50 eq), AcOH (0.5 mL) and the mixture was stirred at r.t. overnight under N$_2$. The mixture was concentrated and purified by flash column chromatography (PE:EA=50:1 to 10:1) to give the title compound as a yellow liquid.

Step 2: 3-Cyclopropyl-3,8-diazabicyclo[3.2.1]octane

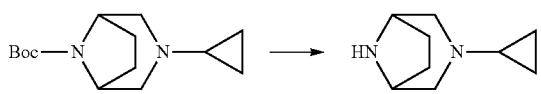 [SMILES: CC(C)(C)OC(=O)N1C2CCC1CN(C1CC1)C2 ; C1CC2CN(C3CC3)CC1N2]

To a solution of tert-butyl 3-cyclopropyl-3,8-diazabicyclo[3.2.1]octane-8-carboxylate (485 mg, 1.92 mmol, 1.00 eq) in EtOAc (3.0 mL) was added EtOAc/HCl (2M, 3.0 mL) and the mixture was stirred at r.t. for 2 hours under N$_2$. The mixture was concentrated to give the title compound as white solid.

Intermediate 27

Synthesis of 7-azabicyclo[2.2.1]heptane-1-carbonitrile

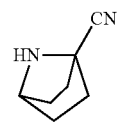

Step 1: Tert-Butyl 7-azabicyclo[2.2.1]heptane-7-carboxylate

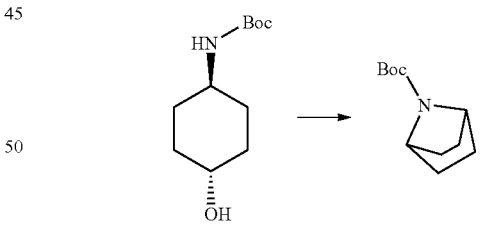

MsCl (9.58 g, 83.61 mmol, 1.50 eq) was added to a solution of tert-butyl ((1r,4r)-4-hydroxycyclohexyl)carbamate (12 g, 55.74 mmol, 1.00 eq) in DCM (200.0 mL) and TEA (8.46 g, 83.61 mmol, 1.50 eq) at 0° C. and the mixture was stirred for 1 h. The mixture was washed with water, brine, and the organic layer was dried over Na$_2$SO$_4$, concentrated to give the product. The resulting product was dissolved in THF (200.0 mL) followed by addition of t-BuOK (6.25 g, 55.74 mmol, 1.00 eq). After 2 h, additional t-BuOK (9.38 g, 83.61 mmol, 1.50 eq) was added and the mixture was stirred at r.t. overnight under N$_2$. The mixture was quenched by 1N HCl aq., extracted with EtOAc and the combined organic layers were washed with water, brine, dried over Na₂SO₄, concentrated. The residue was purified by flash column chromatography (PE:EA=50:1 to 10:1) to give the title compound as a yellow liquid.

Step 2: Tert-Butyl 1-formyl-7-azabicyclo[2.2.1]heptane-7-carboxylate

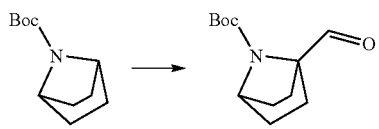 [SMILES: CC(C)(C)OC(=O)N1C2CCC1CC2 ; CC(C)(C)OC(=O)N1C2CCC1(C=O)CC2]

s-BuLi (2.9 mL, 3.80 mmol, 1.50 eq) was added to a solution of tert-butyl 7-azabicyclo-[2.2.1]heptane-7-carboxylate (500 mg, 2.53 mmol, 1.00 eq) and TMEDA (442 mg, 3.80 mmol, 1.50 eq) in Et₂O (5.0 mL) at 0° C. and the mixture was stirred for 1 h under N₂. DMF (370 mg, 5.07 mmol, 2.00 eq) was added and the mixture was stirred at r.t. for 20 h under N₂. The mixture was quenched by sat. NH₄Cl aq., extracted with EtOAc. The combined organic layers were washed with water, brine, dried over Na₂SO₄, concentrated, and the residue was purified by flash column chromatography (EA:PE=0 to 100%) to give the title compound as a yellow liquid.

Step 3: tert-Butyl 1-((hydroximino)methyl)-7-azabicyclo[2.2.1]heptane-7-carboxylate

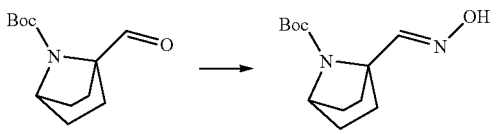 [SMILES: CC(C)(C)OC(=O)N1C2CCC1(C=O)CC2 ; CC(C)(C)OC(=O)N1C2CCC1(/C=N/O)CC2]

To a solution of tert-butyl 1-formyl-7-azabicyclo[2.2.1]heptane-7-carboxylate (1.30 g, 5.77 mmol, 1.00 eq) in MeOH:H₂O=1:1 (30.0 mL) was added NH₂OH HCl (0.48 g, 6.92 mmol, 1.20 eq) and Na₂CO₃ (0.37 g, 3.46 mmol, 0.60 eq) at r.t. and the mixture was stirred for 3 h. The mixture was poured into water, extracted with EtOAc. The combined organic layers were washed with water, brine, dried over Na₂SO₄, concentrated to give the title compound as a yellow oil.

Step 4: tert-Butyl 1-cyano-7-azabicyclo[2.2.1]heptane-7-carboxylate

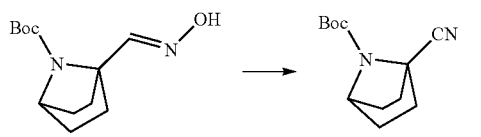 [SMILES: CC(C)(C)OC(=O)N1C2CCC1(/C=N/O)CC2 ; CC(C)(C)OC(=O)N1C2CCC1(C#N)CC2]

To a solution of tert-butyl 1-((hydroxyimino)methyl)-7-azabicyclo[2.2.1]heptane-7-carboxylate (1.39 g, 5.78 mmol, 1.00 eq) in MeCN (50.0 mL) was added Cu(OAc)₂·H₂O (23 mg, 0.12 mmol, 0.02 eq) and the mixture was stirred at 80° C. for 20 h under N₂. The mixture was concentrated and purified by flash column chromatography (EA:PE=0 to 100%) to give the title compound as a white solid.

Step 5: 7-Azabicyclo[2.2.1]heptane-1-carbonitrile

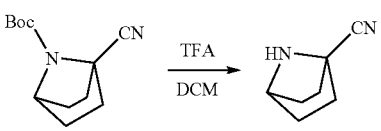 [SMILES: CC(C)(C)OC(=O)N1C2CCC1(C#N)CC2 ; N#CC12CCC(CC1)N2]

TFA (1.0 mL) was added to a solution of tert-butyl 1-cyano-7-azabicyclo[2.2.1]heptane-7-carboxylate (500 mg, 2.25 mmol, 1.00 eq) in DCM (5.0 mL) and the mixture was stirred at r.t. for 2 h. The mixture was concentrated and adjust pH to 8 to 9 by THF/NH₃, then it was concentrated to give the title compound as a yellow solid.

Intermediate 28

Synthesis of 3-(methyl-d3)-3,8-diazabicyclo[3.2.1]octane

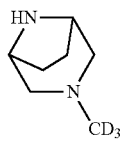

The title compound was prepared by proceeding analogously as described in Intermediate 24, Step 1, using iodomethane-d₃ instead of 1,1,1-trifluoro-3-iodopropane.

Intermediate 29

Synthesis of 2-(difluoromethyl)-6-fluorobenzenesulfonyl Chloride

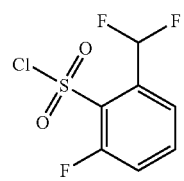 [SMILES: O=S(=O)(Cl)c1c(F)cccc1C(F)F]

Step 1: 2-(Benzylthio)-3-fluorobenzaldehyde

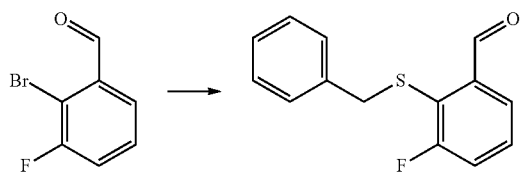 [SMILES: O=Cc1cccc(F)c1Br ; O=Cc1cccc(F)c1SCc1ccccc1]

A mixture of 2-bromo-3-fluorobenzaldehyde (200 mg, 0.99 mmol, 1.00 eq.), phenylmethanethiol (245 mg, 1.97 mmol, 2.00 eq.), Pd₂(dba)₃ (180 mg, 0.20 mmol, 0.20 eq.), XantPhos (114 mg, 0.20 mmol, 0.20 eq.) and DIEA (381 mg, 2.96 mmol, 3.00 eq.) in 1,4-dioxane (4.0 mL) was stirred at 90° C. under N₂ overnight. The mixture was concentrated and purified by column chromatography on silica gel (PE:EA=20:1) to give the title compound as a yellow oil.

Step 2: Benzyl (2-(difluoromethyl)-6-fluorophenyl)sulfane

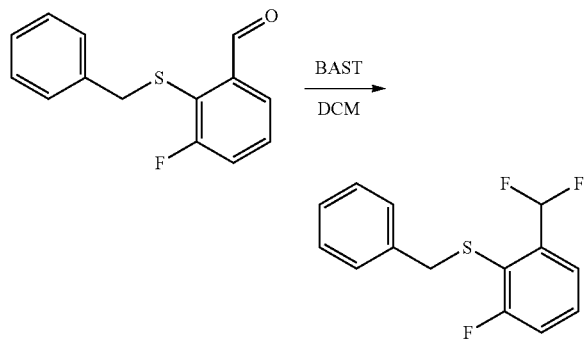

BAST (269 mg, 1.22 mmol, 1.50 eq.) was added to a mixture of 2-(benzylthio)-3-fluorobenzaldehyde (200 mg, 0.81 mmol, 1.00 eq.) in DCM (5.0 mL) portion-wise at 0° C. The mixture was stirred at r.t. under N₂ overnight and then quenched with sat. NaHCO₃, and diluted with DCM. The organic layer was washed with brine, dried over Na₂SO₄, concentrated. The residue was purified by column chromatography on silica gel (PE:EA=20:1) to give the title compound as a colorless oil.

Step 3: 2-(Difluoromethyl)-6-fluorobenzenesulfonyl Chloride

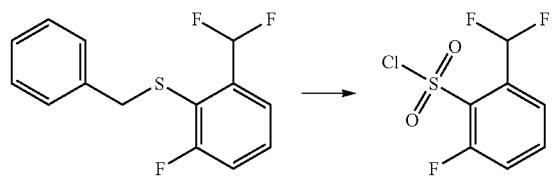 [SMILES: Fc1cccc(C(F)F)c1SCc1ccccc1 ; O=S(=O)(Cl)c1c(F)cccc1C(F)F]

A mixture of benzyl(2-(difluoromethyl)-6-fluorophenyl)sulfane (50 mg, 0.19 mmol, 1.00 eq.) in AcOH/H₂O (1.0 mL/0.4 mL) was added NCS (75 mg, 0.56 mmol, 3.00 eq.) at 0° C. This mixture was stirred at r.t for 3 h before H₂O was added. The mixture was extracted with EtOAc, and the combined organic layers were washed with brine, dried over Na₂SO₄, concentrated to give the crude product as a yellow oil.

Intermediate 30

Synthesis of 3-phenyl-3,8-diazabicyclo[3.2.1]octane

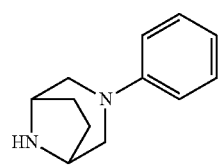 [SMILES: c1ccc(N2CC3CCC(C2)N3)cc1]

Step 1: Tert-Butyl 3-phenyl-3,8-diazabicyclo[3.2.1]octane-8-carboxylate

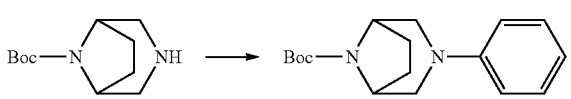

To a stirred solution of bromobenzene (100 mg, 0.637 mmol, 1.00 eq.) in toluene (2.0 mL) was added Pd₂(dba)₃ (29 mg, 0.03 mmol, 0.05 eq.), t-BuOK (214 mg, 1.89 mmol, 3.00 eq), BINAP (19.6 mg, 0.0637 mmol, 0.10 eq) and tert-butyl 3,8-diazabicyclo[3.2.1]octane-8-carboxylate (270 mg, 1.262 mmol, 2.00 eq). The resulting mixture was stirred at 100° C. for 12 h and then concentrated and purified by silica gel column chromatography eluting with PE/EtOAc (10:1) to give title compound as white solid.

Step 2: 3-Phenyl-3,8-diazabicyclo[3.2.1]octane

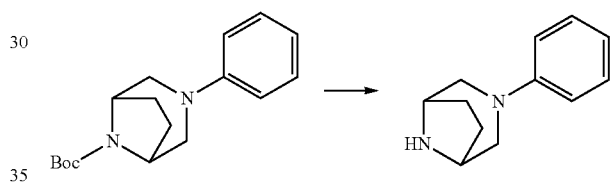

A mixture of tert-butyl 3-phenyl-3,8-diazabicyclo[3.2.1]octane-8-carboxylate (160 mg, 0.50 mmol, 1.00 eq.) in DCM/TFA=5:1 (2.0 mL) was stirred at room temperature for 2 h. The reaction mixture was concentrated to give the crude product as a white solid.

Intermediate 31

Synthesis of 8-(pyridin-2-yl)-3,8-diazabicyclo[3.2.1]octane

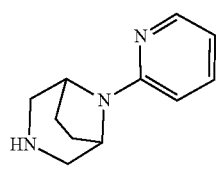 [SMILES: c1ccc(N2C3CCC2CNC3)nc1]

The title compound was prepared by proceeding analogously as described in Intermediate 30, Step 1, using tert-butyl 3,8-diazabicyclo[3.2.1]octane-3-carboxylate instead of tert-butyl 3,8-diazabicyclo[3.2.1]octane-8-carboxylate and 2-iodopyridine instead of bromobenzene.

Intermediate 32

Synthesis of 3-(pyridin-2-yl)-3,8-diazabicyclo[3.2.1]octane

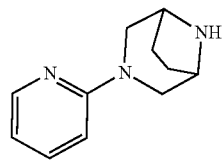 [SMILES: c1ccc(N2CC3CCC(C2)N3)nc1]

The title compound was prepared by proceeding analogously as described in Intermediate 30, Step 1 with 2-iodopyridine instead of bromobenzene.

Intermediate 33

Synthesis of N-(3-(2-bromo-2-(2-chloropyrimidin-4-yl)acetyl)-2-fluorophenyl)-2-chloro-6-(trifluoromethyl)benzenesulfonamide

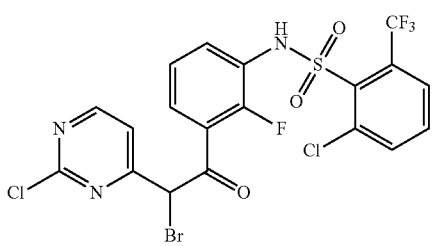

Step 1: 2-Chloro-6-(trifluoromethyl)benzene-1-sulfonyl Chloride

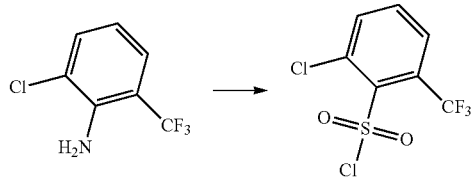 [SMILES: Nc1c(Cl)cccc1C(F)(F)F ; O=S(=O)(Cl)c1c(Cl)cccc1C(F)(F)F]

(Solution A): $SOC_2$ (12.20 g, 102.30 mmol, 4.00 eq.) was added slowly to water (50.0 ml) at 0° C. and the mixture was stirred at room temperature for 18 h under $N_2$. CuCl (100 mg, 0.04 mmol, 0.04 eq.) was added, and the resulting mixture was stirred at 0° C. for 1.5 h.

(Solution B): $NaNO_2$ (1.98 g, 28.70 mmol, 1.12 eq.) in water was added to a mixture of 2-chloro-6-(trifluoromethyl)aniline (5.00 g, 25.60 mmol, 1.00 eq.) in HCl (8.0 ml) and the mixture was stirred at 0° C. for 15 min.

Solution A was added to the solution B at 0° C. and the mixture was stirred at 0° C. for 1.5 h. The mixture was extracted with DCM, and the combined organic layers was washed with brine, dried over $NaSO_4$, concentrated. The residue was purified by silica gel column chromatography PE/EtOAc (3:1) to give the title compound as a yellow solid.

Step 2: Methyl 3-(2-chloro-6-(trifluoromethyl)phenylsulfonamido)-2-fluorobenzoate

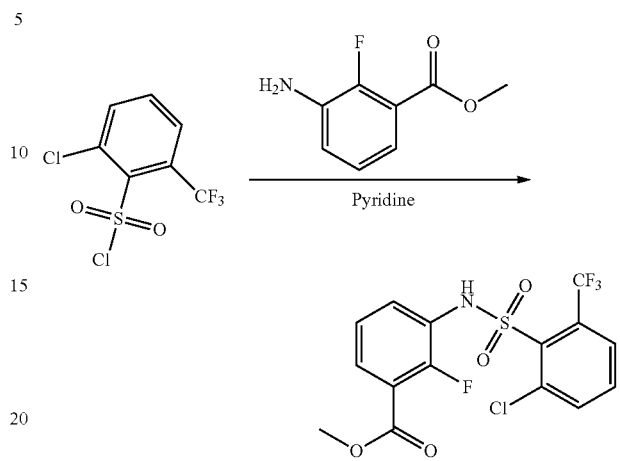

2-Chloro-6-(trifluoromethyl)benzene-1-sulfonyl chloride (500 mg, 1.80 mmol, 1.20 eq.) in DCM was added dropwise to a stirred solution of methyl 3-amino-2-fluorobenzoate (254 mg, 1.50 mmol, 1.00 eq.) and pyridine (356 mg, 4.50 mmol, 3.00 eq.) in DCM at 0° C. under $N_2$, and the resulting mixture was stirred at room temperature overnight under $N_2$. The mixture was diluted with water and exacted with DCM. The combined organic layer was washed with brine, dried over $NaSO_4$, concentrated and purified by silica gel column chromatography PE/EtOAc (3:1) to give the title compound as a yellow solid.

Step 3: 2-Chloro-N-(3-(2-(2-chloropyrimidin-4-yl)acetyl)-2-fluorophenyl)-6-(trifluoromethyl)-benzenesulfonamide

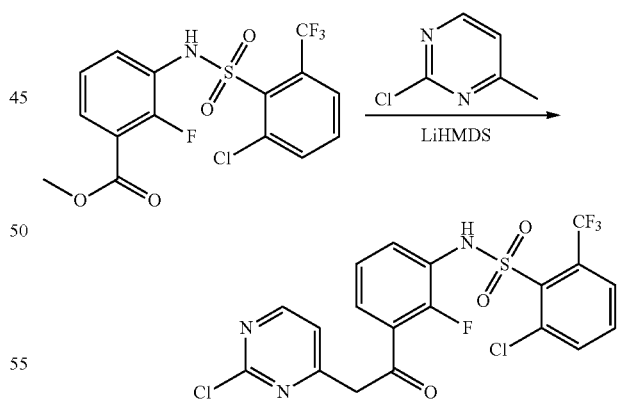

LiHMDS (1M in THF, 16.5 mL, 16.51 mmol, 3.00 eq.) was added to a stirred solution of methyl 3-(2-chloro-6-(trifluoromethyl)phenylsulfonamido)-2-fluorobenzoate (2.25 g, 5.47 mmol, 1.00 eq.) in THF (10.0 ml) at 0° C. A solution of 2-chloro-4-methylpyrimidine (911 mg, 7.12 mmol, 1.30 eq.) in THF (10.0 ml) was added dropwise to the mixture. After 1 h, the mixture was poured in aq. $NH_4Cl$, and exacted with EtOAc. The combined organic layers were washed with brine, dried over $NaSO_4$, concentrated and purified by silica gel column chromatography PE/EtOAc (1:1) to give the title compound as yellow solid.

Step 4: N-(3-(2-bromo-2-(2-chloropyrimidin-4-yl) acetyl)-2-fluorophenyl)-2-chloro-6-(trifluoromethyl)benzenesulfonamide

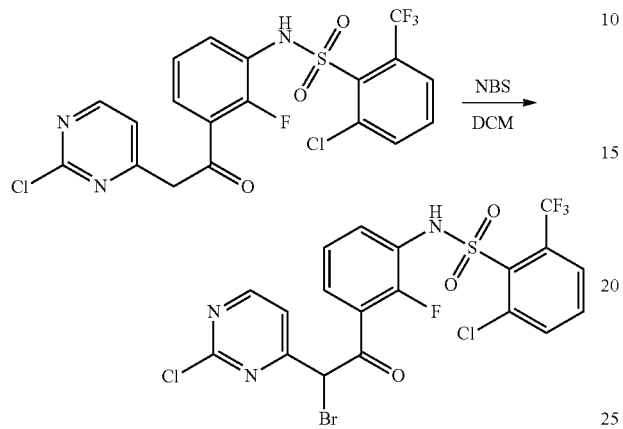

To a stirred solution of 2-chloro-N-(3-(2-(2-chloropyrimidin-4-yl)acetyl)-2-fluorophenyl)-6-(trifluoromethyl)benzenesulfonamide (1.78 g, 3.48 mmol, 1.00 eq.) in DCM was added NBS (411 mg, 3.48 mmol, 1.00 eq.). The mixture was stirred at room temperature for 3 h under N₂ and then poured into water and extracted with DCM. The combined organic layers were dried over NaSO₄, concentrated and purified by silica gel column chromatography PE/EtOAc (1:1) to give the title compound as a yellow solid.

Intermediate 34

Synthesis of 4-methyl-4-(methylsulfonyl)cyclohexan-1-amine Hydrochloride

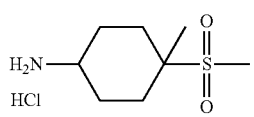

Step 1: Tert-Butyl (4-hydroxy-4-methylcyclohexyl)carbamate

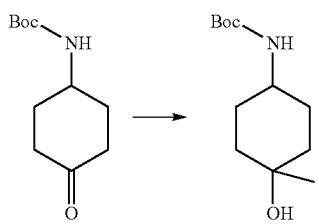 [SMILES: CC(C)(C)OC(=O)NC1CCC(=O)CC1 ; CC1(O)CCC(NC(=O)OC(C)(C)C)CC1]

To a stirred solution of tert-butyl (4-oxocyclohexyl)carbamate (25.00 g, 0.12 mmol, 1.00 eq.) in THF (500.0 mL) was added CH₃MgBr (117 mL, 0.35 mmol, 3.00 eq.) at −78° C. and the mixture was stirred at r.t. 20 h under N₂. The mixture was poured into sat. NH₄Cl aq., and the mixture was extracted with EtOAc, washed with brine. The organic layer was concentrated and purified by silica gel column chromatography eluting with (EA:PE=0 to 100%) to give title compound as a pale yellow solid.

Step 2: 4-((tert-Butoxycarbonyl)amino)-1-methylcyclohexyl Methanesulfonate

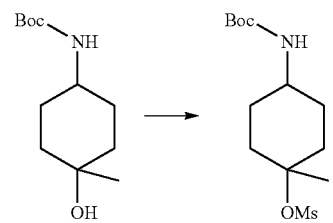 [SMILES: CC1(O)CCC(NC(=O)OC(C)(C)C)CC1 ; CC(C)(C)OC(=O)NC1CCC(C)(OS(C)(=O)=O)CC1]

To a stirred solution of tert-butyl (4-hydroxy-4-methylcyclohexyl)carbamate (8.20 g, 35.81 mmol, 1.00 eq.) in DCM (100.0 mL) was added TEA (15.0 mL, 107.42 mmol, 3.00 eq.), MsCl (3.3 mL, 42.97 mmol, 1.20 eq.) at 0° C. The resulting mixture was stirred at RT for 16 h, and the mixture was washed with brine. The organic layer was dried over Na₂SO₄ and concentrated to give the title compound as yellow solid.

Step 3: Tert-Butyl (4-methyl-4-(methylthio)cyclohexyl)carbamate

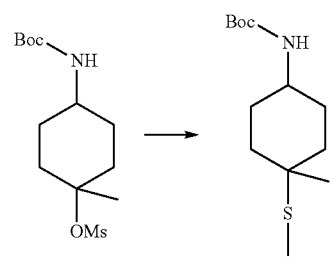 [SMILES: CC(C)(C)OC(=O)NC1CCC(C)(OS(C)(=O)=O)CC1 ; CSC1(C)CCC(NC(=O)OC(C)(C)C)CC1]

To a stirred solution of 4-((tert-butoxycarbonyl)amino)-1-methylcyclohexyl methanesulfonate (11.00 g, 35.83 mmol, 1.00 eq.) in DMF (100.0 mL) was added NaSCH₃ (5.02 g, 71.66 mmol, 2.00 eq.). The reaction mixture was stirred at RT 16 h, and the mixture was quenched with H₂O and then extracted with EtOAc. The organic layer was washed with brine, dried over Na₂SO₄ and concentrated and purified by reverse phase column chromatography to give the title compound as white solid.

211

Step 4: Tert-Butyl (4-methyl-4-(methylsulfonyl)cyclohexyl)carbamate

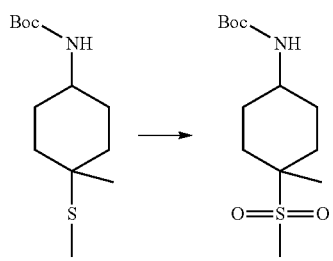 [SMILES: CSC1(C)CCC(NC(=O)OC(C)(C)C)CC1 ; CC(C)(C)OC(=O)NC1CCC(C)(S(C)(=O)=O)CC1]

To a stirred solution of tert-butyl (4-methyl-4-(methylthio)cyclohexyl)carbamate (500 mg, 1.93 mmol, 1.00 eq.) in MeOH:THF:H$_2$O=2:2:1 (20.0 mL) was added oxone (2.37 g, 3.86 mmol, 2.00 eq.). The mixture was stirred at RT 16 h, and the mixture was diluted with water and extracted with DCM. The combined organic layer was washed with brine, and dried over Na$_2$SO$_4$. The organic layer was concentrated to give the title compound as a pale yellow solid.

Step 5: 4-Methyl-4-(methylsulfonyl)cyclohexan-1-amine Hydrochloride

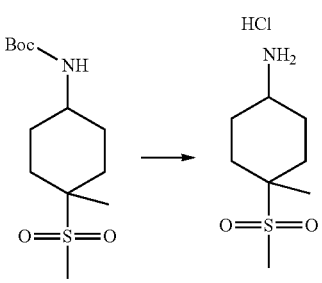 [SMILES: Cl ; CC(C)(C)OC(=O)NC1CCC(C)(S(C)(=O)=O)CC1 ; CC1(S(C)(=O)=O)CCC(N)CC1]

To a stirred solution of tert-butyl (4-methyl-4-(methylsulfonyl)cyclohexyl)carbamate (380 mg, 1.31 mmol, 1.00 eq.) in EA (2.0 mL) was added EA/HCl (2M, 2.0 mL) and stirred 2 h at r.t. under nitrogen atmosphere. The resulting mixture was concentrated to afford the title compound as a white solid.

212

Example 1

Synthesis of N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide

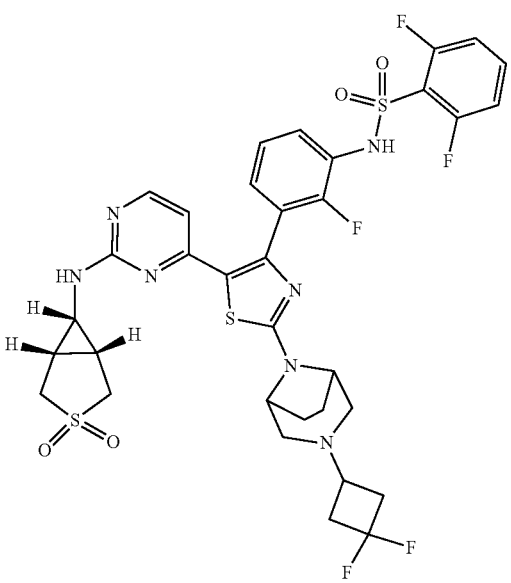 [SMILES: O=S1(=O)C[C@@H]2[C@H](C1)[C@@H]2Nc1nccc(-c2sc(N3C4CCC3CN(C3CC(F)(F)C3)C4)nc2-c2cccc(NS(=O)(=O)c3c(F)cccc3F)c2F)n1]

Step 1: Tert-Butyl (1R,5S)-8-(benzoylcarbamothioyl)-3,8-diazabicyclo[3.2.1]octane-3-carboxylate

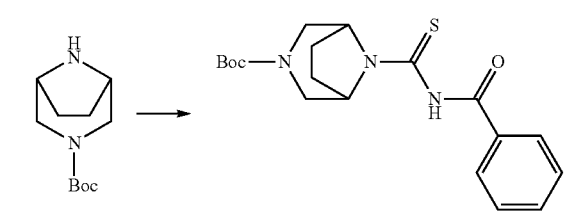 [SMILES: CC(C)(C)OC(=O)N1CC2CCC(C1)N2 ; CC(C)(C)OC(=O)N1CC2CCC(C1)N2C(=S)NC(=O)c1ccccc1]

Benzoyl isothiocyanate (169 mg, 1.03 mmol, 1.10 eq.) was added to a mixture of tert-butyl (1R,5S)-3,8-diazabicyclo[3.2.1]octane-3-carboxylate (200 mg, 0.94 mmol, 1.00 eq.) in THF (5.0 mL) and the mixture was stirred at r.t. under N$_2$ overnight. The mixture was concentrated and purified by column chromatography on silica gel (PE:EA=5:1) to give the title compound as a white solid.

Step 2: Tert-Butyl (1R,5S)-8-carbamothioyl-3,8-diazabicyclo[3.2.1]octane-3-carboxylate

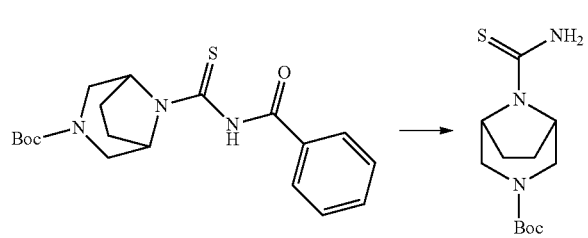 [SMILES: CC(C)(C)OC(=O)N1CC2CCC(C1)N2C(=S)NC(=O)c1ccccc1 ; CC(C)(C)OC(=O)N1CC2CCC(C1)N2C(N)=S]

A mixture of tert-butyl (1R,5S)-8-(benzoylcarbamothioyl)-3,8-diazabicyclo[3.2.1]octane-3-carboxylate (300 mg, 0.80 mmol, 1.00 eq.) and $N_2H_4$ (80%, 5.0 mL) was stirred at r.t. under $N_2$ overnight. Water was added, and the mixture was extracted with DCM. The combined organic layers were washed with brine, dried over $Na_2SO_4$, concentrated and purified by column chromatography on silica gel (PE:EA=1:1) to give the title compound as a white solid.

Step 3: Tert-Butyl 8-(5-(2-chloropyrimidin-4-yl)-4-(3-((2,6-difluorophenyl)sulfonamido)-2-fluorophenyl)thiazol-2-yl)-3,8-diazabicyclo[3.2.1]octane-3-carboxylate

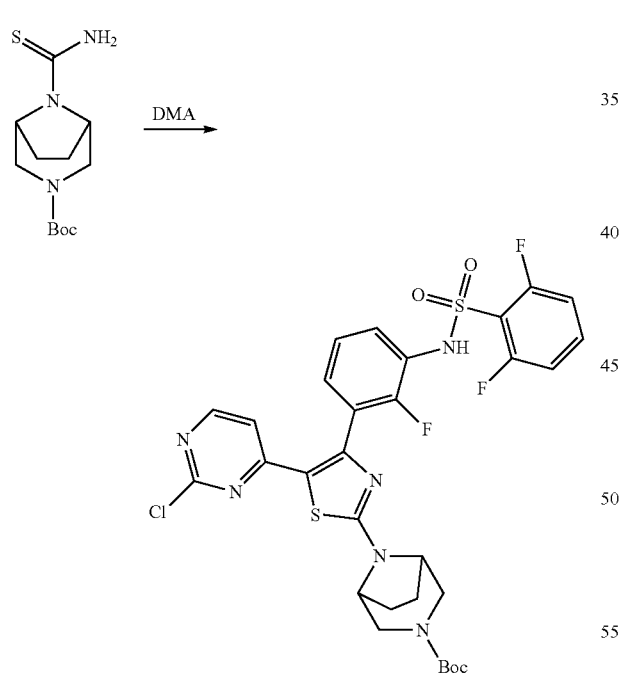

A mixture of N-(3-(2-bromo-2-(2-chloropyrimidin-4-yl)acetyl)-2-fluorophenyl)-2,6-difluorobenzenesulfonamide (Intermediate 9; 384 mg, 0.74 mmol, 1.00 eq.) and tert-butyl (1R,5S)-8-carbamothioyl-3,8-diazabicyclo[3.2.1]octane-3-carboxylate (200 mg, 0.74 mmol, 1.00 eq.) in DMA (5.0 mL) was stirred at r.t. for 30 min and then at 65° C. under $N_2$ overnight. The mixture was concentrated and purified by column chromatography on silica gel (PE:EA=2:1) to give the title compound as a yellow solid.

Step 4: N-(3-(2-(3,8-Diazabicyclo[3.2.1]octan-8-yl)-5-(2-chloropyrimidin-4-yl)thiazol-4-yl)-2-fluorophenyl)-2,6-difluorobenzenesulfonamide

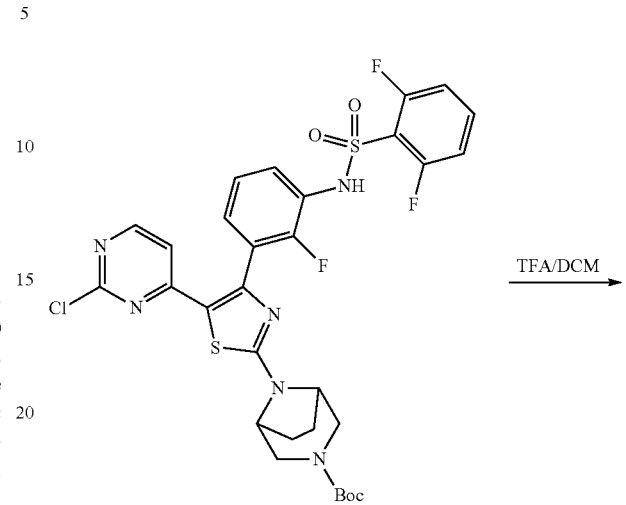

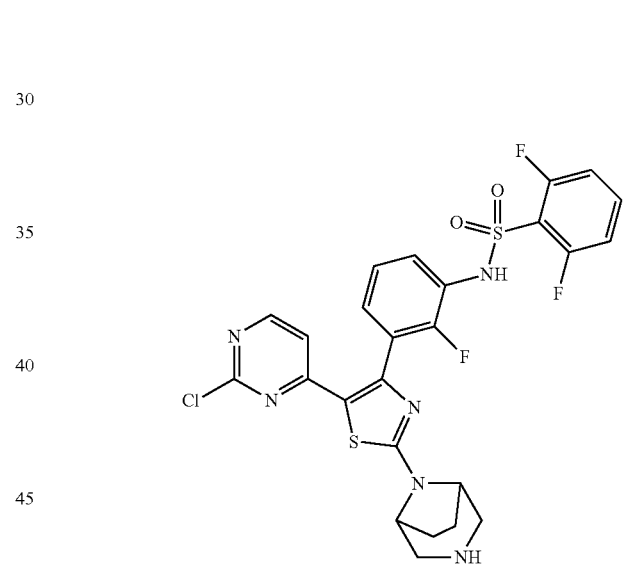

A mixture of tert-butyl 8-(5-(2-chloropyrimidin-4-yl)-4-(3-((2,6-difluorophenyl)-sulfonamido)-2-fluorophenyl)thiazol-2-yl)-3,8-diazabicyclo[3.2.1]octane-3-carboxylate (400 mg, 0.58 mmol, 1.00 eq.) and TFA (4.0 mL) in DCM (10.0 mL) was stirred at 0° C. for 2 h. The mixture was concentrated to give the crude product as a yellow oil.

Step 5: N-(3-(5-(2-Chloropyrimidin-4-yl)-2-(3-(3,3-difluorocyclobutyl)-3,8-diazabicyclo-[3.2.1]octan-8-yl)thiazol-4-yl)-2-fluorophenyl)-2,6-difluorobenzenesulfonamide

Step 6: N-(3-(2-(3-(3,3-Difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide

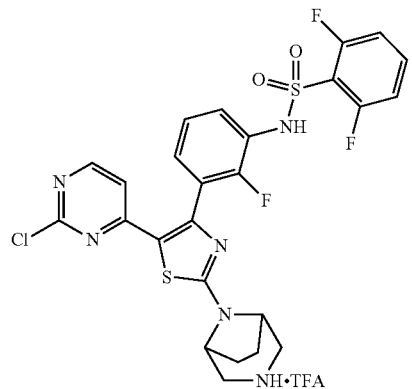
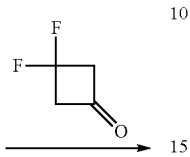
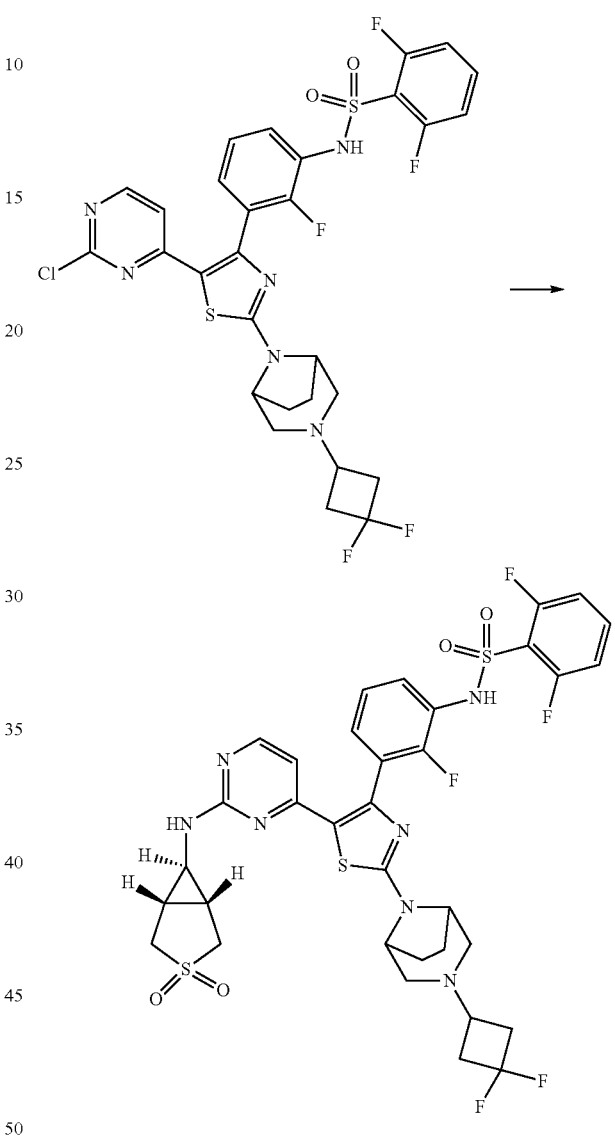

3,3-Difluorocyclobutan-1-one (162 mg, 1.53 mmol, 3.00 eq.) was added to a solution of N-(3-(2-(3,8-diazabicyclo[3.2.1]octan-8-yl)-5-(2-chloropyrimidin-4-yl)thiazol-4-yl)-2-fluorophenyl)-2,6-difluorobenzenesulfonamide (300 mg, 0.51 mmol, 1.00 eq.) in DCE/MeOH (1:1, 6.0 mL) and the mixture was stirred at r.t. under $N_2$ for 1 h. $NaBH_3CN$ (163 mg, 2.55 mmol, 5.00 eq.) was added at 0° C. and the mixture was stirred at r.t. overnight. The mixture was concentrated and purified by column chromatography on silica gel (PE:EA=2:1) to give the title compound as a yellow solid.

A mixture of N-(3-(5-(2-chloropyrimidin-4-yl)-2-(3-(3,3-difluorocyclobutyl)-3,8-diazabicyclo[3.2.1]octan-8-yl)thiazol-4-yl)-2-fluorophenyl)-2,6-difluorobenzenesulfonamide (60 mg, 0.09 mmol, 1.00 eq.), (1R,5S,6r)-6-amino-3-thiabicyclo[3.1.0]hexane 3,3-dioxide (Intermediate 3; 19 mg, 0.13 mmol, 1.50 eq.), RuPhos (20 mg), RuPhos Pd G2 (20 mg) and $Cs_2CO_3$ (86 mg, 0.26 mmol, 3.00 eq) in t-BuOH (1.0 mL) was stirred at 90° C. under $N_2$ overnight. The mixture was concentrated and purified by prep-HPLC to give the title compound as a yellow solid. LCMS (ES, m/z): $[M+1]^+$=794.3.

Proceeding analogously as described in Example 1, the following compounds were prepared.

| Ex # | Structures | Changes in synthetic protocol | LCMS (ES, m/z): [M + 1]+ |
|---|---|---|---|
| 2 | 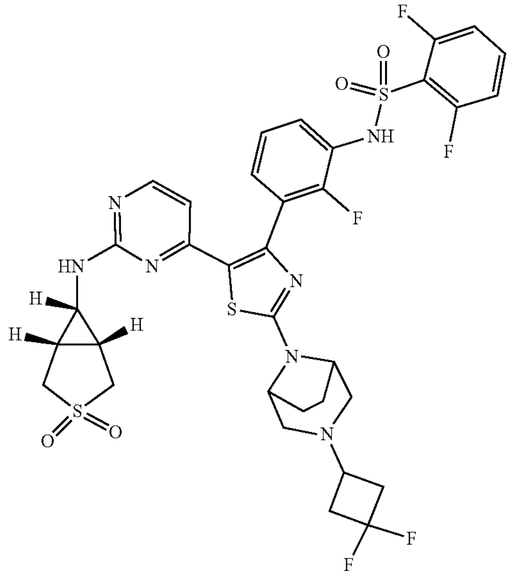 [SMILES: O=S1(=O)C[C@@H]2[C@H](C1)[C@@H]2Nc1nccc(-c2sc(N3C4CCC3CN(C3CC(F)(F)C3)C4)nc2-c2cccc(NS(=O)(=O)c3c(F)cccc3F)c2F)n1] | Intermediate 3 replaced by Intermediate 2 in Step 6. | 794.3 |
| 3 | 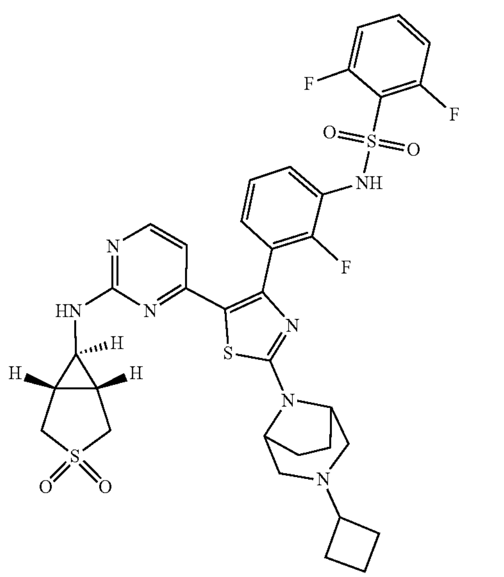 [SMILES: O=S1(=O)C[C@@H]2[C@H](C1)[C@H]2Nc1nccc(-c2sc(N3C4CCC3CN(C3CCC3)C4)nc2-c2cccc(NS(=O)(=O)c3c(F)cccc3F)c2F)n1] | 3,3-difluorocyclobutan-1-one replaced by cyclobutanone in Step 5. | 758.2 |
| 4 | 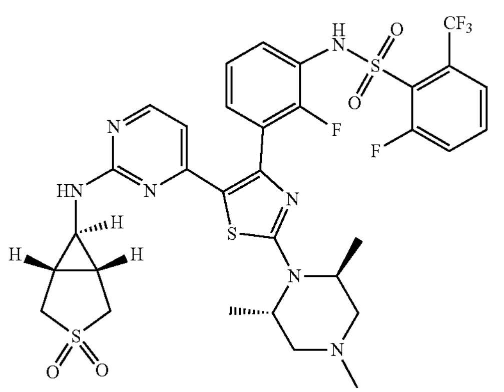 [SMILES: C[C@H]1CN(C)C[C@H](C)N1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1] | 1. tert-butyl (1R,5S)-3,8-diazabicyclo-[3.2.1]octane-3-carboxylate replaced by tert-butyl (3S,5S)-3,5-dimethylpiperazine-1-carboxylate in Step 1.<br>2. Intermediate 9 replaced by Intermediate 8 in Step 3.<br>3. 3,3-difluorocyclobutan-1-one replaced by formaldehyde in Step 5. | 770.2 |

Example 5

Synthesis of N-(3-(2-((3R,5R)-3,5-dimethylmorpholino)-5-(2-(((2,2-dioxido-2-thiaspiro[3.3]heptan-6-yl)amino)pyrimidin-4-yl)thiazol-4-yl)-2-fluorophenyl)-2,6-difluorobenzenesulfonamide

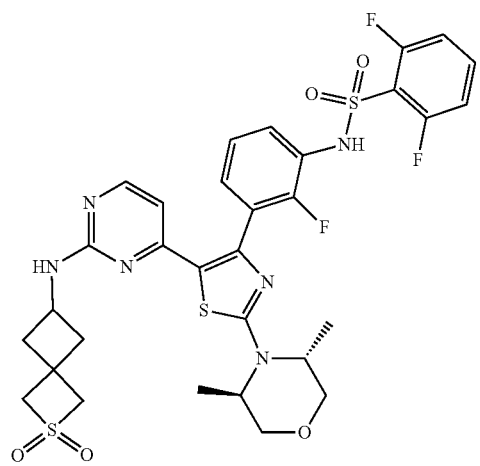 [SMILES: C[C@@H]1COC[C@@H](C)N1c1nc(-c2cccc(NS(=O)(=O)c3c(F)cccc3F)c2F)c(-c2ccnc(NC3CC4(C3)CS(=O)(=O)C4)n2)s1]

Step 1: N-((3R,5R)-3,5-dimethylmorpholine-4-carbonothioyl)benzamide

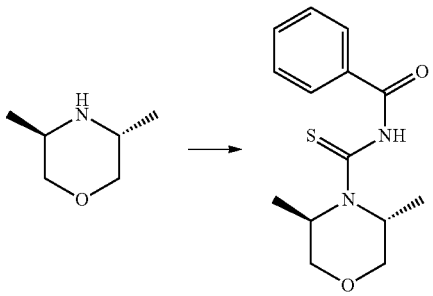

To a stirred solution of (3R,5R)-3,5-dimethylmorpholine (500 mg, 4.34 mmol, 1.00 eq.) in THF (10.0 mL) was added benzoyl isothiocyanate (708 mg, 4.34 mmol, 1.00 eq.), and the mixture was stirred at rt overnight. The reaction mixture was concentrated and purified by silica gel chromatography (EA:PE=1:5) to give the title compound as a white solid.

Step 2: (3R,5R)-3,5-dimethylmorpholine-4-carbothioamide

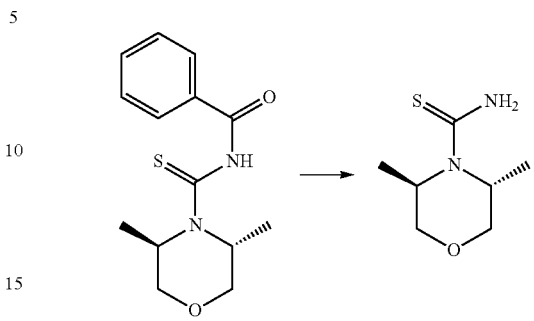

A mixture of N-((3R,5R)-3,5-dimethylmorpholine-4-carbonothioyl)benzamide (975 mg, 3.50 mmol, 1.00 eq.) and $N_2H_4 \cdot H_2O$ (15.0 mL) was stirred at rt overnight. The mixture was diluted with DCM and washed with 10% citric acid, and the organic layer was washed with brine, dried over $Na_2SO_4$, concentrated and purified by silica gel chromatography (EA:PE=1:1) to give the title compound as a white solid.

Step 3: N-(3-(5-(2-chloropyrimidin-4-yl)-2-((3R,5R)-3,5-dimethylmorpholino)thiazol-4-yl)-2-fluorophenyl)-2,6-difluorobenzenesulfonamide

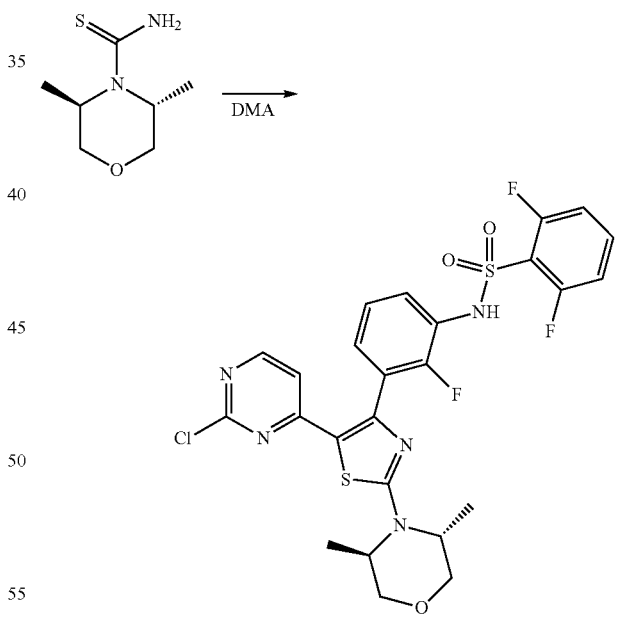

A mixture of N-(3-(2-bromo-2-(2-chloropyrimidin-4-yl)acetyl)-2-fluorophenyl)-2,6-difluorobenzenesulfonamide (Intermediate 9; 449 mg, 0.86 mmol, 1.00 eq.), (3R,5R)-3,5-dimethylmorpholine-4-carbothioamide (150 mg, 0.86 mmol, 1.00 eq.) in DMA (10.0 mL) was stirred at 70° C. under $N_2$ overnight. The reaction mixture was extracted with EtOAc, and the combined organic layer was washed with brine, dried over $Na_2SO_4$, concentrated and purified by flash chromatography to give the title compound as a yellow solid.

Step 4: N-(3-(2-((3R,5R)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

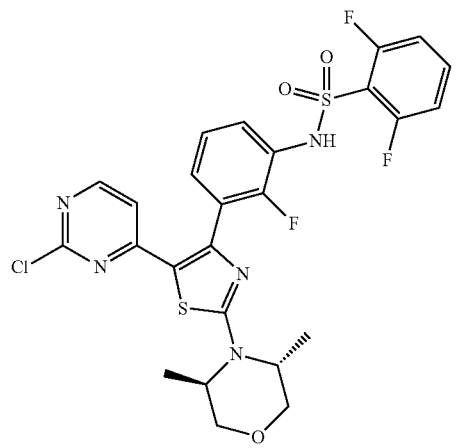

-continued

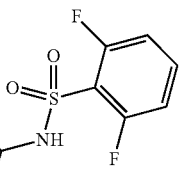

A mixture of N-(3-(5-(2-chloropyrimidin-4-yl)-2-((3R,5R)-3,5-dimethylmorpholino)-thiazol-4-yl)-2-fluorophenyl)-2,6-difluorobenzenesulfonamide (200 mg, 0.34 mmol, 1.00 eq.), 6-amino-2-thiaspiro[3.3]heptane 2,2-dioxide hydrochloride (Intermediate 6, 79 mg, 0.40 mmol, 1.20 eq.), $Cs_2CO_3$ (552 mg, 1.70 mmol, 5.00 eq.), RuPhos (20 mg), RuPhos Pd G2 (20 mg) in t-BuOH (5.0 mL) was stirred at 90° C. under $N_2$ overnight. The reaction mixture was extracted with EtOAc, and the combined organic layer was washed with brine, dried over $Na_2SO_4$, concentrated and purified by silica gel chromatography (PE:EA=1:1) to give the title compound as a yellow solid. MS (ES, m/z): $[M+1]^+=721.3$ Proceeding analogously as described in Example 5, the following compounds were prepared.

| Ex # | Structures | Changes in synthetic protocol | LCMS (ES, m/z): $[M + 1]^+$ |
|---|---|---|---|
| 6 | 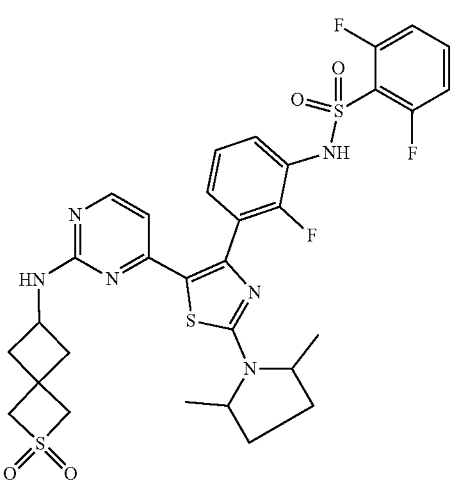 [SMILES: CC1CCC(C)N1c1nc(-c2cccc(NS(=O)(=O)c3c(F)cccc3F)c2F)c(-c2ccnc(NC3CC4(C3)CS(=O)(=O)C4)n2)s1] | (3R,5R)-3,5-dimethylmorpholine replaced by 2,5-dimethylpyrrolidine in Step 1. | 705.3 |

| Ex # | Structures | Changes in synthetic protocol | LCMS (ES, m/z): [M + 1]+ |
|---|---|---|---|
| 7 | 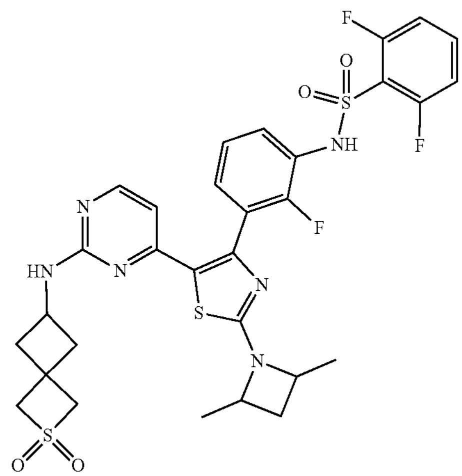 [SMILES: CC1CC(C)N1c1nc(-c2cccc(NS(=O)(=O)c3c(F)cccc3F)c2F)c(-c2ccnc(NC3CC4(C3)CS(=O)(=O)C4)n2)s1] | (3R,5R)-3,5-dimethylmorpholine replaced by 2,4-dimethylazetidine in Step 1. | 691.1 |
| 8 | 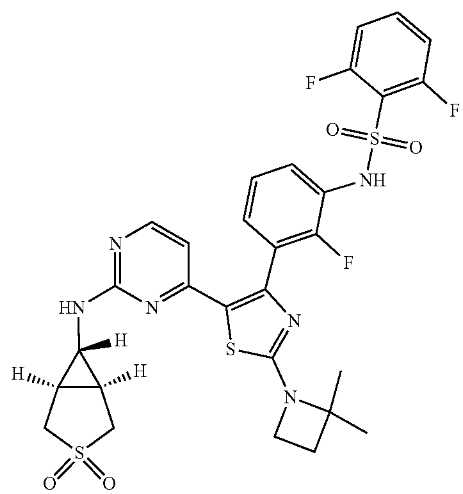 [SMILES: CC1(C)CCN1c1nc(-c2cccc(NS(=O)(=O)c3c(F)cccc3F)c2F)c(-c2ccnc(N[C@H]3[C@@H]4CS(=O)(=O)C[C@@H]43)n2)s1] | 1. (3R,5R)-3,5-dimethylmorpholine replaced by 2,2-dimethylazetidine in Step 1.<br>2. Intermediate 6 replaced by Intermediate 3 in Step 4. | 677.2 |
| 9 | 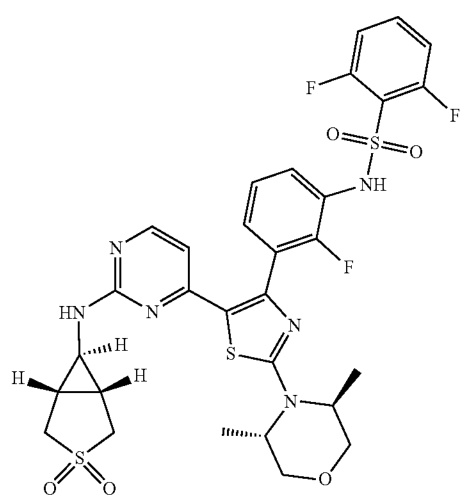 [SMILES: C[C@H]1COC[C@H](C)N1c1nc(-c2cccc(NS(=O)(=O)c3c(F)cccc3F)c2F)c(-c2ccnc(N[C@H]3[C@@H]4CS(=O)(=O)C[C@@H]43)n2)s1] | 1. (3R,5R)-3,5-dimethylmorpholine replaced by (3S,5S)-3,5-dimethylmorpholine in Step 1.<br>2. Intermediate 6 replaced by Intermediate 3 in Step 4. | 707.2 |

| Ex # | Structures | Changes in synthetic protocol | LCMS (ES, m/z): [M + 1]+ |
|---|---|---|---|
| 10 | 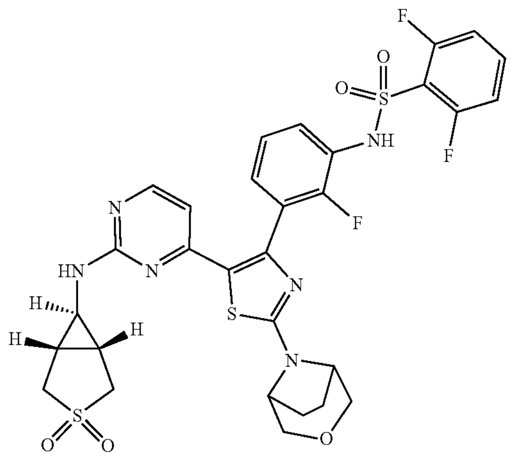 [SMILES: O=S1(=O)C[C@@H]2[C@H](C1)[C@H]2Nc1nccc(-c2sc(N3C4CCC3COC4)nc2-c2cccc(NS(=O)(=O)c3c(F)cccc3F)c2F)n1] | 1. (3R,5R)-3,5-dimethylmorpholine replaced by 3-oxa-8-azabicyclo-[3.2.1]octane in Step 1.<br>2. Intermediate 6 replaced by Intermediate 3 in Step 4. | 705.1 |
| 11 | 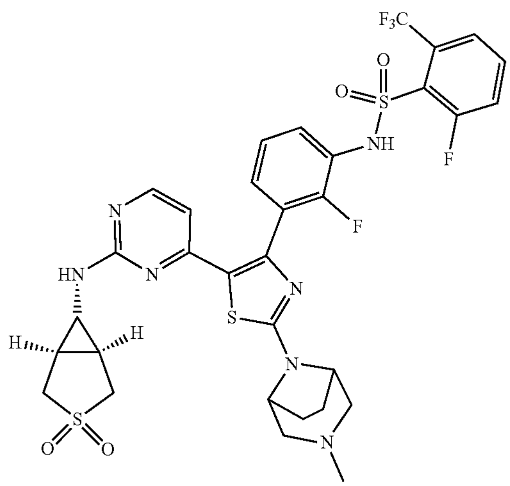 | 1. (3R,5R)-3,5-dimethylmorpholine replaced by 3-methyl-3,8-diazabicyclo[3.2.1]octane in Step 1.<br>2. Intermediate 9 was replaced by Intermediate 8 in Step 3.<br>3. Intermediate 6 replaced by Intermediate 3 in Step 4. | 768.3 |
| 12 | 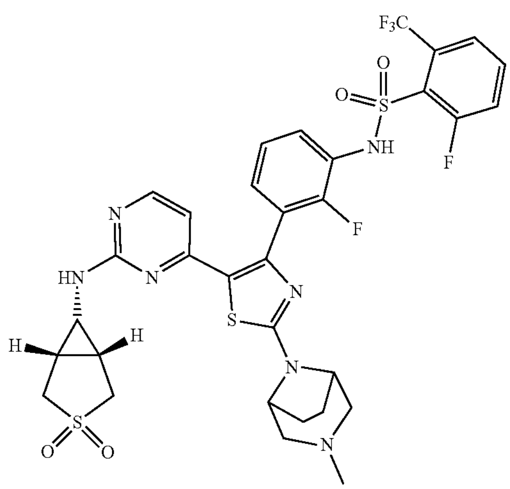 | 1. (3R,5R)-3,5-dimethylmorpholine replaced by 3-methyl-3,8-diazabicyclo[3.2.1]octane in Step 1.<br>2. Intermediate 9 was replaced by Intermediate 8 in Step 3.<br>3. Intermediate 6 replaced by Intermediate 2 in Step 4. | 768.3 |

| Ex # | Structures | Changes in synthetic protocol | LCMS (ES, m/z): [M + 1]+ |
|---|---|---|---|
| 13 | 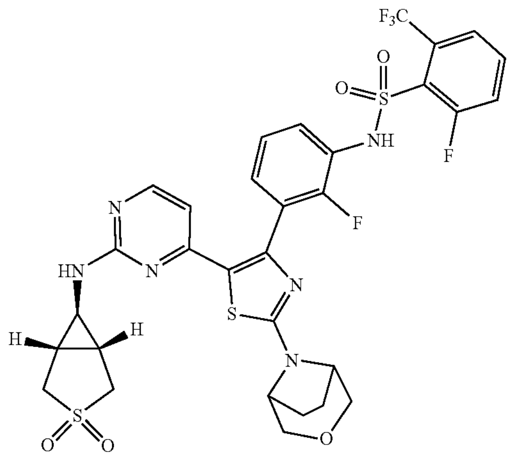 [SMILES: O=S1(=O)C[C@@H]2[C@H](C1)[C@H]2Nc1nccc(-c2sc(N3C4CCC3COC4)nc2-c2cccc(NS(=O)(=O)c3c(F)cccc3C(F)(F)F)c2F)n1] | 1. (3R,5R)-3,5-dimethylmorpholine replaced by 3-oxa-8-azabicyclo[3.2.1]octane in Step 1.<br>2. Intermediate 9 was replaced by Intermediate 8 in Step 3.<br>3. Intermediate 6 replaced by Intermediate 3 in Step 4. | 755.2 |
| 14 | 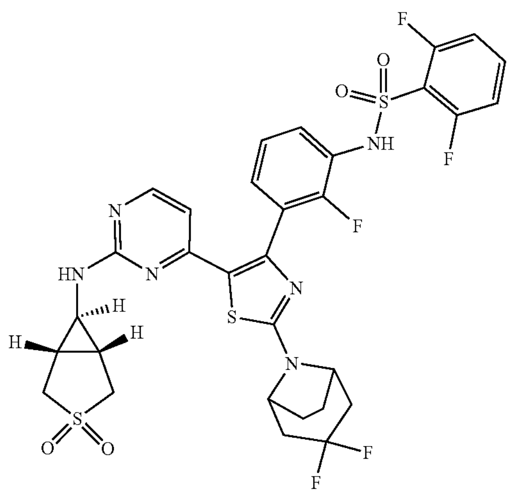 [SMILES: O=S1(=O)C[C@@H]2[C@H](C1)[C@H]2Nc1nccc(-c2sc(N3C4CCC3CC(F)(F)C4)nc2-c2cccc(NS(=O)(=O)c3c(F)cccc3F)c2F)n1] | 1. (3R,5R)-3,5-dimethylmorpholine replaced by 3,3-difluoro-8-azabicyclo[3.2.1]octane in Step 1.<br>2. Intermediate 6 replaced by Intermediate 3 in Step 4. | 739.2 |
| 15 | 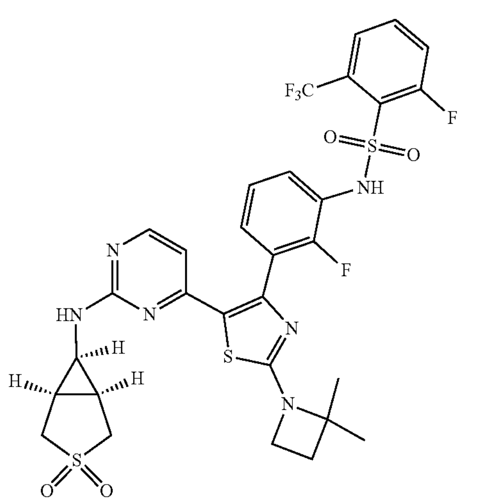 [SMILES: CC1(C)CCN1c1nc(-c2cccc(NS(=O)(=O)c3c(F)cccc3C(F)(F)F)c2F)c(-c2ccnc(N[C@@H]3[C@@H]4CS(=O)(=O)C[C@@H]43)n2)s1] | 1. (3R,5R)-3,5-dimethylmorpholine replaced by 2,2-dimethylazetidine in Step 1.<br>2. Intermediate 9 was replaced by Intermediate 8 in Step 3.<br>3. Intermediate 6 replaced by Intermediate 2 in Step 4. | 727.2 |

| Ex # | Structures | Changes in synthetic protocol | LCMS (ES, m/z): [M + 1]+ |
|---|---|---|---|
| 16 | 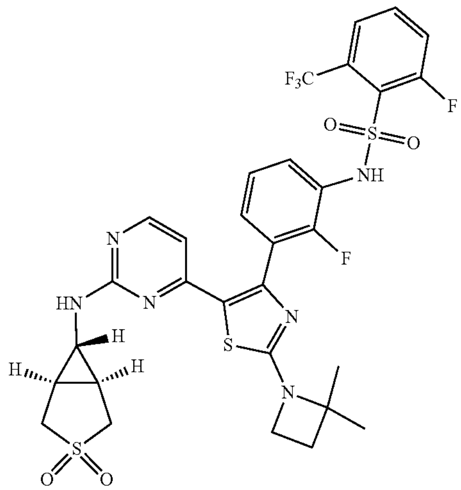 [SMILES: CC1(C)CCN1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1] | 1. (3R,5R)-3,5-dimethylmorpholine replaced by 2,2-dimethylazetidine in Step 1.<br>2. Intermediate 9 was replaced by Intermediate 8 in Step 3.<br>3. Intermediate 6 replaced by Intermediate 3 in Step 4. | 727.2 |
| 17 | 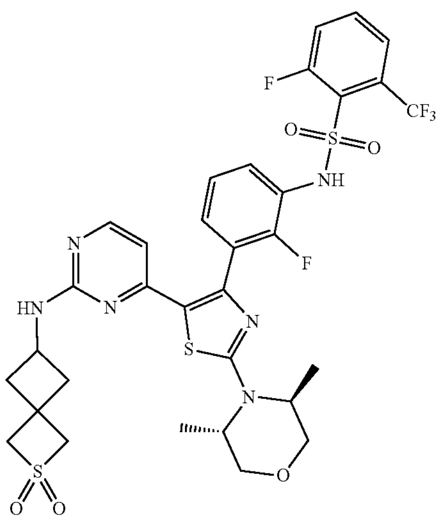 [SMILES: C[C@H]1COC[C@H](C)N1c1nc(-c2cccc(NS(=O)(=O)c3c(F)cccc3C(F)(F)F)c2F)c(-c2ccnc(NC3CC4(C3)CS(=O)(=O)C4)n2)s1] | 1. (3R,5R)-3,5-dimethylmorpholine replaced by (3S,5S)-3,5-dimethylmorpholine in Step 1.<br>2. Intermediate 9 was replaced by Intermediate 8 in Step 3. | 770.9 |
| 18 | 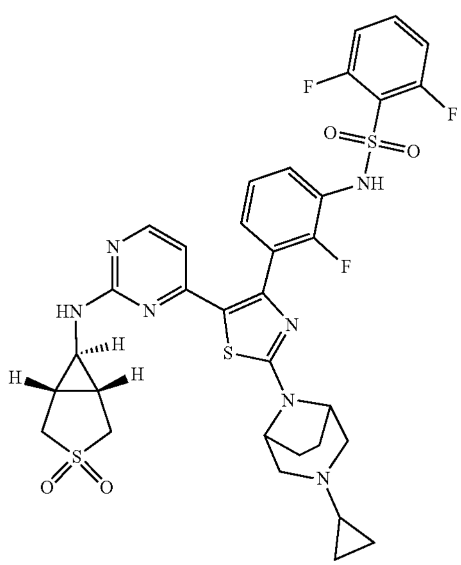 [SMILES: O=S1(=O)C[C@@H]2[C@H](C1)[C@H]2Nc1nccc(-c2sc(N3C4CCC3CN(C3CC3)C4)nc2-c2cccc(NS(=O)(=O)c3c(F)cccc3F)c2F)n1] | 1. (3R,5R)-3,5-dimethylmorpholine replaced by Intermediate 26 in Step 1.<br>2. Intermediate 6 replaced by Intermediate 3 in Step 4. | 744.1 |

| Ex # | Structures | Changes in synthetic protocol | LCMS (ES, m/z): [M + 1]+ |
|---|---|---|---|
| 19 | (structure) | 1. (3R,5R)-3,5-dimethylmorpholine replaced by Intermediate 27 in Step 1. | 728.1 |

Additional compound prepared by proceeding analogously as described in Example 5, are:

| Ex # | Structures | Changes in synthetic protocol | LCMS (ES, m/z): [M + 1]+ |
|---|---|---|---|
| 130 | (structure) | 1. (3R,5R)-3,5-dimethylmorpholine replaced by (3S,5S)-3,5-dimethylmorpholine in Step 1.<br>2. Intermediate 9 replaced by Intermediate 8 in Step 3.<br>3. Intermediate 6 replaced by Intermediate 3 in Step 4. | 757.2 |

-continued

| Ex # | Structures | Changes in synthetic protocol | LCMS (ES, m/z): [M + 1]+ |
|---|---|---|---|
| 131 | 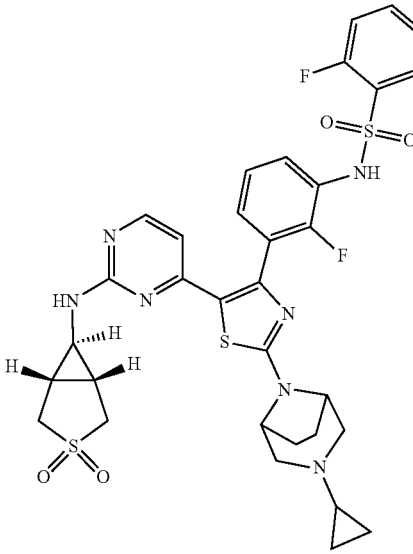 | 1. (3R,5R)-3,5-dimethylmorpholine replaced by replaced by Intermediate 26 in Step 1.<br>2. Intermediate 9 replaced by Intermediate 8 in Step 3.<br>3. Intermediate 6 replaced by Intermediate 3 in Step 4. | 794.3 |
| 132 | 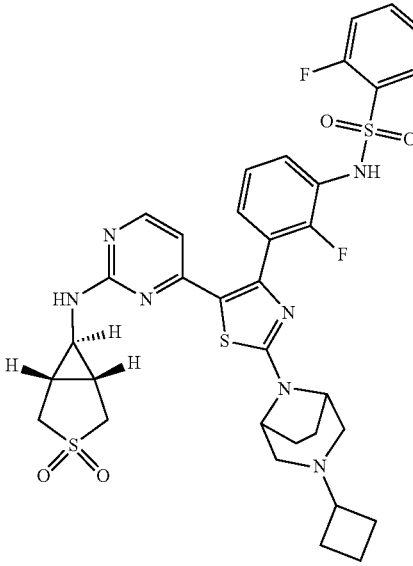 | 1. (3R,5R)-3,5-dimethylmorpholine replaced by 3-cyclobutyl-3,8-diazabicyclo[3.2.1]octane in Step 1<br>2. Intermediate 9 replaced by Intermediate 8 in Step 3.<br>3. Intermediate 6 replaced by Intermediate 3 in Step 4. | 808.3 |

-continued

| Ex # | Structures | Changes in synthetic protocol | LCMS (ES, m/z): [M + 1]⁺ |
|---|---|---|---|
| 133 | 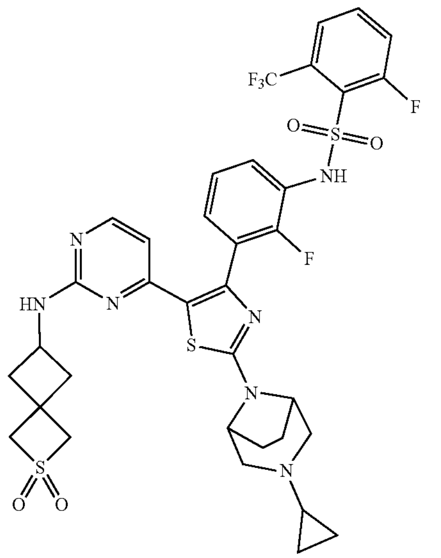 [SMILES: O=S1(=O)CC2(CC(Nc3nccc(-c4sc(N5C6CCC5CN(C5CC5)C6)nc4-c4cccc(NS(=O)(=O)c5c(F)cccc5C(F)(F)F)c4F)n3)C2)C1] | 1. (3R,5R)-3,5-dimethylmorpholine replaced by Intermediate 26 in Step 1<br>2. Intermediate 9 replaced by Intermediate 8 in Step 3. | 808.3 |
| 134 | 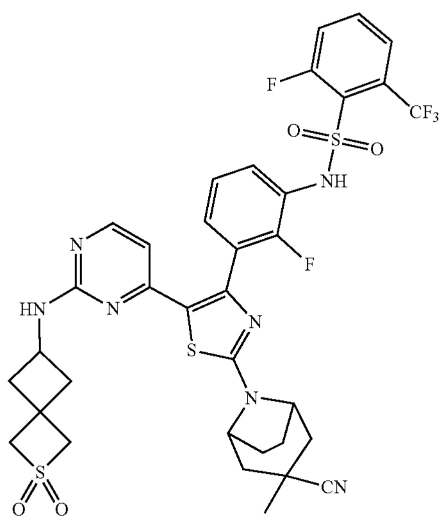 [SMILES: CC1(C#N)CC2CCC(C1)N2c1nc(-c2cccc(NS(=O)(=O)c3c(F)cccc3C(F)(F)F)c2F)c(-c2ccnc(NC3CC4(C3)CS(=O)(=O)C4)n2)s1] | 1. (3R,5R)-3,5-dimethylmorpholine replaced by Intermediate 21 in Step 1.<br>2. Intermediate 9 replaced by Intermediate 8 in Step 3. | 806.3 |
| 135 | 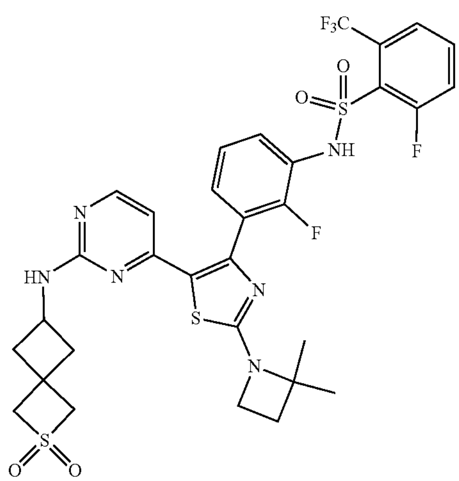 [SMILES: CC1(C)CCN1c1nc(-c2cccc(NS(=O)(=O)c3c(F)cccc3C(F)(F)F)c2F)c(-c2ccnc(NC3CC4(C3)CS(=O)(=O)C4)n2)s1] | 1. (3R,5R)-3,5-dimethylmorpholine replaced by 2,2-dimethylazetidine in Step 1<br>2. Intermediate 9 replaced by Intermediate 8 in Step 3. | 741.3 |

Example 20

Synthesis of N-(3-(5-(2-((2,2-dioxido-2-thiaspiro[3.3]heptan-6-yl)amino)pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide

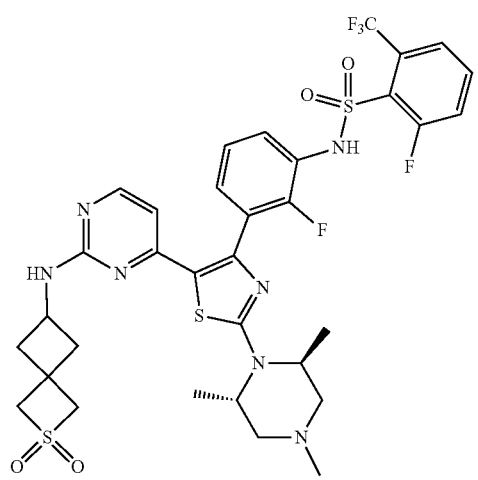 [SMILES: C[C@H]1CN(C)C[C@H](C)N1c1nc(-c2cccc(NS(=O)(=O)c3c(F)cccc3C(F)(F)F)c2F)c(-c2ccnc(NC3CC4(C3)CS(=O)(=O)C4)n2)s1]

Step 1: Tert-Butyl (3S,5S)-4-carbamothioyl-3,5-dimethylpiperazine-1-carboxylate

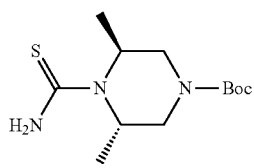

The title compound was synthesized by proceeding analogously as described in Example 5, Step 1, using tert-butyl (3S,5S)-3,5-dimethylpiperazine-1-carboxylate instead of (3R,5R)-3,5-dimethylmorpholine.

Step 2: Tert-Butyl (3S,5S)-4-(4-(3-acetamido-2-fluorophenyl)-5-(2-chloropyrimidin-4-yl)thiazol-2-yl)-3,5-dimethylpiperazine-1-carboxylate

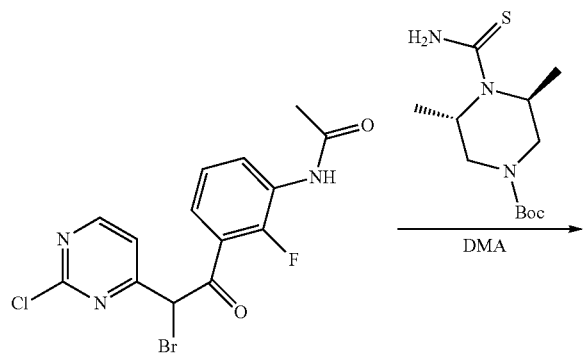

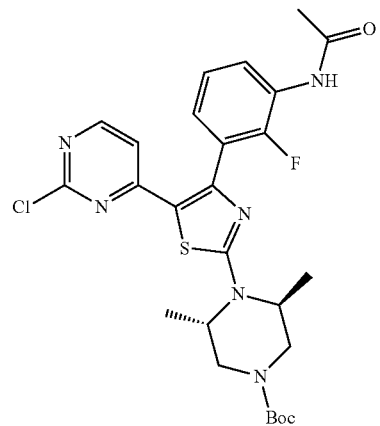

A mixture of N-(3-(2-bromo-2-(2-chloropyrimidin-4-yl)acetyl)-2-fluorophenyl)-acetamide (Intermediate 10; 462 mg, 1.20 mmol, 1.20 eq.) and (3S,5S)-tert-butyl 4-carbamothioyl-3,5-dimethylpiperazine-1-carboxylate (273 mg, 1.00 mmol, 1.00 eq.) in DMA (10.0 mL) was stirred at 70° C. under $N_2$ overnight. The reaction mixture was extracted with EtOAc, and the combined organic layer was washed with brine, dried over $Na_2SO_4$, concentrated and purified by flash chromatography to give the title compound as a yellow solid.

Step 3: Tert-Butyl (3S,5S)-4-(4-(3-acetamido-2-fluorophenyl)-5-(2-((2,2-dioxido-2-thiaspiro[3.3]heptan-6-yl)amino)pyrimidin-4-yl)thiazol-2-yl)-3,5-dimethylpiperazine-1-carboxylate

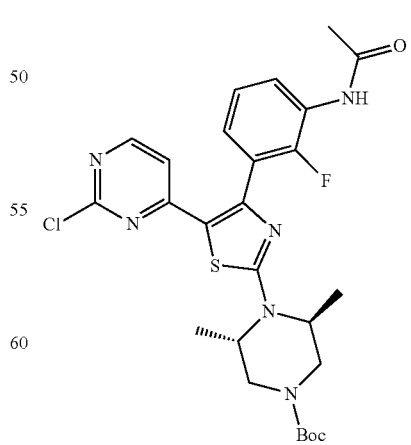

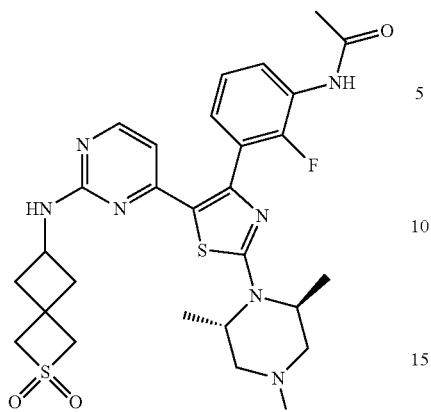

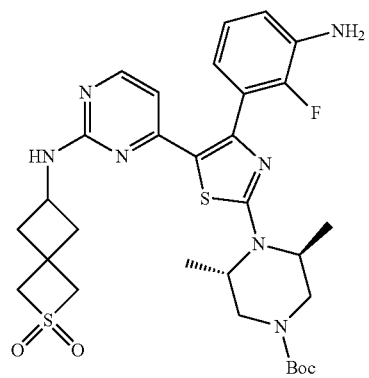

A mixture of (tert-butyl (3S,5S)-4-(4-(3-acetamido-2-fluorophenyl)-5-(2-chloropyrimidin-4-yl)thiazol-2-yl)-3,5-dimethylpiperazine-1-carboxylate (180 mg, 0.32 mmol, 1.00 eq.), 6-amino-2-thiaspiro[3.3]heptane 2,2-dioxide hydrochloride (70 mg, 0.36 mmol, 1.20 eq.), Cs₂CO₃ (520 mg, 1.60 mmol, 5.00 eq.), RuPhos (30 mg), RuPhos Pd G2 (30 mg) in t-BuOH (5.0 mL) was stirred at 90° C. under N₂ overnight. The reaction mixture was extracted with EtOAc, and the combined organic layer was washed with brine, dried over Na₂SO₄, concentrated and the residue was purified by silica gel chromatography (PE:EA=1:1) to give the title compound as a yellow solid.

Step 4: Tert-Butyl (3S,5S)-4-(4-(3-amino-2-fluorophenyl)-5-(2-((2,2-dioxido-2-thiaspiro[3.3]-heptan-6-yl)amino)pyrimidin-4-yl)thiazol-2-yl)-3,5-dimethylpiperazine-1-carboxylate To a stirred solution of tert-butyl (3S,5S)-4-(4-(3-acetamido-2-fluorophenyl)-5-(2-((2,2-dioxido-2-thiaspiro[3.3]heptan-6-yl)amino)pyrimidin-4-yl)thiazol-2-yl)-3,5-dimethylpiperazine-1-carboxylate (130 mg, 0.19 mmol, 1.00 eq.) in EtOH (3.0 mL) was added NaOH (120 mg, 3.00 mmol, 1M), the resulting mixture was stirred at 80° C. under N₂ overnight. The reaction mixture was extracted with EtOAc, and the combined organic layer was washed with brine, dried over Na₂SO₄, concentrated to give the title compound as a brown oil.

Step 5: Tert-Butyl (3S,5S)-4-(5-(2-((2,2-dioxido-2-thiaspiro[3.3]heptan-6-yl)amino)-pyrimidin-4-yl)-4-(2-fluoro-3-((2-fluoro-6-(trifluoromethyl)phenyl)sulfonamido)-phenyl)thiazol-2-yl)-3,5-dimethylpiperazine-1-carboxylate

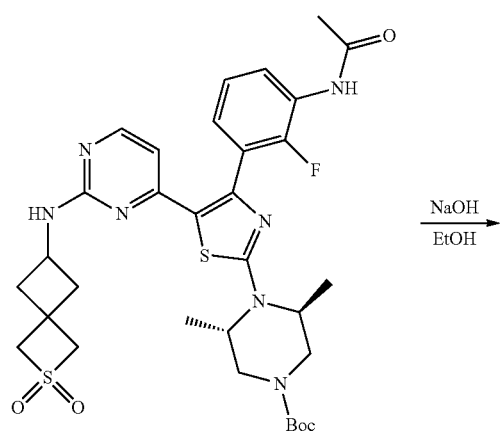

NaOH
EtOH

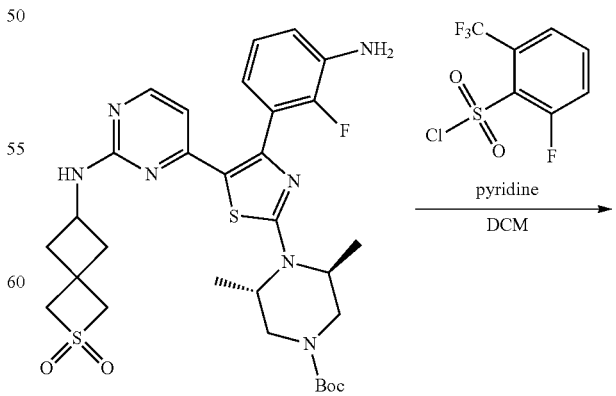

pyridine
DCM

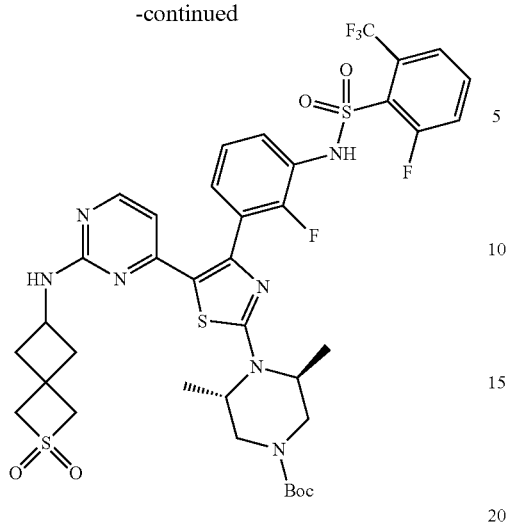

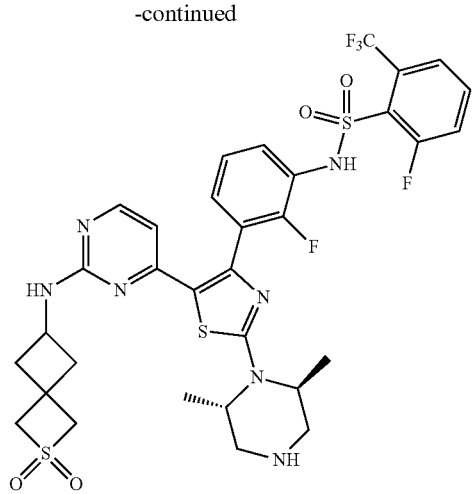

2-Fluoro-6-(trifluoromethyl)benzene-1-sulfonyl chloride (79 mg, 0.30 mmol, 1.50 eq.) was added to a stirred solution of tert-butyl (3S,5S)-4-(4-(3-amino-2-fluorophenyl)-5-(2-((2,2-dioxido-2-thiaspiro[3.3]heptan-6-yl)amino)pyrimidin-4-yl)thiazol-2-yl)-3,5-dimethylpiperazine-1-carboxylate (122 mg, 0.19 mmol, 1.00 eq.) in DCM (4.0 mL) and pyridine (90 mg, 1.14 mmol, 6.00 eq.), and the resulting mixture was stirred at 45° C. under $N_2$ overnight. The mixture was extracted with DCM, and the combined organic layer was washed with brine, dried over $Na_2SO_4$, concentrated and purified by flash chromatography to give the title compound as a yellow solid.

Step 6: N-(3-(2-((2S,6S)-2,6-dimethylpiperazin-1-yl)-5-(2-((2,2-dioxido-2-thiaspiro[3.3]-heptan-6-yl)amino)pyrimidin-4-yl)thiazol-4-yl)-2-fluorophenyl)-2-fluoro-6-(trifluoromethyl)-benzenesulfonamide To a stirred solution of tert-butyl (3S,5S)-4-(5-(2-((2,2-dioxido-2-thiaspiro[3.3]-heptan-6-yl)amino)pyrimidin-4-yl)-4-(2-fluoro-3-(2-fluoro-6-(trifluoromethyl)-phenylsulfonamido)phenyl)-thiazol-2-yl)-3,5-dimethylpiperazine-1-carboxylate (50 mg, 0.06 mmol, 1.00 eq.) in DCM (2.0 mL) was added TFA (0.5 mL), and the resulting mixture was stirred at rt for 2 h. The mixture was concentrated to give the title compound as a yellow oil.

Step 7: N-(3-(5-(2-((2,2-dioxido-2-thiaspiro[3.3] heptan-6-yl)amino)pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide

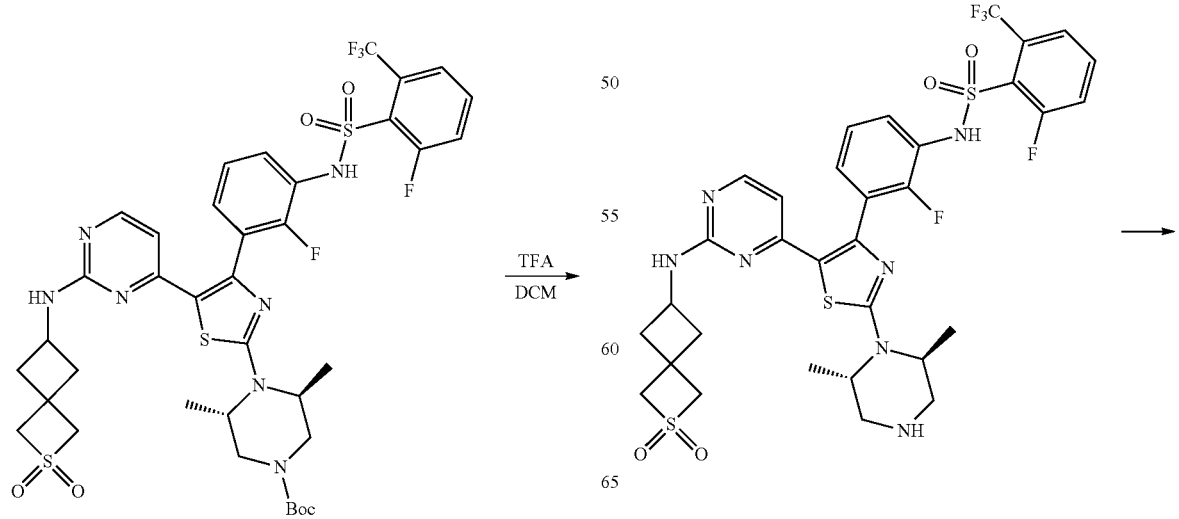

243

-continued

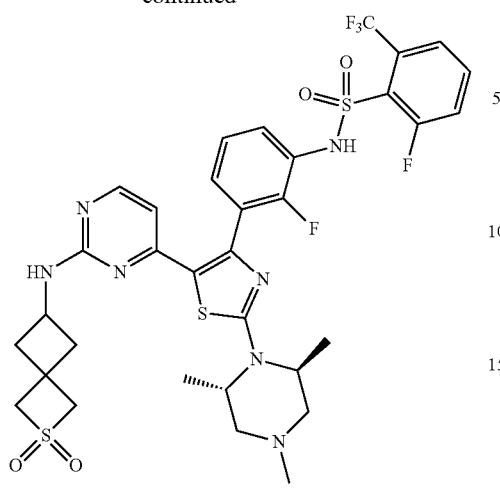

To a stirred solution of N-(3-(2-((2S,6S)-2,6-dimethylpiperazin-1-yl)-5-(2-(((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide (44 mg, 0.06 mmol, 1.00 eq.) in MeOH (2.0 mL) was added HCHO (25 mg, 0.30 mmol, 5.00 eq., 35%) and AcOH (1 drop), the resulting mixture was stirred at rt for 30 min. NaBH$_3$CN (8 mg, 0.12 mmol, 2.00 eq.) was added, and the mixture was stirred at rt overnight. The solution was diluted with water and extracted with EtOAc. The combined organic layer was washed with brine, dried over Na$_2$SO$_4$, concentrated and purified by prep-HPLC to give the title compound as a yellow solid. MS (ES, m/z): [M+1]$^+$=784.3

Example 21

Synthesis of N-(3-(5-(2-((2,2-dioxido-2-thiaspiro[3.3]heptan-6-yl)amino)pyrimidin-4-yl)-2-(2,4,6-trimethylpiperazin-1-yl)thiazol-4-yl)-2-fluorophenyl)-2,6-difluorobenzenesulfonamide

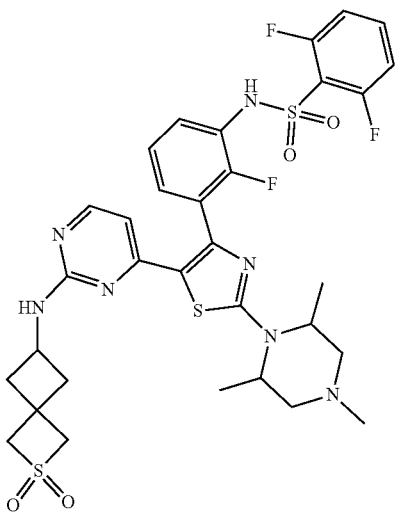 [SMILES: CC1CN(C)CC(C)N1c1nc(-c2cccc(NS(=O)(=O)c3c(F)cccc3F)c2F)c(-c2ccnc(NC3CC4(C3)CS(=O)(=O)C4)n2)s1]

244

Step 1: Tert-Butyl 4-(benzoylcarbamothioyl)-3,5-dimethylpiperazine-1-carboxylate

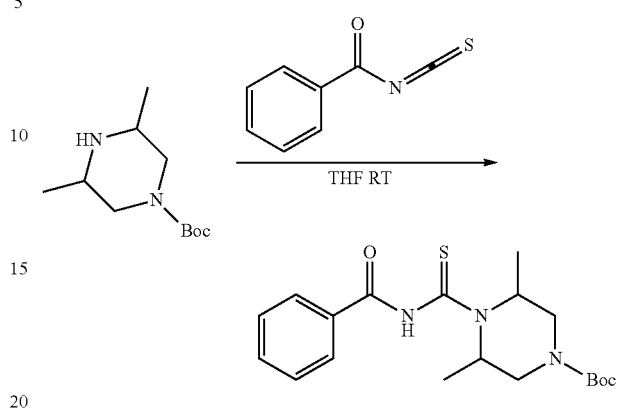

To a stirred solution of tert-butyl 3,5-dimethylpiperazine-1-carboxylate (2.00 g, 9.34 mmol, 1.00 eq.) in THF (30.0 mL) was added benzoyl isothiocyanate (1.67 g, 10.28 mmol, 1.10 eq.), and the mixture was stirred at rt overnight. The mixture was concentrated and purified by silica gel chromatography (EA:PE=1:5) to give the title compound as a yellow solid.

Step 2: Tert-Butyl 4-carbamothioyl-3,5-dimethylpiperazine-1-carboxylate

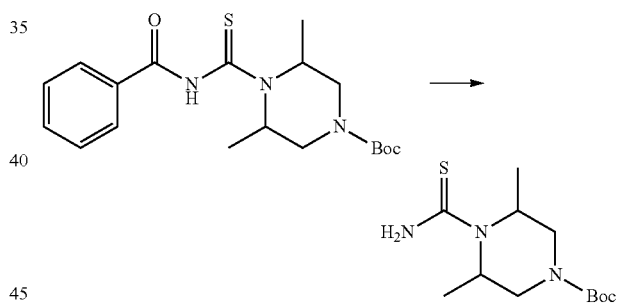

A mixture of tert-butyl 4-(benzoylcarbamothioyl)-3,5-dimethylpiperazine-1-carboxylate (2.80 g, 7.43 mmol, 1.00 eq.) and N$_2$H$_4$·H$_2$O (30.0 mL) was stirred at rt overnight. The mixture was diluted with DCM and the organic layer was washed with 10% citric acid, brine, dried over Na$_2$SO$_4$, concentrated and purified by silica gel chromatography (EA:PE=1:3) to give the title compound as a white solid.

Step 3: Tert-Butyl 4-(5-(2-chloropyrimidin-4-yl)-4-(3-(2,6-difluorophenylsulfonamido)-2-fluorophenyl)thiazol-2-yl)-3,5-dimethylpiperazine-1-carboxylate

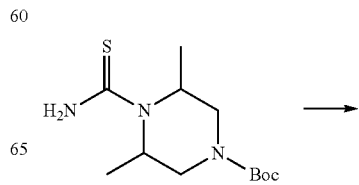

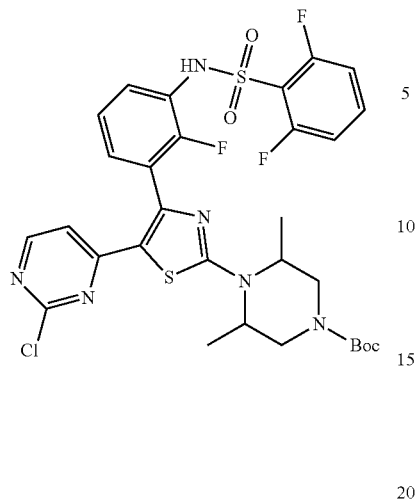

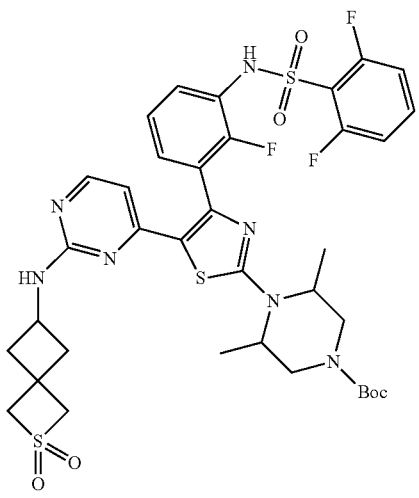

A mixture of N-(3-(2-bromo-2-(2-chloropyrimidin-4-yl)acetyl)-2-fluorophenyl)-2,6-difluorobenzenesulfonamide (Intermediate 9; 1.14 g, 2.20 mmol, 1.00 eq.) and tert-butyl 4-carbamothioyl-3,5-dimethylpiperazine-1-carboxylate (600 mg, 2.20 mmol, 1.00 eq.) in DMA (12.0 mL) was stirred at 70° C. under $N_2$ overnight. The reaction mixture was extracted with EtOAc, and the combined organic layer was washed with brine, dried over $Na_2SO_4$, concentrated and purified by flash chromatography to give the title compound as a yellow solid.

Step 4: Tert-Butyl 4-(4-(3-(2,6-difluorophenylsulfonamido)-2-fluorophenyl)-5-(2-((2,2-dioxido-2-thiaspiro[3.3]heptan-6-yl)amino)pyrimidin-4-yl)thiazol-2-yl)-3,5-dimethyl-piperazine-1-carboxylate A mixture of tert-butyl 4-(5-(2-chloropyrimidin-4-yl)-4-(3-(2,6-difluorophenyl-sulfonamido)-2-fluorophenyl)thiazol-2-yl)-3,5-dimethylpiperazine-1-carboxylate (200 mg, 0.29 mmol, 1.00 eq.), 6-amino-2-thiaspiro[3.3]heptane 2,2-dioxide hydrochloride (Intermediate 6; 68 mg, 0.35 mmol, 1.20 eq.), $Cs_2CO_3$ (471 mg, 1.45 mmol, 5.00 eq.), RuPhos (20 mg), RuPhos Pd G2 (20 mg) in t-BuOH (5.0 mL) was stirred at 90° C. under $N_2$ overnight. The reaction mixture was extracted with EtOAc, and the combined organic layer was washed with brine, dried over $Na_2SO_4$, concentrated and purified by silica gel chromatography (PE:EA=1:1) to give the title compound as a yellow solid.

Step 5: N-(3-(2-(2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

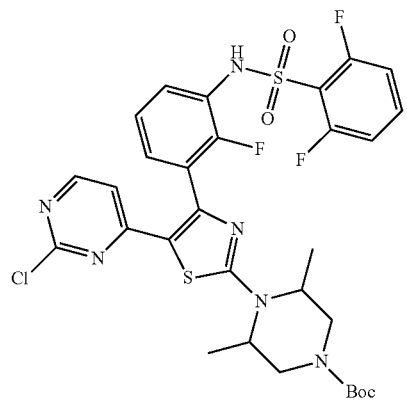

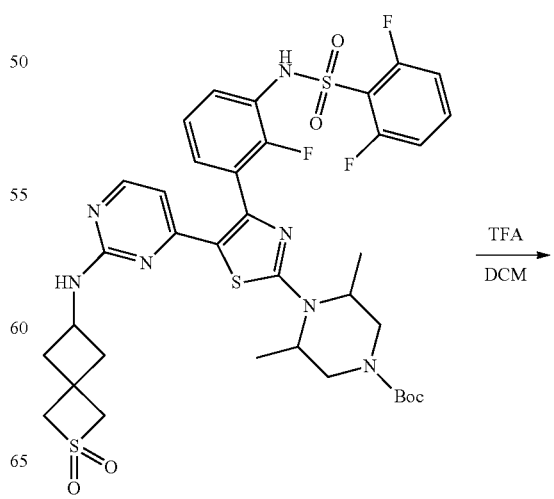

247

-continued

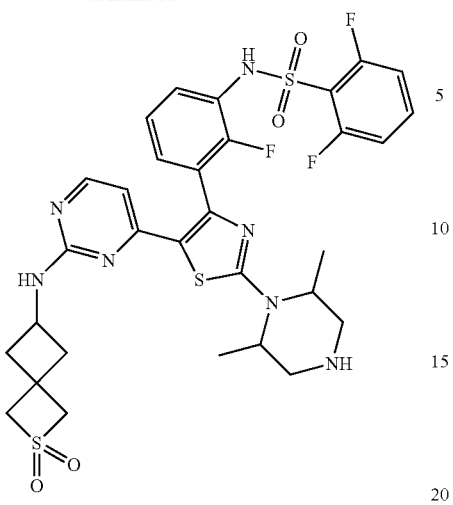

To a stirred solution of tert-butyl 4-(4-(3-(2,6-difluorophenylsulfonamido)-2-fluorophenyl)-5-(2-((2,2-dioxido-2-thiaspiro[3.3]heptan-6-yl)amino)pyrimidin-4-yl)thiazol-2-yl)-3,5-dimethylpiperazine-1-carboxylate (50 mg, 0.06 mmol, 1.00 eq.) in DCM (2.0 mL) was added TFA (0.5 mL). The resulting mixture was stirred at rt for 2 h and then concentrated to give the title compound as a yellow oil.

Step 6: N-(3-(5-(2-((2,2-dioxido-2-thiaspiro[3.3]heptan-6-yl)amino)pyrimidin-4-yl)-2-(2,4,6-trimethylpiperazin-1-yl)thiazol-4-yl)-2-fluorophenyl)-2,6-difluorobenzenesulfonamide

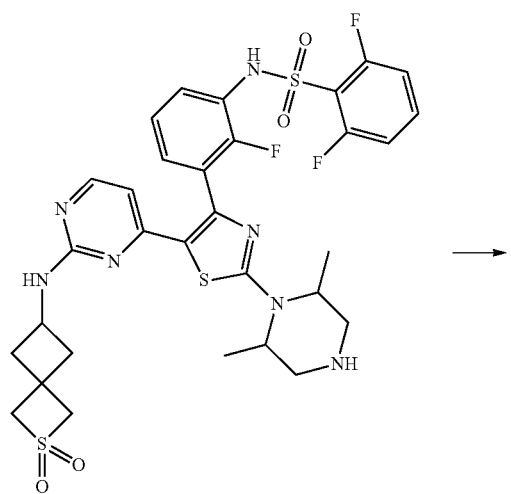

248

-continued

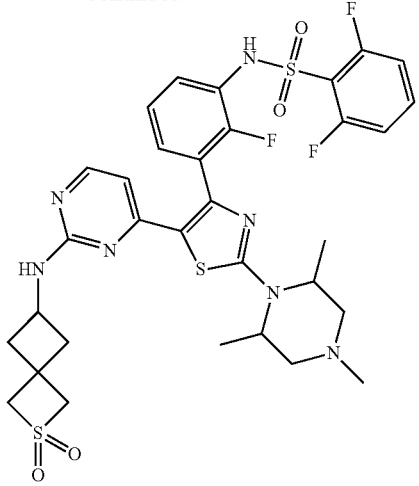

To a stirred solution of N-(3-(2-(2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide (44 mg, 0.06 mmol, 1.00 eq.) in MeOH (2.0 mL) was added HCHO (25 mg, 0.30 mmol, 5.00 eq., 35%) and AcOH (1 drop), the resulting mixture was stirred at rt for 30 min., and NaBH$_3$CN (8 mg, 0.12 mmol, 2.00 eq.) was added. The mixture was stirred at rt overnight. The mixture was diluted with water and extracted with EtOAc, and the combined organic layer was washed with brine, dried over Na$_2$SO$_4$, concentrated and purified by prep-HPLC to give the title compound as a yellow solid. MS (ES, m/z): [M+1]$^+$=734.3

Proceeding analogously as described in Example 21, the following compounds were prepared.

| Ex # | Structures | Changes in synthetic protocol | LCMS (ES, m/z): [M + 1]+ |
|---|---|---|---|
| 22 | 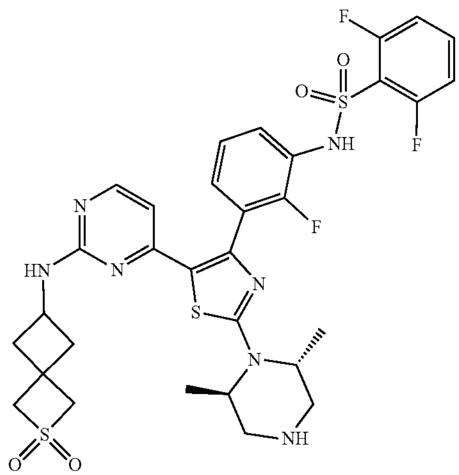 [SMILES: C[C@@H]1CNC[C@@H](C)N1c1nc(-c2cccc(NS(=O)(=O)c3c(F)cccc3F)c2F)c(-c2ccnc(NC3CC4(C3)CS(=O)(=O)C4)n2)s1] | tert-butyl 3,5-dimethylpiperazine-1-carboxylate replaced by tert-butyl (3R,5R)-3,5-dimethylpiperazine-1-carboxylate in Step 1 without performing Step 6. | 720.1 |
| 23 | 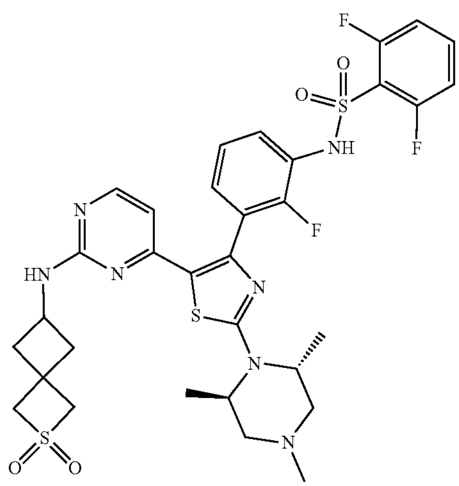 [SMILES: C[C@@H]1CN(C)C[C@@H](C)N1c1nc(-c2cccc(NS(=O)(=O)c3c(F)cccc3F)c2F)c(-c2ccnc(NC3CC4(C3)CS(=O)(=O)C4)n2)s1] | tert-butyl 3,5-dimethylpiperazine-1-carboxylate replaced by tert-butyl (3R,5R)-3,5-dimethylpiperazine-1-carboxylate in Step 1. | 734.1 |
| 24 | 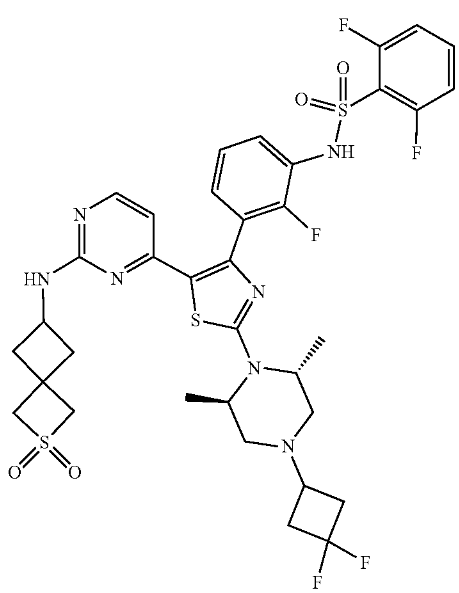 [SMILES: C[C@@H]1CN(C2CC(F)(F)C2)C[C@@H](C)N1c1nc(-c2cccc(NS(=O)(=O)c3c(F)cccc3F)c2F)c(-c2ccnc(NC3CC4(C3)CS(=O)(=O)C4)n2)s1] | 1. tert-butyl 3,5-dimethylpiperazine-1-carboxylate replaced by tert-butyl (3R,5R)-3,5-dimethylpiperazine-1-carboxylate in Step 1.<br>2. formaldehyde replaced by 3,3-difluorocyclobutan-1-one in Step 6. | 810.1 |

| Ex # | Structures | Changes in synthetic protocol | LCMS (ES, m/z): [M + 1]+ |
|---|---|---|---|
| 25 | 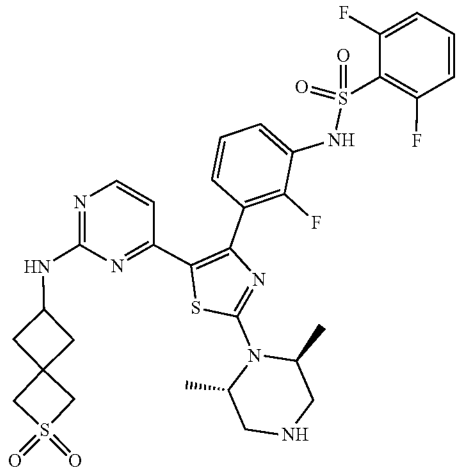 [SMILES: C[C@H]1CNC[C@H](C)N1c1nc(-c2cccc(NS(=O)(=O)c3c(F)cccc3F)c2F)c(-c2ccnc(NC3CC4(C3)CS(=O)(=O)C4)n2)s1] | tert-butyl 3,5-dimethylpiperazine-1-carboxylate replaced by tert-butyl (3S,5S)-3,5-dimethylpiperazine-1-carboxylate in Step 1 without performing Step 6. | 720.1 |
| 26 | 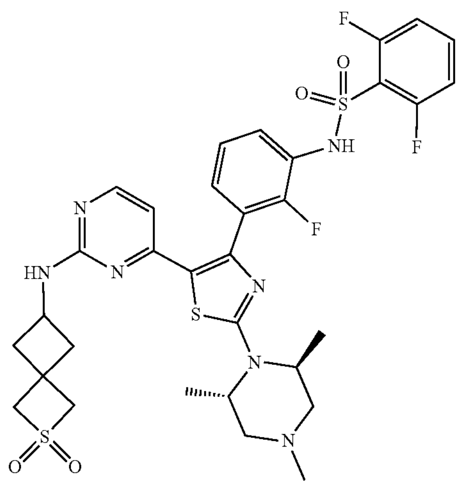 [SMILES: C[C@H]1CN(C)C[C@H](C)N1c1nc(-c2cccc(NS(=O)(=O)c3c(F)cccc3F)c2F)c(-c2ccnc(NC3CC4(C3)CS(=O)(=O)C4)n2)s1] | tert-butyl 3,5-dimethylpiperazine-1-carboxylate replaced by tert-butyl (3S,5S)-3,5-dimethylpiperazine-1-carboxylate in Step 1. | 734.3 |
| 27 | 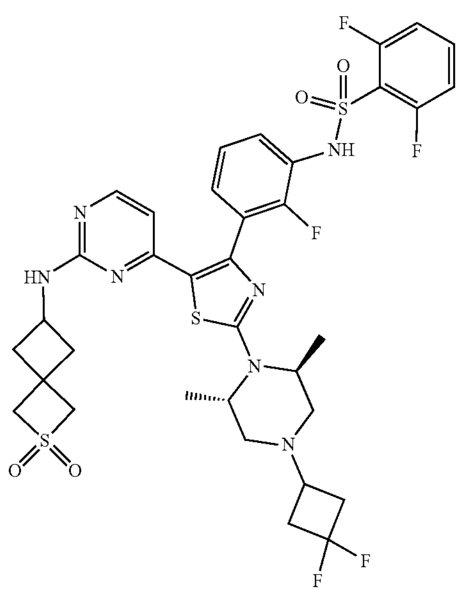 [SMILES: C[C@H]1CN(C2CC(F)(F)C2)C[C@H](C)N1c1nc(-c2cccc(NS(=O)(=O)c3c(F)cccc3F)c2F)c(-c2ccnc(NC3CC4(C3)CS(=O)(=O)C4)n2)s1] | 1. tert-butyl 3,5-dimethylpiperazine-1-carboxylate replaced by tert-butyl (3S,5S)-3,5-dimethylpiperazine-1-carboxylate in Step 1.<br>2. formaldehyde replaced by 3,3-difluorocyclobutan-1-one in Step 6. | 810.3 |

| Ex # | Structures | Changes in synthetic protocol | LCMS (ES, m/z): [M + 1]+ |
|---|---|---|---|
| 28 | 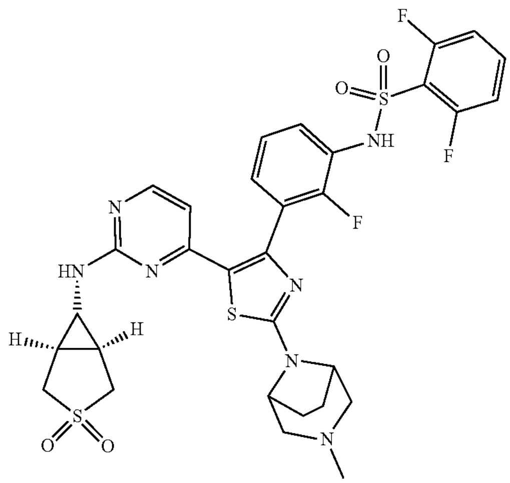 | 1. tert-butyl 3,5-dimethylpiperazine-1-carboxylate replaced by tert-butyl 3,8-diazabicyclo[3.2.1]octane-3-carboxylate in Step 1.<br>2. Intermediate 6 replaced by Intermediate 3 in Step 4. | 718.1 |
| 29 | 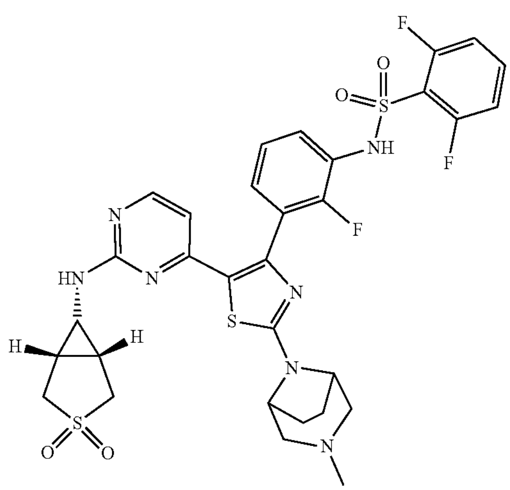 | 1. tert-butyl 3,5-dimethylpiperazine-1-carboxylate replaced by tert-butyl 3,8-diazabicyclo[3.2.1]octane-3-carboxylate in Step 1.<br>2. Intermediate 6 replaced by intermediate 2 in Step 4. | 718.1 |

Example 30

Synthesis of 2-fluoro-N-(2-fluoro-3-(5-(2-(((1r,4r)-4-(methylsulfonyl)cyclohexyl)-amino)pyrimidin-4-yl)-2-(3-(trifluoromethyl)bicyclo[1.1.1]pentan-1-yl)thiazol-4-yl)phenyl)-6-(trifluoromethyl)benzenesulfonamide

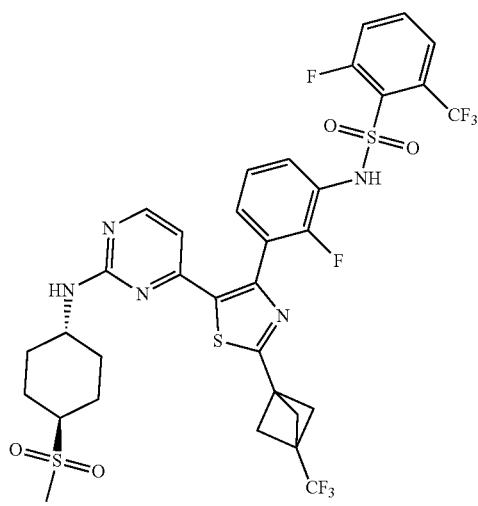 [SMILES: CS(=O)(=O)[C@H]1CC[C@H](Nc2nccc(-c3sc(C45CC(C(F)(F)F)(C4)C5)nc3-c3cccc(NS(=O)(=O)c4c(F)cccc4C(F)(F)F)c3F)n2)CC1]

Step 1: 3-(Trifluoromethyl)bicyclo[1.1.1]pentane-1-carboxamide

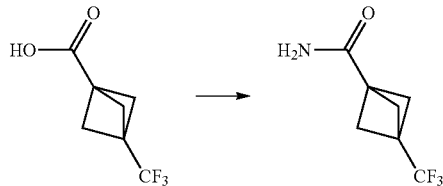

Oxalyl chloride (641 mg, 5.05 mmol, 1.30 eq.) and DMF (1 drop) were added to a mixture of 3-(trifluoromethyl)bicyclo[1.1.1]pentane-1-carboxylic acid (700 mg, 3.89 mmol, 1.00 eq) in DCM (14.0 mL) dropwise at 0° C. and the mixture was stirred at rt under $N_2$ for 2 h. Then $NH_3$ (gas) was bubbled into the reaction mixture at −10° C. After stirring the mixture at rt overnight, it was filtered, and the filtrate was concentrated to give the crude product as white solid.

Step 2: 3-(Trifluoromethyl)bicyclo[1.1.1]pentane-1-carbothioamide

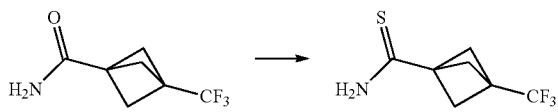 [SMILES: NC(=O)C12CC(C(F)(F)F)(C1)C2 ; NC(=S)C12CC(C(F)(F)F)(C1)C2]

Lawesson's reagent (1.57 g, 3.89 mmol, 1.00 eq.) was added to a mixture of (trifluoromethyl)bicyclo[1.1.1]pentane-1-carboxamide (697 mg, 3.89 mmol, 1.00 eq) in THF (28.0 mL) and the mixture was stirred at 65° C. under $N_2$ overnight. The mixture was concentrated and purified by column chromatography on silica gel (PE:EA=5:1) to give the title compound as white solid.

Step 3: N-(3-(5-(2-chloropyrimidin-4-yl)-2-(3-(trifluoromethyl)bicyclo[1.1.1]pentan-1-yl)thiazol-4-yl)-2-fluorophenyl)-2-fluoro-6-(trifluoromethyl)benzenesulfonamide

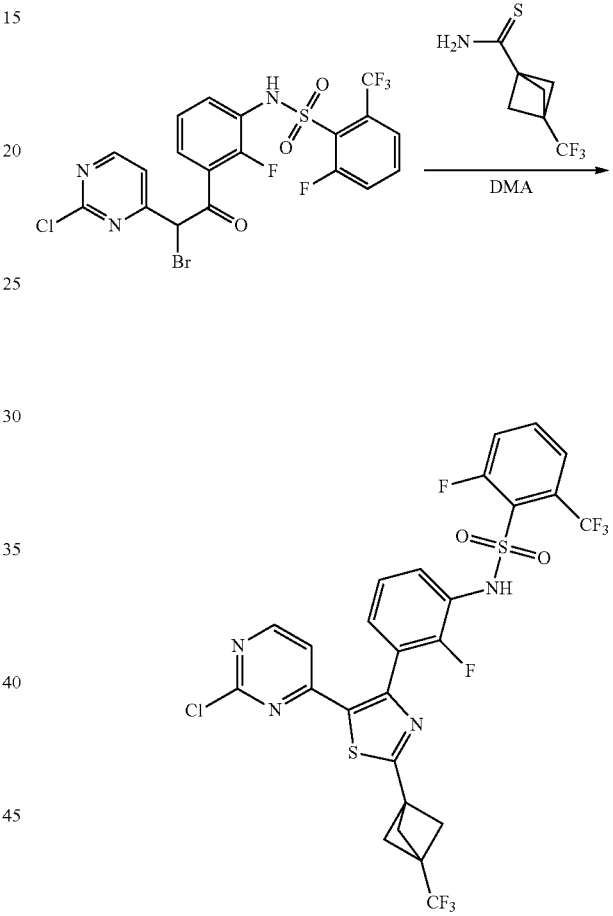

A mixture of N-(3-(2-bromo-2-(2-chloropyrimidin-4-yl)acetyl)-2-fluorophenyl)-2-fluoro-6-(trifluoromethyl)benzenesulfonamide (Intermediate 8; 876 mg, 1.54 mmol, 1.00 eq.) and 3-(trifluoromethyl)bicyclo[1.1.1]pentane-1-carbothioamide (300 mg, 1.54 mmol, 1.00 eq.) in DMA (36.0 mL) was stirred at r.t. under $N_2$ for 30 min. The mixture was stirred at 65° C. under $N_2$ overnight, then diluted with $H_2O$ and extracted with EtOAc. The combined organic layers were washed with brine, dried over $Na_2SO_4$, concentrated. The residue was purified by column chromatography on silica gel (PE:EA=2:1) to give the title product as a pale yellow solid.

Step 4: 2-Fluoro-N-(2-fluoro-3-(5-(2-(((1r,4r)-4-(methylsulfonyl)cyclohexyl)amino)-pyrimidin-4-yl)-2-(3-(trifluoromethyl)bicyclo[1.1.1]pentan-1-yl)thiazol-4-yl)phenyl)-6-(trifluoromethyl)-benzenesulfonamide

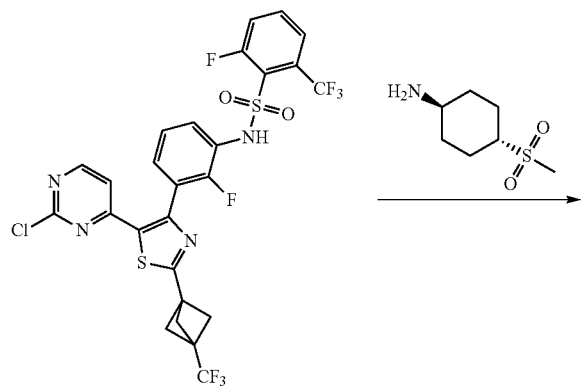

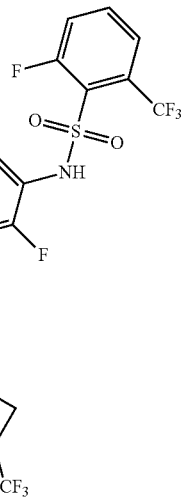

A mixture of N-(3-(5-(2-chloropyrimidin-4-yl)-2-(3-(trifluoromethyl)bicyclo[1.1.1]-pentan-1-yl)thiazol-4-yl)-2-fluorophenyl)-2-fluoro-6-(trifluoromethyl)benzenesulfonamide (200 mg, 0.30 mmol, 1.00 eq.), (1r,4r)-4-(methylsulfonyl)cyclohexan-1-amine trifluoroacetate (Intermediate 5; 131 mg, 0.45 mmol, 1.50 eq), Ruphos (50 mg), RuPhos Pd G2 (50 mg) and $Cs_2CO_3$ (293 mg, 0.90 mmol, 3.00 eq.) in NMP/t-BuOH (1.0 mL/3.0 mL) was stirred at 90° C. under $N_2$ overnight. The mixture was diluted with $H_2O$ and extracted with EtOAc. The combined organic layers were washed with brine, dried over $Na_2SO_4$, and concentrated. The residue was purified by column chromatography on silica gel (DCM:MeOH=30:1) and prep-TLC (DCM:MeOH=30:1) to give the title compound. The title compound was triturated with ether/MeOH (20:1) for 1 h, the solid was filtered, and the filter cake was washed with ether. The filtrate was freeze-dried to give title compound as a pale-yellow solid. MS (ES, m/z): [M+1]+=808.1

Proceeding analogously as described in Example 30, the following compounds were prepared.

| Ex # | Structures | Changes in synthetic protocol | LCMS (ES, m/z): [M + 1]+ |
|---|---|---|---|
| 31 | 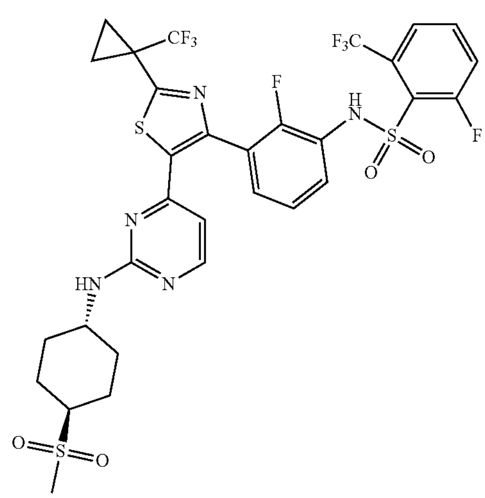 [SMILES: CS(=O)(=O)[C@H]1CC[C@H](Nc2nccc(-c3sc(C4(C(F)(F)F)CC4)nc3-c3cccc(NS(=O)(=O)c4c(F)cccc4C(F)(F)F)c3F)n2)CC1] | 3-(trifluoromethyl)bicyclo[1.1.1]pentane-1-carboxylic acid replaced by 1-(trifluoromethyl)cyclopropane-1-carboxylic acid in Step 1. | 782.1 |

| Ex # | Structures | Changes in synthetic protocol | LCMS (ES, m/z): [M + 1]+ |
|---|---|---|---|
| 32 | 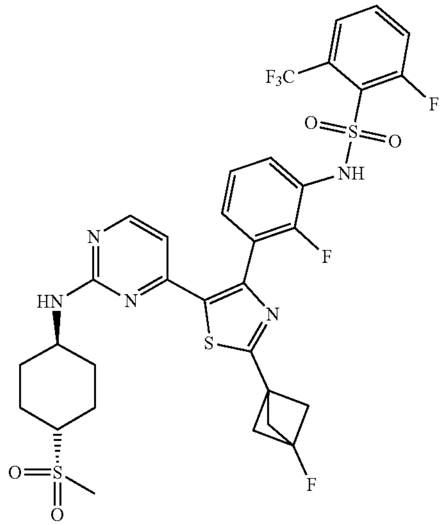 | 3-(trifluoromethyl)bicyclo[1.1.1]pentane-1-carboxylic acid replaced by 3-fluorobicyclo[1.1.1]pentane-1-carboxylic acid in Step 1. | 757.1 |
| 33 | 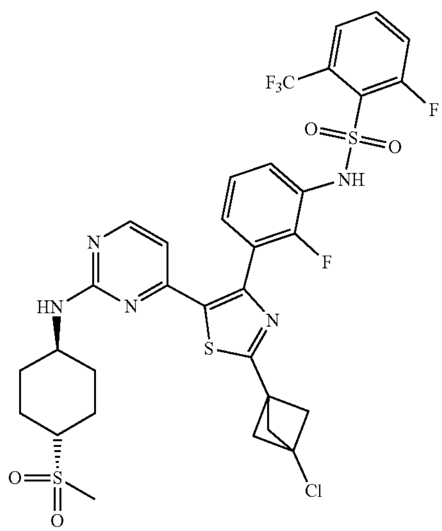 | 3-(trifluoromethyl)bicyclo[1.1.1]pentane-1-carboxylic acid replaced by Intermediate 18 in Step 1. | 773.9 |
| 34 | 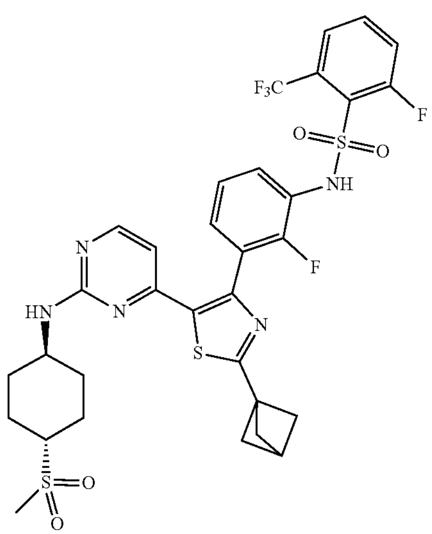 [SMILES: CS(=O)(=O)[C@H]1CC[C@H](Nc2nccc(-c3sc(C45CC(C4)C5)nc3-c3cccc(NS(=O)(=O)c4c(F)cccc4C(F)(F)F)c3F)n2)CC1] | 3-(trifluoromethyl)bicyclo[1.1.1]pentane-1-carboxylic acid replaced by Intermediate 15 in Step 1. | 740.2 |

| Ex # | Structures | Changes in synthetic protocol | LCMS (ES, m/z): [M + 1]+ |
|---|---|---|---|
| 35 | 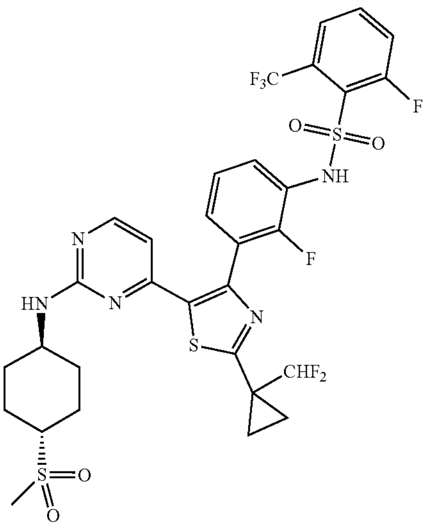 [SMILES: CS(=O)(=O)[C@H]1CC[C@H](Nc2nccc(-c3sc(C4(C(F)F)CC4)nc3-c3cccc(NS(=O)(=O)c4c(F)cccc4C(F)(F)F)c3F)n2)CC1] | 3-(trifluoromethyl)bicyclo[1.1.1]pentane-1-carboxylic acid replaced by Intermediate 16 in Step 1. | 764.1 |

Example 36

Synthesis of N-(3-(5-(2-((2,2-dioxido-2-thiaspiro[3.3]heptan-6-yl)amino)pyrimidin-4-yl)-2-(3-(trifluoromethyl)bicyclo[1.1.1]pentan-1-yl)thiazol-4-yl)-2-fluorophenyl)-2-fluoro-6-(trifluoromethyl)benzenesulfonamide

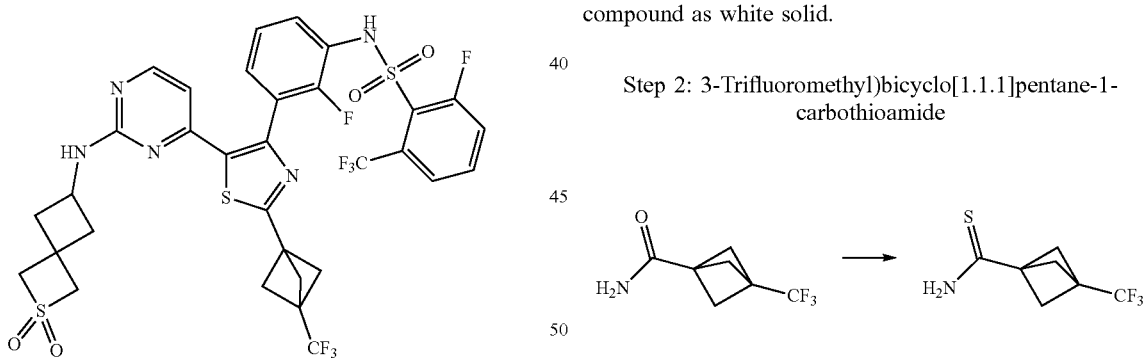

Step 1: 3-(Trifluoromethyl)bicyclo[1.1.1]pentane-1-carboxamide

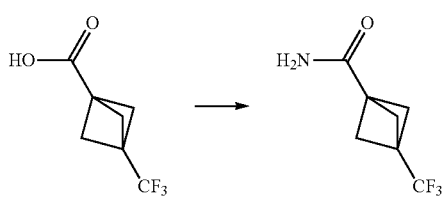

Oxalyl chloride (641 mg, 5.05 mmol, 1.30 eq.) and DMF (1 drop) were added to a mixture of 3-(trifluoromethyl)bicyclo[1.1.1]pentane-1-carboxylic acid (700 mg, 3.89 mmol, 1.00 eq) in DCM (14.0 mL) dropwise at 0° C. and the mixture was stirred at r.t. under $N_2$ for 2 h. $NH_3$ (gas) was bubbled into the reaction mixture at −10° C. and the mixture was warmed to r.t. and stirred overnight. The mixture was filtered, and the filtrate was concentrated to give crude title compound as white solid.

Step 2: 3-Trifluoromethyl)bicyclo[1.1.1]pentane-1-carbothioamide

Lawesson's reagent (1.57 g, 3.89 mmol, 1.00 eq.) was added to a mixture of (trifluoromethyl)bicyclo[1.1.1]pentane-1-carboxamide (697 mg, 3.89 mmol, 1.00 eq) in THF (28.0 mL) and the mixture was stirred at 65° C. under $N_2$ overnight. The mixture was concentrated and purified by column chromatography on silica gel (PE:EA=5:1) to give the title compound as white solid.

263

Step 3: N-(3-(5-(2-chloropyrimidin-4-yl)-2-(3-(trifluoromethyl)bicyclo[1.1.1]pentan-1-yl)-thiazol-4-yl)-2-fluorophenyl)-2-fluoro-6-(trifluoromethyl)benzenesulfonamide

264

Step 4: N-(3-(5-(2-((2,2-dioxido-2-thiaspiro[3.3]heptan-6-yl)amino)pyrimidin-4-yl)-2-(3-(trifluoromethyl)bicyclo[1.1.1]pentan-1-yl)thiazol-4-yl)-2-fluorophenyl)-2-fluoro-6-(trifluoromethyl)benzenesulfonamide

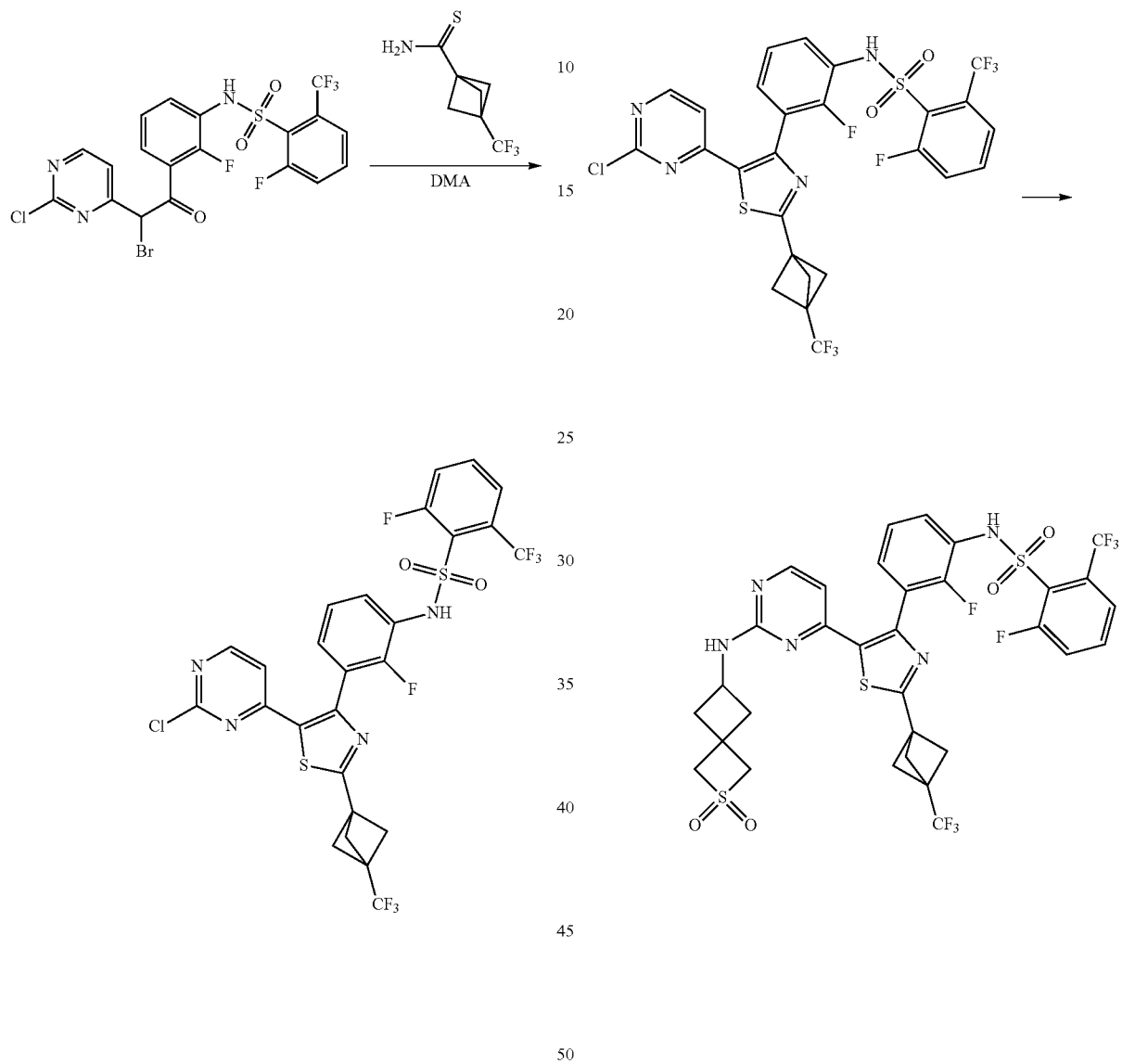

A mixture of N-(3-(2-bromo-2-(2-chloropyrimidin-4-yl)acetyl)-2-fluorophenyl)-2-fluoro-6-(trifluoromethyl)benzenesulfonamide (Intermediate 8, 876 mg, 1.54 mmol, 1.00 eq.) and 3-(trifluoromethyl)bicyclo[1.1.1]pentane-1-carbothioamide (300 mg, 1.54 mmol, 1.00 eq.) in DMA (36.0 mL) was stirred at r.t. under $N_2$ for 30 min. The mixture was stirred at 65° C. under $N_2$ overnight, then diluted with $H_2O$ and extracted with EtOAc. The combined organic layers were washed with brine, dried over $Na_2SO_4$, concentrated. The residue was purified by column chromatography on silica gel (PE:EA=2:1) to give the title compound as a pale yellow solid.

A mixture of N-(3-(5-(2-chloropyrimidin-4-yl)-2-(3-(trifluoromethyl)bicyclo[1.1.1]-pentan-1-yl)thiazol-4-yl)-2-fluorophenyl)-2-fluoro-6-(trifluoromethyl)benzenesulfonamide (300 mg, 0.45 mmol, 1.00 eq.), 6-amino-2-thiaspiro[3.3]heptane 2,2-dioxide (Intermediate 6; 133 mg, 0.68 mmol, 1.50 eq.), RuPhos (60 mg), RuPhos Pd G2 (60 mg) and $Cs_2CO_3$ (440 mg, 1.35 mmol, 3.00 eq.) in NMP/t-BuOH (1.5 mL/6.0 mL) was stirred at 90° C. under $N_2$ overnight. The mixture was diluted with $H_2O$ and extracted with EtOAc. The combined organic layers were washed with brine, dried over $Na_2SO_4$, concentrated. The residue was purified by prep-TLC (DCM:EtOAc=1:2) to give the title compound as a white solid. LCMS (ES, m/z): [M+1]$^+$=792.1

Proceeding analogously as described in Example 36, the following compounds were prepared.

| Ex # | Structures | Changes in synthetic protocol | LCMS (ES, m/z): [M + 1]+ |
|---|---|---|---|
| 37 | 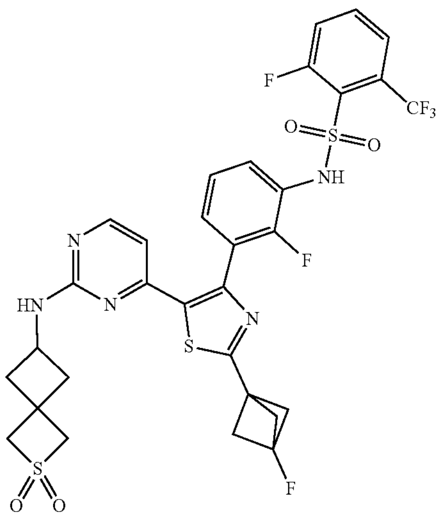 [SMILES: O=S1(=O)CC2(CC(Nc3nccc(-c4sc(C56CC(F)(C5)C6)nc4-c4cccc(NS(=O)(=O)c5c(F)cccc5C(F)(F)F)c4F)n3)C2)C1] | 3-(trifluoromethyl)bicyclo[1.1.1]pentane-1-carboxylic acid replaced by 3-fluorobicyclo[1.1.1]pentane-1-carboxylic acid in Step 1 | 742.2 |
| 38 | 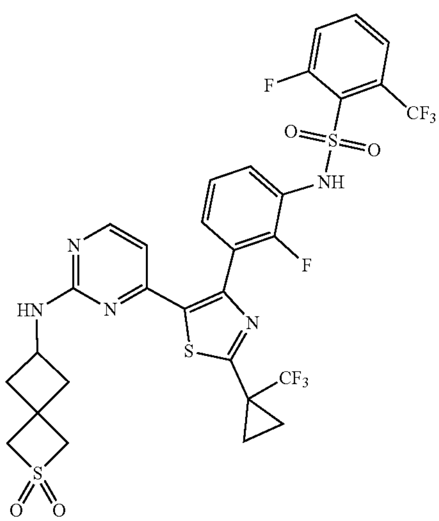 [SMILES: O=S1(=O)CC2(CC(Nc3nccc(-c4sc(C5(C(F)(F)F)CC5)nc4-c4cccc(NS(=O)(=O)c5c(F)cccc5C(F)(F)F)c4F)n3)C2)C1] | 3-(trifluoromethyl)bicyclo[1.1.1]pentane-1-carboxylic acid replaced by 1-(trifluoromethyl)cyclopropane-1-carboxylic acid in Step 1. | 766.1 |
| 39 | 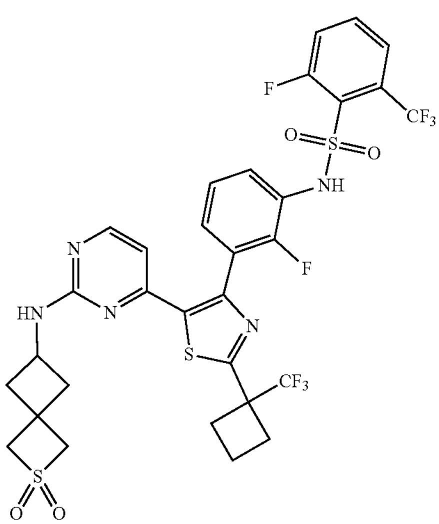 [SMILES: O=S1(=O)CC2(CC(Nc3nccc(-c4sc(C5(C(F)(F)F)CCC5)nc4-c4cccc(NS(=O)(=O)c5c(F)cccc5C(F)(F)F)c4F)n3)C2)C1] | 3-(trifluoromethyl)bicyclo[1.1.1]pentane-1-carboxylic acid replaced by 1-(trifluoromethyl)cyclobutane-1-carboxylic acid in Step 1. | 780.2 |

| Ex # | Structures | Changes in synthetic protocol | LCMS (ES, m/z): [M + 1]+ |
|---|---|---|---|
| 40 | 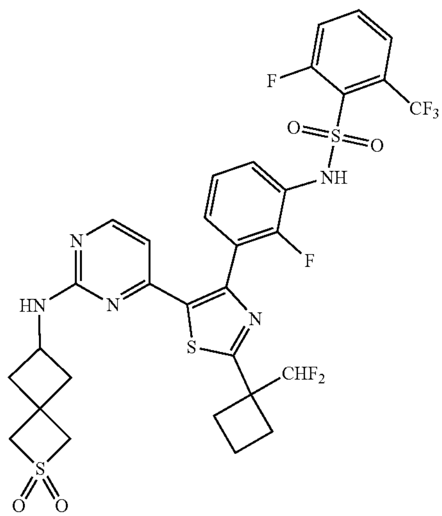 [SMILES: O=S1(=O)CC2(CC(Nc3nccc(-c4sc(C5(C(F)F)CCC5)nc4-c4cccc(NS(=O)(=O)c5c(F)cccc5C(F)(F)F)c4F)n3)C2)C1] | 3-(trifluoromethyl)bicyclo[1.1.1]pentane-1-carboxylic acid replaced by Intermediate 17 in Step 1. | 762.1 |
| 41 | 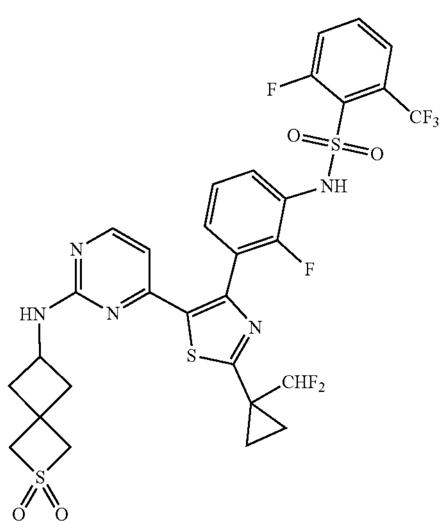 [SMILES: O=S1(=O)CC2(CC(Nc3nccc(-c4sc(C5(C(F)F)CC5)nc4-c4cccc(NS(=O)(=O)c5c(F)cccc5C(F)(F)F)c4F)n3)C2)C1] | 3-(trifluoromethyl)bicyclo[1.1.1]pentane-1-carboxylic acid replaced by Intermediate 16 in Step 1. | 748.1 |

Additional compound prepared by proceeding analogously as described in Example 36, are:

| Ex # | Structures | Changes in synthetic protocol | LCMS (ES, m/z): [M + 1]+ |
|---|---|---|---|
| 119 | 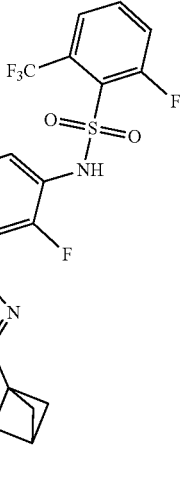 | 1. 3-(trifluoromethyl)bicyclo[1.1.1]pentane-1-carboxylic acid replaced by Intermediate 15 in Step 1.<br>2. Intermediate 6 replaced by Intermediate 2 in Step 4. | 710.2 |
| 120 | 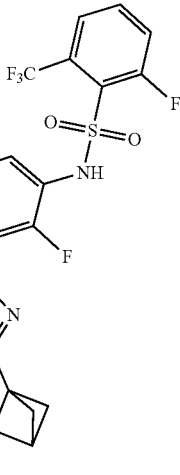 | 1. 3-(trifluoromethyl)bicyclo[1.1.1]pentane-1-carboxylic acid replaced by Intermediate 15 in Step 1.<br>2. Intermediate 6 replaced by Intermediate 3 in Step 4. | 709.9 |
| 121 | 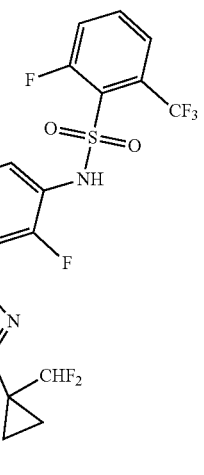 | 1. 3-(trifluoromethyl)bicyclo[1.1.1]pentane-1-carboxylic acid replaced by Intermediate 16 in Step 1.<br>2. Intermediate 6 replaced by Intermediate 3 in Step 4. | 734.0 |

| Ex # | Structures | Changes in synthetic protocol | LCMS (ES, m/z): [M + 1]+ |
|---|---|---|---|
| 122 | 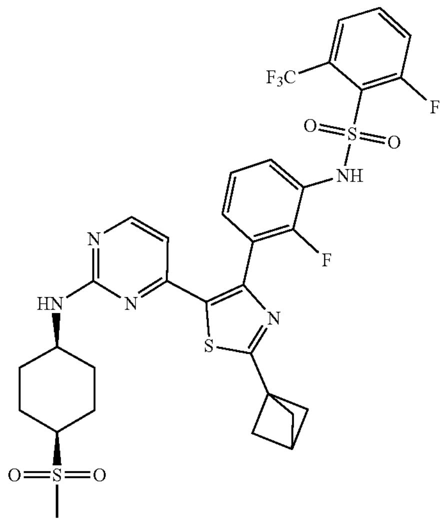 [SMILES: CS(=O)(=O)[C@H]1CC[C@@H](Nc2nccc(-c3sc(C45CC(C4)C5)nc3-c3cccc(NS(=O)(=O)c4c(F)cccc4C(F)(F)F)c3F)n2)CC1] | 1. 3-(trifluoromethyl)bicyclo-[1.1.1]pentane-1-carboxylic acid replaced by Intermediate 15 in Step 1.<br>2. Intermediate 6 replaced by Intermediate 4 in Step 4. | 740.1 |
| 123 | 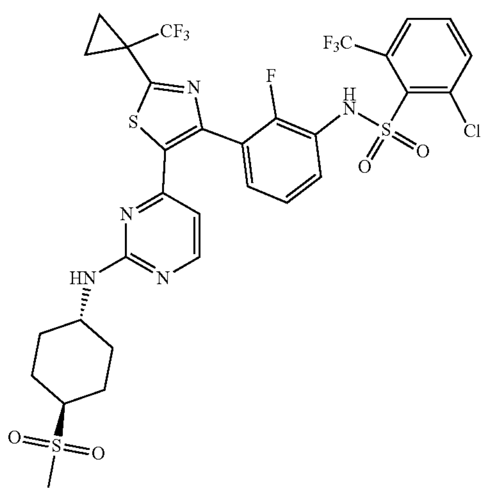 [SMILES: CS(=O)(=O)[C@H]1CC[C@H](Nc2nccc(-c3sc(C4(C(F)(F)F)CC4)nc3-c3cccc(NS(=O)(=O)c4c(Cl)cccc4C(F)(F)F)c3F)n2)CC1] | 1. 3-(trifluoromethyl)bicyclo[1.1.1]pentane-1-carboxylic acid replaced by 1-(trifluoromethyl)cyclopropane-1-carboxylic acid in Step 1.<br>2. Intermediate 8 replaced by Intermediate 33 in step 3.<br>3. Intermediate 6 replaced by Intermediate 5 in Step 4. | 798.1 |
| 124 | 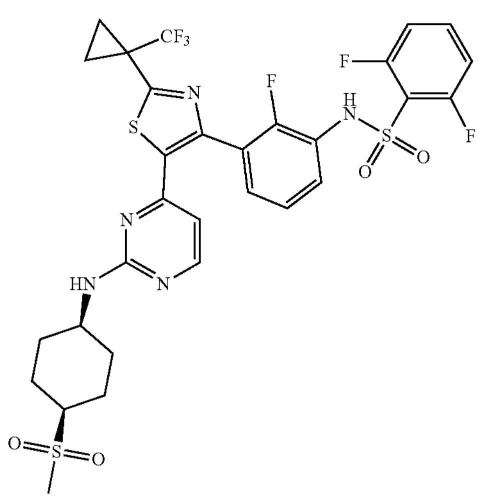 [SMILES: CS(=O)(=O)[C@H]1CC[C@@H](Nc2nccc(-c3sc(C4(C(F)(F)F)CC4)nc3-c3cccc(NS(=O)(=O)c4c(F)cccc4F)c3F)n2)CC1] | 1. 3-(trifluoromethyl)bicyclo[1.1.1]pentane-1-carboxylic acid replaced by 1-(trifluoromethyl)cyclopropane-1-carboxylic acid in Step 1.<br>2. Intermediate 8 replaced by Intermediate 9 in step 3.<br>3. Intermediate 6 replaced by Intermediate 4 in Step 4. | 732.1 |

| Ex # | Structures | Changes in synthetic protocol | LCMS (ES, m/z): [M + 1]+ |
|---|---|---|---|
| 125 | 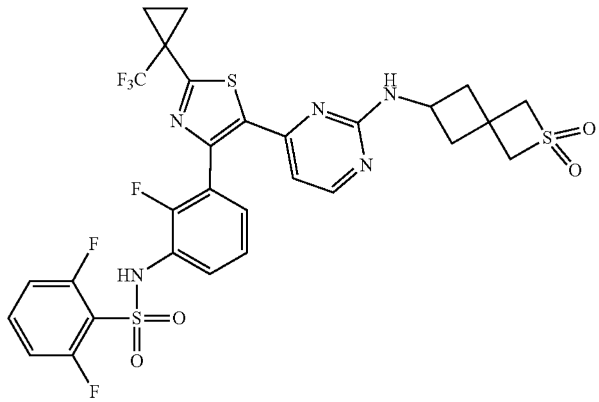 [SMILES: O=S1(=O)CC2(CC(Nc3nccc(-c4sc(C5(C(F)(F)F)CC5)nc4-c4cccc(NS(=O)(=O)c5c(F)cccc5F)c4F)n3)C2)C1] | 1. 3-(trifluoromethyl)bicyclo[1.1.1]pentane-1-carboxylic acid replaced by 1-(trifluoromethyl)cyclopropane-1-carboxylic acid in Step 1.<br>2. Intermediate 8 replaced by Intermediate 9 in step 3. | 716.1 |

Example 42

Synthesis of N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

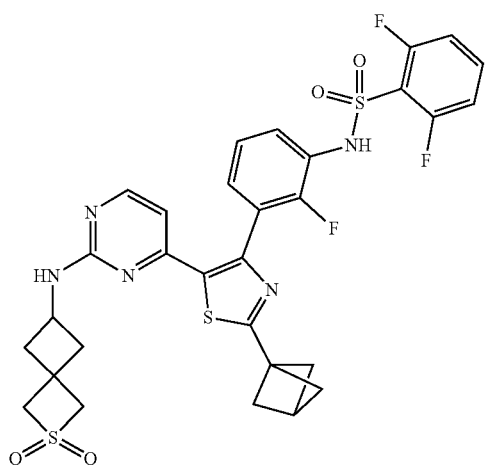 [SMILES: O=S1(=O)CC2(CC(Nc3nccc(-c4sc(C56CC(C5)C6)nc4-c4cccc(NS(=O)(=O)c5c(F)cccc5F)c4F)n3)C2)C1]

Step 1: Bicyclo[1.1.1]pentane-1-carboxamide

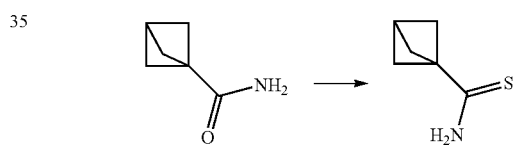

Oxalyl chloride (294 mg, 2.32 mmol, 1.30 eq.) and DMF (1 drop) was added to a mixture of bicyclo[1.1.1]pentane-1-carboxylic acid (Intermediate 15; 200 mg, 1.78 mmol, 1.00 eq.) in DCM (2.0 mL) at 0° C. The mixture was warmed to r.t. and stirred under $N_2$ for 2 h. The mixture was added dropwise to a solution of $NH_3·H_2O$ (1.90 g, 53.52 mmol, 30.00 eq.) in THF (3.0 mL) and stirred at r.t. overnight. The mixture was diluted with $H_2O$ and extracted with DCM. The combined organic layers were dried over $Na_2SO_4$, concentrated to give the title compound as a yellow solid.

Step 2: Bicyclo[1.1.1]pentane-1-carbothioamide

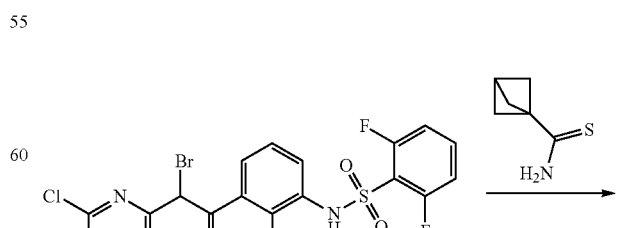

Lawesson's reagent (655 mg, 1.62 mmol, 1.00 eq.) was added to a mixture of bicyclo[1.1.1]pentane-1-carboxamide (180 mg, 1.62 mmol, 1.00 eq.) in THF (10.0 mL) and the mixture was stirred at 60° C. under $N_2$ for 3 h. The mixture was concentrated and purified by column chromatography on silica gel (PE:EA=2:1) to give the title compound as a yellow solid.

Step 3: N-(3-(2-(Bicyclo[1.1.1]pentan-1-yl)-5-(2-chloropyrimidin-4-yl)thiazol-4-yl)-2-fluoro-phenyl)-2,6-difluorobenzenesulfonamide 275
-continued

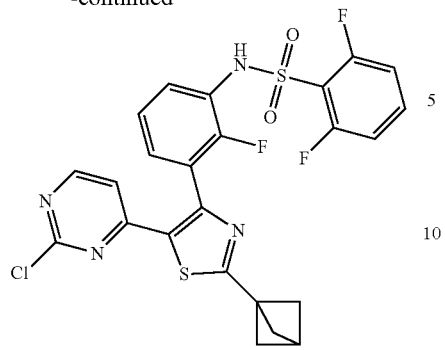

A mixture of N-(3-(2-bromo-2-(2-chloropyrimidin-4-yl)acetyl)-2-fluorophenyl)-2,6-difluorobenzenesulfonamide (Intermediate 9; 260 mg, 0.50 mmol, 1.00 eq.) and bicyclo[1.1.1]pentane-1-carbothioamide (64 mg, 0.50 mmol, 1.00 eq) in DMA (5.0 mL) was stirred at r.t. for 30 min. The mixture was stirred at 75° C. overnight and then concentrated. The residue was purified by column chromatography on silica gel (PE:EA=2:1) to give the title compound as a yellow solid.

Step 4: N-(3-(2-(Bicyclo[1.1.1]pentan-1-yl)-5-(2-((2,2-dioxido-2-thiaspiro[3.3]heptan-6-yl)-amino)pyrimidin-4-yl)thiazol-4-yl)-2-fluorophenyl)-2,6-difluorobenzenesulfonamide

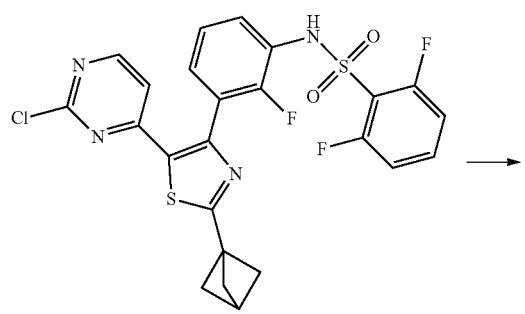

276
-continued

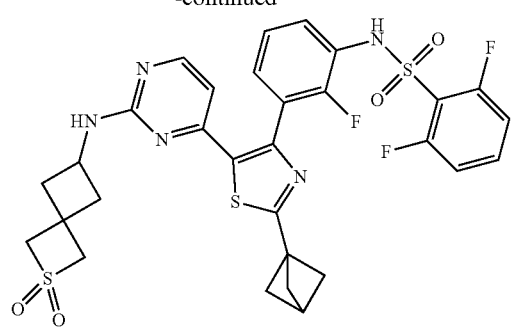

A mixture of N-(3-(2-(bicyclo[1.1.1]pentan-1-yl)-5-(2-chloropyrimidin-4-yl)thiazol-4-yl)-2-fluorophenyl)-2,6-difluorobenzenesulfonamide (50 mg, 0.09 mmol, 1.00 eq.), 6-amino-2-thiaspiro[3.3]heptane 2,2-dioxide (Intermediate 6; 18 mg, 0.11 mmol, 1.20 eq.) and DIEA (35 mg, 0.27 mmol, 3.00 eq) in t-BuOH (2.0 mL) was stirred overnight at 130° C. under $N_2$. The mixture was cooled to rt and concentrated. The residue was purified by prep-HPLC to give the title compound as a white solid. LCMS (ES, m/z): $[M+H]^+$=674.2.

Proceeding analogously as described in Example 42, the following compounds were prepared.

| Ex# | Structures | Changes in synthetic protocol | LCMS (ES, m/z): [M + 1]+ |
|---|---|---|---|
| 43 | 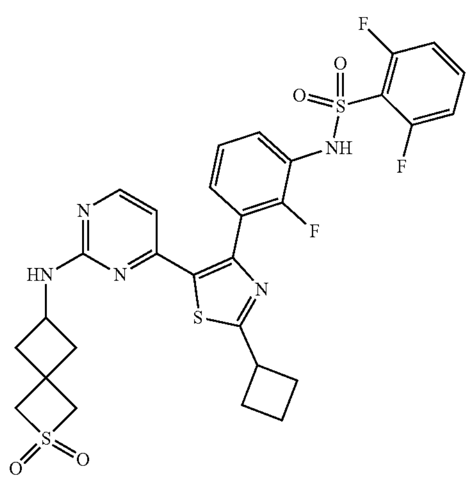 [SMILES: O=S1(=O)CC2(CC(Nc3nccc(-c4sc(C5CCC5)nc4-c4cccc(NS(=O)(=O)c5c(F)cccc5F)c4F)n3)C2)C1] | bicyclo[1.1.1]pentane-1-carboxylic acid replaced by cyclobutanecarboxylic acid in Step 1. | 662.1 |

| Ex# | Structures | Changes in synthetic protocol | LCMS (ES, m/z): [M + 1]+ |
|---|---|---|---|
| 44 | 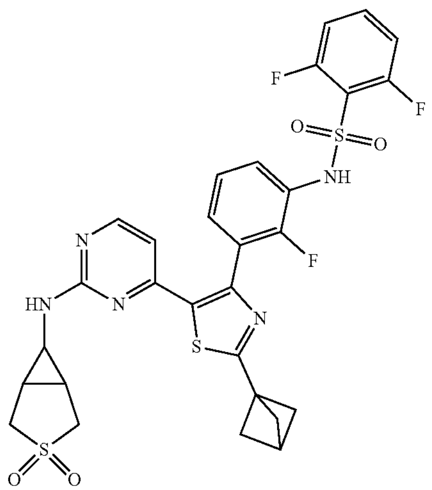 [SMILES: O=S1(=O)CC2C(C1)C2Nc1nccc(-c2sc(C34CC(C3)C4)nc2-c2cccc(NS(=O)(=O)c3c(F)cccc3F)c2F)n1] | Intermediate 6 replaced by 6-amino-3-thiabicyclo[3.1.0]hexane 3,3-dioxide in Step 4. | 660.1 |
| 45 | 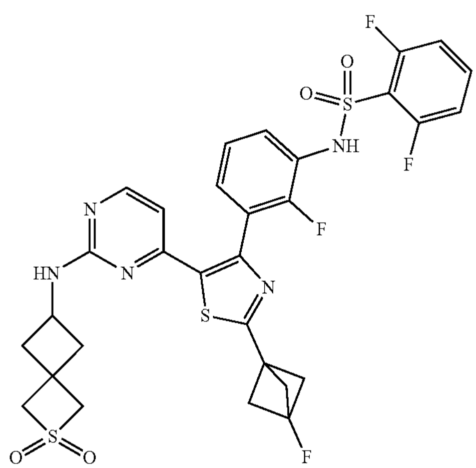 [SMILES: O=S1(=O)CC2(CC(Nc3nccc(-c4sc(C56CC(F)(C5)C6)nc4-c4cccc(NS(=O)(=O)c5c(F)cccc5F)c4F)n3)C2)C1] | bicyclo[1.1.1]pentane-1-carboxylic acid replaced by 3-fluorobicyclo[1.1.1]-pentane-1-carboxylic acid in Step 1. | 692.1 |
| 46 | 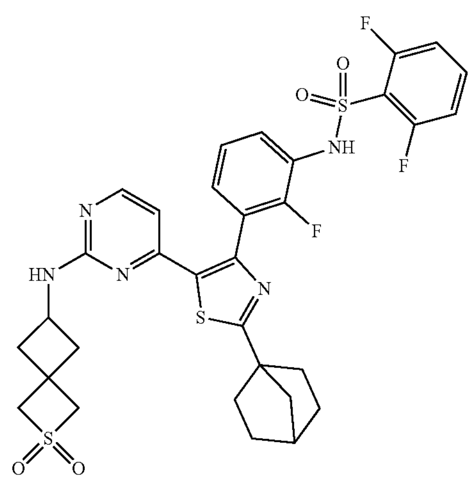 [SMILES: O=S1(=O)CC2(CC(Nc3nccc(-c4sc(C56CCC(CC5)C6)nc4-c4cccc(NS(=O)(=O)c5c(F)cccc5F)c4F)n3)C2)C1] | bicyclo[1.1.1]pentane-1-carboxylic acid replaced by bicyclo[2.2.1]heptane-1-carboxylic acid in Step 1. | 702.3 |

| Ex# | Structures | Changes in synthetic protocol | LCMS (ES, m/z): [M + 1]+ |
|---|---|---|---|
| 47 | 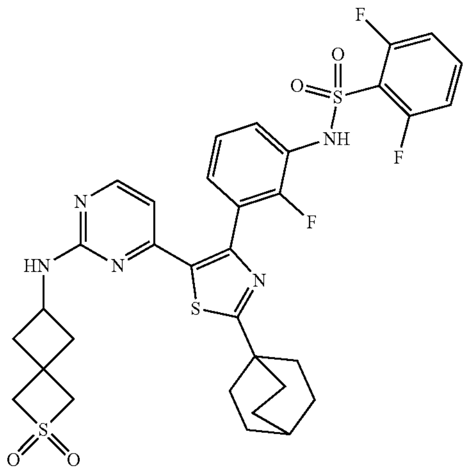 [SMILES: O=S1(=O)CC2(CC(Nc3nccc(-c4sc(C56CCC(CC5)CC6)nc4-c4cccc(NS(=O)(=O)c5c(F)cccc5F)c4F)n3)C2)C1] | bicyclo[1.1.1]pentane-1-carboxylic acid replaced by bicyclo[2.2.2]octane-1-carboxylic acid in Step 1. | 716.2 |
| 48 | 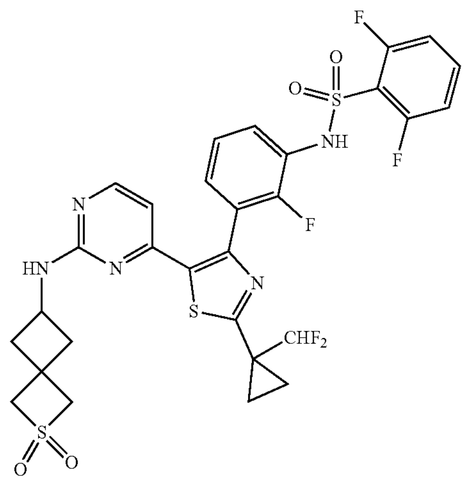 [SMILES: O=S1(=O)CC2(CC(Nc3nccc(-c4sc(C5(C(F)F)CC5)nc4-c4cccc(NS(=O)(=O)c5c(F)cccc5F)c4F)n3)C2)C1] | bicyclo[1.1.1]pentane-1-carboxylic acid replaced by Intermediate 17 in Step 1. | 698.1 |
| 49 | 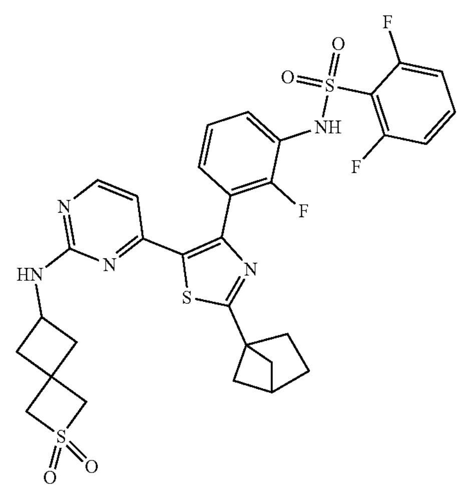 [SMILES: O=S1(=O)CC2(CC(Nc3nccc(-c4sc(C56CCC(C5)C6)nc4-c4cccc(NS(=O)(=O)c5c(F)cccc5F)c4F)n3)C2)C1] | bicyclo[1.1.1]pentane-1-carboxylic acid replaced by bicyclo[2.1.1]hexane-1-carboxylic acid in Step 1. | 688.1 |

-continued

| Ex# | Structures | Changes in synthetic protocol | LCMS (ES, m/z): [M + 1]+ |
|---|---|---|---|
| 50 | 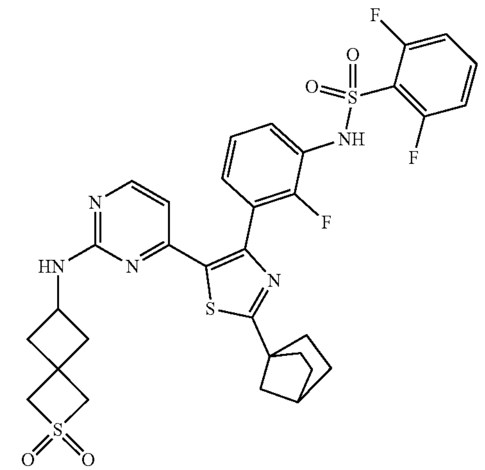 [SMILES: O=S1(=O)CC2(CC(Nc3nccc(-c4sc(C56CCC(CC5)C6)nc4-c4cccc(NS(=O)(=O)c5c(F)cccc5F)c4F)n3)C2)C1] | bicyclo[1.1.1]pentane-1-carboxylic acid replaced by bicyclo[2.2.1]heptane-1-carboxylic acid in Step 1. | 702.1 |
| 51 | 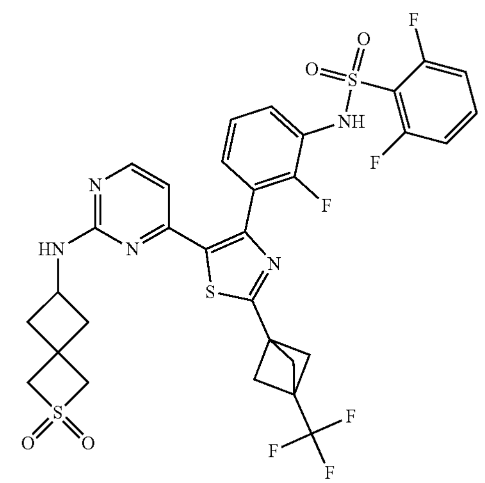 [SMILES: O=S1(=O)CC2(CC(Nc3nccc(-c4sc(C56CC(C(F)(F)F)(C5)C6)nc4-c4cccc(NS(=O)(=O)c5c(F)cccc5F)c4F)n3)C2)C1] | bicyclo[1.1.1]pentane-1-carboxylic acid replaced by 3-(trifluoromethyl)bicyclo-[1.1.1]pentane-1-carboxylic acid in Step 1. | 742.1 |
| 52 | 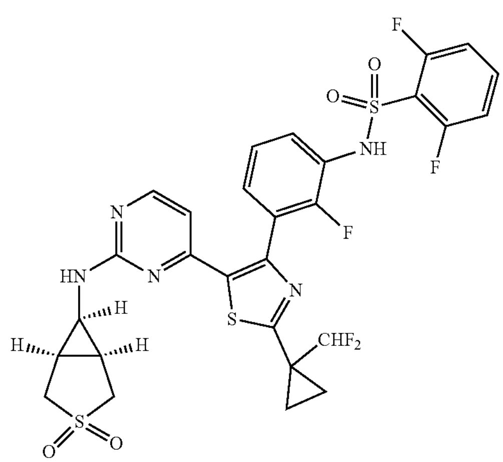 [SMILES: O=S1(=O)C[C@@H]2[C@H](C1)[C@@H]2Nc1nccc(-c2sc(C3(C(F)F)CC3)nc2-c2cccc(NS(=O)(=O)c3c(F)cccc3F)c2F)n1] | 1. bicyclo[1.1.1]pentane-1-carboxylic acid replaced by Intermediate 17 in Step 1.<br>2. Intermediate 6 replaced by Intermediate 2 in Step 4. | 684.2 |

-continued

| Ex# | Structures | Changes in synthetic protocol | LCMS (ES, m/z): [M + 1]⁺ |
|---|---|---|---|
| 53 | 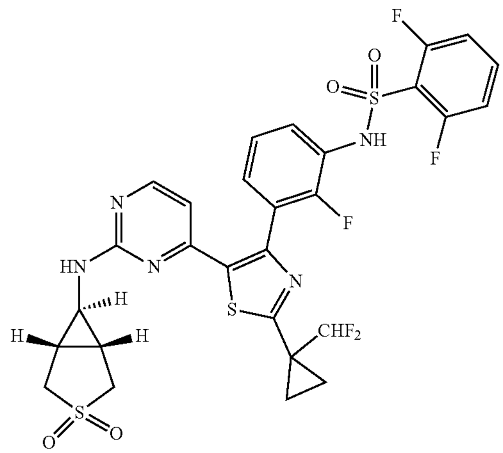 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3F)c2F)n1] | 1. bicyclo[1.1.1]pentane-1-carboxylic acid replaced by Intermediate 17 in Step 1.<br>2. Intermediate 6 replaced by Intermediate 3 in Step 4. | 684.2 |
| 54 | 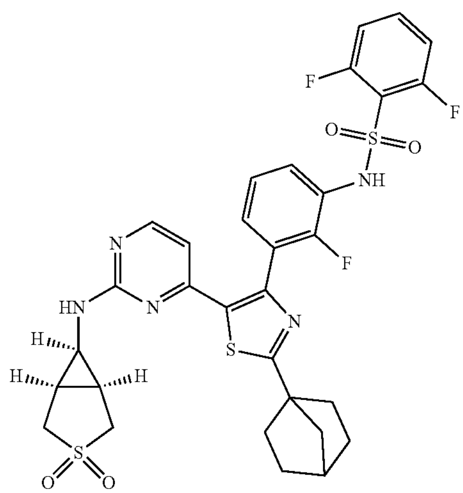 [SMILES: O=S1(=O)C[C@@H]2[C@H](C1)[C@@H]2Nc1nccc(-c2sc(C34CCC(CC3)C4)nc2-c2cccc(NS(=O)(=O)c3c(F)cccc3F)c2F)n1] | 1. bicyclo[1.1.1]pentane-1-carboxylic acid replaced by bicyclo[2.2.1]heptane-1-carboxylic acid in Step 1.<br>2. Intermediate 6 replaced by Intermediate 2 in Step 4. | 688.2 |
| 55 | 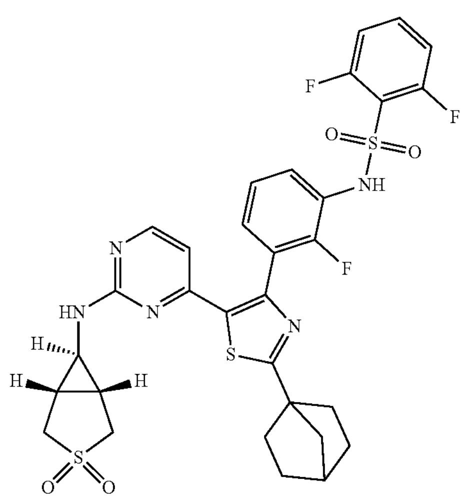 [SMILES: O=S1(=O)C[C@@H]2[C@H](C1)[C@H]2Nc1nccc(-c2sc(C34CCC(CC3)C4)nc2-c2cccc(NS(=O)(=O)c3c(F)cccc3F)c2F)n1] | 1. bicyclo[1.1.1]pentane-1-carboxylic acid replaced by bicyclo[2.2.1]heptane-1-carboxylic acid in Step 1.<br>2. Intermediate 6 replaced by Intermediate 3 in Step 4. | 688.3 |

-continued

| Ex# | Structures | Changes in synthetic protocol | LCMS (ES, m/z): [M + 1]+ |
|---|---|---|---|
| 56 | 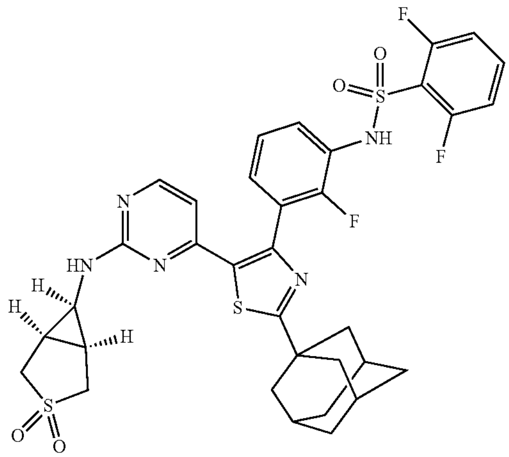 [SMILES: O=S1(=O)C[C@@H]2[C@H](C1)[C@@H]2Nc1nccc(-c2sc(C34CC5CC(CC(C5)C3)C4)nc2-c2cccc(NS(=O)(=O)c3c(F)cccc3F)c2F)n1] | 1. bicyclo[1.1.1]pentane-1-carboxylic acid replaced by adamantane-1-carboxylic acid in Step 1.<br>2. Intermediate 6 replaced by Intermediate 2 in Step 4. | 728.2 |
| 57 | 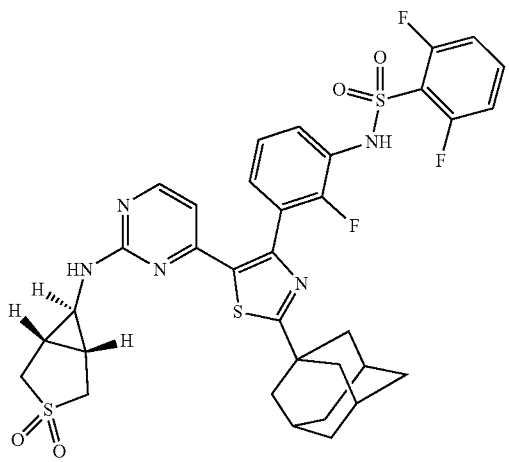 [SMILES: O=S1(=O)C[C@@H]2[C@H](C1)[C@H]2Nc1nccc(-c2sc(C34CC5CC(CC(C5)C3)C4)nc2-c2cccc(NS(=O)(=O)c3c(F)cccc3F)c2F)n1] | 1. bicyclo[1.1.1]pentane-1-carboxylic acid replaced by adamantane-1-carboxylic acid in Step 1.<br>2. Intermediate 6 replaced by Intermediate 3 in Step 4. | 728.2 |
| 58 | 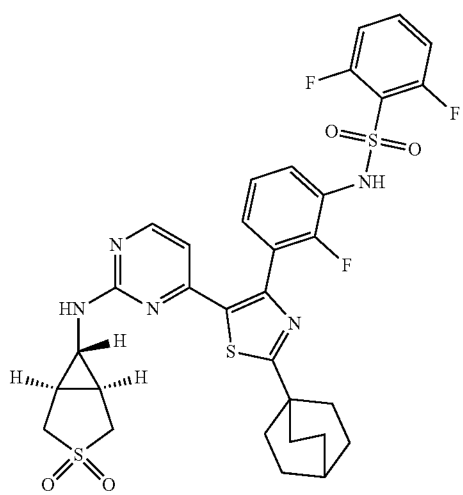 [SMILES: O=S1(=O)C[C@@H]2[C@H](C1)[C@H]2Nc1nccc(-c2sc(C34CCC(CC3)CC4)nc2-c2cccc(NS(=O)(=O)c3c(F)cccc3F)c2F)n1] | 1. bicyclo[1.1.1]pentane-1-carboxylic acid replaced by bicyclo[2.2.2]octane-1-carboxylic acid in Step 1.<br>2. Intermediate 6 replaced by Intermediate 3 in Step 4. | 702.3 |

| Ex# | Structures | Changes in synthetic protocol | LCMS (ES, m/z): [M + 1]+ |
|---|---|---|---|
| 59 | 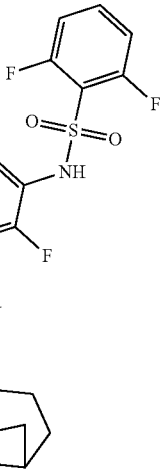 | 1. bicyclo[1.1.1]pentane-1-carboxylic acid replaced by bicyclo[2.2.2]octane-1-carboxylic acid in Step 1.<br>2. Intermediate 6 replaced by Intermediate 2 in Step 4. | 702.2 |
| 60 | 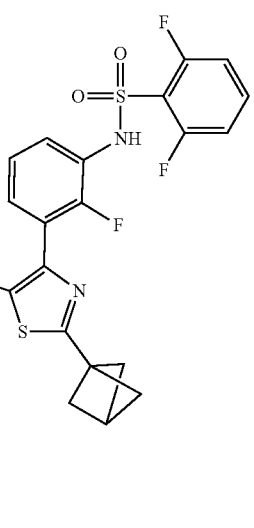 | Intermediate 6 replaced by Intermediate 1 in Step 4. | 688.2 |
| 61* | 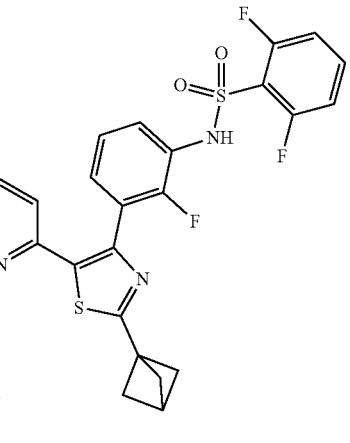 | Intermediate 6 replaced by Intermediate 7 in Step 4. | 688.1 |

-continued

| Ex# | Structures | Changes in synthetic protocol | LCMS (ES, m/z): [M + 1]+ |
|---|---|---|---|
| 62* | 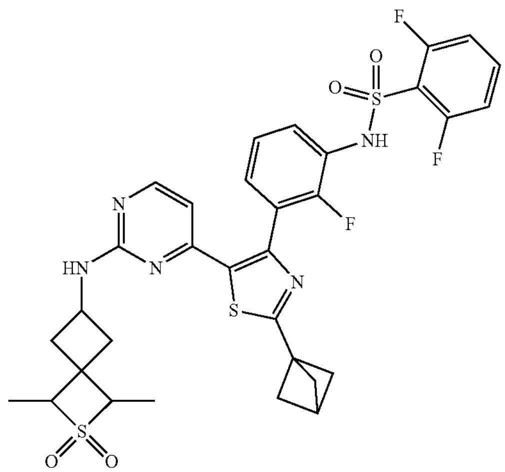 [SMILES: CC1C2(CC(Nc3nccc(-c4sc(C56CC(C5)C6)nc4-c4cccc(NS(=O)(=O)c5c(F)cccc5F)c4F)n3)C2)C(C)S1(=O)=O] | Intermediate 6 replaced by Intermediate 7 in Step 4. | 701.3 |

*61 and 62 were prepared using Intermediate 7 as a mixture, then 61 and 62 were separated.

Additional compound prepared by proceeding analogously as described in Example 42 are:

| Ex # | Structures | Changes in synthetic protocol | LCMS (ES, m/z): [M + 1]+ |
|---|---|---|---|
| 64 | 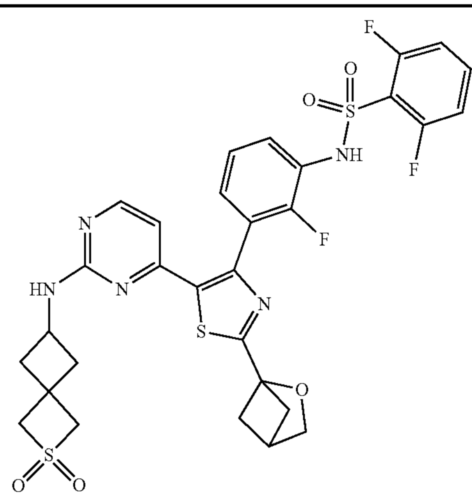 | bicyclo[1.1.1]pentane-1-carboxylic acid replaced by 2-oxabicyclo[2.1.1]-hexane-1-carboxylic acid in Step 1. | 690.2 |
| 65 | 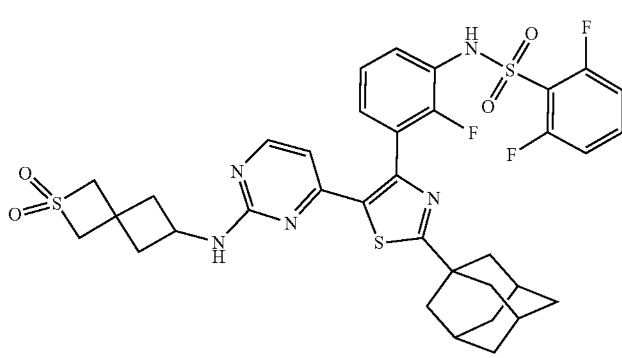 [SMILES: O=S1(=O)CC2(CC(Nc3nccc(-c4sc(C56CC7CC(CC(C7)C5)C6)nc4-c4cccc(NS(=O)(=O)c5c(F)cccc5F)c4F)n3)C2)C1] | bicyclo[1.1.1]pentane-1-carboxylic acid replaced by -adamantane-1-carboxylic acid in Step 1. | 742.2 |

| Ex # | Structures | Changes in synthetic protocol | LCMS (ES, m/z): [M + 1]+ |
|---|---|---|---|
| 66 | 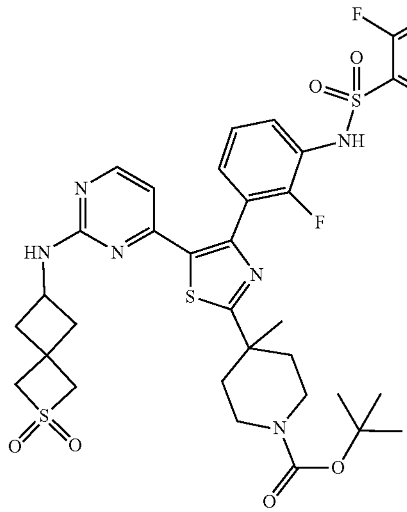 | bicyclo[1.1.1]pentane-1-carboxylic acid replaced by (1-(tert-butoxy-carbonyl)-4-methylpiperidine-4-carboxylic acid in Step 1. | 805.3 |

Example 63

Synthesis of N-(3-(5-(2-((2,2-dioxido-2-thiaspiro[3.3]heptan-6-yl)amino)pyrimidin-4-yl)-2-(3-(hydroxymethyl)bicyclo[1.1.1]pentan-1-yl)thiazol-4-yl)-2-fluorophenyl)-2,6-difluorobenzenesulfonamide Step 1: N-(3-(2-(3-(((tert-butyldiphenylsilyl)oxy)methyl)bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

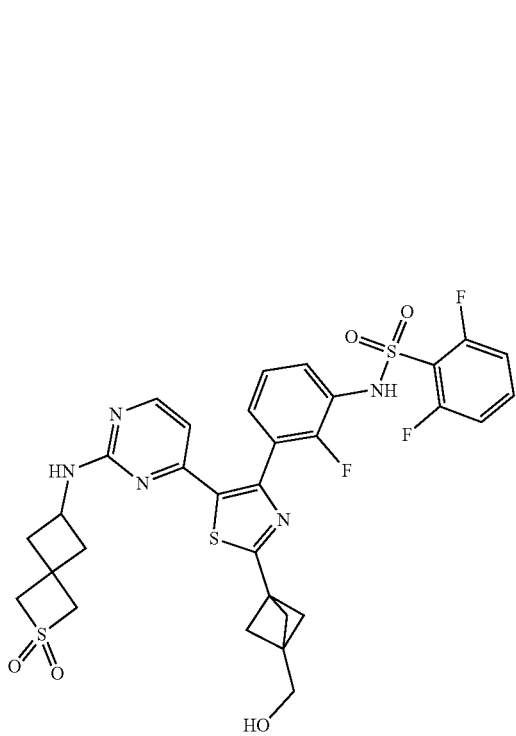 [SMILES: O=S1(=O)CC2(CC(Nc3nccc(-c4sc(C56CC(CO)(C5)C6)nc4-c4cccc(NS(=O)(=O)c5c(F)cccc5F)c4F)n3)C2)C1]

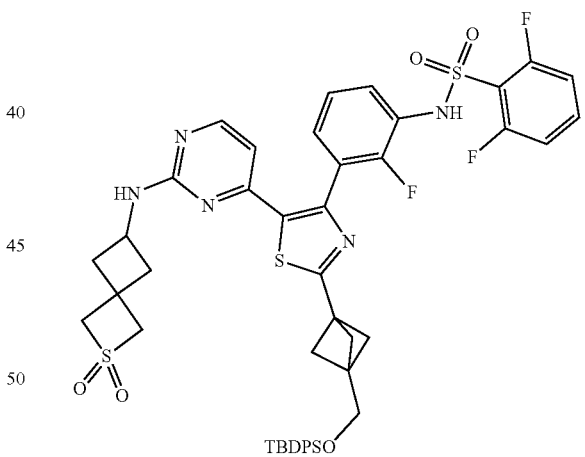

The title compound was synthesized with 3-(((tert-butyldiphenylsilyl)oxy)methyl)-bicyclo[1.1.1]pentane-1-carboxylic acid (Intermediate 14) replacing bicyclo[1.1.1]pentane-1-carboxylic acid and proceeding analogously as described in Example 42, Steps 1-4.

Step 2: N-(3-(5-(2-((2,2-dioxido-2-thiaspiro[3.3] heptan-6-yl)amino)pyrimidin-4-yl)-2-(3-(hydroxymethyl)bicyclo[1.1.1]pentan-1-yl)thiazol-4-yl)-2-fluorophenyl)-2,6-difluoro-benzenesulfonamide

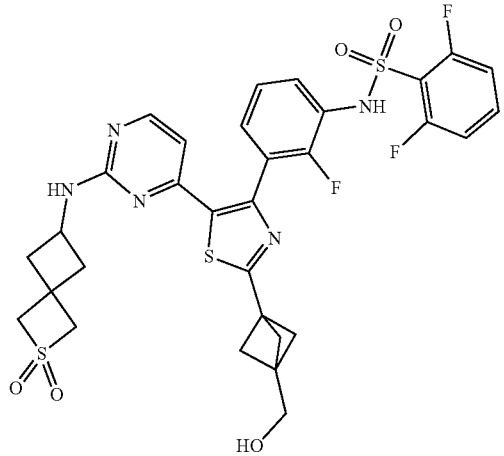 [SMILES: O=S1(=O)CC2(CC(Nc3nccc(-c4sc(C56CC(CO)(C5)C6)nc4-c4cccc(NS(=O)(=O)c5c(F)cccc5F)c4F)n3)C2)C1]

TBAF (5.0 mL in THF 1M) was added to a stirred solution of N-(3-(2-(3-(((tert-butyl-diphenylsilyl)oxy)methyl)bicycle [1.1.1]pentan-1-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzene-sulfonamide (310 mg, 0.33 mmol, 1.00 eq.) in THF (50.0 mL) at rt under N$_2$. The resulting mixture was stirred at rt for 16 h and then concentrated and purified by silica gel chromatography (EA:PE=1:1) to give the title compound. MS (ES, m/z): [M+1]$^+$=704.2

Example 67

Synthesis of N-(3-(5-(2-((2,2-dioxido-2-thiaspiro [3.3]heptan-6-yl)amino)pyrimidin-4-yl)-2-(4-methylpiperidin-4-yl)thiazol-4-yl)-2-fluorophenyl)-2,6-difluorobenzenesulfonamide

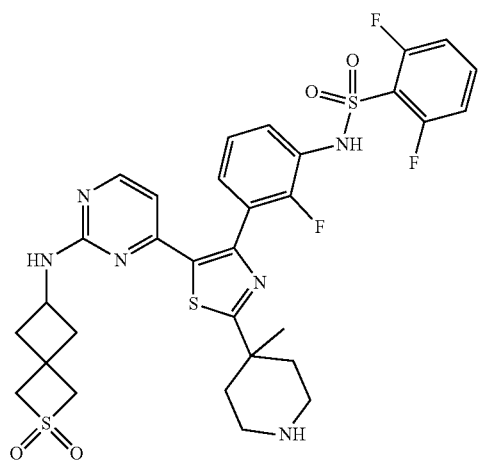 [SMILES: CC1(c2nc(-c3cccc(NS(=O)(=O)c4c(F)cccc4F)c3F)c(-c3ccnc(NC4CC5(C4)CS(=O)(=O)C5)n3)s2)CCNCC1]

To a solution of tert-butyl 4-(4-(3-(2,6-difluorophenylsulfonamido)-2-fluorophenyl)-5-(2-((2,2-dioxido-2-thiaspiro[3.3]heptan-6-yl)amino)pyrimidin-4-yl)thiazol-2-yl)-4-methylpiperidine-1-carboxylate (150 mg, 0.19 mmol, 1.00 eq.) in DCM (4.0 mL) was added TFA (1.0 mL). The mixture was stirred at rt for 2 h and then concentrated to give the title compound. MS (ES, m/z): [M+1]$^+$=705.1

Example 68

Synthesis of N-(3-(2-(1,4-dimethylpiperidin-4-yl)-5-(2-((2,2-dioxido-2-thiaspiro[3.3]heptan-6-yl)amino) pyrimidin-4-yl)thiazol-4-yl)-2-fluorophenyl)-2,6-difluorobenzenesulfonamide

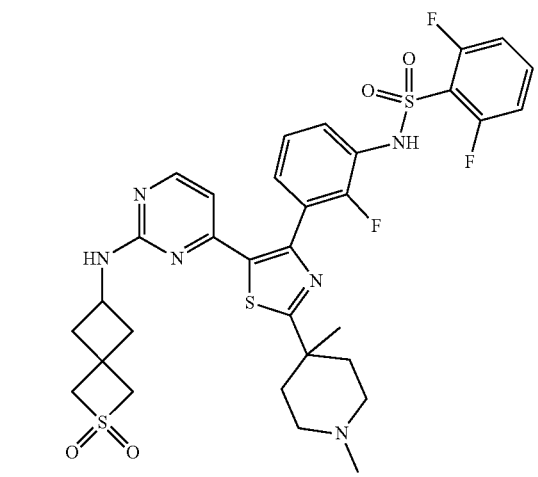 [SMILES: CN1CCC(C)(c2nc(-c3cccc(NS(=O)(=O)c4c(F)cccc4F)c3F)c(-c3ccnc(NC4CC5(C4)CS(=O)(=O)C5)n3)s2)CC1]

To a solution of N-(3-(5-(2-((2,2-dioxido-2-thiaspiro[3.3] heptan-6-yl)amino)-pyrimidin-4-yl)-2-(4-methylpiperidin-4-yl)thiazol-4-yl)-2-fluorophenyl)-2,6-difluoro-benzene-sulfonamide (50 mg, 0.07 mmol, 1.00 eq.) and NaBH(OAc)$_3$ (45 mg, 0.21 mmol, 3.00 eq.) was added HCHO (35% in H$_2$O, 24 mg, 0.28 mmol, 4.00 eq.) at 0° C. The mixture was stirred at rt for 3 h and then concentrated and purified by prep-HPLC to give the title compound. MS (ES, m/z): [M+1]$^+$=719.2.

Example 69

Synthesis of N-(3-(2-(bicyclo[1.1.1]pentan-1-yl)-5-(2-((2,2-dioxido-2-thiaspiro[3.3]heptan-6-yl)amino) pyrimidin-4-yl)thiazol-4-yl)-2-fluorophenyl)-2,6-dichlorobenzenesulfonamide

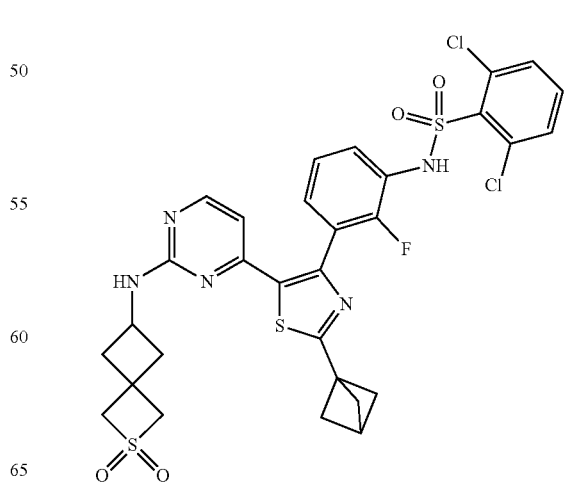

Step 1: N-(3-(2-(Bicyclo[1.1.1]pentan-1-yl)-5-(2-chloropyrimidin-4-yl)thiazol-4-yl)-2-fluorophenyl)acetamide

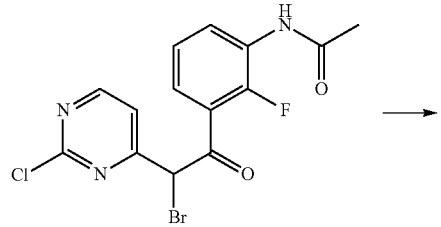

A mixture of bicyclo[1.1.1]pentane-1-carbothioamide (2.00 g, 15.70 mmol, 1.00 eq) and N-(3-(2-bromo-2-(2-chloropyrimidin-4-yl)acetyl)-2-fluorophenyl)acetamide (Int. 10; 6.00 g, 15.70 mmol, 1.00 eq) in DMA (100.0 mL) was stirred at r.t. for 1 h, and then stirred at 65° C. overnight under $N_2$. The mixture was extracted with EtOAc, and the combined organic layers were washed with water, brine, dried over $Na_2SO_4$, and concentrated to give the title compound as a yellow solid.

Step 2: N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)acetamide

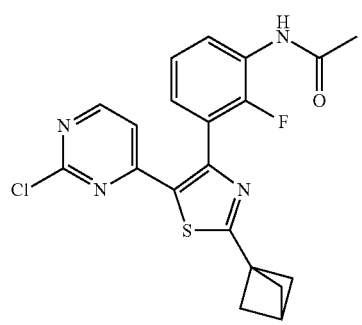

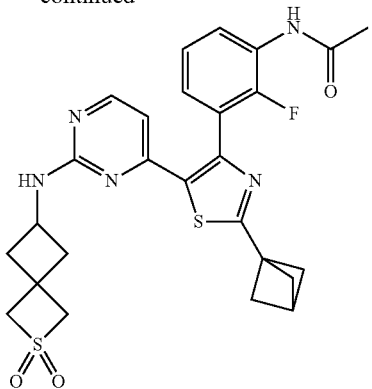

To a solution of N-(3-(2-(bicyclo[1.1.1]pentan-1-yl)-5-(2-chloropyrimidin-4-yl)thiazol-4-yl)-2-fluorophenyl)acetamide (4.75 g, 11.47 mmol, 1.00 eq) in n-BuOH (100.0 mL) was added 2-thiaspiro[3.3]heptan-6-amine (Intermediate 6; 3.39 g, 17.21 mmol, 1.50 eq), DIEA (8.88 g, 68.84 mmol, 6.00 eq) and the mixture was stirred at 130° C. overnight under $N_2$. The mixture was concentrated and purification by column chromatography on silica gel (PE:EA=2:1 to 1:2) to give the title compound as a yellow solid.

Step 3: 6-((4-(4-(3-Amino-2-fluorophenyl)-2-(bicyclo[1.1.1]pentan-1-yl)thiazol-5-yl)pyrimidin-2-yl)amino)-2-thiaspiro[3.3]heptane 2,2-dioxide

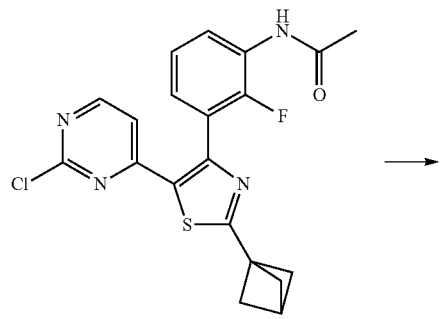

To a solution of N-(3-(2-(bicyclo[1.1.1]pentan-1-yl)-5-(2-((2,2-dioxido-2-thiaspiro[3.3]-heptan-6-yl)amino)pyrimidin-4-yl)thiazol-4-yl)-2-fluorophenyl)acetamide (1.50 g, 2.78 mmol) in MeOH (15.0 mL) was added MeOH/HCl (2M, 10.0 mL) and the mixture was stirred at 50° C. for 2 h under N₂. The mixture was concentrated and pH was adjusted to 9 by addition of 1N NaOH aq. The mixture was extracted with EtOAc and the combined organic layers were washed with water, brine, dried over Na₂SO₄, concentrated to give the title compound as a yellow solid.

Step 4: N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-dichlorobenzenesulfonamide

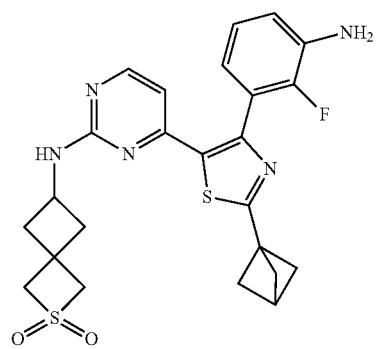
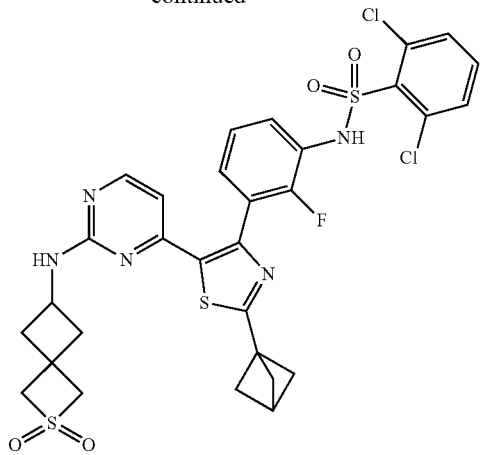

2,6-Dichlorobenzenesulfonyl chloride (197 mg, 0.80 mmol, 2.00 eq.) was added to a mixture of 6-((4-(4-(3-amino-2-fluorophenyl)-2-(bicyclo[1.1.1]pentan-1-yl)thiazol-5-yl)-pyrimidin-2-yl)amino)-2-thiaspiro[3.3]heptane 2,2-dioxide (200 mg, 0.40 mmol, 1.00 eq.) and pyridine (95 mg, 1.21 mmol, 3.00 eq.) in DCM (4.0 mL) at 0° C. The mixture was slowly warmed to r.t. and stirred overnight. The mixture was concentrated and purified by column chromatography on silica gel (DCM:MeOH=20:1) to give the title compound as a yellow solid. MS (ES, m/z): [M+1]⁺=706.1.

Proceeding analogously as described in Example 69, the following compounds were prepared.

| Ex # | Structures | Changes in synthetic protocol | LCMS (ES, m/z): [M + 1]⁺ |
|---|---|---|---|
| 70 | 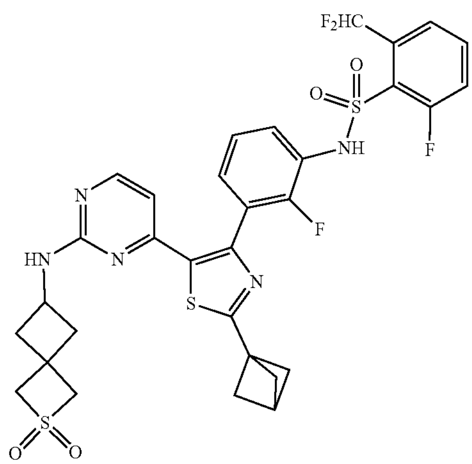 [SMILES: O=S1(=O)CC2(CC(Nc3nccc(-c4sc(C56CC(C5)C6)nc4-c4cccc(NS(=O)(=O)c5c(F)cccc5C(F)F)c4F)n3)C2)C1] | 2,6-dichlorobenzenesulfonyl chloride replaced by Intermediate 29 in Step 4. | 706.1 |

| Ex # | Structures | Changes in synthetic protocol | LCMS (ES, m/z): [M + 1]+ |
|---|---|---|---|
| 71 | 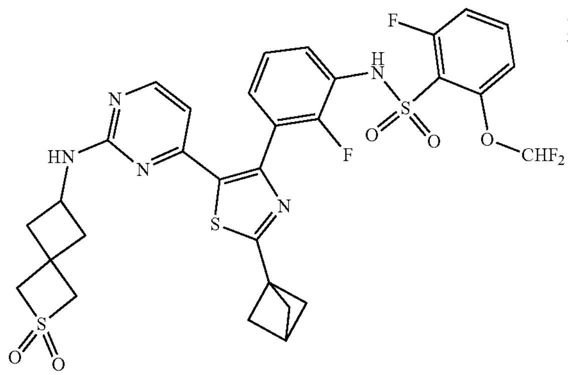 [SMILES: O=S1(=O)CC2(CC(Nc3nccc(-c4sc(C56CC(C5)C6)nc4-c4cccc(NS(=O)(=O)c5c(F)cccc5OC(F)F)c4F)n3)C2)C1] | 2,6-dichlorobenzenesulfonyl chloride replaced by Intermediate 12 in Step 4. | 722.2 |
| 72 | 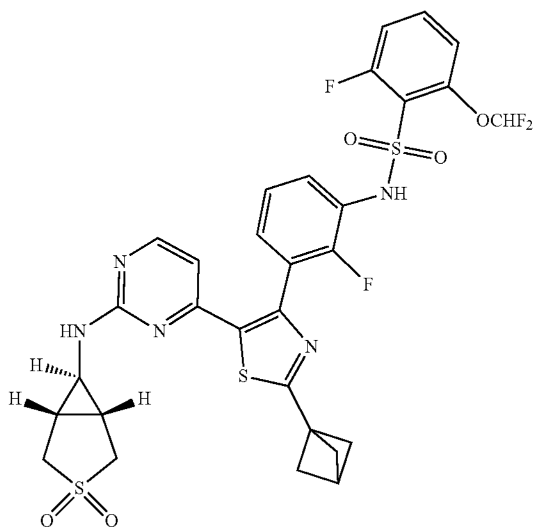 [SMILES: O=S1(=O)C[C@@H]2[C@H](C1)[C@H]2Nc1nccc(-c2sc(C34CC(C3)C4)nc2-c2cccc(NS(=O)(=O)c3c(F)cccc3OC(F)F)c2F)n1] | 1. Intermediate 6 replaced by Intermediate 3 in Step 2.<br>2. 2,6-dichlorobenzenesulfonyl chloride replaced by Intermediate 12 in Step 4. | 708.1 |
| 73 | 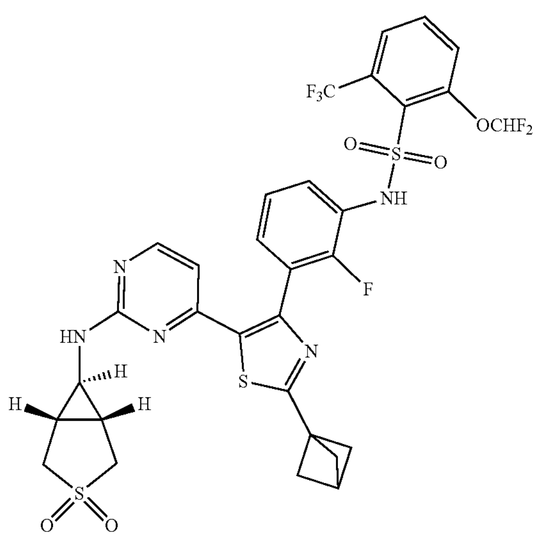 [SMILES: O=S1(=O)C[C@@H]2[C@H](C1)[C@H]2Nc1nccc(-c2sc(C34CC(C3)C4)nc2-c2cccc(NS(=O)(=O)c3c(OC(F)F)cccc3C(F)(F)F)c2F)n1] | 1. Intermediate 6 replaced by Intermediate 3 in Step 2.<br>2. 2,6-dichlorobenzenesulfonyl chloride replaced with Intermediate 11 in Step 4. | 758.2 |

| Ex # | Structures | Changes in synthetic protocol | LCMS (ES, m/z): [M + 1]+ |
|---|---|---|---|
| 74 | 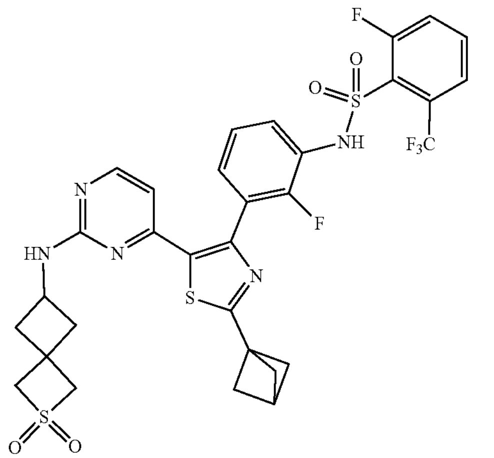 [SMILES: O=S1(=O)CC2(CC(Nc3nccc(-c4sc(C56CC(C5)C6)nc4-c4cccc(NS(=O)(=O)c5c(F)cccc5C(F)(F)F)c4F)n3)C2)C1] | 2,6-dichlorobenzenesulfonyl chloride replaced by 2-fluoro-6-(trifluoromethyl)benzenesulfonyl chloride in Step 4. | 724.2 |
| 75 | 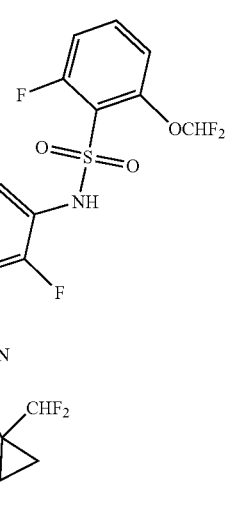 | 1 bicyclo[1.1.1]pentane-1-carboxylic acid replaced by Intermediate 16 in Step 1<br>2 2,6-dichlorobenzenesulfonyl chloride replaced by Intermediate 12 in Step 4. | 746.2 |
| 76 | 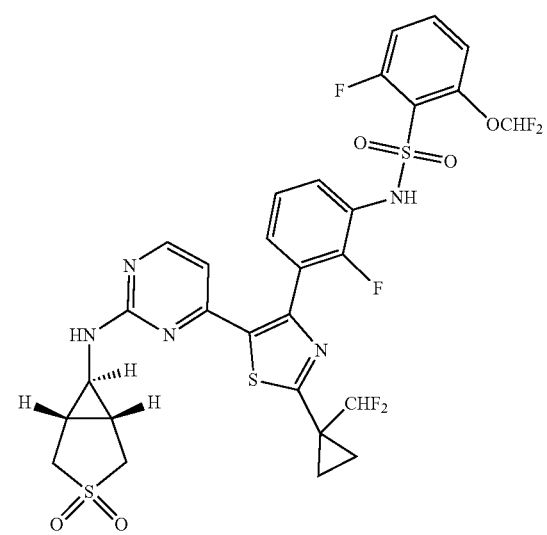 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3OC(F)F)c2F)n1] | 1. bicyclo[1.1.1]pentane-1-carboxylic acid replaced by Intermediate 16 in Step 1<br>2. Intermediate 6 replaced by Intermediate 3 in Step 2.<br>3. 2,6-dichlorobenzenesulfonyl chloride replaced by Intermediate 12 in Step 4. | 732.2 |

Example 78

Synthesis of N-(3-(2-(3-oxa-8-azabicyclo[3.2.1]octan-8-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzenesulfonamide

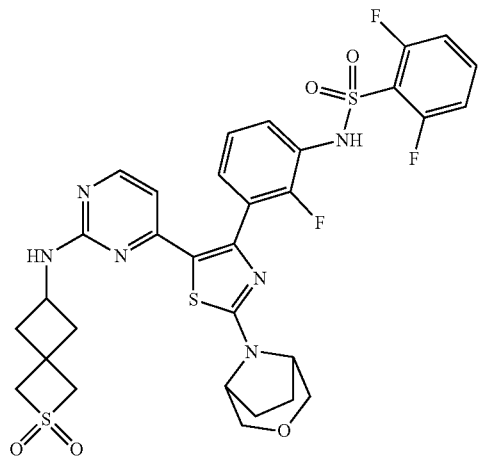 [SMILES: O=S1(=O)CC2(CC(Nc3nccc(-c4sc(N5C6CCC5COC6)nc4-c4cccc(NS(=O)(=O)c5c(F)cccc5F)c4F)n3)C2)C1]

Step 1: N-(3-(2-amino-5-(2-chloropyrimidin-4-yl)-2,3-dihydrothiazol-4-yl)-2-fluorophenyl)-2,6-difluorobenzenesulfonamide

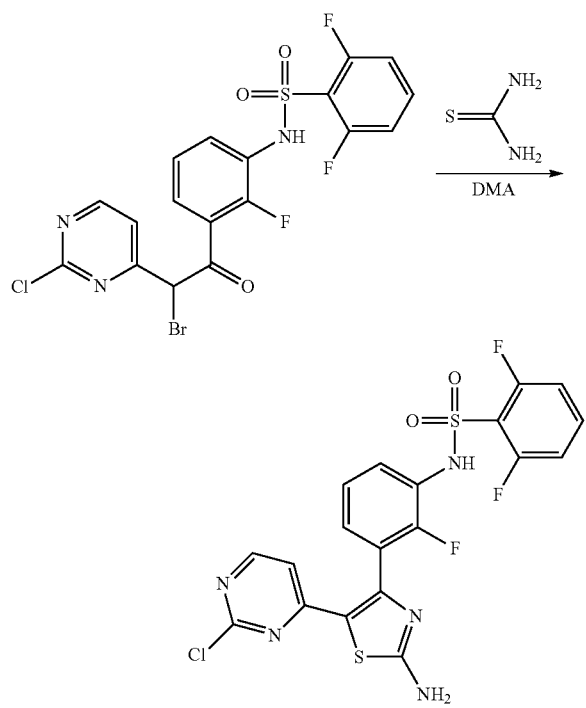

A mixture of N-(3-(2-bromo-2-(2-chloropyrimidin-4-yl)acetyl)-2-fluorophenyl)-2,6-difluorobenzenesulfonamide (Intermediate 9; 15.00 g, 28.85 mmol, 1.00 eq.) and thiourea (2.20 g, 3.72 mmol, 1.00 eq.) in DMA (150.0 mL) was stirred at rt for 30 mins. and then heated to 70° C. under $N_2$ for 4 h. The mixture was poured into water, filtered to give the title compound as a yellow solid.

Step 2: N-(3-(2-amino-5-(2-(methylthio)pyrimidin-4-yl)thiazol-4-yl)-2-fluorophenyl)-2,6-difluorobenzenesulfonamide

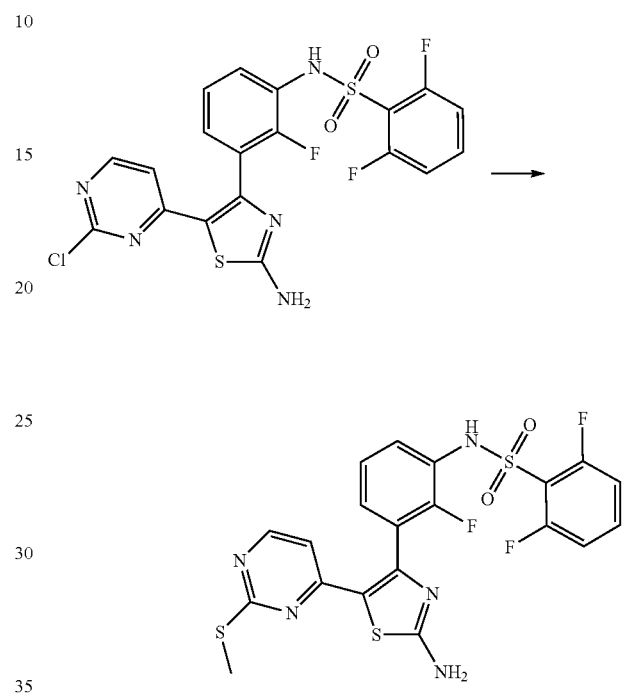

Sodium methanethiolate (196 mg, 2.80 mmol, 2.00 eq) was added to a mixture of N-(3-(2-amino-5-(2-chloropyrimidin-4-yl)thiazol-4-yl)-2-fluorophenyl)-2,6-difluorobenzene-sulfonamide (700 mg, 1.40 mmol, 1.00 eq) in DMSO (10.0 ml) at rt and the mixture was stirred at rt overnight. The mixture was diluted with water and extracted with EtOAc. The combined organic layer was washed with brine, dried over $Na_2SO_4$, and concentrated. The residue was purified by chromatograph on silica gel (DCM/MeOH=20/1) to give the title compound as a yellow solid.

Step 3: N-(3-(2-bromo-5-(2-(methylthio)pyrimidin-4-yl)thiazol-4-yl)-2-fluorophenyl)-2,6-difluorobenzenesulfonamide

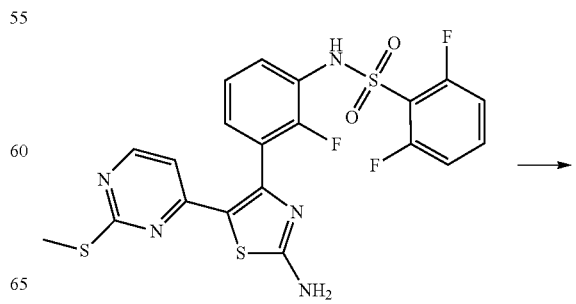

305

-continued

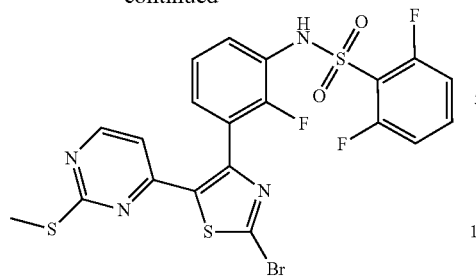

tert-Butyl nitrite (91 mg, 0.89 mmol, 1.50 eq) was added to a mixture of N-(3-(2-amino-5-(2-(methylthio)pyrimidin-4-yl)thiazol-4-yl)-2-fluorophenyl)-2,6-difluorobenzenesulfonamide (300 mg, 0.59 mmol, 1.00 eq) and CuBr$_2$ (158 mg, 0.71 mmol. 1.20 eq) in MeCN (6.0 ml) at 0° C. The mixture was stirred at rt overnight, and extracted with EtOAc. The combined organic layer was washed with brine and dried over Na$_2$SO$_4$. Then the residue was purified by chromatograph on silica gel (DCM/MeOH=100/1) to give the title compound as a yellow solid.

Step 4: N-(3-(2-(3-oxa-8-azabicyclo[3.2.1]octan-8-yl)-5-(2-(methylthio)pyrimidin-4-yl)thiazol-4-yl)-2-fluorophenyl)-2,6-difluorobenzenesulfonamide

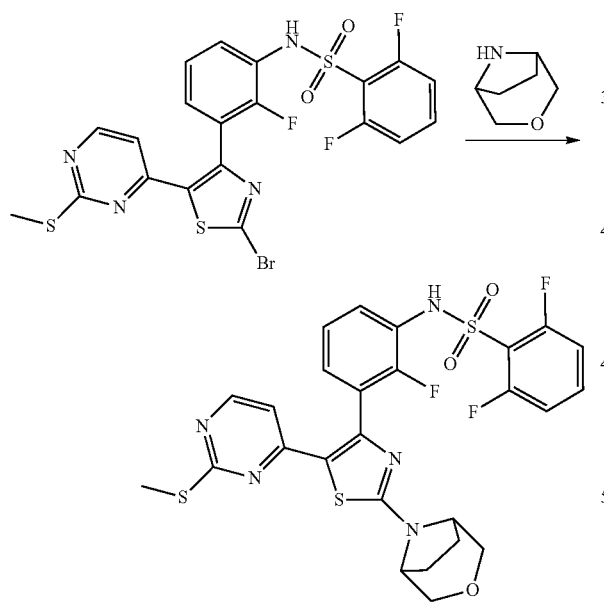

A mixture of N-(3-(2-bromo-5-(2-(methylthio)pyrimidin-4-yl)thiazol-4-yl)-2-fluorophenyl)-2,6-difluorobenzenesulfonamide (100 mg, 0.18 mol, 1.00 eq), 3-oxa-8-azabicyclo[3.2.1]octane (131 mg, 0.90 mmol 5.00 eq), and TEA (111 mg, 1.10 mmol, 6.00 eq) in DMA (2.0 ml) was stirred at 120° C. under microwave irradiation for 3 h. Then the mixture was diluted with water and extracted with EtOAc. The combined organic layer was washed with brine and dried over Na$_2$SO$_4$ and concentrated. The residue was purified by chromatograph on silica gel (DCM/MeOH=50/1) to give the title compound as a yellow solid.

306

Step 5: N-(3-(2-(3-oxa-8-azabicyclo[3.2.1]octan-8-yl)-5-(2-(methylsulfonyl)pyrimidin-4-yl)thiazol-4-yl)-2-fluorophenyl)-2,6-difluorobenzenesulfonamide

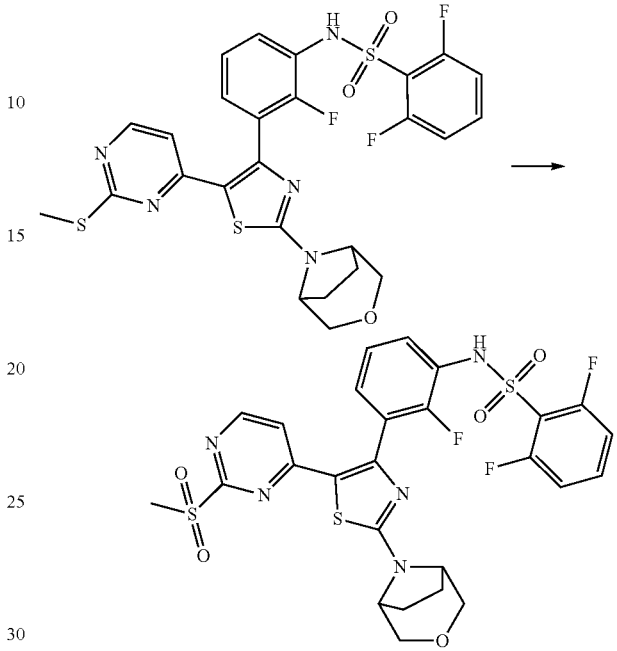

Oxone (246 mg, 0.40 mmol, 2.00 eq) was added to a mixture of N-(3-(2-(3-oxa-8-azabicyclo[3.2.1]octan-8-yl)-5-(2-(methylthio)pyrimidin-4-yl)thiazol-4-yl)-2-fluorophenyl)-2,6-difluorobenzenesulfonamide (120 mg, 0.20 mmol 1.00 eq) in THF/H$_2$O=4/1 (2.0 ml) at rt and the mixture was stirred overnight. The mixture was extracted with EtOAc and the combined organic layer was washed with brine and dried over Na$_2$SO$_4$ and concentrated. The residue was purified by prep-HPLC to give the title compound as a yellow solid.

Step 6: N-(3-(2-(3-Oxa-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

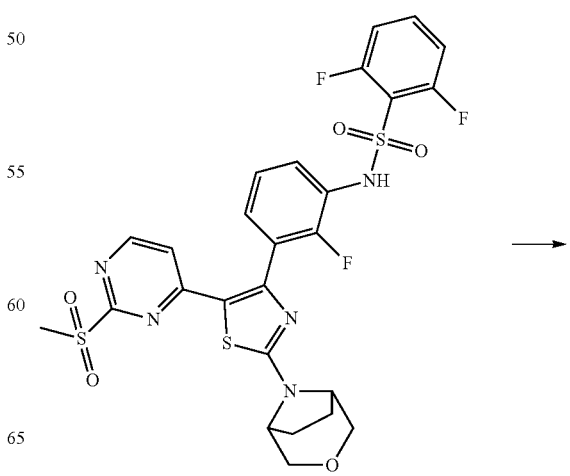

307
-continued

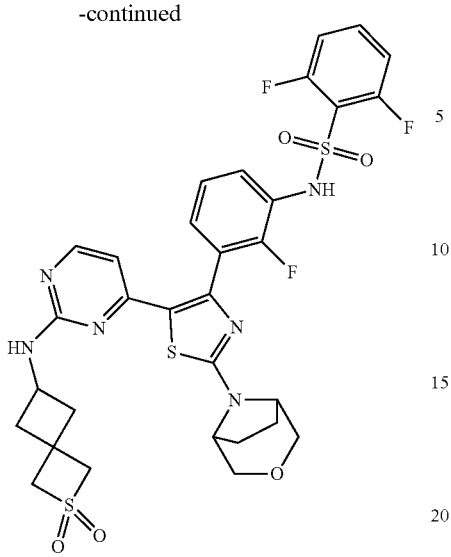

A mixture of N-(3-(2-(3-oxa-8-azabicyclo[3.2.1]octan-8-yl)-5-(2-(methylsulfonyl)-pyrimidin-4-yl)thiazol-4-yl)-2-fluorophenyl)-2,6-difluorobenzenesulfonamide (70 mg, 0.11 mmol, 1.00 eq), 6-amino-2-thiaspiro[3.3]heptane 2,2-dioxide (Intermediate 6; 27 mg, 0.17 mmol, 1.50 eq), DIEA (43 mg, 0.33 mmol, 3.00 eq) in DMSO (1 ml) was stirred at 70° C. overnight. The mixture was purified by chromatograph on silica gel to give the title compound as a yellow solid.

LCMS (ES, m/z): $[M+H]^+=719.2$

Proceeding analogously as described in Example 78, the following compounds were prepared.

| Ex# | Structures | Changes in synthetic protocol | LCMS (ES, m/z): $[M + 1]^+$ |
|---|---|---|---|
| 79 | 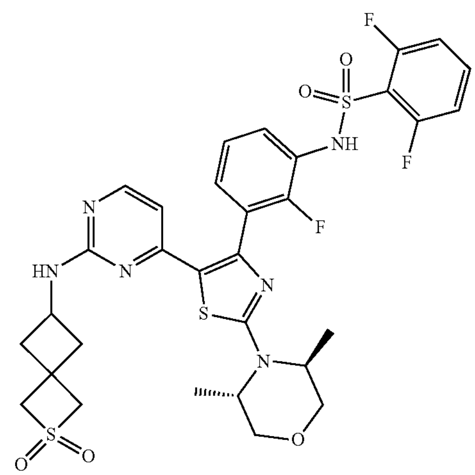 [SMILES: C[C@H]1COC[C@H](C)N1c1nc(-c2cccc(NS(=O)(=O)c3c(F)cccc3F)c2F)c(-c2ccnc(NC3CC4(C3)CS(=O)(=O)C4)n2)s1] | 3-oxa-8-azabicyclo[3.2.1]octane replaced by (3S,5S)-3,5-dimethylmorpholine in Step 4. | 721.3 |
| 80 | 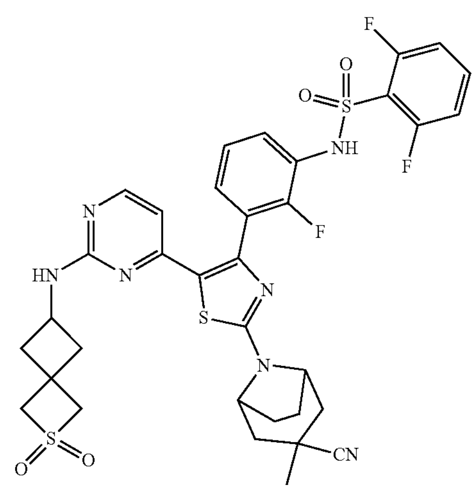 [SMILES: CC1(C#N)CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | 3-oxa-8-azabicyclo[3.2.1]octane replaced by Intermediate 21 in Step 4. | 756.3 |

Example 81

Synthesis of N-(3-(5-(2-((2,2-dioxido-2-thiaspiro[3.3]heptan-6-yl)amino)pyrimidin-4-yl)-2-(3-methyl-3,8-diazabicyclo[3.2.1]octan-8-yl)thiazol-4-yl)-2-fluorophenyl)-2,6-difluorobenzenesulfonamide

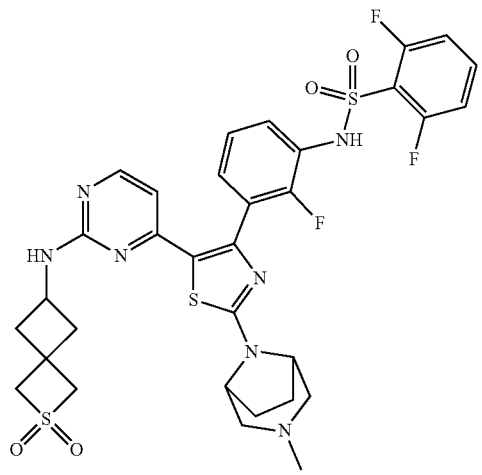 [SMILES: CN1CC2CCC(C1)N2c1nc(-c2cccc(NS(=O)(=O)c3c(F)cccc3F)c2F)c(-c2ccnc(NC3CC4(C3)CS(=O)(=O)C4)n2)s1]

Step 1: N-(3-(2-amino-5-(2-chloropyrimidin-4-yl)-2,3-dihydrothiazol-4-yl)-2-fluorophenyl)-2,6-difluorobenzenesulfonamide

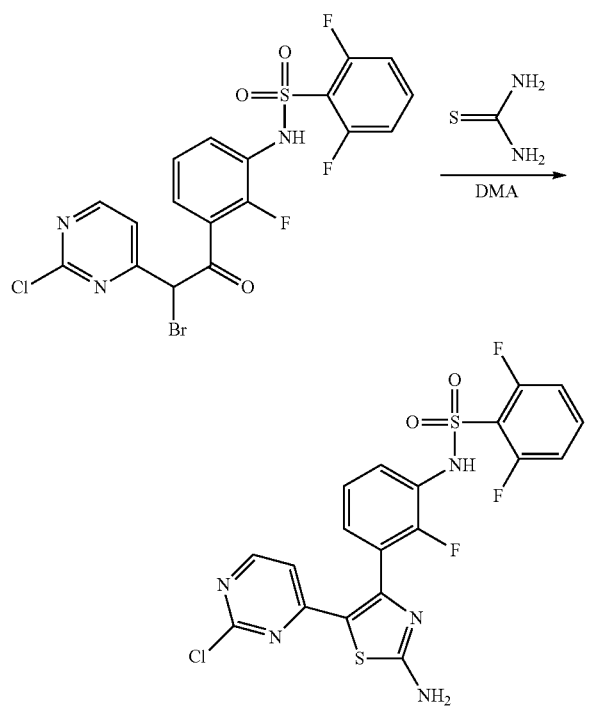

A mixture of N-(3-(2-bromo-2-(2-chloropyrimidin-4-yl)acetyl)-2-fluorophenyl)-2,6-difluorobenzenesulfonamide (Intermediate 9; 15.00 g, 28.85 mmol, 1.00 eq.) and thiourea (2.20 g, 3.72 mmol, 1.00 eq.) in DMA (150.0 mL) was stirred at rt for 30 mins, then the mixture was heated to 70° C. under $N_2$ for 4 h. The mixture was poured into water, filtered to give the title compound as a yellow solid.

Step 2: N-(3-(2-amino-5-(2-(methylthio)pyrimidin-4-yl)thiazol-4-yl)-2-fluorophenyl)-2,6-difluorobenzenesulfonamide

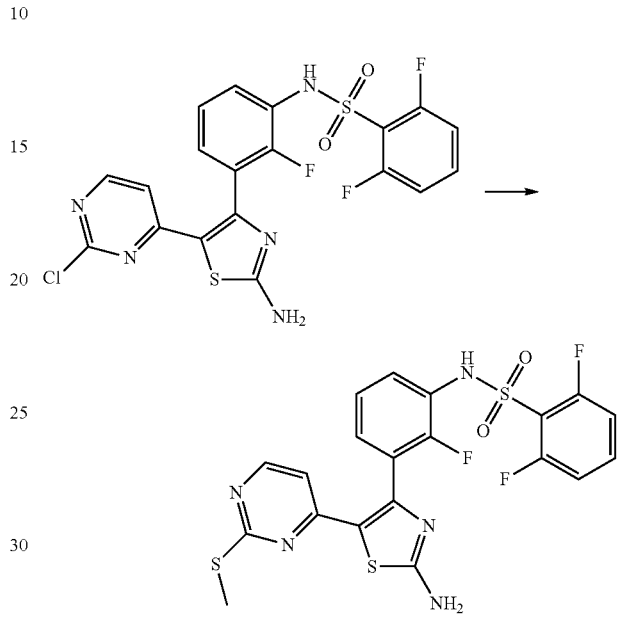

Sodium methanethiolate (196 mg, 2.80 mmol, 2.00 eq) was added to a mixture of N-(3-(2-amino-5-(2-chloropyrimidin-4-yl)thiazol-4-yl)-2-fluorophenyl)-2,6-difluorobenzenesulfonamide (700 mg, 1.40 mmol, 1.00 eq) in DMSO (10.0 ml) at rt and the mixture was stirred overnight. The mixture was diluted with water and extracted with EtOAc. The combined organic layer was washed with brine, dried over $Na_2SO_4$ and concentrated. The residue was purified by chromatograph on silica gel (DCM/MeOH=20/1) to give the title compound as a yellow solid.

Step 3: N-(3-(2-bromo-5-(2-(methylthio)pyrimidin-4-yl)thiazol-4-yl)-2-fluorophenyl)-2,6-difluorobenzenesulfonamide

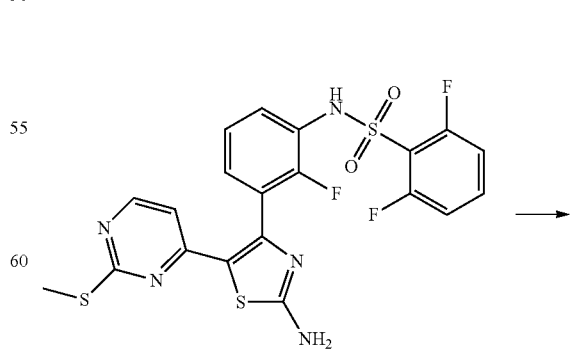

-continued

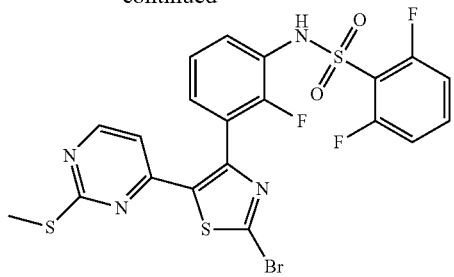

tert-Butyl nitrite (91 mg, 0.89 mmol, 1.50 eq) was added to a mixture of N-(3-(2-amino-5-(2-(methylthio)pyrimidin-4-yl)thiazol-4-yl)-2-fluorophenyl)-2,6-difluorobenzene-sulfonamide (300 mg, 0.59 mmol, 1.00 eq) and CuBr$_2$ (158 mg, 0.71 mmol. 1.20 eq) in MeCN (6.0 ml) at 0° C. and the mixture was stirred at rt overnight. The mixture was diluted with water and extracted with EtOAc. The combined organic layer was washed with brine, dried over Na$_2$SO$_4$, and concentrated. The residue was purified by chromatograph on silica gel (DCM/MeOH=100/1) to give the title compound as a yellow solid.

Step 4: 2,6-Difluoro-N-(2-fluoro-3-(2-(3-methyl-3,8-diazabicyclo[3.2.1]octan-8-yl)-5-(2-(methylthio)pyrimidin-4-yl)thiazol-4-yl)phenyl)benzenesulfonamide

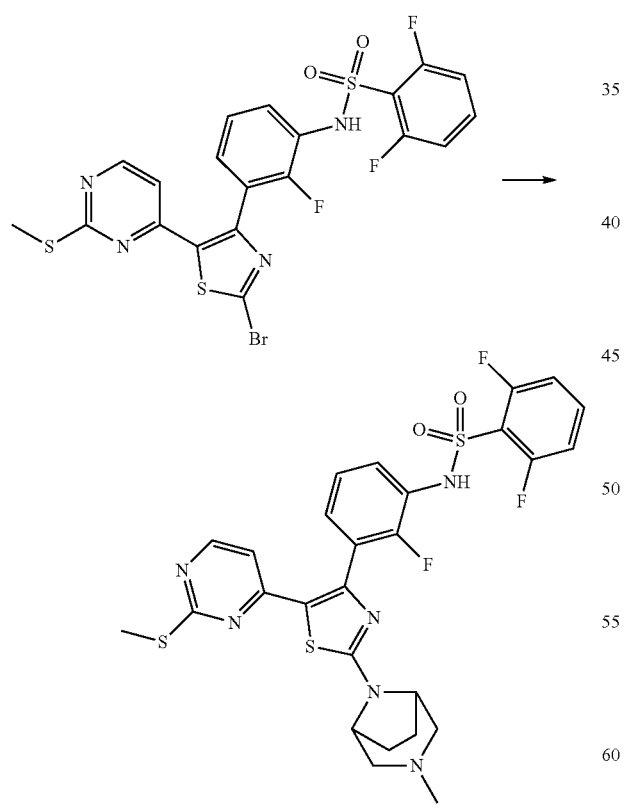

A mixture of N-(3-(2-bromo-5-(2-(methylthio)pyrimidin-4-yl)thiazol-4-yl)-2-fluoro-phenyl)-2,6-difluorobenzene-sulfonamide (500 mg, 0.87 mmol, 1.00 eq), 3-methyl-3,8-diaza-bicyclo[3.2.1]octane hydrochloride (425 mg, 2.62 mmol, 3.0 eq), TEA (796 mg, 7.87 mmol, 9.00 eq) in DMA (6.0 mL) was stirred at 120° C. for 3 h under microwave irradiation. The mixture was concentrated and the residue was purified by flash column chromatography (EA: PE=0~100%) to give the title compound as a yellow oil.

Step 5: 2,6-Difluoro-N-(2-fluoro-3-(2-(3-methyl-3,8-diazabicyclo[3.2.1]octan-8-yl)-5-(2-(methylsulfonyl)pyrimidin-4-yl)thiazol-4-yl)phenyl)benzene-sulfonamide

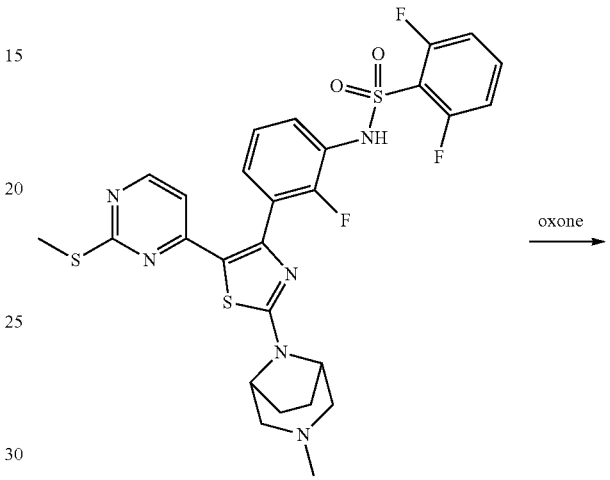

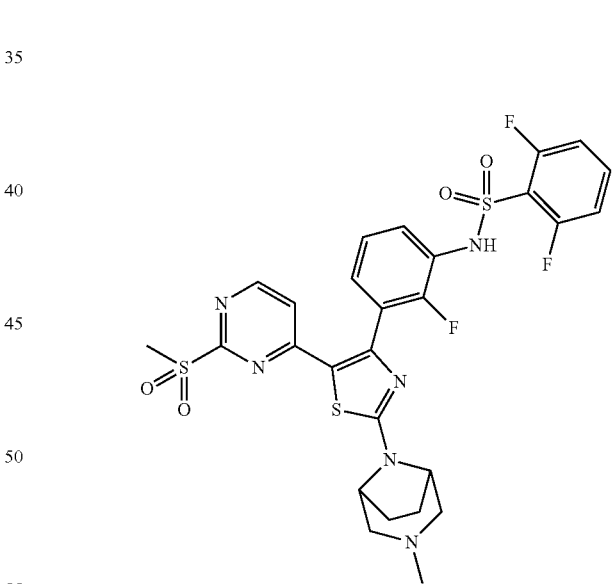

To a solution of 2,6-difluoro-N-(2-fluoro-3-(2-(3-methyl-3,8-diazabicyclo[3.2.1]-octan-8-yl)-5-(2-(methylthio)pyrimidin-4-yl)thiazol-4-yl)phenyl)benzenesulfonamide (513 mg, 0.83 mmol, 1.00 eq) in MeOH:THF:H$_2$O=2:2:1 (15.0 mL) was added oxone (1.50 g, 2.49 mmol, 3.00 eq). The mixture was stirred at 35° C. overnight and then diluted with H$_2$O and extracted with EtOAc. The combined organic layers were washed with water, brine, dried over Na$_2$SO$_4$, concentrated to give the title compound as a yellow oil, which was used directly for the next step without purification.

313

Step 6: N-(3-(5-(2-((2,2-dioxido-2-thiaspiro[3.3]heptan-6-yl)amino)pyrimidin-4-yl)-2-(3-methyl-3,8-diazabicyclo[3.2.1]octan-8-yl)thiazol-4-yl)-2-fluoro-phenyl)-2,6-difluoro-benzenesulfonamide

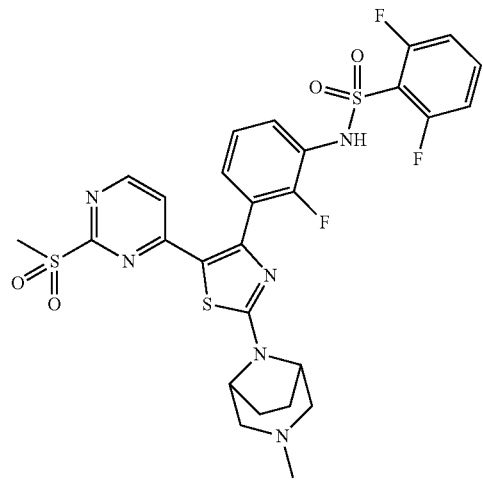

314

-continued

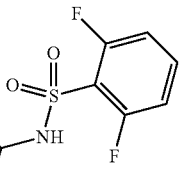

A mixture of 2,6-difluoro-N-(2-fluoro-3-(2-(3-methyl-3,8-diazabicyclo[3.2.1]octan-8-yl)-5-(2-(methylsulfonyl)pyrimidin-4-yl)thiazol-4-yl)phenyl)benzenesulfonamide (520 mg, 0.80 mmol, 1.00 eq), 6-amino-2-thiaspiro[3.3]heptane 2,2-dioxide (Intermediate 6; 237 mg, 1.20 mmol, 1.50 eq), DIEA (620 mg, 4.80 mmol, 6.00 eq) in DMSO (15.0 mL) was stirred at 65° C. overnight under $N_2$. The mixture was poured into water, and the mixture was extracted with EtOAc. The combined organic layer was washed with water, brine, dried over $Na_2SO_4$, concentrated. The residue was purified by prep-HPLC to give the title compound as a pale-yellow solid. MS (ES, m/z): [M+1]$^+$=732.2.

Proceeding analogously as described in Example 81, the following compounds were prepared.

| Ex# | Structures | Changes in synthetic protocol | LCMS (ES, m/z): [M + 1]$^+$ |
|---|---|---|---|
| 82 | 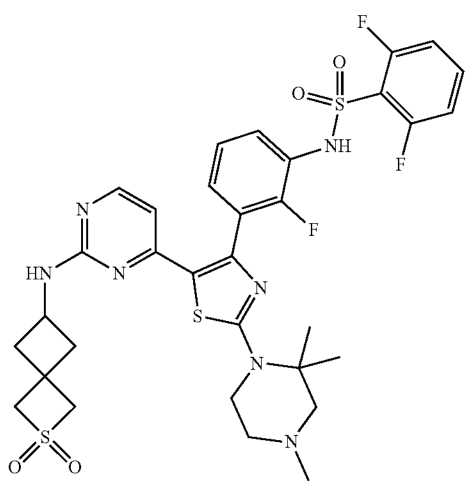 [SMILES: CN1CCN(c2nc(-c3cccc(NS(=O)(=O)c4c(F)cccc4F)c3F)c(-c3ccnc(NC4CC5(C4)CS(=O)(=O)C5)n3)s2)C(C)(C)C1] | 3-methyl-3,8-diazabicyclo[3.2.1]-octane replaced by 1,3,3-trimethylpiperazine in Step 4. | 734.3 |

-continued

| Ex# | Structures | Changes in synthetic protocol | LCMS (ES, m/z): [M + 1]+ |
|---|---|---|---|
| 83 | 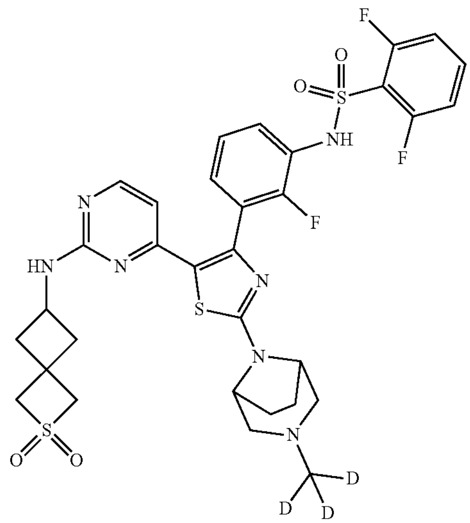 [SMILES: [2H]C([2H])([2H])N1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by Intermediate 28 in Step 4. | 735.3 |
| 84 | 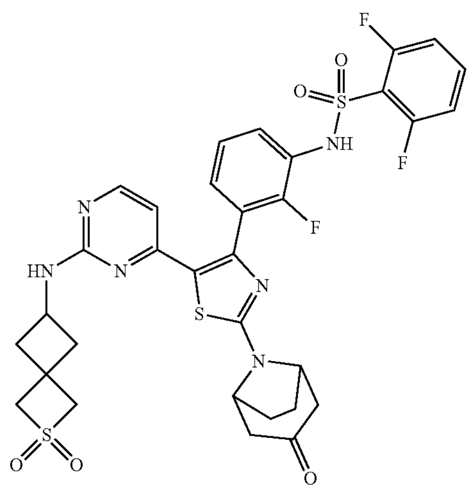 [SMILES: O=C1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by 8-azabicyclo-[3.2.1]octan-3-one in Step 4. | 731.2 |
| 85 | 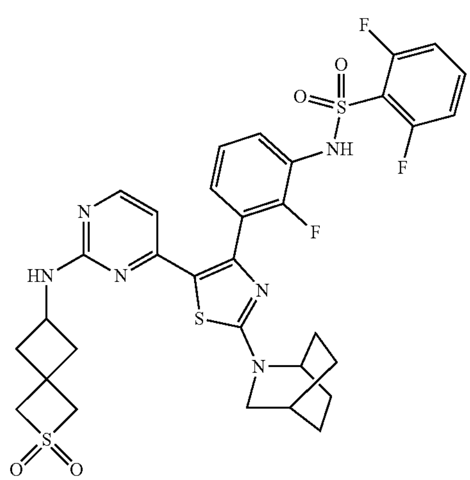 [SMILES: O=S1(=O)CC2(CC(Nc3nccc(-c4sc(N5CC6CCC5CC6)nc4-c4cccc(NS(=O)(=O)c5c(F)cccc5F)c4F)n3)C2)C1] | 3-methyl-3,8-diazabicyclo[3.2.1]-octane replaced by 2-azabicyclo-[2.2.2]octane in Step 4. | 717.2 |

-continued

| Ex# | Structures | Changes in synthetic protocol | LCMS (ES, m/z): [M + 1]+ |
|---|---|---|---|
| 86 | 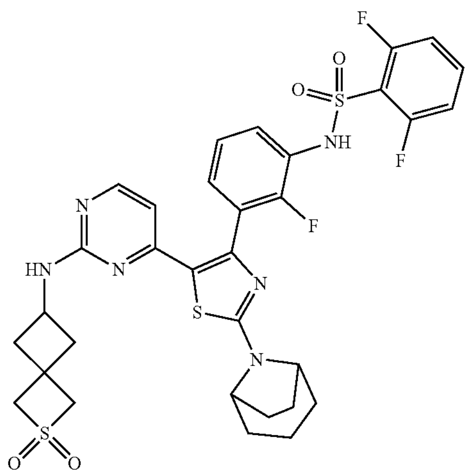 [SMILES: O=S1(=O)CC2(CC(Nc3nccc(-c4sc(N5C6CCCC5CC6)nc4-c4cccc(NS(=O)(=O)c5c(F)cccc5F)c4F)n3)C2)C1] | 3-methyl-3,8-diazabicyclo[3.2.1]-octane replaced by 8-azabicyclo-[3.2.1]octane in Step 4. | 717.2 |
| 87 | 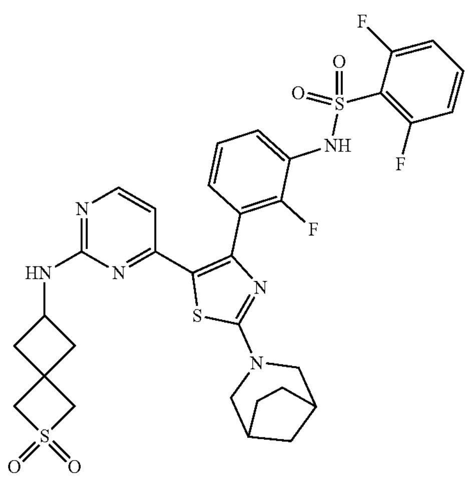 [SMILES: O=S1(=O)CC2(CC(Nc3nccc(-c4sc(N5CC6CCC(C6)C5)nc4-c4cccc(NS(=O)(=O)c5c(F)cccc5F)c4F)n3)C2)C1] | 3-methyl-3,8-diazabicyclo[3.2.1]-octane replaced by 3-azabicyclo-[3.2.2]nonane in Step 4. | 731.2 |
| 88 | 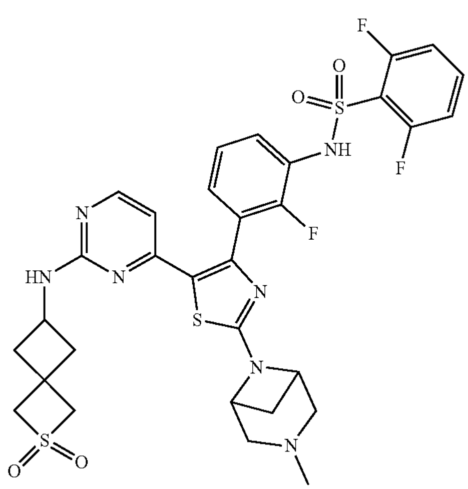 [SMILES: CN1CC2CC(C1)N2c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by 3-methyl-3,6-diazabicyclo[3.1.1]heptane in Step 4. | 718.2 |

-continued

| Ex# | Structures | Changes in synthetic protocol | LCMS (ES, m/z): [M + 1]+ |
|---|---|---|---|
| 89 | 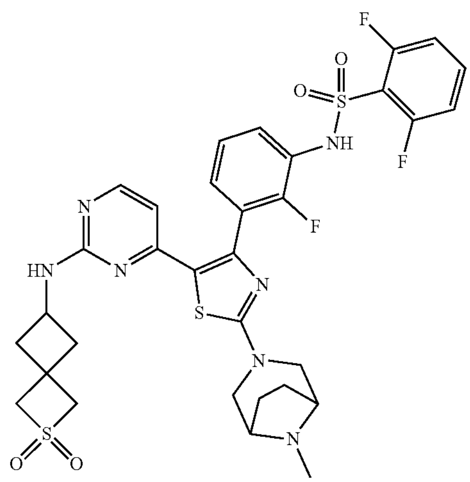 [SMILES: CN1C2CCC1CN(c1nc(-c3cccc(NS(=O)(=O)c4c(F)cccc4F)c3F)c(-c3ccnc(NC4CC5(C4)CS(=O)(=O)C5)n3)s1)C2] | 3-methyl-3,8-diazabicyclo[3.2.1]-octane replaced by 8-methyl-3,8-diazabicyclo[3.2.1]octane in Step 4. | 732.2 |
| 90 | 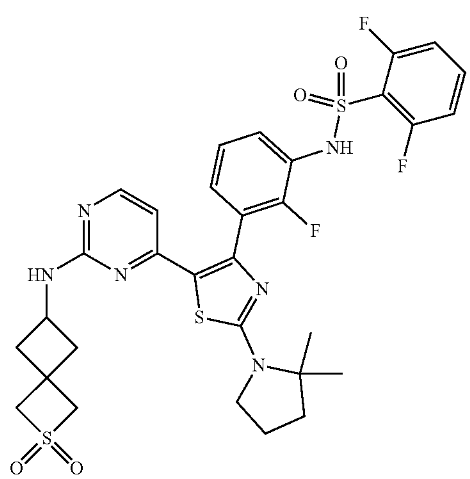 [SMILES: CC1(C)CCCN1c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by 2,2-dimethylpyrrolidine in Step 4. | 705.2 |
| 91 | 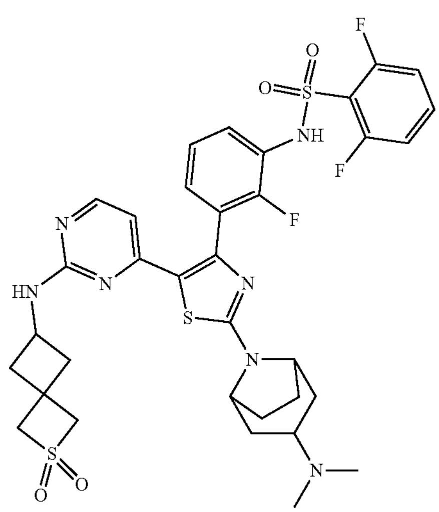 [SMILES: CN(C)C1CC2CCC(C1)N2c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by N,N-dimethyl-8-azabicyclo[3.2.1]octan-3-amine in Step 4. | 760.2 |

| Ex# | Structures | Changes in synthetic protocol | LCMS (ES, m/z): [M + 1]+ |
|---|---|---|---|
| 92 | 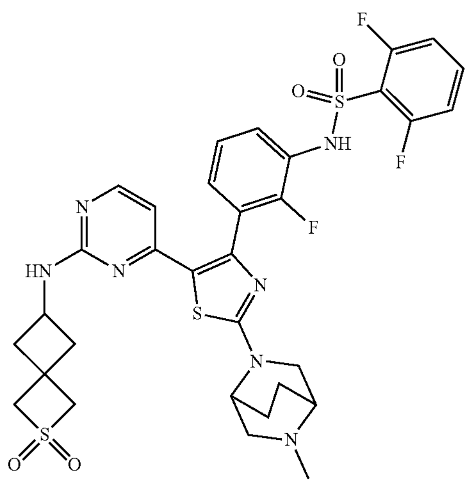 [SMILES: CN1CC2CCC1CN2c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by 2-methyl-2,5-diazabicyclo[2.2.2]octane in Step 4. | 732.2 |
| 93 | 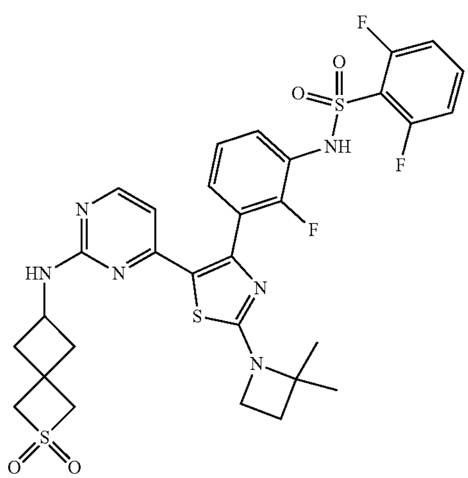 [SMILES: CC1(C)CCN1c1nc(-c2cccc(NS(=O)(=O)c3c(F)cccc3F)c2F)c(-c2ccnc(NC3CC4(C3)CS(=O)(=O)C4)n2)s1] | 3-methyl-3,8-diazabicyclo[3.2.1]-octane replaced by 2,2-dimethylazetidine in Step 4. | 691.2 |
| 94 | 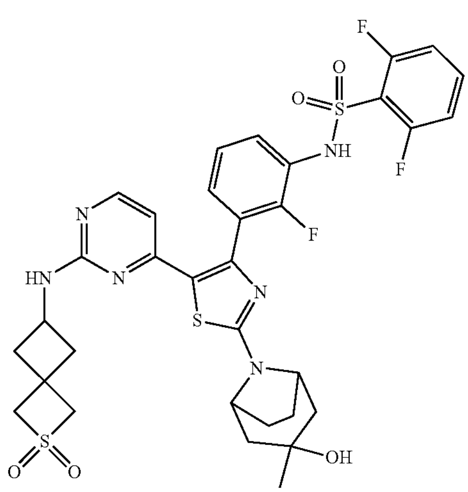 | 3-methyl-3,8-diazabicyclo[3.2.1]-octane replaced by 3-methyl-8-azabicyclo[3.2.1]octan-3-ol in Step 4. | 747.3 |

Example 95

Synthesis of N-(3-(2-(3,8-diazabicyclo[3.2.1]octan-8-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzenesulfonamide

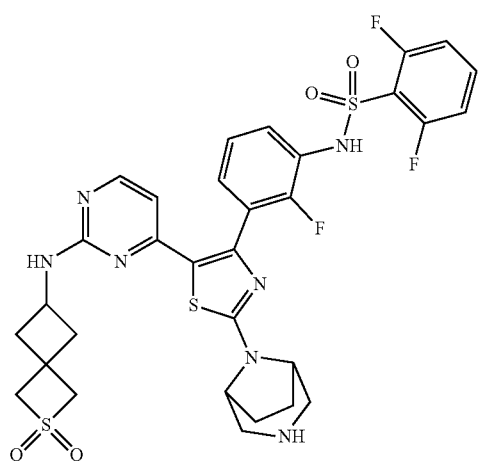 [SMILES: O=S1(=O)CC2(CC(Nc3nccc(-c4sc(N5C6CCC5CNC6)nc4-c4cccc(NS(=O)(=O)c5c(F)cccc5F)c4F)n3)C2)C1]

Step 1: N-(3-(2-amino-5-(2-((2,2-dioxido-2-thiaspiro[3.3]heptan-6-yl)amino)pyrimidin-4-yl)-2,3-dihydrothiazol-4-yl)-2-fluorophenyl)-2,6-difluorobenzenesulfonamide

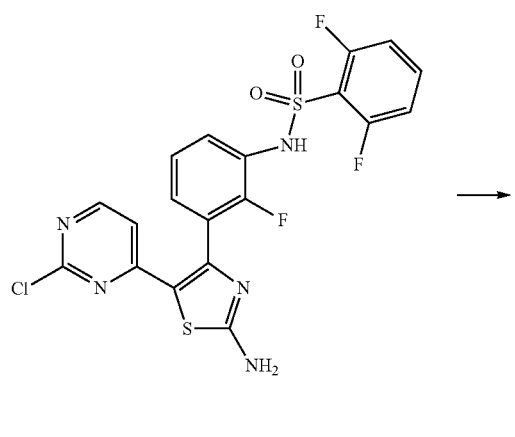

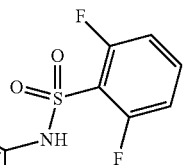

A mixture of N-(3-(2-amino-5-(2-chloropyrimidin-4-yl)-2,3-dihydrothiazol-4-yl)-2-fluorophenyl)-2,6-difluorobenzenesulfonamide (10.00 g, 20.10 mmol, 1.00 eq.), 6-amino-2-thiaspiro[3.3]heptane 2,2-dioxide (Intermediate 6; 4.40 g, 22.10 mmol, 1.10 eq.) and DIEA (13.00 g, 100.50 mmol, 5.00 eq.) in n-BuOH (100.0 mL) was stirred at 130° C. under N₂ overnight. The mixture was concentrated, and the residue was purified by column chromatography on silica gel (DCM/MeOH=40:1) to give the title compound as yellow solid.

Step 2: N-(3-(2-bromo-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

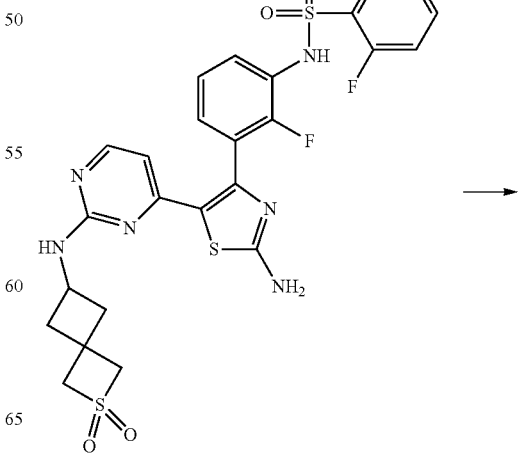

325
-continued

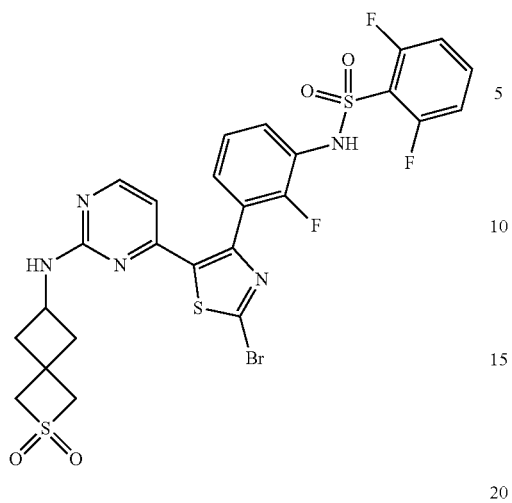

tert-Butyl nitrite (2.20 g, 21.70 mmol, 1.50 eq.) was added to a mixture of N-(3-(2-amino-5-(2-((2,2-dioxido-2-thiaspiro[3.3]heptan-6-yl)amino)pyrimidin-4-yl)-2,3-dihydrothiazol-4-yl)-2-fluorophenyl)-2,6-difluorobenzenesulfonamide (9.00 g, 14.47 mmol, 1.00 eq.) and CuBr$_2$ (4.20 g, 18.81 mmol, 1.30 eq.) in MeCN (100.0 mL) at 0° C. The mixture was warmed to rt and stirred for 2 h. The mixture was diluted with EtOAc, and the organic layer was washed with water, brine, dried over Na$_2$SO$_4$, concentrated. The residue was purified by column chromatography on silica gel (PE/EA=1:1) to give the tilted compound as yellow solid.

Step 3: tert-Butyl 8-(4-(3-(2,6-difluorophenylsulfonamido)-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate

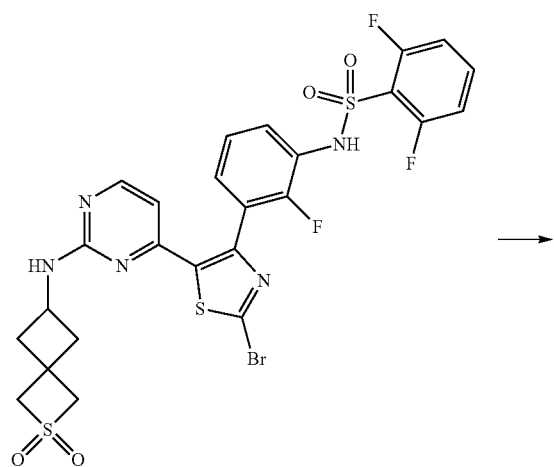

326
-continued

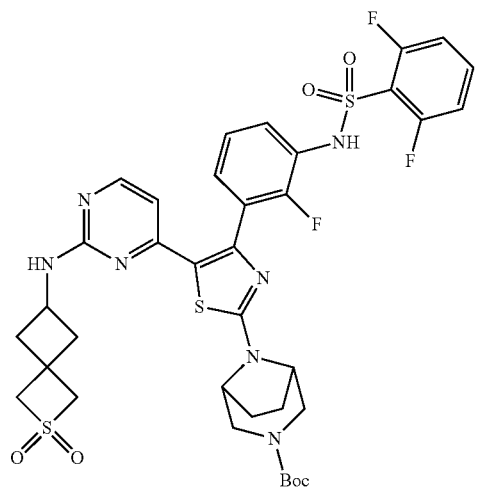

A mixture of N-(3-(2-bromo-5-(2-((2,2-dioxido-2-thiaspiro[3.3]heptan-6-yl)amino)-pyrimidin-4-yl)thiazol-4-yl)-2-fluorophenyl)-2,6-difluorobenzenesulfonamide (5.00 g, 7.28 mmol, 1.00 eq) and tert-butyl 3,8-diazabicyclo[3.2.1]octane-3-carboxylate (2.32 g, 10.92 mmol, 1.50 eq), TEA (4.42 g, 43.70 mmol, 6.00 eq) in DMA (30.0 mL) was stirred at 120° C. overnight under N$_2$. The mixture was poured into water and extracted with EtOAc. The combined organic layer was washed with water, brine, dried over Na$_2$SO$_4$, concentrated. The residue was purified by column chromatography on silica gel (DCM:MeOH=50:1 to 10:1) to give the title compound as a yellow oil.

Step 4: N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

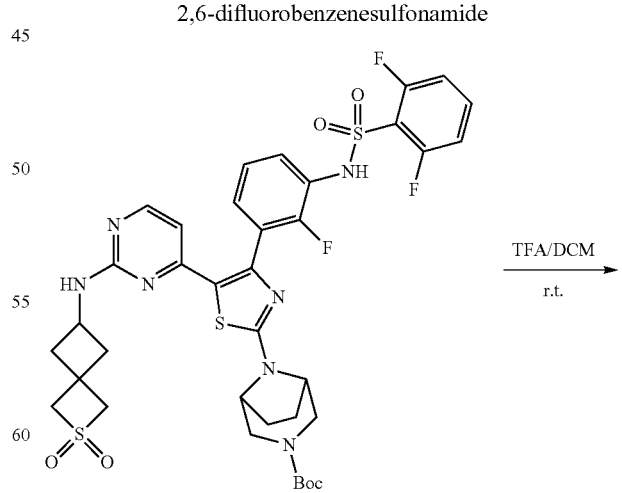

327
-continued

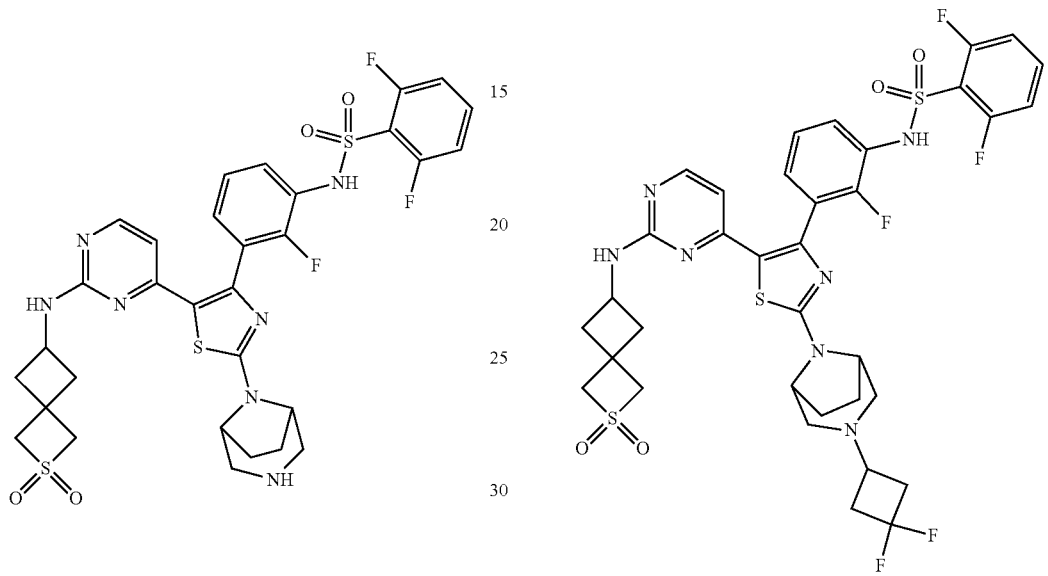

To a solution of tert-butyl 8-(4-(3-(2,6-difluorophenylsulfonamido)-2-fluorophenyl)-5-(2-((2,2-dioxido-2-thiaspiro[3.3]heptan-6-yl)amino)pyrimidin-4-yl)thiazol-2-yl)-3,8-diazabicyclo-[3.2.1]octane-3-carboxylate (10 g, 12.20 mmol) in DCM (10.0 mL) was added TFA (4.0 mL) and the mixture was stirred at rt for 3 h. The mixture was concentrated to give the title compound as a yellow oil. MS (ES, m/z): [M+1]$^+$=718.0.

328

Example 96

Synthesis of N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide To a solution of N-(3-(2-(3,8-diazabicyclo[3.2.1]octan-8-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzene-sulfonamide (300 mg, 0.37 mmol, 1.00 eq) in MeOH:THIF=1:1 (5 mL) was added 3,3-difluoro-cyclobutanone (117 mg, 1.10 mmol, 3.00 eq), AcOH (3 drop) and the mixture was stirred at rt for 15 min NaBH$_3$CN (116 mg, 1.84 mmol, 5.00 eq.) was added and the mixture was stirred at rt overnight under N$_2$. The mixture was poured into water, and pH was adjusted to 7~8 by 1N NaOH. The mixture was extracted with EtOAc, washed with water, brine, dried over Na$_2$SO$_4$, and concentrated. The residue was purified by column chromatography on silica gel (EA:PE=0 to 1000%) and then purification by reverse column to give the title compound as a yellow solid. MS (ES, m/z): [M+H]$^+$=808.3.

Proceeding analogously as described in Example 96, the following compounds were prepared.

| Ex# | Structures | Changes in synthetic protocol | LCMS (ES, m/z): [M + 1]+ |
|---|---|---|---|
| 97 | 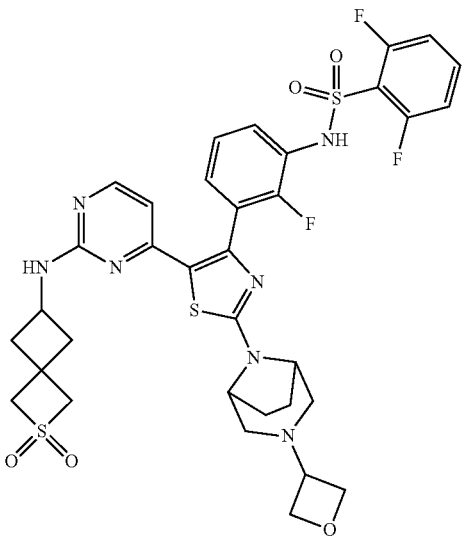 [SMILES: O=S1(=O)CC2(CC(Nc3nccc(-c4sc(N5C6CCC5CN(C5COC5)C6)nc4-c4cccc(NS(=O)(=O)c5c(F)cccc5F)c4F)n3)C2)C1] | 3,3-difluorocyclobutan-1-one was replaced by oxetan-3-one. | 774.3 |
| 98 | 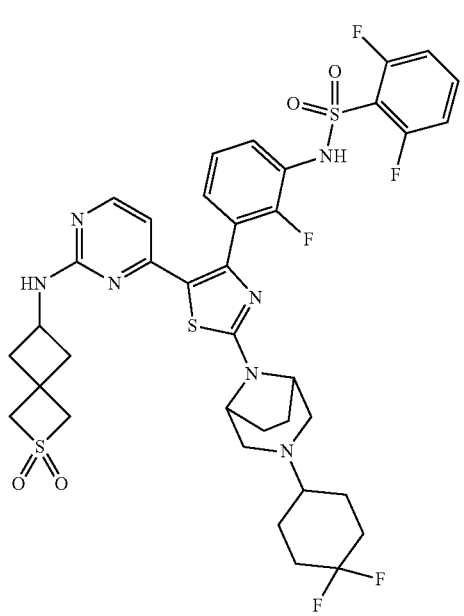 [SMILES: O=S1(=O)CC2(CC(Nc3nccc(-c4sc(N5C6CCC5CN(C5CCC(F)(F)CC5)C6)nc4-c4cccc(NS(=O)(=O)c5c(F)cccc5F)c4F)n3)C2)C1] | 3,3-difluorocyclobutan-1-one was replaced by 4,4-difluorocyclohexanone. | 836.3 |

-continued

| Ex# | Structures | Changes in synthetic protocol | LCMS (ES, m/z): [M + 1]+ |
|---|---|---|---|
| 99 | 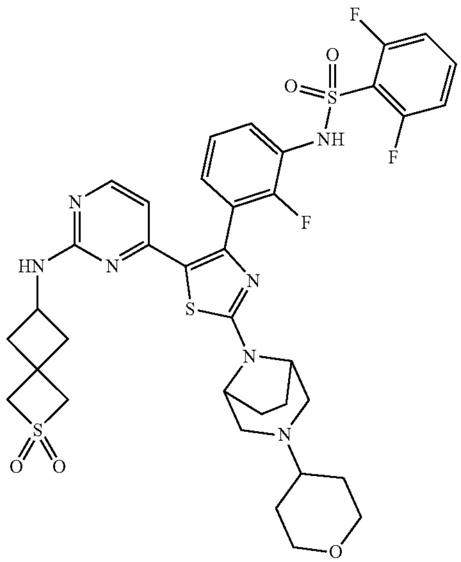 [SMILES: O=S1(=O)CC2(CC(Nc3nccc(-c4sc(N5C6CCC5CN(C5CCOCC5)C6)nc4-c4cccc(NS(=O)(=O)c5c(F)cccc5F)c4F)n3)C2)C1] | 3,3-difluorocyclobutan-1-one was replaced by tetrahydro-4H-pyran-4-one. | 802.3 |
| 100 | 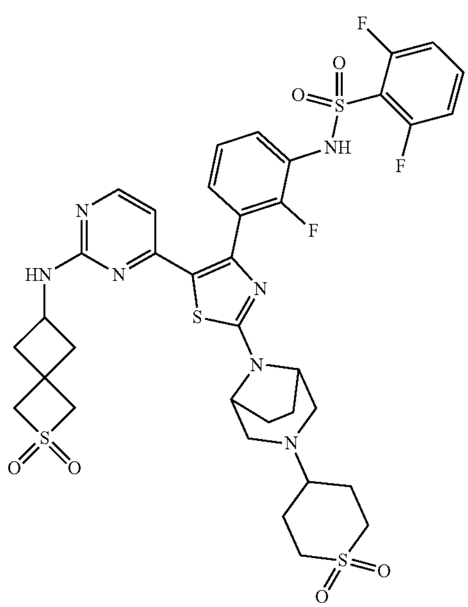 [SMILES: O=S1(=O)CCC(N2CC3CCC(C2)N3c2nc(-c3cccc(NS(=O)(=O)c4c(F)cccc4F)c3F)c(-c3ccnc(NC4CC5(C4)CS(=O)(=O)C5)n3)s2)CC1] | 3,3-difluorocyclobutan-1-one was replaced by tetrahydro-4H-thiopyran-4-one 1,1-dioxide. | 850.2 |

-continued
| Ex# | Structures | Changes in synthetic protocol | LCMS (ES, m/z): [M + 1]+ |
|---|---|---|---|
| 101 | 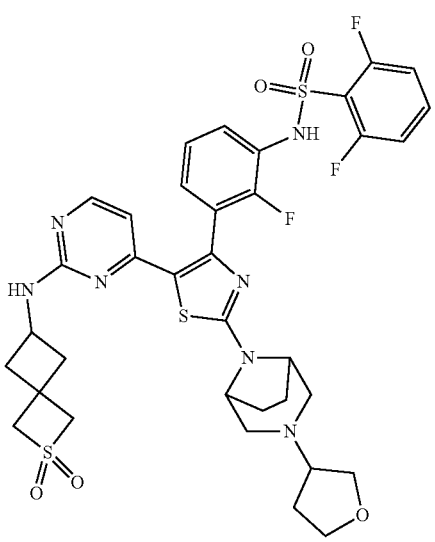 [SMILES: O=S1(=O)CC2(CC(Nc3nccc(-c4sc(N5C6CCC5CN(C5CCOC5)C6)nc4-c4cccc(NS(=O)(=O)c5c(F)cccc5F)c4F)n3)C2)C1] | 3,3-difluorocyclobutan-1-one was replaced by dihydrofuran-3(2H)-one. | 788.2 |
| 102 | 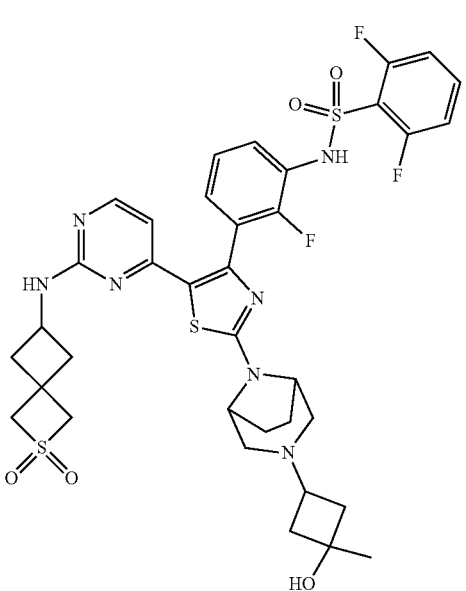 [SMILES: CC1(O)CC(N2CC3CCC(C2)N3c2nc(-c3cccc(NS(=O)(=O)c4c(F)cccc4F)c3F)c(-c3ccnc(NC4CC5(C4)CS(=O)(=O)C5)n3)s2)C1] | 3,3-difluorocyclobutan-1-one was replaced by Intermediate 13. | 802.3 |

| Ex# | Structures | Changes in synthetic protocol | LCMS (ES, m/z): [M + 1]+ |
|---|---|---|---|
| 103 | 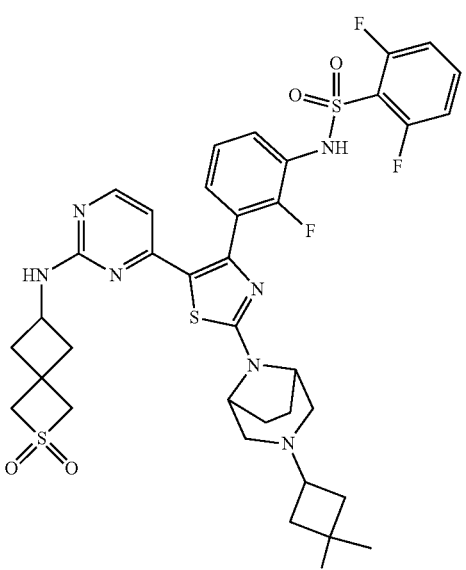 | 3,3-difluorocyclobutan-1-one was replaced by Intermediate 19. | 811.4 |
| 104 | 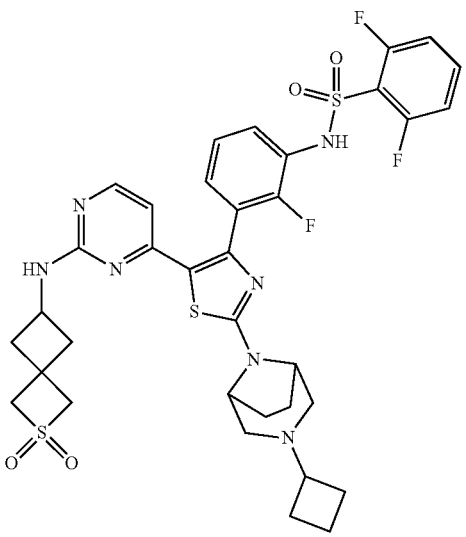 [SMILES: O=S1(=O)CC2(CC(Nc3nccc(-c4sc(N5C6CCC5CN(C5CCC5)C6)nc4-c4cccc(NS(=O)(=O)c5c(F)cccc5F)c4F)n3)C2)C1] | 3,3-difluorocyclobutan-1-one was replaced by cyclobutanone. | 772.4 |

Example 105

Synthesis of N-(3-(2-(7-azabicyclo[2.2.1]heptan-7-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide

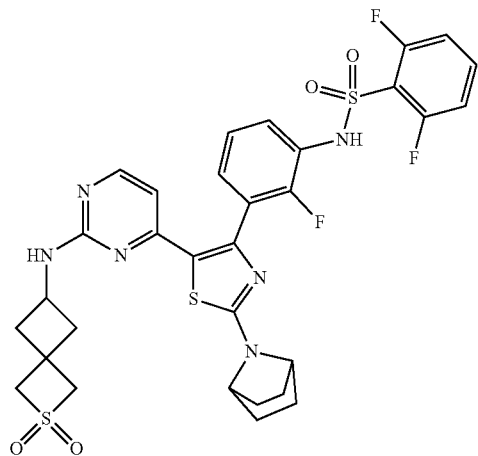 [SMILES: O=S1(=O)CC2(CC(Nc3nccc(-c4sc(N5C6CCC5CC6)nc4-c4cccc(NS(=O)(=O)c5c(F)cccc5F)c4F)n3)C2)C1]

A mixture of N-(3-(2-bromo-5-(2-((2,2-dioxido-2-thiaspiro[3.3]heptan-6-yl)amino)-pyrimidin-4-yl)thiazol-4-yl)-2-fluorophenyl)-2,6-difluorobenzenesulfonamide (0.5 g, 0.73 mmol, 1.00 eq.) and 7-azabicyclo[2.2.1]heptane (0.11 g, 1.1 mmol, 1.50 eq.), TEA (0.44 g, 4.3 mmol, 6.00 eq.) in DMA (3.0 mL) was stirred at 120° C. overnight under $N_2$. The mixture was poured into water, extracted with EtOAc. The combined organic layer was washed with water, brine, dried over $Na_2SO_4$, concentrated. The residue was purified by column chromatography on silica gel (DCM:MeOH=50:1 to 10:1) to give the title compound as yellow solid. LCMS (ES, m/z): $[M+1]^+$=703.2

Proceeding analogously as described in Example 105, the following compounds were prepared.

| Ex# | Structures | Changes in synthetic protocol | LCMS (ES, m/z): $[M + 1]^+$ |
|---|---|---|---|
| 106 | 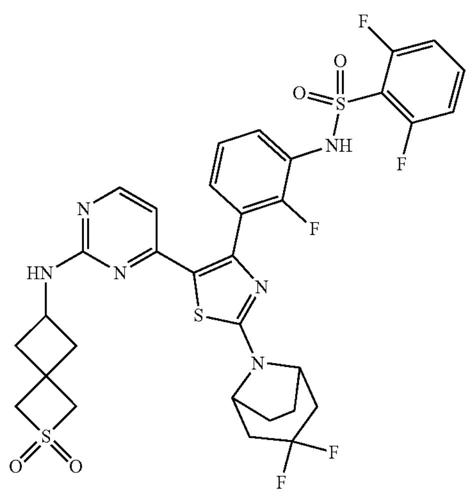 [SMILES: O=S1(=O)CC2(CC(Nc3nccc(-c4sc(N5C6CCC5CC(F)(F)C6)nc4-c4cccc(NS(=O)(=O)c5c(F)cccc5F)c4F)n3)C2)C1] | 7-azabicyclo[2.2.1]heptane was replaced by 3,3-difluoro-8-azabicyclo-[3.2.1]octane. | 753.1 |

-continued
| Ex# | Structures | Changes in synthetic protocol | LCMS (ES, m/z): [M + 1]+ |
|---|---|---|---|
| 107 | 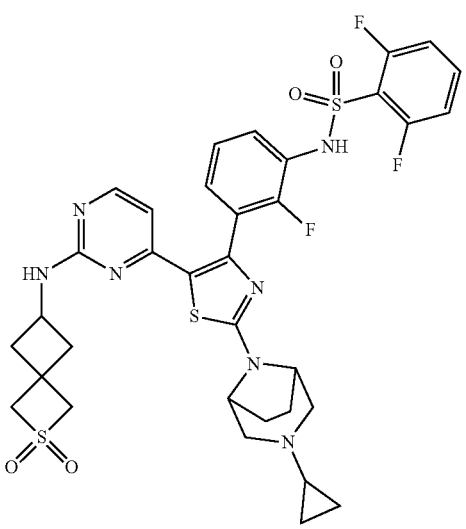 [SMILES: O=S1(=O)CC2(CC(Nc3nccc(-c4sc(N5C6CCC5CN(C5CC5)C6)nc4-c4cccc(NS(=O)(=O)c5c(F)cccc5F)c4F)n3)C2)C1] | 7-azabicyclo[2.2.1]heptane was replaced by Intermediate 26. | 758.2 |
| 108 | 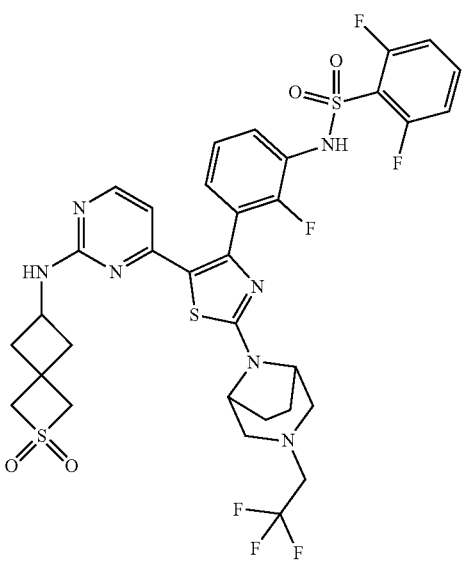 [SMILES: O=S1(=O)CC2(CC(Nc3nccc(-c4sc(N5C6CCC5CN(CC(F)(F)F)C6)nc4-c4cccc(NS(=O)(=O)c5c(F)cccc5F)c4F)n3)C2)C1] | 7-azabicyclo[2.2.1]heptane was replaced by Intermediate 22. | 800.2 |

-continued
| Ex# | Structures | Changes in synthetic protocol | LCMS (ES, m/z): [M + 1]+ |
|---|---|---|---|
| 109 | 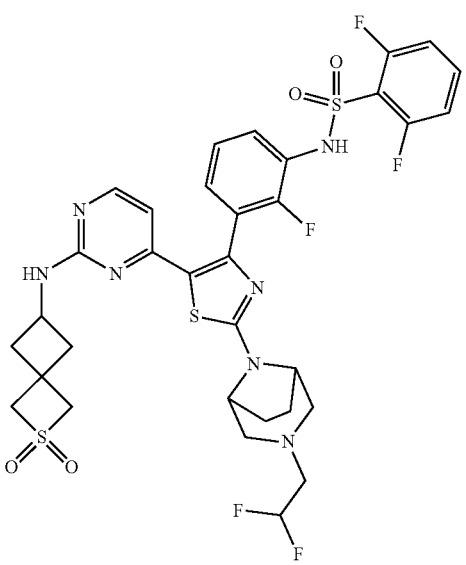 [SMILES: O=S1(=O)CC2(CC(Nc3nccc(-c4sc(N5C6CCC5CN(CC(F)F)C6)nc4-c4cccc(NS(=O)(=O)c5c(F)cccc5F)c4F)n3)C2)C1] | 7-azabicyclo[2.2.1]heptane was replaced by Intermediate 23. | 782.3 |
| 110 | 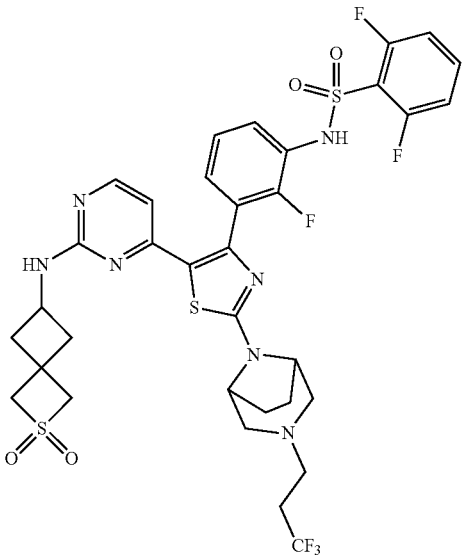 [SMILES: O=S1(=O)CC2(CC(Nc3nccc(-c4sc(N5C6CCC5CN(CCC(F)(F)F)C6)nc4-c4cccc(NS(=O)(=O)c5c(F)cccc5F)c4F)n3)C2)C1] | 7-azabicyclo[2.2.1]heptane was replaced by Intermediate 24. | 814.3 |

| Ex# | Structures | Changes in synthetic protocol | LCMS (ES, m/z): [M + 1]+ |
|---|---|---|---|
| 111 | 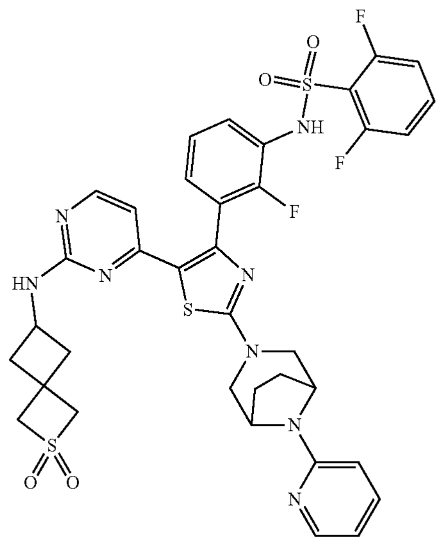 [SMILES: O=S1(=O)CC2(CC(Nc3nccc(-c4sc(N5CC6CCC(C5)N6c5ccccn5)nc4-c4cccc(NS(=O)(=O)c5c(F)cccc5F)c4F)n3)C2)C1] | 7-azabicyclo[2.2.1]heptane was replaced by Intermediate 31. | 795.2 |
| 112 | 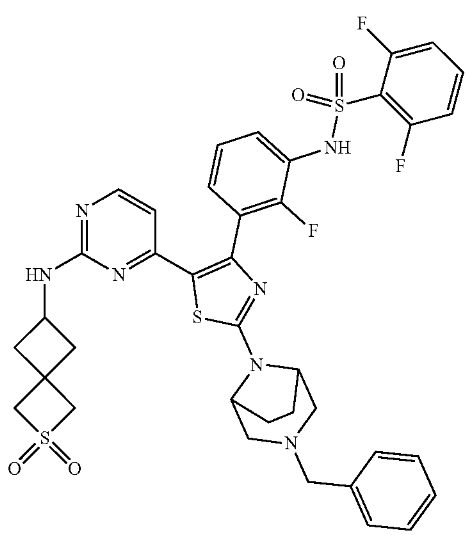 [SMILES: O=S1(=O)CC2(CC(Nc3nccc(-c4sc(N5C6CCC5CN(Cc5ccccc5)C6)nc4-c4cccc(NS(=O)(=O)c5c(F)cccc5F)c4F)n3)C2)C1] | 7-azabicyclo[2.2.1]heptane was replaced by Intermediate 25. | 808.2 |

-continued

| Ex# | Structures | Changes in synthetic protocol | LCMS (ES, m/z): [M + 1]+ |
|---|---|---|---|
| 113 | 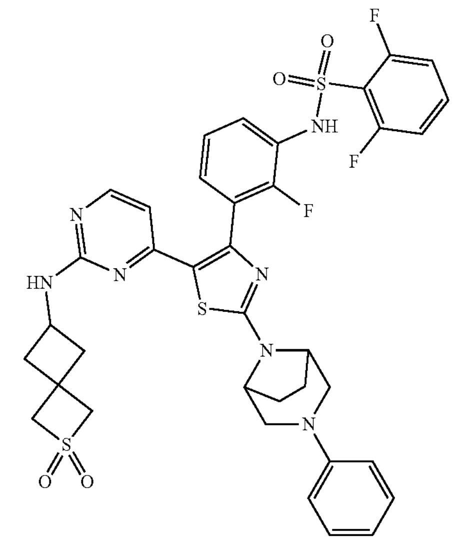 [SMILES: O=S1(=O)CC2(CC(Nc3nccc(-c4sc(N5C6CCC5CN(c5ccccc5)C6)nc4-c4cccc(NS(=O)(=O)c5c(F)cccc5F)c4F)n3)C2)C1] | 7-azabicyclo[2.2.1]heptane was replaced by Intermediate 30. | 794.3 |
| 114 | 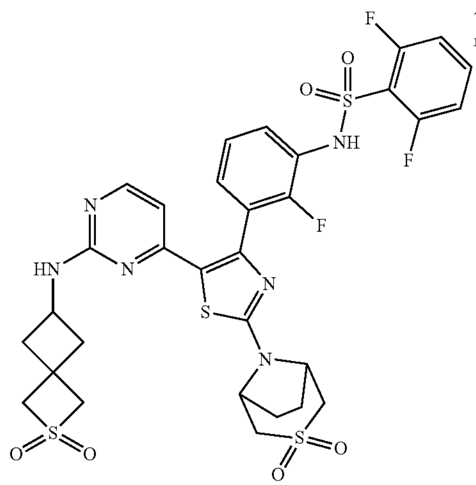 | 7-azabicyclo[2.2.1]heptane was replaced by Intermediate 20. | 767.2 |
| 115 | 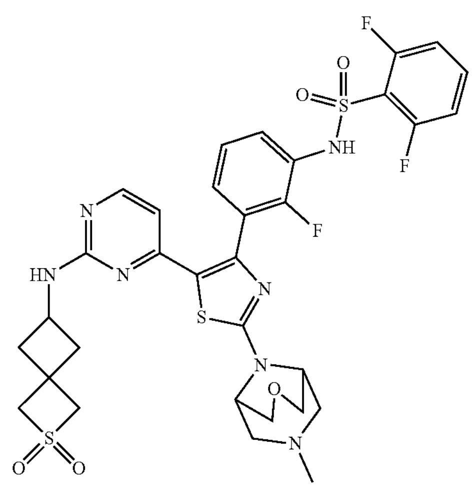 [SMILES: CN1CC2COCC(C1)N2c1nc(-c2cccc(NS(=O)(=O)c3c(F)cccc3F)c2F)c(-c2ccnc(NC3CC4(C3)CS(=O)(=O)C4)n2)s1] | 7-azabicyclo[2.2.1]heptane was replaced by 7-methyl-3-oxa-7,9-diazabicyclo[3.3.1]. | 748.3 |

| Ex# | Structures | Changes in synthetic protocol | LCMS (ES, m/z): [M + 1]+ |
|---|---|---|---|
| 116 | 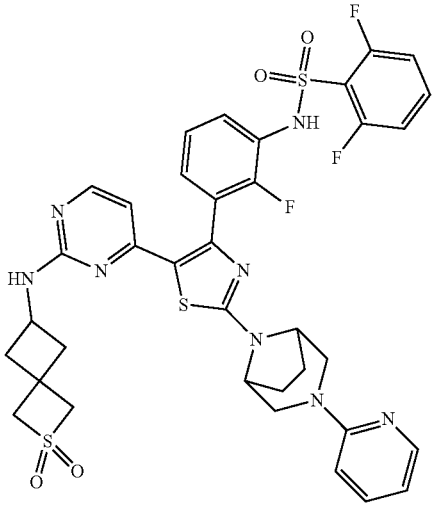 [SMILES: O=S1(=O)CC2(CC(Nc3nccc(-c4sc(N5C6CCC5CN(c5ccccn5)C6)nc4-c4cccc(NS(=O)(=O)c5c(F)cccc5F)c4F)n3)C2)C1] | 7-azabicyclo[2.2.1]heptane was replaced by Intermediate 32. | 795.1 |

Example 117

Synthesis of N-(3-(5-(2-((2,2-dioxido-2-thiaspiro [3.3]heptan-6-yl)amino)pyrimidin-4-yl)-2-(3-(1,1-dioxidothietan-3-yl)-3,8-diazabicyclo[3.2.1]octan-8-yl)thiazol-4-yl)-2-fluorophenyl)-2,6-difluorobenzenesulfonamide Step 1: 6 N-(3-(5-(2-((2,2-dioxido-2-thiaspiro[3.3] heptan-6-yl)amino)pyrimidin-4-yl)-2-(3-(thietan-3-yl)-3,8-diazabicyclo[3.2.1]octan-8-yl)thiazol-4-yl)-2-fluorophenyl)-2,6-difluorobenzenesulfonamide

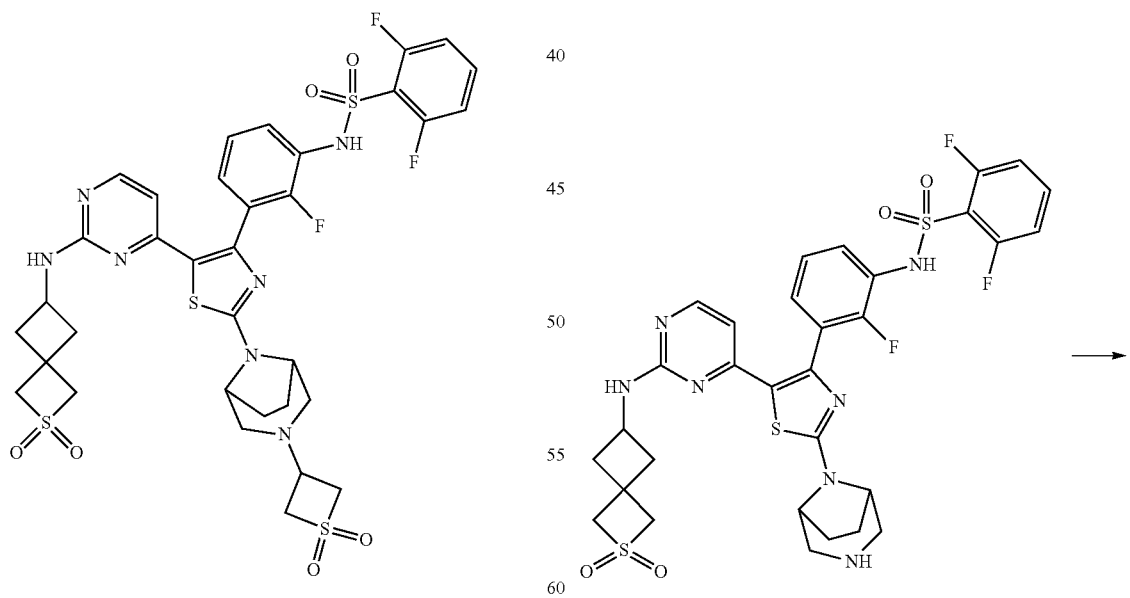

349
-continued

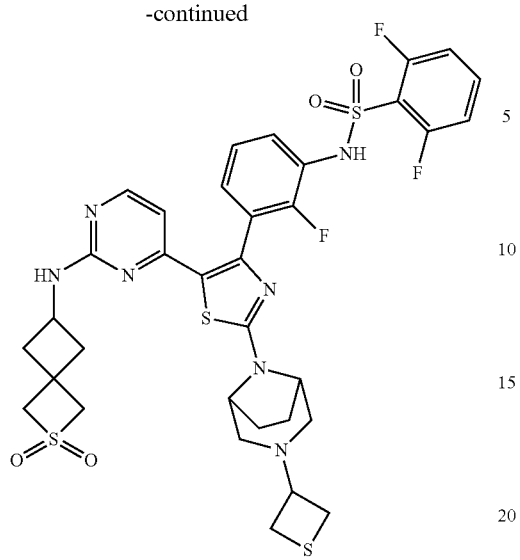

To a solution of N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide (100 mg, 0.14 mmol, 1.00 eq.) in MeOH/THF (2.0 mL, 1:1) was added thietan-3-one (61 mg, 0.70 mmol, 5.00 eq.) and AcOH (1 drop). The mixture was stirred at rt for 20 mins. NaBH$_3$CN (44 mg, 0.70 mmol, 5.00 eq.) was added and the mixture was stirred at rt overnight. The mixture was diluted with water and extracted with DCM. The combined organic layers were washed with water, brine, dried over Na$_2$SO$_4$, and concentrated. The residue was purified by silica flash column DCM/MeOH (20:1) to give the title compound as a yellow solid.

Step 2: N-(3-(5-(2-((2,2-dioxido-2-thiaspiro[3.3]heptan-6-yl)amino)pyrimidin-4-yl)-2-(3-(1,1-dioxidothietan-3-yl)-3,8-diazabicyclo[3.2.1]octan-8-yl)thiazol-4-yl)-2-fluorophenyl)-2,6-difluorobenzenesulfonamide 350
-continued

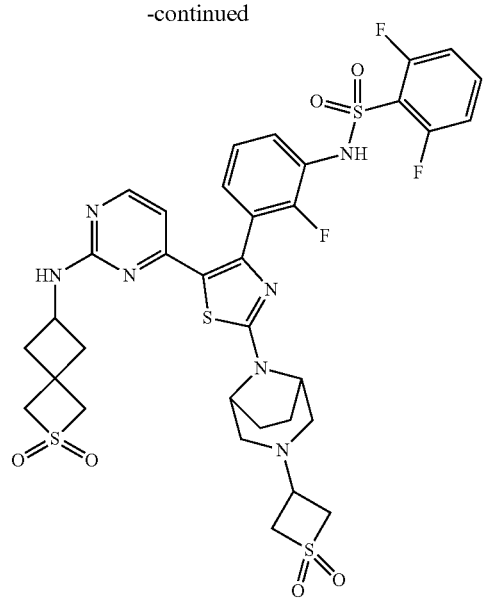

Oxone (93 mg, 0.15 mmol, 3.00 eq.) was added to a mixture of 6 N-(3-(5-(2-((2,2-dioxido-2-thiaspiro[3.3]heptan-6-yl)amino)pyrimidin-4-yl)-2-(3-(thietan-3-yl)-3,8-diazabicyclo[3.2.1]-octan-8-yl)thiazol-4-yl)-2-fluorophenyl)-2,6-difluorobenzenesulfonamide (40 mg, 0.05 mmol, 1.00 eq.) in MeOH:THF:H$_2$O (2.0 mL, 2:2:1) and the mixture was stirred at rt 1 h. The mixture was extracted with DCM, and the combined organic layers were washed with water, brine, dried over Na$_2$SO$_4$, and concentrated. The residue was purified by prep-HPLC to give the title compound as yellow solid. MS (ES, m/z): [M+H]$^+$=822.1

Example 126

Synthesis of N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide

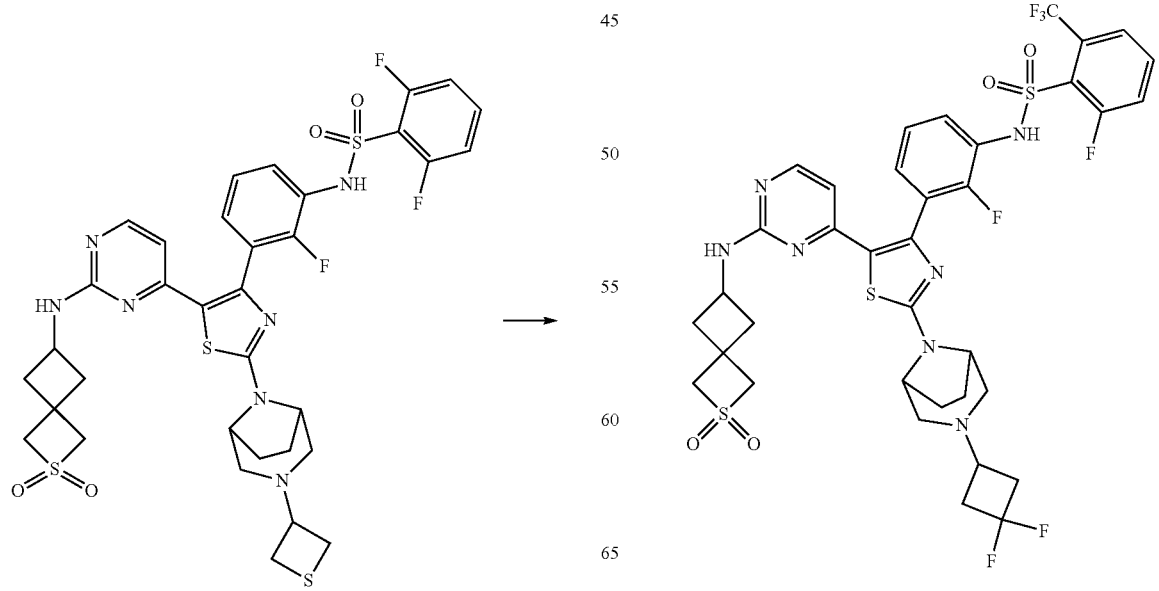

Step 1: N-(3-(2-amino-5-(2-chloropyrimidin-4-yl)thiazol-4-yl)-2-fluorophenyl)acetamide

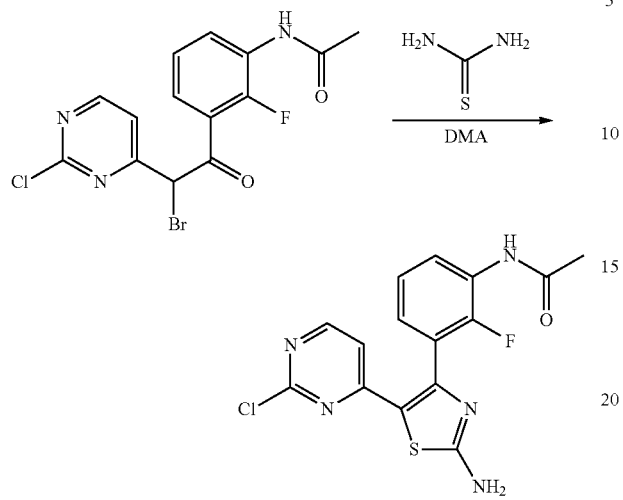

A mixture of N-(3-(2-bromo-2-(2-chloropyrimidin-4-yl)acetyl)-2-fluorophenyl)-acetamide (Int. 10; 6.32 g, 16.40 mmol, 1.00 eq), thiourea (1.25 g, 16.40 mmol, 1.00 eq) in DMA (70.0 mL) was stirred at 65° C. for 3 h under $N_2$. The mixture was poured into water, and the mixture was extracted with EtOAc. The combined organic layers were washed with water, brine, dried over $Na_2SO_4$, concentrated to give the title compound as a yellow solid.

Step 2: N-(3-(2-amino-5-(2-((2,2-dioxido-2-thiaspiro[3.3]heptan-6-yl)amino)pyrimidin-4-yl)-thiazol-4-yl)-2-fluorophenyl)acetamide A mixture of N-(3-(2-amino-5-(2-chloropyrimidin-4-yl)thiazol-4-yl)-2-fluorophenyl)-acetamide (5.05 g, 13.90 mmol, 1.00 eq), 2-thiaspiro[3.3]heptan-6-amine hydrochloride (Intermediate 6; 3.30 g, 16.70 mmol, 1.50 eq), DIEA (8.90 g, 69.60 mmol, 5.00 eq) in n-BuOH (100.0 mL) was stirred at 130° C. overnight under $N_2$. The mixture was poured into water and extracted with EtOAc. The combined organic layers were washed with water, brine, dried over $Na_2SO_4$, concentrated. The residue was purified by column chromatography on silica gel (PE:EA=1:1 to DCM:MeOH=20:1) to give the title compound as a yellow solid.

Step 3: N-(3-(2-bromo-5-(2-((2,2-dioxido-2-thiaspiro[3.3]heptan-6-yl)amino)pyrimidin-4-yl)thiazol-4-yl)-2-fluorophenyl)acetamide

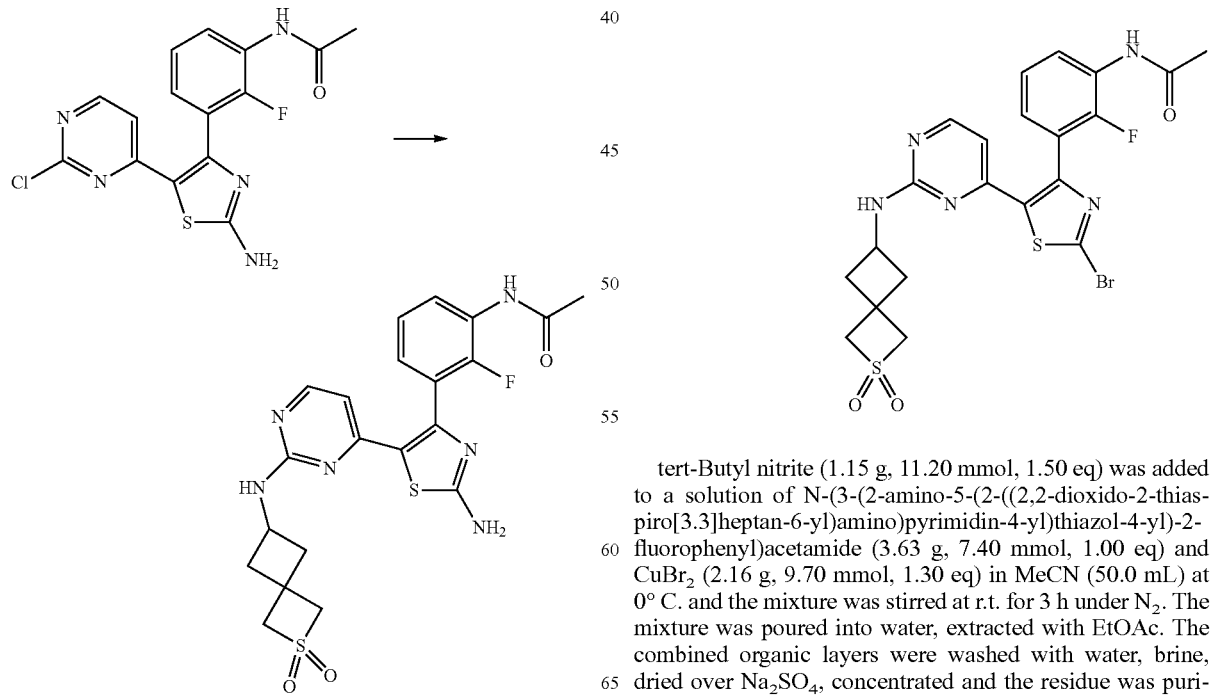

tert-Butyl nitrite (1.15 g, 11.20 mmol, 1.50 eq) was added to a solution of N-(3-(2-amino-5-(2-((2,2-dioxido-2-thiaspiro[3.3]heptan-6-yl)amino)pyrimidin-4-yl)thiazol-4-yl)-2-fluorophenyl)acetamide (3.63 g, 7.40 mmol, 1.00 eq) and $CuBr_2$ (2.16 g, 9.70 mmol, 1.30 eq) in MeCN (50.0 mL) at 0° C. and the mixture was stirred at r.t. for 3 h under $N_2$. The mixture was poured into water, extracted with EtOAc. The combined organic layers were washed with water, brine, dried over $Na_2SO_4$, concentrated and the residue was purified by column chromatography (PE:EA=1:1 to DCM:MeOH=20:1) to give the title compound as a yellow solid.

353

Step 4: tert-Butyl 8-(4-(3-acetamido-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate

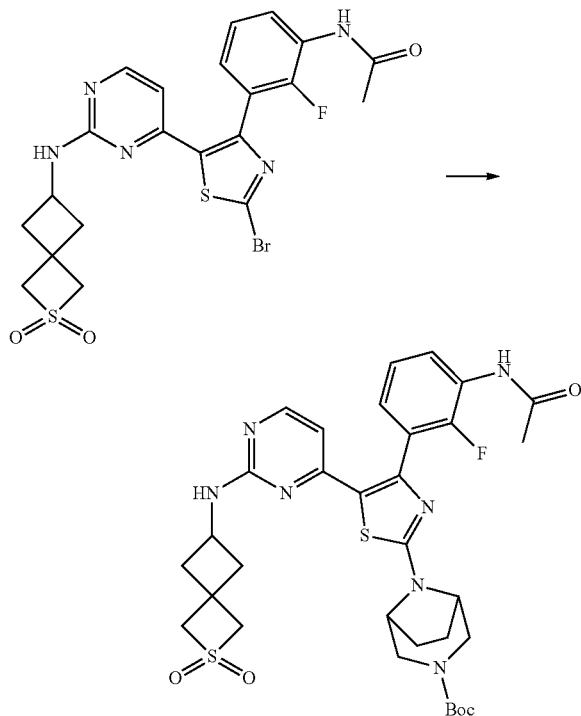

A mixture of N-(3-(2-bromo-5-(2-((2,2-dioxido-2-thiaspiro[3.3]heptan-6-yl)amino)-pyrimidin-4-yl)thiazol-4-yl)-2-fluorophenyl)acetamide (800 mg, 1.45 mmol, 1.00 eq.), tert-butyl 3,8-diazabicyclo[3.2.1]octane-3-carboxylate (400 mg, 1.88 mmol, 1.30 eq.) and TEA (439 mg, 4.38 mmol, 3.00 eq.) in DMA (10.0 mL) was stirred at 120° C. overnight. The mixture was diluted with water and extracted with EtOAc. The combined organic layers were washed with water, brine, dried over Na₂SO₄, and concentrated. The residue was purified by silica flash column PE/EtOAc (1:2) to give the title compound as a yellow solid.

Step 5: Tert-Butyl 8-(4-(3-amino-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate

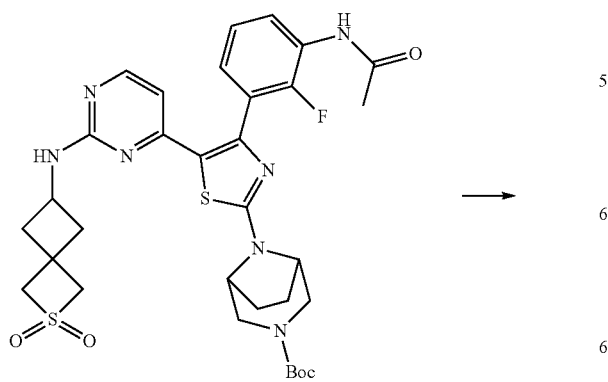

354

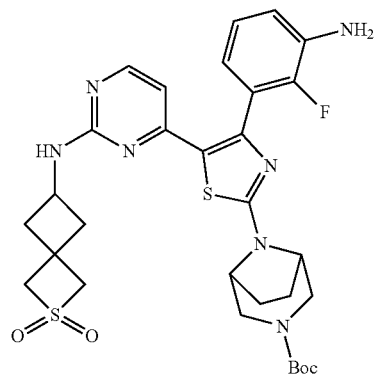

To a solution of tert-butyl 8-(4-(3-acetamido-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate (900 mg, 1.32 mmol, 1.00 eq.) in EtOH (10.0 mL) was added NaOH (105 mg, 2.64 mmol, 2.00 eq.) and the mixture was stirred at 80° C. overnight. The mixture was diluted with water and extracted with EtOAc. The combined organic layers was washed with brine, dried over Na₂SO₄ and concentrated to give the title compound as a yellow solid.

Step 6: Tert-Butyl 8-(5-(2-((2,2-dioxido-2-thiaspiro[3.3]heptan-6-yl)amino)pyrimidin-4-yl)-4-(2-fluoro-3-(2-fluoro-6-(trifluoromethyl)phenylsulfonamido)phenyl)thiazol-2-yl)-3,8-diazabicyclo[3.2.1]octane-3-carboxylate

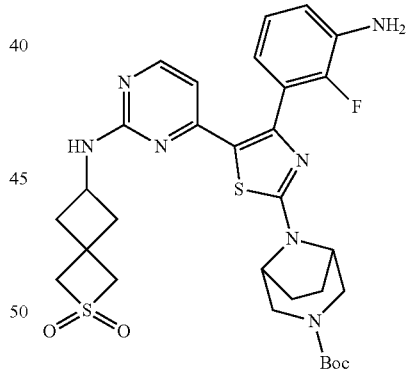

+

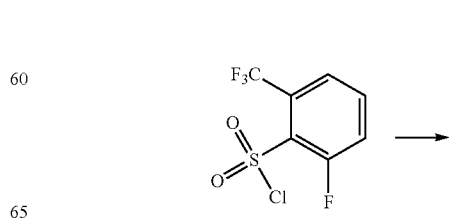

355

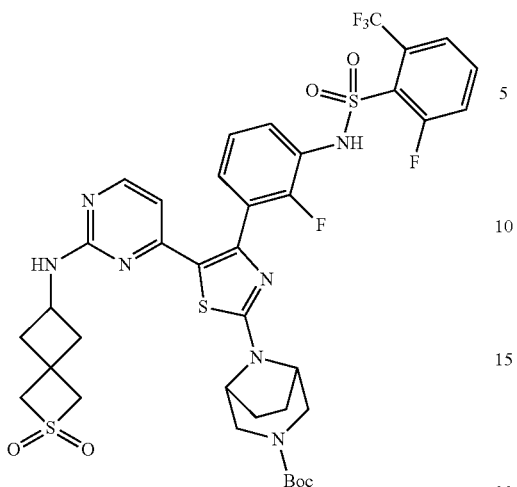

2-Fluoro-6-(trifluoromethyl)benzene-1-sulfonyl chloride (536 mg, 2.05 mmol, 1.60 eq.) was added to a solution of tert-butyl 8-(4-(3-amino-2-fluorophenyl)-5-(2-((2,2-di-oxido-2-thiaspiro[3.3]heptan-6-yl)amino)pyrimidin-4-yl) thiazol-2-yl)-3,8-diazabicyclo[3.2.1]octane-3-carboxylate (820 mg, 1.28 mmol, 1.00 eq.) and pyridine (303 mg, 3.84 mmol, 3.00 eq.) in DCM (20.0 mL) and the mixture was stirred at 40° C. overnight. The mixture was concentrated and the residue was purified by silica flash column DCM/MeOH (20:1) to give the title compound as a yellow solid.

Step 7: N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide

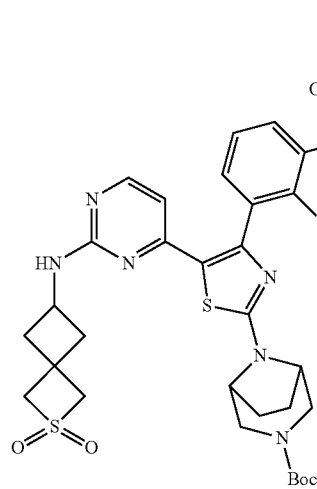

356

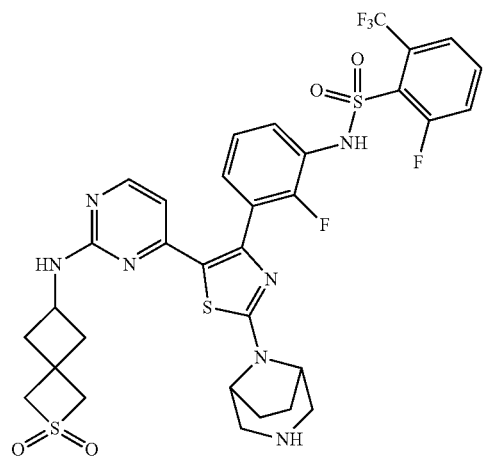

To a solution of tert-butyl 8-(5-(2-((2,2-dioxido-2-thiaspiro[3.3]heptan-6-yl)amino)-pyrimidin-4-yl)-4-(2-fluoro-3-(2-fluoro-6-(trifluoromethyl)phenylsulfonamido)-phenyl) thiazol-2-yl)-3,8-diazabicyclo[3.2.1]octane-3-carboxylate (540 mg, 0.62 mmol, 1.00 eq.) in DCM (4.0 mL) was added TFA (1.0 mL) and the mixture was stirred at rt for 2 h. The mixture was concentrated to give the title compound as a yellow oil.

Step 8: N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl) thiazol-4-yl)-2-fluorophenyl)-2-fluoro-6-(trifluoromethyl)benzenesulfonamide

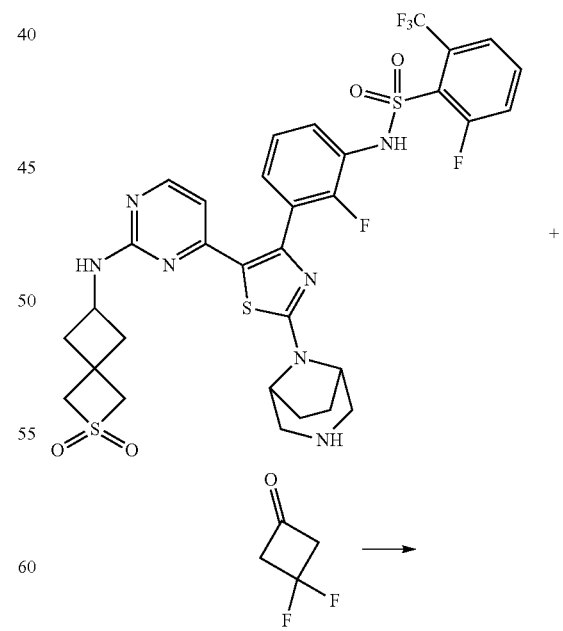

357
-continued

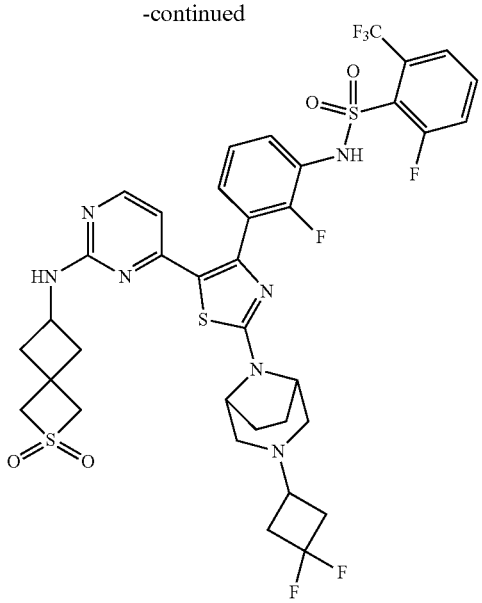

358

A mixture of N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide (200 mg, 0.26 mmol, 1.00 eq.), AcOH (2 drops) and 3,3-difluorocyclobutanone (138 mg, 1.30 mmol, 5.00 eq.) in MeOH/THF (4.0 mL, 1:1) was stirred at rt for 0.5 h. NaBH$_3$CN (82 mg, 1.30 mmol, 5.00 eq.) was added and the mixture was stirred at rt overnight. The mixture was extracted with DCM and the combined organic layers was washed with brine, dried over Na$_2$SO$_4$ and concentrated. The residue was purified by silica flash column to give the title compound as a yellow solid.

Proceeding analogously as described in Example 126, the following compounds were prepared.

| Ex# | Structures | Changes in synthetic protocol | LCMS (ES, m/z): [M + 1]$^+$ |
|---|---|---|---|
| 127 | 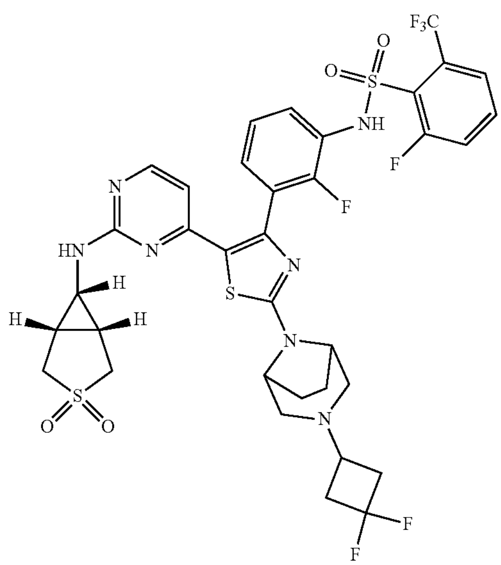 [SMILES: O=S1(=O)C[C@@H]2[C@H](C1)[C@@H]2Nc1nccc(-c2sc(N3C4CCC3CN(C3CC(F)(F)C3)C4)nc2-c2cccc(NS(=O)(=O)c3c(F)cccc3C(F)(F)F)c2F)n1] | Intermediate 6 replaced by Intermediate 2 in Step 2. | 844.3 |

-continued
| Ex# | Structures | Changes in synthetic protocol | LCMS (ES, m/z): [M + 1]+ |
|---|---|---|---|
| 128 | 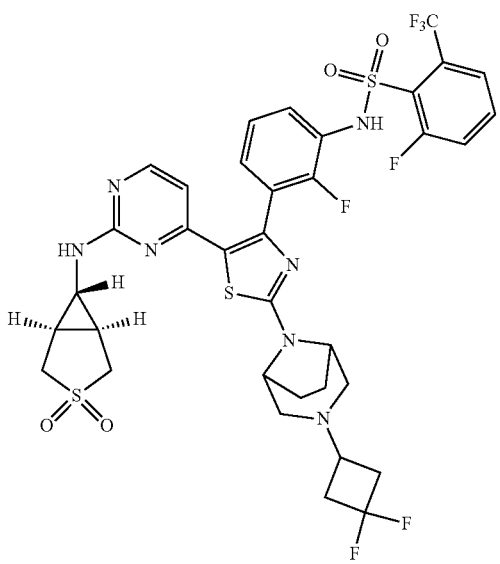 [SMILES: O=S1(=O)C[C@@H]2[C@H](C1)[C@H]2Nc1nccc(-c2sc(N3C4CCC3CN(C3CC(F)(F)C3)C4)nc2-c2cccc(NS(=O)(=O)c3c(F)cccc3C(F)(F)F)c2F)n1] | Intermediate 6 replaced by Intermediate 3 in Step 2. | 844.3 |
| 129 | 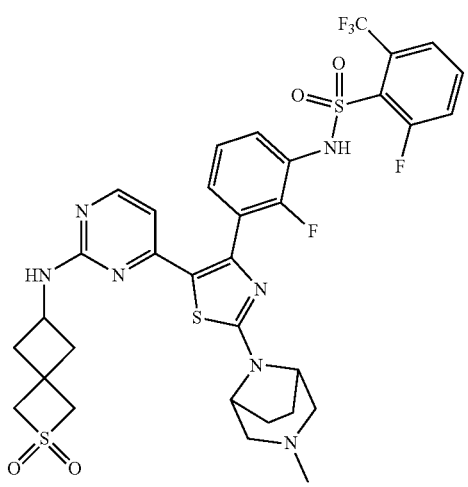 [SMILES: CN1CC2CCC(C1)N2c1nc(-c2cccc(NS(=O)(=O)c3c(F)cccc3C(F)(F)F)c2F)c(-c2ccnc(NC3CC4(C3)CS(=O)(=O)C4)n2)s1] | 3,3-difluorocyclobutanone replaced by formaldehyde in Step 8 | 782.3 |

Example 136

Synthesis of N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-(difluoromethyl)-6-fluorobenzenesulfonamide Step 1: N-(3-(2-amino-5-(2-((2,2-dioxido-2-thiaspiro[3.3]heptan-6-yl)amino)pyrimidin-4-yl)thiazol-4-yl)-2-fluorophenyl)acetamide A mixture of N-(3-(2-amino-5-(2-chloropyrimidin-4-yl)thiazol-4-yl)-2-fluorophenyl)-acetamide (5.05 g, 13.90 mmol, 1.00 eq), 2-thiaspiro[3.3]heptan-6-amine hydrochloride (Intermediate 6; 3.30 g, 16.70 mmol, 1.50 eq), DIEA (8.90 g, 69.60 mmol, 5.00 eq) in n-BuOH (100.0 mL) was stirred at 130° C. overnight under $N_2$. The mixture was poured into water and extracted with EtOAc. The combined organic layers were washed with water, brine, dried over $Na_2SO_4$. and concentrated. The residue was purified by column chromatography on silica gel (PE:EA=1:1 to DCM:MeOH=20:1) to give the title compound as a yellow solid.

Step 2: N-(3-(2-bromo-5-(2-((2,2-dioxido-2-thiaspiro[3.3]heptan-6-yl)amino)pyrimidin-4-yl)thiazol-4-yl)-2-fluorophenyl)acetamide

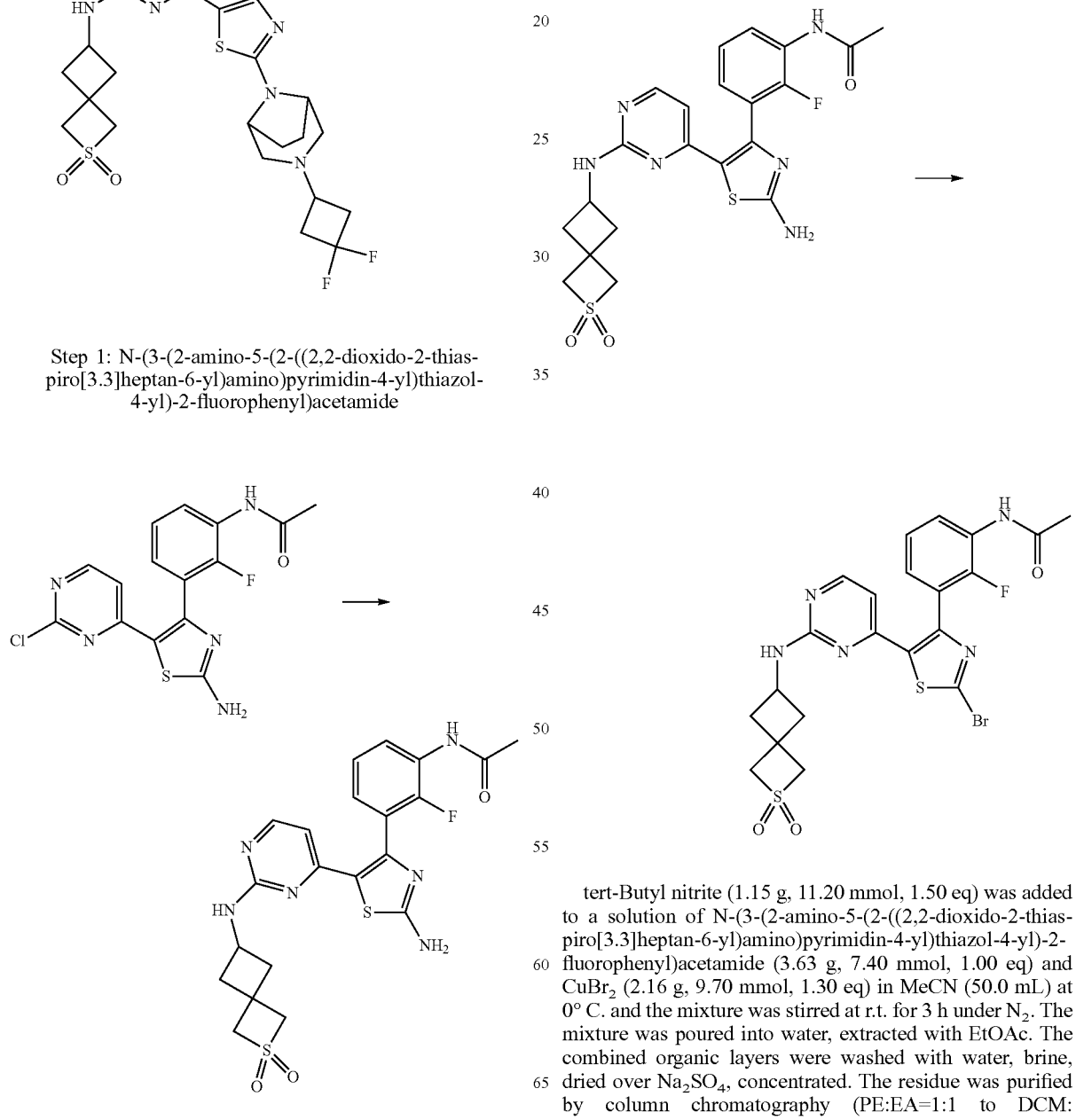

tert-Butyl nitrite (1.15 g, 11.20 mmol, 1.50 eq) was added to a solution of N-(3-(2-amino-5-(2-((2,2-dioxido-2-thiaspiro[3.3]heptan-6-yl)amino)pyrimidin-4-yl)thiazol-4-yl)-2-fluorophenyl)acetamide (3.63 g, 7.40 mmol, 1.00 eq) and $CuBr_2$ (2.16 g, 9.70 mmol, 1.30 eq) in MeCN (50.0 mL) at 0° C. and the mixture was stirred at r.t. for 3 h under $N_2$. The mixture was poured into water, extracted with EtOAc. The combined organic layers were washed with water, brine, dried over $Na_2SO_4$, concentrated. The residue was purified by column chromatography (PE:EA=1:1 to DCM:MeOH=20:1) to give the title compound as a yellow solid.

363

Step 3: Tert-Butyl 8-(4-(3-acetamido-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate

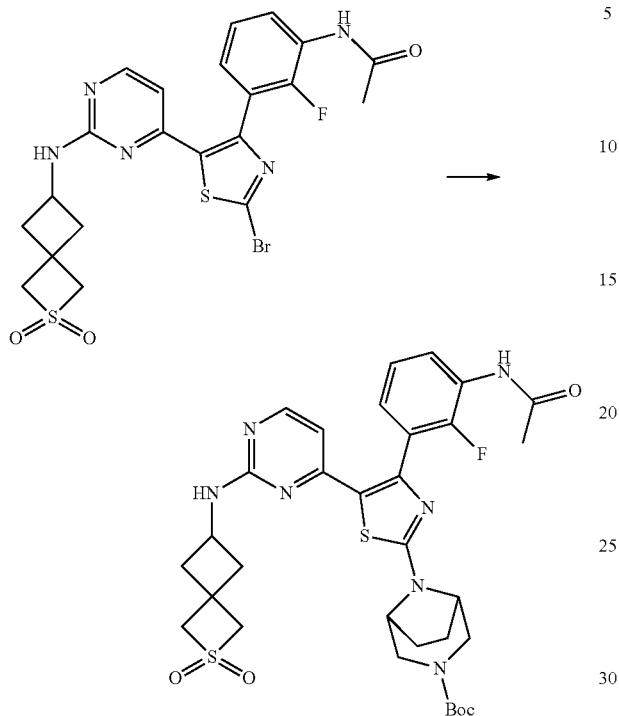

A mixture of N-(3-(2-bromo-5-(2-((2,2-dioxido-2-thiaspiro[3.3]heptan-6-yl)amino)-pyrimidin-4-yl)thiazol-4-yl)-2-fluorophenyl)acetamide (800 mg, 1.45 mmol, 1.00 eq.), tert-butyl 3,8-diazabicyclo[3.2.1]octane-3-carboxylate (400 mg, 1.88 mmol, 1.30 eq.) and TEA (439 mg, 4.38 mmol, 3.00 eq.) in DMA (10.0 mL) was stirred at 120° C. overnight. The mixture was diluted with water and extracted with EtOAc. The combined organic layers were washed with water, brine, dried over Na₂SO₄, concentrated. The residue was purified by silica flash column PE/EtOAc (1:2) to give the title compound as a yellow solid.

Step 4: N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)acetamide

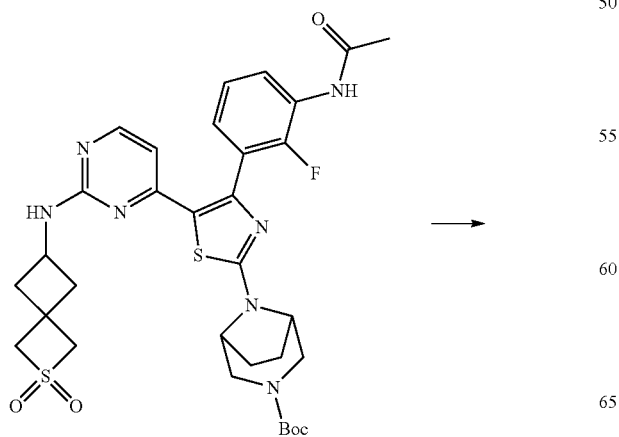

364

-continued

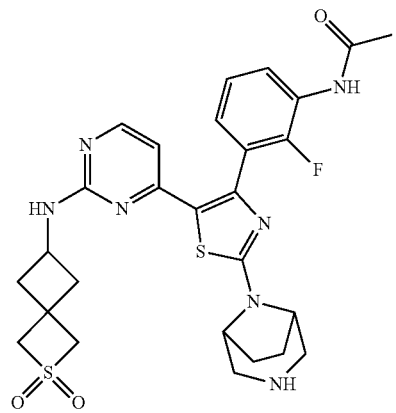

TFA (1.0 mL) was added to a mixture of tert-butyl 8-(4-(3-acetamido-2-fluorophenyl)-5-(2-((2,2-dioxido-2-thiaspiro[3.3]heptan-6-yl)amino)pyrimidin-4-yl)thiazol-2-yl)-3,8-diazabicyclo[3.2.1]octane-3-carboxylate (450 mg, 0.66 mmol, 1.00 eq.) in DCM (5.0 mL) at 0° C. This mixture was stirred at rt under N₂ for 2 h and then concentrated to give crude product as a brown solid.

Step 5: N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)acetamide

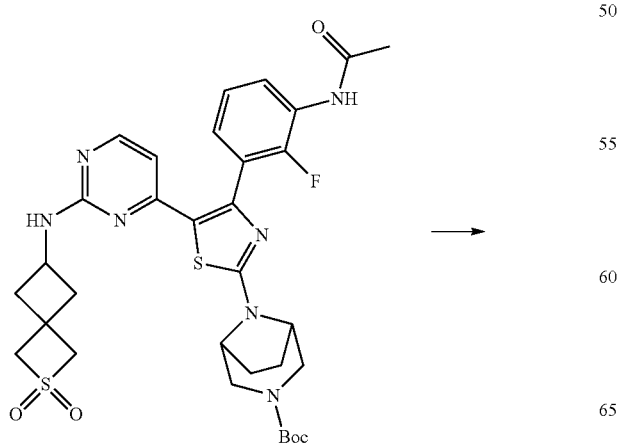 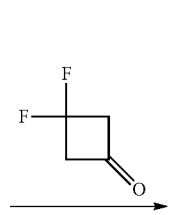

365
-continued

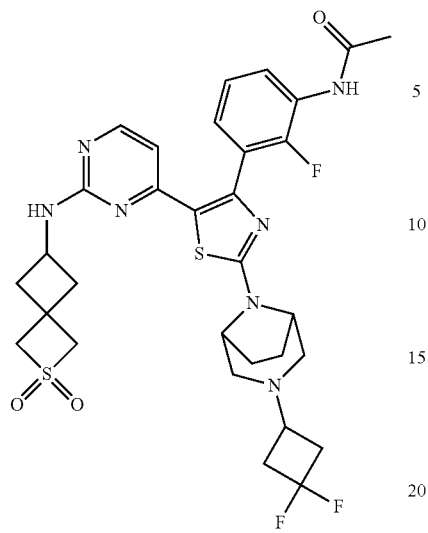

A mixture of N-(3-(2-(3,8-diazabicyclo[3.2.1]octan-8-yl)-5-(2-((2,2-dioxido-2-thiaspiro[3.3]heptan-6-yl)amino) pyrimidin-4-yl)thiazol-4-yl)-2-fluorophenyl)acetamide (350 mg, 0.50 mmol, 1.00 eq.) and 3,3-difluorocyclobutan-1-one (160 mg, 1.506 mmol, 3.00 eq.) in DCE/MeOH (1:1, 7.0 mL) was stirred at r.t. for 1 h. NaBH$_3$CN (158 mg, 2.51 mmol, 5.00 eq.) was added and the mixture was stirred at r.t. under N$_2$ overnight. The mixture was concentrated and the residue was purified by column chromatography on silica gel (DCM:MeOH=20:1) to give the title compound as a yellow solid.

Step 6: 6-((4-(4-(3-Amino-2-fluorophenyl)-2-(3-(3, 3-difluorocyclobutyl)-3,8-diazabicyclo-[3.2.1]octan-8-yl)thiazol-5-yl)pyrimidin-2-yl)amino)-2-thiaspiro [3.3]heptane 2,2-dioxide 366
-continued

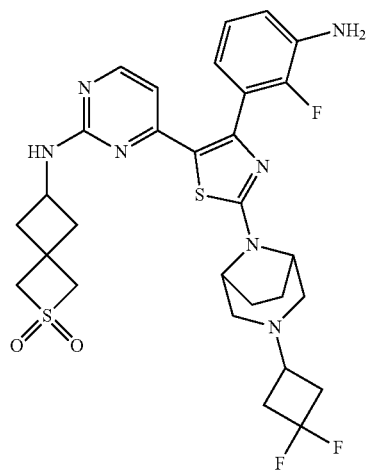

A mixture of N-(3-(2-(3-(3,3-difluorocyclobutyl)-3,8-diazabicyclo[3.2.1]octan-8-yl)-5-(2-((2,2-dioxido-2-thiaspiro [3.3]heptan-6-yl)amino)pyrimidin-4-yl)thiazol-4-yl)-2-fluorophenyl)-acetamide (325 mg, 0.48 mmol, 1.00 eq.) in HCl/MeOH (2M, 10.0 mL) was stirred at 50° C. under N$_2$ for 3 h. The mixture was concentrated to give the crude title compound which was used in next step without further purification.

Step 7: N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl) thiazol-4-yl)-2-fluorophenyl)-2-(difluoromethyl)-6-fluorobenzenesulfonamide

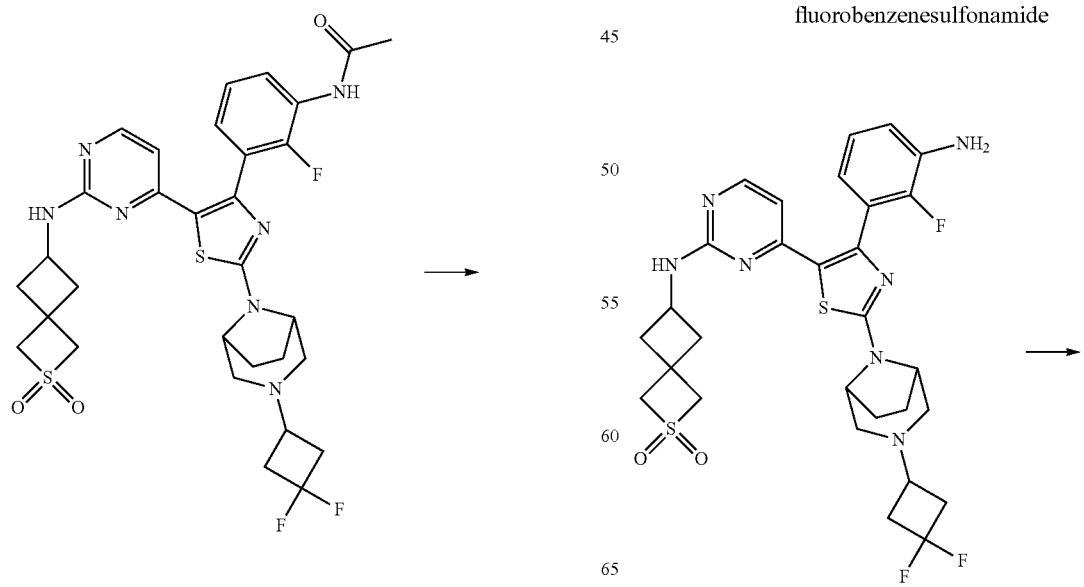

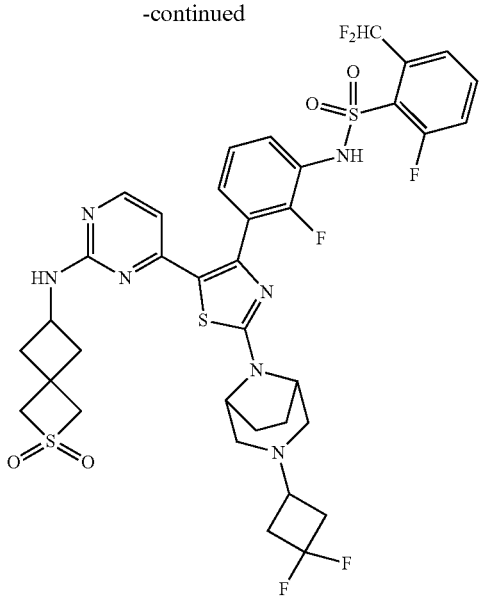

2-(Difluoromethyl)-6-fluorobenzenesulfonyl chloride (Intermediate 29; 180 mg, 0.74 mmol, 3.00 eq.) was added to a mixture of 6-((4-(4-(3-amino-2-fluorophenyl)-2-(3-(3,3-difluorocyclobutyl)-3,8-diazabicyclo[3.2.1]octan-8-yl)thiazol-5-yl)pyrimidin-2-yl)amino)-2-thiaspiro[3.3]heptane 2,2-dioxide (155 mg, 0.25 mmol, 1.00 eq.), pyridine (97 mg, 1.23 mmol, 5.00 eq.) in DCM (5.0 mL) and the mixture was stirred at rt under $N_2$ overnight. The mixture was concentrated and the residue was purified by prep-HPLC to give the title compound as a yellow solid. MS (ES, m/z): [M+1]=840.3.

Proceeding analogously as described in Example 136, the following compounds were prepared.

| Ex# | Structures | Changes in synthetic protocol | LCMS (ES, m/z): [M + 1]+ |
|---|---|---|---|
| 137 | 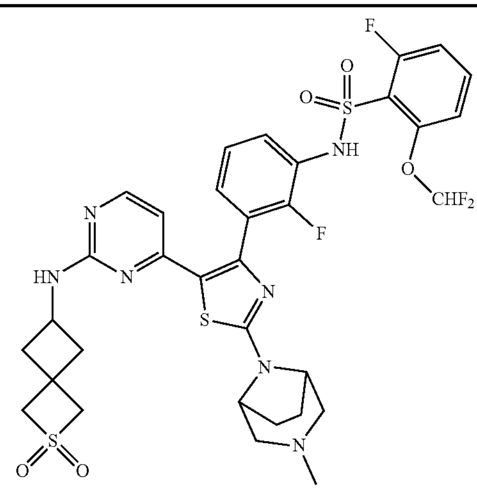 | 1. 3,3-difluorocyclobutan-1-one replaced by formaldehyde in Step 5<br>2. Intermediate 29, replaced by Intermediate 12 in Step 7. | 780.3 |
| 138 | 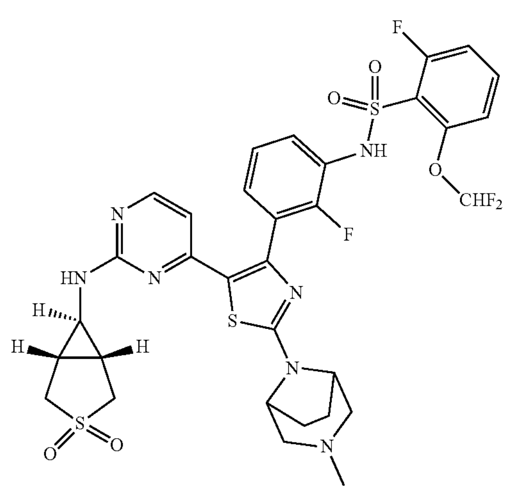 [SMILES: CN1CC2CCC(C1)N2c1nc(-c2cccc(NS(=O)(=O)c3c(F)cccc3OC(F)F)c2F)c(-c2ccnc(N[C@H]3[C@@H]4CS(=O)(=O)C[C@@H]43)n2)s1] | 1. Intermediate 6 replaced by Intermediate 3 in Step 1.<br>2. 3,3-difluorocyclobutan-1-one replaced by formaldehyde in Step 5<br>3. Intermediate 29, replaced by Intermediate 12 in Step 7. | 766.3 |

| Ex# | Structures | Changes in synthetic protocol | LCMS (ES, m/z): [M + 1]+ |
|---|---|---|---|
| 139 | 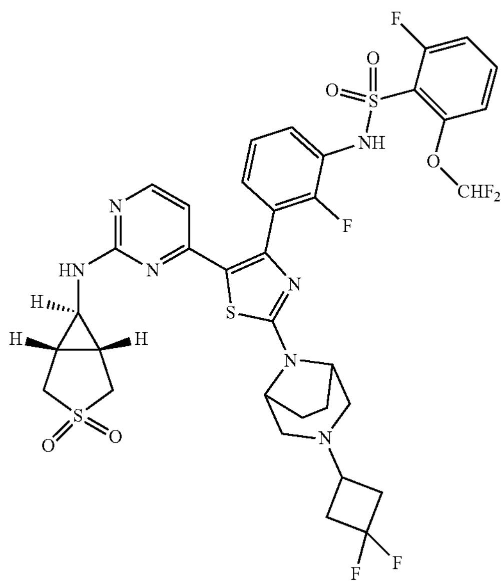 [SMILES: O=S1(=O)C[C@@H]2[C@H](C1)[C@H]2Nc1nccc(-c2sc(N3C4CCC3CN(C3CC(F)(F)C3)C4)nc2-c2cccc(NS(=O)(=O)c3c(F)cccc3OC(F)F)c2F)n1] | 1. Intermediate 6 replaced by Intermediate 3 in Step 1. 2. Intermediate 29, replaced by Intermediate 12 in Step 7. | 842.0 |

Example 140

Synthesis of N-(3-(2-(bicyclo[1.1.1]pentan-1-yl)-5-(2-((2,2-dioxido-2-thiaspiro[3.3]heptan-6-yl)-amino)pyrimidin-4-yl)thiazol-4-yl)-2-fluorophenyl)-2-fluoro-6-methoxybenzenesulfonamide

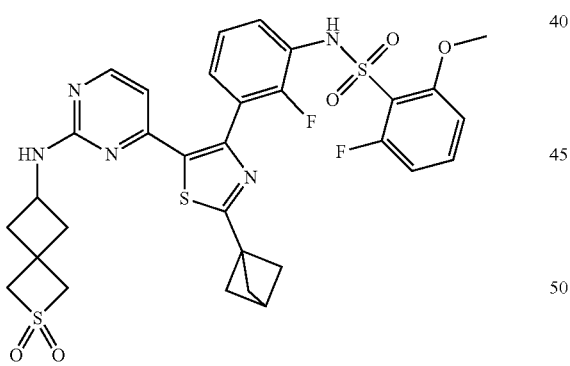

To a stirred solution of N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide (Example 42; 50 mg, 0.07 mmol, 1.00 eq.) in THF (2.0 mL) was added NaH (60%) (14.8 mg, 0.37 mmol, 5.00 eq.) at 0° C. The mixture was stirred at rt for 30 min. MeOH (9.6 mg, 0.30 mmol, 14.00 eq.) was added at rt and the mixture was stirred overnight. The mixture was diluted with water and extracted with EtOAc. The combined organic layers were washed with brine, dried over $Na_2SO_4$, and concentrated. The residue was purified by prep-TlPLC to give the title compound as a white solid. LCMS (ES, m/z): [M+H]+=686.2

Proceeding analogously as described in Example 140, the following compounds were prepared.

| Ex# | Structures | Changes in synthetic protocol | LCMS (ES, m/z): [M + 1]+ |
|---|---|---|---|
| 141 | 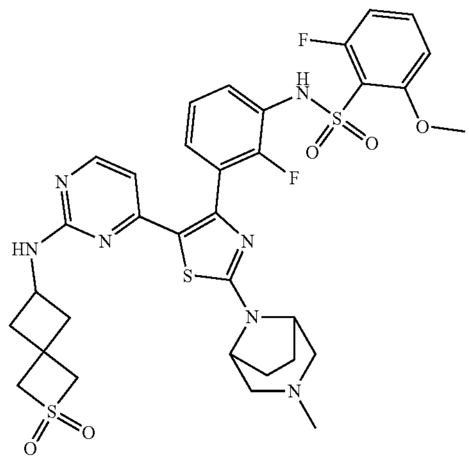 [SMILES: COc1cccc(F)c1S(=O)(=O)Nc1cccc(-c2nc(N3C4CCC3CN(C)C4)sc2-c2ccnc(NC3CC4(C3)CS(=O)(=O)C4)n2)c1F] | N-(3-(2-(bicyclo[1.1.1]pentan-1-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzenesulfonamide replaced by title compound of Example 81 | 744.4 |
| 142 | 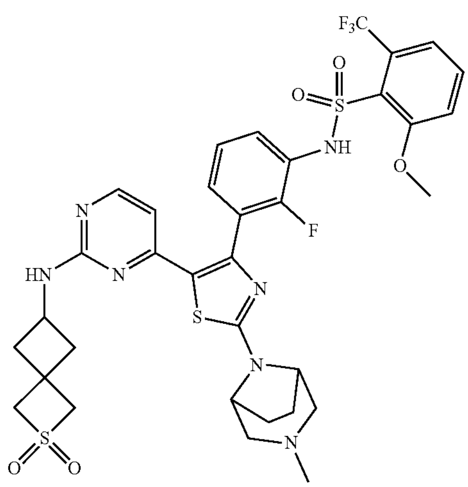 [SMILES: COc1cccc(C(F)(F)F)c1S(=O)(=O)Nc1cccc(-c2nc(N3C4CCC3CN(C)C4)sc2-c2ccnc(NC3CC4(C3)CS(=O)(=O)C4)n2)c1F] | N-(3-(2-(bicyclo[1.1.1]pentan-1-yl)-5-(2-((2,2-dioxido-2-thiaspiro-[3.3]heptan-6-yl)amino)pyrimidin-4-yl)thiazol-4-yl)-2-fluorophenyl)-2,6-difluorobenzenesulfonamide replaced by title compound of Example 129 | 794.3 |

Example 143

Synthesis of N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-cyclopropyl-6-fluorobenzenesulfonamide

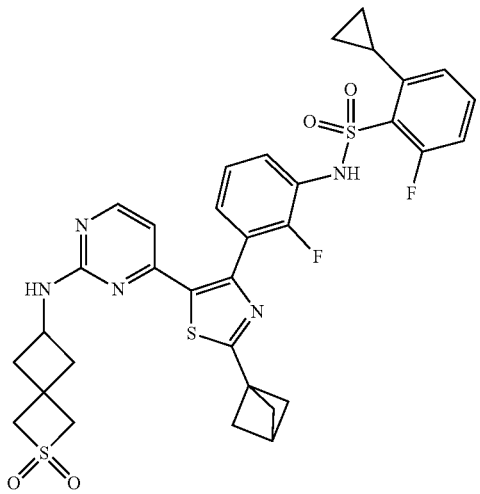 [SMILES: O=S1(=O)CC2(CC(Nc3nccc(-c4sc(C56CC(C5)C6)nc4-c4cccc(NS(=O)(=O)c5c(F)cccc5C5CC5)c4F)n3)C2)C1]

Step 1: 2-Bromo-6-fluorobenzene-1-sulfonyl Chloride

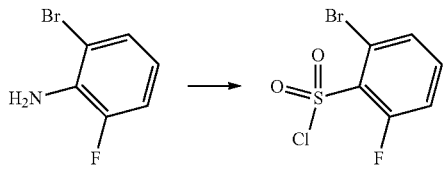 [SMILES: Nc1c(F)cccc1Br ; O=S(=O)(Cl)c1c(F)cccc1Br]

(Solution A) SOC$_2$ (1.70 g, 14.47 mmol, 5.50 eq.) was added dropwise to H$_2$O (7.5 mL) at 0° C., then the reaction was stirred at rt overnight. CuCl (130 mg, 1.32 mmol, 0.50 eq.) was added to the reaction mixture.

(Solution B) To a 100 mL three necked flask was added HCl (6.0 mL) and 2-bromo-6-fluoroaniline (500 mg, 2.63 mmol, 1.00 eq.) at 0° C. Then NaNO$_2$ (272 mg, 3.95 mmol, 1.50 eq.) in H$_2$O (5.0 mL) was added dropwise at 0° C. The mixture was stirred for 1 h.

Solution A was added to Solution B dropwise at 0° C. and the mixture was stirred at rt for 1 h. The mixture was diluted with water and extracted with DCM. The combined organic layers were dried over Na$_2$SO$_4$ and concentrated to give the title compound as a yellow oil.

Step 2: N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-bromo-6-fluorobenzenesulfonamide

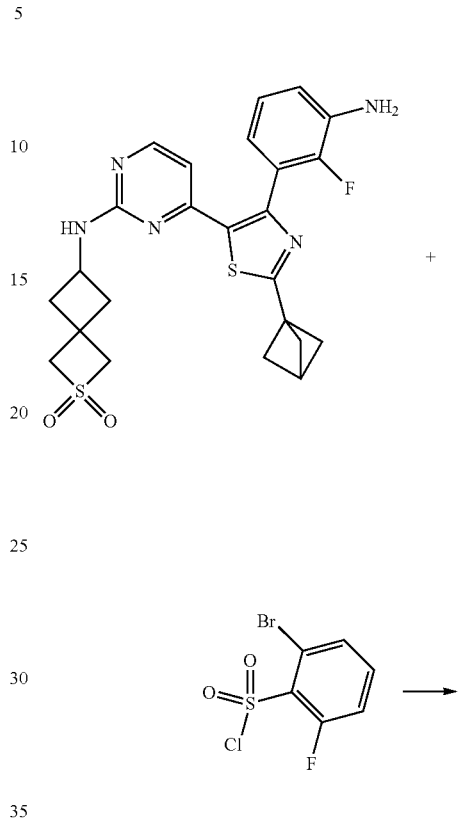

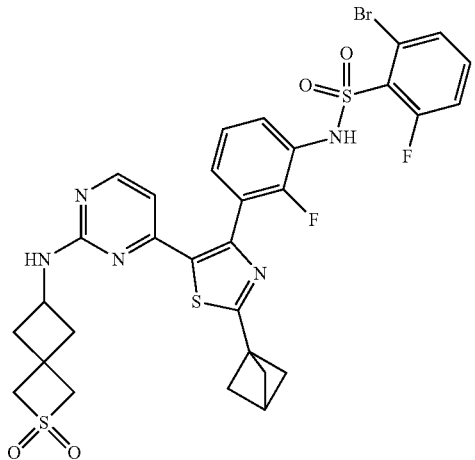

2-Bromo-6-fluorobenzene-1-sulfonyl chloride (165 mg, 0.60 mmol, 2.0 eq.) was added to a solution of 6-((4-(4-(3-amino-2-fluorophenyl)-2-(bicyclo[1.1.1]pentan-1-yl)thiazol-5-yl)pyrimidin-2-yl)amino)-2-thiaspiro[3.3]heptane 2,2-dioxide (150 mg, 0.30 mmol, 1.00 eq.) and pyridine (71 mg, 0.90 mmol, 3.00 eq.) in DCM (2.0 mL). The mixture was stirred at 40° C. overnight. The mixture was concentrated and the residue was purified by silica gel flash column PE/EtOAc (1:2) to give the title compound as a white solid.

Step 3: N-(3-(2-(bicyclo[1.1.1]pentan-1-yl)-5-(2-((2,2-dioxido-2-thiaspiro[3.3]heptan-6-yl)-amino)pyrimidin-4-yl)thiazol-4-yl)-2-fluorophenyl)-2-cyclopropyl-6-fluorobenzenesulfonamide

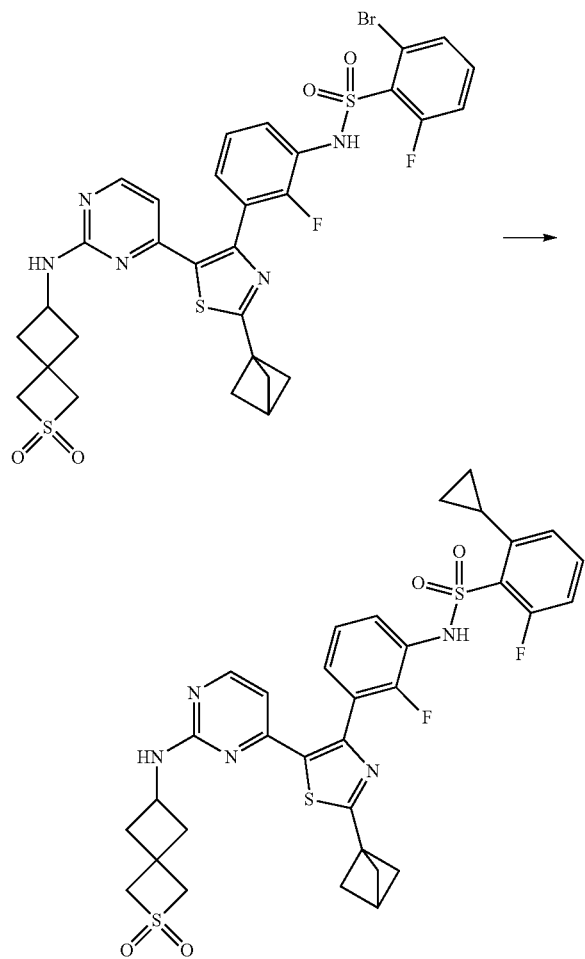

A mixture of cyclopropylboronic acid (35 mg, 0.41 mmol, 3.00 eq.), $Cs_2CO_3$ (133 mg, 0.41 mmol, 3.00 eq.), Pd(dppf)$Cl_2$ (30 mg), N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-bromo-6-fluorobenzenesulfonamide (100 mg, 0.14 mmol, 1.00 eq.) in dioxane/$H_2O$ (2.0 mL, 5:1) was stirred at 100° C. under microwave irradiation for 2 h. The mixture was extracted with DCM and the combined organic layers were dried over $Na_2SO_4$, and concentrated. Then the residue was purified by prep-HPLC to give the title compound as a white solid. MS (ES, m/z): $[M+1]^+=696.1$

BIOLOGICAL EXAMPLES

Example 1: Phospho-$R^B$ Measurement in OVCAR3 Cells

The ability of compounds of Formula (I) to inhibit CDK2 was determined in OVCAR3 cells. Phosphorylation of RB protein at S807/811 were measured using HTRF phospho-RB cellular kits (Cat #64RBS807PEG) from Cisbio.

On Day 1, OVCAR3 cells were seeded into 96-well tissue-culture treated plates at 20,000 cells/well in 200 μL and incubated overnight at 37° C. in $CO_2$ atmosphere. On Day 2, the cells were treated with test compounds at concentrations from 0.3 to 10,000 nM using HP D300 digital dispenser. Twenty-four hours after compound treatment, cell culture media was removed by flicking the plate and tapping the plate against clean paper towel. Immediately 30 μL 1× lysis buffer was supplemented from the kit and the plate was incubated at room temperature on shaker for 30 min. After homogenization by pipetting up and down, 8 μL cell lysate from 96-well cell culture plate was transferred to 384-well small volume white detection plate. 2 μL premixed detection solution was added and the plate was covered with sealer. To prepare the detection solution, d2 conjugated-phospho-RB antibody and Eu-cryptate conjugated phosphor-RB antibody were diluted into detection buffer following manufacturer's instruction.

Detection plates were incubated for 4 h at room temperature and read on ClarioStar (BMG Labtech) in TR-FRET mode (665 nM and 620 nM). The TR-FRET ratio (665 nM1/620 nM) was plotted against the compound concentration and normalized to DMSO controls. Half maximal inhibition concentration ($IC_{50}$) values are calculated with a four-parameter logistic fit using GraphPad Prism (version 8; La Jolla, CA).

CDK2 $IC_{50}$ data for compounds in Compound Table 1 are provided in Table 2 below.

TABLE 2

| Cpd No. from Cpd. Table 1 | pRb (uM) | Cpd No. from Cpd. Table 1 | pRb (uM) | Cpd No. from Cpd. Table 1 | pRb (uM) |
|---|---|---|---|---|---|
| 1 | 1.68 | 52 | 0.08 | 105 | 0.12 |
| 2 | 0.15 | 53 | 0.04 | 106 | 0.68 |
| 3 | 0.12 | 54 | 0.2 | 107 | 0.15 |
| 4 | 0.13 | 55 | 1.35 | 108 | 0.10 |
| 5 | 0.52 | 56 | 0.11 | 109 | 0.09 |
| 6 | 0.080 | 57 | 0.60 | 110 | 0.04 |
| 7 | 0.39 | 58 | 0.09 | 111 | 0.08 |
| 8 | 0.24 | 59 | 3.01 | 112 | 0.03 |
| 9 | 0.10 | 60 | 0.90 | 113 | 0.07 |
| 10 | 0.055 | 61 | 0.34 | 114 | 0.30 |
| 11 | 0.11 | 62 | 3.86 | 115 | 0.05 |
| 12 | 0.068 | 63 | 0.13 | 116 | 0.09 |
| 13 | 0.73 | 64 | 0.17 | 117 | 0.90 |
| 14 | 18.14 | 65 | 0.39 | 118 | 0.73 |
| 15 | 3.20 | 66 | 0.15 | 119 | 1.34 |
| 16 | 0.13 | 67 | 0.03 | 120 | 0.29 |
| 17 | 0.48 | 68 | 0.05 | 121 | 0.05 |
| 18 | 0.079 | 69 | 1.28 | 122 | 0.04 |
| 19 | 0.19 | 70 | 0.03 | 123 | 0.17 |
| 20 | 0.24 | 71 | 18.89 | 124 | 0.04 |
| 21 | 0.24 | 72 | 0.061 | 125 | 4.51 |
| 22 | 0.44 | 73 | 0.6 | 126 | 0.07 |
| 23 | 1.74 | 74 | 0.63 | 127 | 0.06 |
| 24 | 1.46 | 75 | 0.85 | 128 | 0.05 |
| 25 | 1.55 | 76 | 0.87 | 129 | 0.09 |
| 26 | 0.016 | 77 | 0.24 | 130 | 0.45 |
| 27 | 0.066 | 78 | 3.79 | 131 | 0.12 |
| 28 | 1.17 | 79 | 0.06 | 132 | 0.05 |
| 29 | 0.27 | 80 | 0.06 | 133 | 0.12 |
| 30 | 0.24 | 81 | 0.14 | 134 | 0.08 |
| 31 | 0.07 | 82 | 0.13 | 135 | 0.07 |
| 32 | 0.08 | 83 | 0.04 | 136 | 1.35 |
| 33 | 0.10 | 84 | 0.03 | 137 | 0.10 |
| 34 | 2.01 | 85 | 0.03 | 138 | 0.18 |
| 35 | 0.29 | 86 | 0.040 | 139 | 0.13 |
| 36 | 0.09 | 87 | 0.077 | 140 | 0.07 |
| 37 | 0.42 | 88 | 0.09 | 141 | 6.70 |
| 38 | 8.12 | 89 | 0.12 | 142 | 0.32 |
| 39 | 0.35 | 91 | 0.15 | 143 | 0.11 |
| 40 | 1.70 | 92 | 0.04 | 144 | 0.24 |

TABLE 2-continued

| Cpd No. from Cpd. Table 1 | pRb (uM) | Cpd No. from Cpd. Table 1 | pRb (uM) | Cpd No. from Cpd. Table 1 | pRb (uM) |
|---|---|---|---|---|---|
| 41 | 0.36 | 93 | 0.04 | 146 | 0.20 |
| 42 | 0.25 | 94 | 0.28 | 147 | 0.91 |
| 43 | 0.46 | 95 | 0.07 | 148 | 0.40 |
| 44 | 0.66 | 96 | 3.99 | 149 | 0.09 |
| 45 | 4.14 | 98 | 0.13 | 150 | 0.17 |
| 46 | 1.36 | 99 | 0.06 | 151 | 0.051 |
| 47 | 0.05 | 100 | 0.10 | 152 | 0.15 |
| 48 | 7.13 | 101 | 0.17 | 153 | 0.060 |
| 49 | 1.13 | 102 | 0.19 | 154 | 0.095 |
| 50 | 0.19 | 103 | 0.10 | | |
| 51 | 0.04 | 104 | 0.08 | | |

Formulation Examples

The following are representative pharmaceutical formulations containing a compound of the present disclosure.

Tablet Formulation

The following ingredients are mixed intimately and pressed into single scored tablets.

| Ingredient | Quantity per tablet (mg) |
|---|---|
| compound Formula (I) | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule (mg) |
|---|---|
| compound Formula (I) | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:

1. A compound of Formula (I):

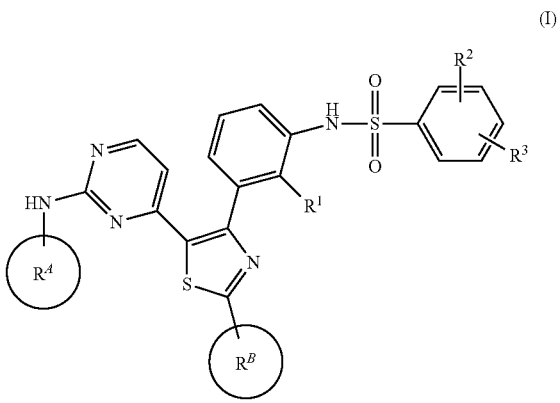

(I)

wherein:
$R^1$ is hydrogen or halo;
ring $R^A$ is a ring of formula (i), (ii), (iii), or (iv):

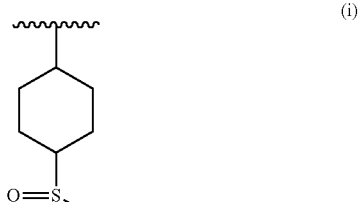

(i)

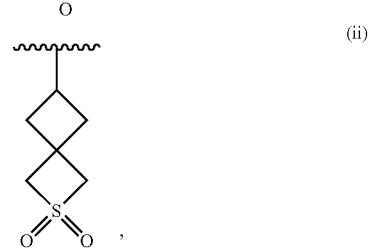

(ii)

-continued

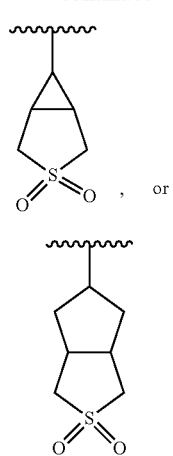

where alk is alkyl and each ring of $R^A$ is substituted with $R^4$ and $R^5$ independently selected from hydrogen, alkyl, and halo;

$R^2$ and $R^3$ are independently selected from hydrogen, alkyl, cycloalkyl, alkoxy, halo, haloalkyl, and haloalkoxy;

ring $R^B$ is cycloalkyl, bridged cycloalkyl, heterocyclyl, or bridged heterocyclyl, wherein:

(A) cycloalkyl and bridged cycloalkyl of ring $R^B$ are substituted with $R^a$ selected from hydrogen, halo, haloalkyl, and hydroxalkyl;

(B) heterocyclyl of ring $R^B$ is substituted with $R^b$, $R^c$, and $R^d$ where $R^b$ and $R^c$ are independently selected from hydrogen, alkyl, alkoxy, hydroxy, cyano, halo, haloalkyl, and haloalkoxy and $R^d$ is hydrogen, alkyl, deuteroalkyl, cycloalkyl (optionally substituted with one or two substituents independently selected from alkyl, halo, hydroxy, and cyano), alkoxy, halo, haloalkyl, haloalkoxy, alkoxycarbonyl, amino, alkylamino, dialkylamino, aryl, aralkyl, heterocyclyl, or heteroaryl; and (C) bridged heterocyclyl of ring $R^B$ is substituted with $R^e$, $R^f$, and $R^g$ where $R^e$ and $R^f$ are independently selected from hydrogen, alkyl, alkoxy, hydroxy, cyano, halo, haloalkyl, and haloalkoxy and $R^g$ is hydrogen, alkyl, deuteroalkyl, cycloalkyl (optionally substituted with one or two substituents independently selected from alkyl, halo, hydroxy, or cyano), alkoxy, halo, haloalkyl, haloalkoxy, alkoxycarbonyl, oxo, amino, alkylamino, dialkylamino, aryl, aralkyl, heterocyclyl, or heteroaryl; or a pharmaceutically acceptable salt thereof.

2. The compound of claim 1, or a pharmaceutically acceptable salt thereof, wherein ring $R^B$ is bridged cycloalkyl substituted with $R^a$.

3. The compound of claim 1, or a pharmaceutically acceptable salt thereof, wherein ring $R^B$ is cycloalkyl substituted with $R^a$.

4. The compound of claim 1, or a pharmaceutically acceptable salt thereof, wherein ring $R^B$ is bridged heterocyclyl substituted with $R^e$, $R^f$, and $R^g$.

5. The compound of claim 1, or a pharmaceutically acceptable salt thereof, wherein ring $R^B$ is heterocyclyl substituted with $R^b$, $R^c$, and $R^d$.

6. The compound of claim 2, or a pharmaceutically acceptable salt thereof, wherein the bridged cycloalkyl of $R^B$ is selected from:

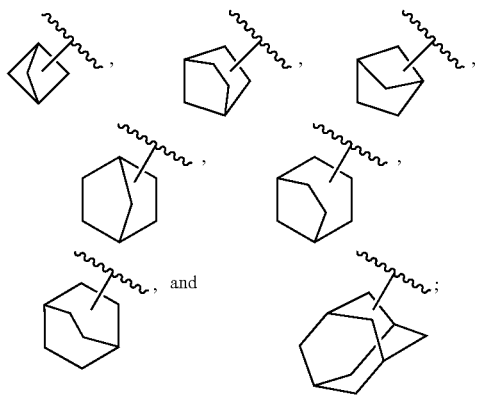

wherein each bridged cycloalkyl is substituted with $R^a$.

7. The compound of claim 3, or a pharmaceutically acceptable salt thereof, wherein the cycloalkyl of ring $R^B$ is selected from:

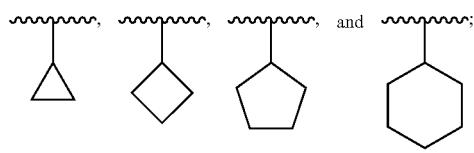

wherein each cycloalkyl ring is substituted with $R^a$.

8. The compound of claim 5, or a pharmaceutically acceptable salt thereof, wherein the heterocyclyl of ring $R^B$ is selected from:

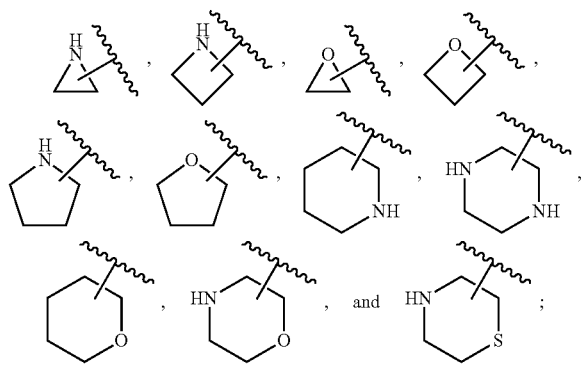

wherein each heterocyclyl is substituted with $R^b$, $R^c$, and $R^d$.

9. The compound of claim 4, or a pharmaceutically acceptable salt thereof, wherein the bridged heterocyclyl of ring $R^B$ is selected from:

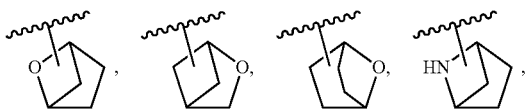

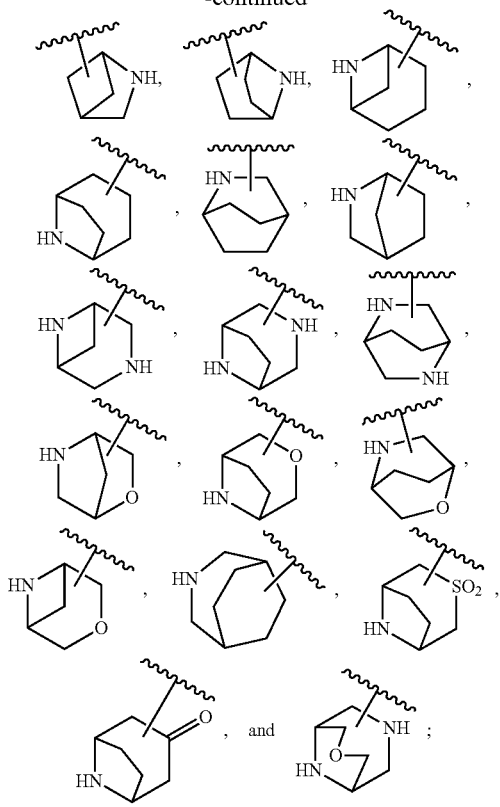

wherein each bridged heterocyclyl is substituted with $R^e$, $R^f$, and $R^g$.

10. The compound of claim 9, or a pharmaceutically acceptable salt thereof, wherein the bridged heterocyclyl of ring $R^B$ is selected from:

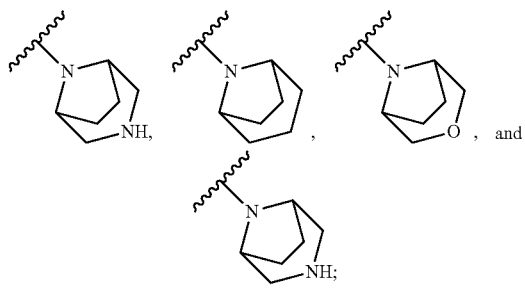

wherein each bridged heterocyclyl is substituted with $R^e$, $R^f$, and $R^g$.

11. The compound of claim 6, or a pharmaceutically acceptable salt thereof, wherein $R^a$ is hydrogen, chloro, fluoro, difluoromethyl, trifluoromethyl, or hydroxymethyl.

12. The compound of claim 6, or a pharmaceutically acceptable salt thereof, wherein $R^a$ is halo or haloalkyl.

13. The compound of claim 7, or a pharmaceutically acceptable salt thereof, wherein $R^a$ is halo or haloalkyl.

14. The compound of claim 6, or a pharmaceutically acceptable salt thereof, wherein ring $R^B$ is bicyclo[1.1.1]pentan-1-yl, 3-fluorobicyclo[1.1.1]pentan-1-yl, 3-chlorobicyclo-[1.1.1]pentan-1-yl, 3-(hydroxymethyl)-bicyclo[1.1.1]pentan-1-yl, 3-(trifluoromethyl)-bicyclo[1.1.1]pentan-1-yl, or 3-(difluoromethyl)bicyclo[1.1.1]pentan-1-yl.

15. The compound of claim 7, or a pharmaceutically acceptable salt thereof, wherein ring $R^B$ is cyclobutyl, cyclopropyl, 1-(difluoromethyl)cyclobutyl, 1-(trifluoromethyl)cyclobutyl, 1-(difluoromethyl)-cyclopropyl, or 1-(trifluoromethyl)cyclopropyl.

16. The compound of claim 8, or a pharmaceutically acceptable salt thereof, wherein $R^b$ and $R^c$ are independently selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^d$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl.

17. The compound of claim 9, or a pharmaceutically acceptable salt thereof, wherein $R^e$ and $R^f$ are independently selected from hydrogen, methyl, fluoro, chloro, difluoromethyl, trifluoromethyl, 2,2-difluoroethyl, 2,2,2-trifluoroethyl, 3,3,3-trifluoropropyl, hydroxy, and cyano, and $R^g$ is selected from hydrogen, methyl, trideuteromethyl, cyclopropyl, cyclobutyl, cyclopentyl, cyclohexyl, 2,2-difluoroethyl, 2,2,2-trifluoroethyl, 3,3,3-trifluoropropyl, amino, dimethylamino, diethylamino, 3,3-difluorocyclobutyl, 4,4-difluorocyclohexyl, 3-hydroxy-3-methylcyclobutyl, 3-cyano-3-methylcyclobutyl, oxetan-3-yl, tetrahydrofuran-2-yl, tetrahydropyran-4-yl, 1,1-dioxidothietan-3-yl, 1,1-dioxidotetrahydro-2H-thiopyran-4-yl, benzyl, phenyl, pyridin-2-yl, pyridin-3-yl, and pyridin-4-yl.

18. The compound of claim 2, selected from the group consisting of:

N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-((3r,5r,7r)-adamantan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-fluorobicyclo[1.1.1]pentan-1-yl)thiazol-4-yl)-2-fluorophenyl)-2,6-difluorobenzenesulfonamide;
N-(3-(2-(3-chlorobicyclo[1.1.1]pentan-1-yl)-5-(2-(((1s,4s)-4-(methylsulfonyl)cyclohexyl)amino)pyrimidin-4-yl)thiazol-4-yl)-2-fluoro-6-(trifluoromethyl)benzenesulfonamide;
N-(3-(2-(bicyclo[2.2.1]heptan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(bicyclo[2.2.2]octan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(bicyclo[2.1.1]hexan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;

-continued

N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
2-fluoro-N-(2-fluoro-3-(2-(3-fluorobicyclo[1.1.1]pentan-1-yl)-5-(2-(((1s,4s)-4-(methylsulfonyl)cyclohexyl)amino)pyrimidin-4-yl)thiazol-4-yl)phenyl)-6-(trifluoromethyl)benzenesulfonamide;
N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2,6-dichlorobenzenesulfonamide;
N-(3-(2-(bicyclo[2.2.1]heptan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-(hydroxymethyl)bicyclo[1.1.1]pentan-1-yl)thiazol-4-yl)-2-fluorophenyl)-2,6-difluorobenzenesulfonamide;
2-fluoro-N-(2-fluoro-3-(5-(2-(((1r,4r)-4-(methylsulfonyl)-cyclohexyl)amino)pyrimidin-4-yl)-2-(3-(trifluoromethyl)-bicyclo[1.1.1]pentan-1-yl)thiazol-4-yl)phenyl)-6-(trifluoromethyl)-benzenesulfonamide;
N-(3-(2-(bicyclo[1.1.1]pentan-1-yl)-5-(2-(((1r,4r)-4-(methylsulfonyl)cyclohexyl)amino)pyrimidin-4-yl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-(3-(trifluoromethyl)bicyclo[1.1.1]pentan-1-yl)thiazol-4-yl)-2-fluorophenyl)-2,6-difluorobenzenesulfonamide;
N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-cyclopropyl-6-fluorobenzenesulfonamide;
N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-(difluoromethyl)-6-fluorobenzenesulfonamide;
N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-methoxybenzenesulfonamide
N-(3-(2-(bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-(difluoromethoxy)-6-fluorobenzenesulfonamide;
N-(3-(2-(bicyclo[2.2.1]heptan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-((3R,5R,7R)-adamantan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-((3R,5R,7R)-adamantan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-fluorobicyclo[1.1.1]pentan-1-yl)thiazol-4-yl)-2-fluorophenyl)-2-fluoro-6-(trifluoromethyl)benzenesulfonamide;
2-fluoro-N-(2-fluoro-3-(2-(3-fluorobicyclo[1.1.1]pentan-1-yl)-5-(2-(((1s,4s)-4-(methylsulfonyl)cyclohexyl)-amino)pyrimidin-4-yl)thiazol-4-yl)phenyl)-6-(trifluoromethyl)benzenesulfonamide;
N-(3-(5-(2-((2,2-dioxido-2-thiaspiro[3.3]heptan-6-yl)amino)-pyrimidin-4-yl)-2-(3-(trifluoromethyl)bicyclo[1.1.1]pentan-1-yl)thiazol-4-yl)-2-fluorophenyl)-2-fluoro-6-(trifluoromethyl)-benzenesulfonamide;
2-chloro-N-(3-(5-(2-((2,2-dioxido-2-thiaspiro[3.3]heptan-6-yl)amino)pyrimidin-4-yl)-2-(3-(trifluoromethyl)bicyclo-[1.1.1]pentan-1-yl)thiazol-4-yl)-2-fluorophenyl)-6-(trifluoromethyl)benzenesulfonamide;
N-(3-(2-(3-(difluoromethyl)bicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
N-(3-(2-(bicyclo[1.1.1]pentan-1-yl)-5-(2-((3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(bicyclo[2.2.1]heptan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(bicyclo[1.1.1]pentan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-fluorobenzenesulfonamide;
N-(3-(2-(bicyclo[2.2.2]octan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide
2-chloro-N-(2-fluoro-3-(5-(2-(((1s,4s)-4-(methylsulfonyl)-cyclohexyl)amino)pyrimidin-4-yl)-2-(3-(trifluoromethyl)bicyclo-[1.1.1]pentan-1-yl)thiazol-4-yl)phenyl)-6-(trifluoromethyl)-benzenesulfonamide;
N-(3-(2-(bicyclo[2.2.2]octan-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(bicyclo[1.1.1]pentan-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-(trifluoromethyl)-benzenesulfonamide;
N-(3-(2-(bicyclo[1.1.1]pentan-1-yl)-5-(2-(((1s,4s)-4-(methylsulfonyl)cyclohexyl)amino)pyrimidin-4-yl)thiazol-4-yl)-2-fluorophenyl)-2-fluoro-6-(trifluoromethyl)benzenesulfonamide;

N-(3-(2-(3-(difluoromethyl)bicyclo[1.1.1]pentan-1-yl)-5-(2-(((1r,4r)-4-(methylsulfonyl)cyclohexyl)-amino)pyrimidin-4-yl)thiazol-4-yl)-2-fluorophenyl)-2-fluoro-6-(trifluoromethyl)benzenesulfonamide;
N-(3-(2-(3-chlorobicyclo[1.1.1]pentan-1-yl)-5-(2-(((1s,4s)-4-(methylsulfonyl)cyclohexyl)amino)pyrimidin-4-yl)thiazol-4-yl)-2-fluorophenyl)-2-fluoro-6-(trifluoromethyl)benzenesulfonamide;
N-(3-(2-(3-chlorobicyclo[1.1.1]pentan-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
N-(3-(2-(bicyclo[1.1.1]pentan-1-yl)-5-(2-(((3aR,5s,6aS)-2,2-dioxidohexahydro-1H-cyclopenta[c]thiophen-5-yl)amino)pyrimidin-4-yl)thiazol-4-yl)-2-fluorophenyl)-2,6-difluorobenzenesulfonamide;
N-(3-(2-(bicyclo[1.1.1]pentan-1-yl)-5-(2-((1-methyl-2,2-dioxido-2-thiaspiro[3.3]heptan-6-yl)amino)pyrimidin-4-yl)thiazol-4-yl)-2-fluorophenyl)-2,6-difluorobenzenesulfonamide; and
N-(3-(2-(bicyclo[1.1.1]pentan-1-yl)-5-(2-((1,3-dimethyl-2,2-dioxido-2-thiaspiro[3.3]heptan-6-yl)amino)pyrimidin-4-yl)thiazol-4-yl)-2-fluorophenyl)-2,6-difluorobenzenesulfonamide;

or a pharmaceutically acceptable salt thereof.

19. The compound of claim 3, selected from the group consisting of:

N-(3-(2-cyclobutyl-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
2-(difluoromethoxy)-N-(3-(2-(1-(difluoromethyl)cyclopropyl)-5-(2-((2,2-dioxido-2-thiaspiro[3.3]heptan-6-yl)amino)pyrimidin-4-yl)thiazol-4-yl)-2-fluorophenyl)-6-fluorobenzenesulfonamide;
N-(3-(2-(1-(difluoromethyl)cyclobutyl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-(1-(trifluoromethyl)cyclobutyl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-(1-(trifluoromethyl)cyclopropyl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-(1-(trifluoromethyl)cyclopropyl)thiazol-4-yl)-2-fluorophenyl)-2,6-difluorobenzenesulfonamide;
N-(3-(2-(1-(difluoromethyl)cyclopropyl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(1-(difluoromethyl)cyclopropyl)-5-(2-(((1r,4r)-4-(methylsulfonyl)cyclohexyl)amino)pyrimidin-4-yl)thiazol-4-yl)-2-fluorophenyl)-2-fluoro-6-(trifluoromethyl)benzenesulfonamide;
N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
2-fluoro-N-(2-fluoro-3-(5-(2-(((1r,4r)-4-(methylsulfonyl)-cyclohexyl)amino)pyrimidin-4-yl)-2-(1-(trifluoromethyl)-cyclopropyl)thiazol-4-yl)phenyl)-6-(trifluoromethyl)benzenesulfonamide;
2,6-difluoro-N-(2-fluoro-3-(5-(2-(((1s,4s)-4-(methylsulfonyl)-cyclohexyl)amino)pyrimidin-4-yl)-2-(1-(trifluoromethyl)-cyclopropyl)thiazol-4-yl)phenyl)benzenesulfonamide;
N-(3-(2-(1-(difluoromethyl)cyclopropyl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)-benzenesulfonamide;
2-(difluoromethoxy)-N-(3-(2-(1-(difluoromethyl)cyclopropyl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-6-fluorobenzene-sulfonamide and;
2-chloro-N-(2-fluoro-3-(5-(2-(((1r,4r)-4-(methylsulfonyl)-cyclohexyl)amino)pyrimidin-4-yl)-2-(1-(trifluoromethyl)-cyclopropyl)thiazol-4-yl)phenyl)-6-(trifluoromethyl)benzene-sulfonamide;

or a pharmaceutically acceptable salt thereof.

20. The compound of claim 4, selected from the group consisting of:

N-(3-(2-(3-oxa-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(2-oxabicyclo[2.1.1]hexan-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(7-azabicyclo[2.2.1]heptan-7-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(3,3-difluoro-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-ox0-8-azabicyclo[3.2.1]octan-8-yl)thiazol-4-yl)-2-fluorophenyl)-2,6-difluorobenzenesulfonamide;
N-(3-(2-(2-azabicyclo[2.2.2]octan-2-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(3-azabicyclo[3.2.2]nonan-3-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-methyl-3,6-diazabicyclo[3.1.1]heptan-6-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(8-methyl-3,8-diazabicyclo[3.2.1]octan-3-yl)thiazol-4-yl)-2-fluorophenyl)-2,6-difluorobenzenesulfonamide;
N-(3-(2-(3-(dimethylamino)-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(5-methyl-2,5-diazabicyclo[2.2.2]octan-2-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-hydroxy-3-methyl-8-azabicyclo[3.2.1]octan-8-yl)thiazol-4-yl)-2-fluorophenyl)-2,6-difluorobenzenesulfonamide;
N-(3-(2-(3-cyano-3-methyl-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(8-(pyridin-2-y])-3,8-diazabicyclo[3.2.1]octan-3-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(1,1-dioxidotetrahydro-2H-thiopyran-4-yl)-3,8-diazabicyclo[3.2.1]octan-8-yl)thiazol-4-yl)-2-fluorophenyl)-2,6-difluorobenzenesulfonamide;
N-(3-(2-(3-benzyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-phenyl-3,8-diazabicyclo[3.2.1]octan-8-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(pyridin-2-y])-3,8-diazabicyclo[3.2.1]octan-8-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(tetrahydrofuran-3-yl)-3,8-diazabicyclo-[3.2.1]octan-8-yl)thiazol-4-yl)-2-fluorophenyl)-2,6-difluoro-benzenesulfonamide;
N-(3-(5-(2-((2,2-dioxido-2-thiaspiro[3.3]heptan-6-yl)amino)-pyrimidin-4-yl)-2-(3-(1,1-dioxidothietan-3-yl)-3,8-diazabicyclo[3.2.1]octan-8-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(3-hydroxy-3-methylcyclobutyl)-3,8-diazabicyclo[3.2.1]octan-8-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3,3-dioxido-3-thia-8-azabicyclo[3.2.1]octan-8-yl)thiazol-4-yl)-2-fluorophenyl)-2,6-difluorobenzenesulfonamide;
N-(3-(2-(3-(3-cyano-3-methylcyclobutyl)-3,8-diazabicyclo-[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-(difluoromethyl)-6-fluorobenzenesulfonamide;
N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-fluoro-6-(trifluoromethyl)-benzenesulfonamide;
N-(3-(2-(3-cyclobutyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(1-cyano-7-azabicyclo[2.2.1]heptan-7-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-fluoro-6-methoxybenzenesulfonamide;
2-(difluoromethoxy)-N-(3-(5-(2-((2,2-dioxido-2-thiaspiro[3.3]-heptan-6-yl)amino)pyrimidin-4-yl)-2-(3-methyl-3,8-diazabicyclo[3.2.1]octan-8-yl)thiazol-4-yl)-2-fluorophenyl)-6-fluorobenzenesulfonamide;
N-(3-(5-(2-(((1S,5S)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2,6-difluorobenzenesulfonamide;
N-(3-(5-(2-(((1R,5S,6s)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2,6-difluorobenzenesulfonamide;

N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2-methoxy-6-(trifluoromethyl)benzenesulfonamide;
2-(difluoromethoxy)-N-(3-(5-(2-((2,2-dioxido-2-thiaspiro[3.3]heptan-6-yl)amino)pyrimidin-4-yl)-2-(3-methyl-3,8-diazabicyclo[3.2.1]octan-8-yl)thiazol-4-yl)-2-fluorophenyl)-6-(trifluoromethyl)benzenesulfonamide;
N-(3-(5-(2-((2,2-dioxido-2-thiaspiro[3.3]heptan-6-yl)amino)-pyrimidin-4-yl)-2-(7-methyl-3-oxa-7,9-diazabicyclo[3.3.1]nonan-9-yl)thiazol-4-yl)-2-fluorophenyl)-2,6-difluorobenzenesulfonamide;
N-(3-(2-(3-cyclopropyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluoro-6-(trifluoromethyl)benzenesulfonamide;
N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(3-oxa-8-azabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(5-(2-(((1S,5S)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2-fluoro-6-(trifluoromethyl)benzenesulfonamide;
N-(3-(5-(2-(((1R,5S,6s)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-2-fluoro-6-(trifluoromethyl)benzenesulfonamide;
N-(3-(2-(3-oxa-8-azabicyclo[3.2.1]octan-8-yl)-5-(2-((3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(3,3-difluoro-8-azabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
2-(difluoromethoxy)-N-(3-(5-(2-(((1R,5S,6r)-3,3-dioxido-3-thiabicyclo[3.1.0]hexan-6-yl)amino)pyrimidin-4-yl)-2-(3-methyl-3,8-diazabicyclo[3.2.1]octan-8-yl)thiazol-4-yl)-2-fluorophenyl)-6-fluorobenzenesulfonamide;
N-(3-(2-(3-(3,3-difluorocyclobutyl)-3,8-diazabicyclo[3.2.1]octan-8-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-(difluoromethoxy)-6-fluorobenzenesulfonamide;
N-(3-(2-(3-cyclobutyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2,6-difluorobenzenesulfonamide;
N-(3-(2-(3-cyclopropyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2,6-difluorobenzene-sulfonamide;
N-(3-(2-(3-cyclopropyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2-fluoro-6-(trifluoromethyl)benzenesulfonamide;
N-(3-(2-(3-cyclobutyl-3,8-diazabicyclo[3.2.1]octan-8-yl)-5-(2-(((1R,5S,6r)-3,3-dioxido-3-thiabicyclo[3.1.0]hexan-6-yl)amino)-pyrimidin-4-yl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-(3-methyl-3,8-diazabicyclo[3.2.1]octan-8-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(methyl-d3)-3,8-diazabicyclo[3.2.1]octan-8-yl)thiazol-4-yl)-2-fluorophenyl)-2,6-difluorobenzenesulfonamide;
N-(3-(2-(3-cyclopropyl-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(2,2,2-trifluoroethyl)-3,8-diazabicyclo-[3.2.1]octan-8-yl)thiazol-4-yl)-2-fluorophenyl)-2,6-difluoro-benzenesulfonamide;
N-(3-(2-(3-(2,2-difluoroethyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;

-continued

N-(3-(5-(2-((2,2-dioxido-2-thiaspiro[3.3]heptan-6-yl)amino)-pyrimidin-4-yl)-2-(3-(3,3,3-trifluoropropyl)-3,8-diazabicyclo-[3.2.1]octan-8-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(3-(oxetan-3-y])-3,8-diazabicyclo[3.2.1]octan-8-yl)thiazol-4-yl)-2-fluorophenyl)-2,6-difluorobenzenesulfonamide;
N-(3-(2-(3-(4,4-difluorocyclohexyl)-3,8-diazabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)pyrimidin-4-yl)-2-(3-(tetrahydro-2H-pyran-4-yl)-3,8-diazabicyclo[3.2.1]octan-8-yl)thiazol-4-yl)-2-fluorophenyl)-2,6-difluorobenzenesulfonamide;
N-(3-(2-(3-(3,3-difluorocyclobutyl)-3,8-diazabicyclo[3.2.1]octan-8-yl)-5-(2-((2,2-dioxido-2-thiaspiro[3.3 ]heptan-6-yl)amino)pyrimidin-4-yl)thiazol-4-yl)-2-fluorophenyl)-2-fluoro-6-(trifluoromethyl)benzenesulfonamide; and
N-(3-(2-(3-cyano-3-methyl-8-azabicyclo[3.2.1]octan-8-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;

or a pharmaceutically acceptable salt thereof.

21. The compound of claim 5, selected from the group consisting of:

N-(3-(2-((3S,5S)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
tert-butyl 4-(4-(3-((2,6-difluorophenyl)sulfonamido)-2-fluorophenyl)-5-(2-((2,2-dioxido-2-thiaspiro[3.3]heptan-6-yl)amino)pyrimidin-4-yl)thiazol-2-yl)-4-methylpiperidine-1-carboxylate;
N-(3-(5-(2-((2,2-dioxido-2-thiaspiro[3.3]heptan-6-yl)amino)pyrimidin-4-yl)-2-(4-methylpiperidin-4-yl)thiazol-4-yl)-2-fluorophenyl)-2,6-difluorobenzenesulfonamide;
N-(3-(2-(1,4-dimethylpiperidin-4-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(2,2-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-(2,4,6-trimethylpiperazin-1-yl)thiazol-4-yl)-2-fluorophenyl)-2,6-difluorobenzenesulfonamide;
N-(3-(2-((3R,5R)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-((2R,6R)-2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-((2R,6R)-2,4,6-trimethylpiperazin-1-yl)thiazol-4-yl)-2-fluorophenyl)-2,6-difluorobenzenesulfonamide;
N-(3-(2-((2R,6R)-4-(3,3-difluorocyclobutyl)-2,6-dimethylpiperazin-1-yl)-5-(2-((2,2-dioxido-2-thiaspiro[3.3]heptan-6-yl)amino)-pyrimidin-4-yl)thiazol-4-yl)-2-fluorophenyl)-2,6-difluoro-benzenesulfonamide;
N-(3-(2-((2S,6S)-2,6-dimethylpiperazin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(5-(2-((2,2-dioxido-2-thiaspiro[3.3]heptan-6-yl)amino)-pyrimidin-4-yl)-2-((2S,6S)-2,4,6-trimethylpiperazin-1-yl)thiazol-4-yl)-2-fluorophenyl)-2,6-difluorobenzenesulfonamide;
N-(3-(2-((2S,6S)-4-(3,3-difluorocyclobutyl)-2,6-dimethylpiperazin-1-yl)-5-(2-((2,2-dioxido-2-thiaspiro[3.3]heptan-6-yl)amino)-pyrimidin-4-yl)thiazol-4-yl)-2-fluorophenyl)-2,6-difluoro-benzenesulfonamide;
N-(3-(2-(2,5-dimethylpyrrolidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-(2,2-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
N-(3-(5-(2-((2,2-dioxido-2-thiaspiro[3.3]heptan-6-yl)amino)-pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide;
N-(3-(2-(2,4-dimethylazetidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;
N-(3-(2-((3S,5S)-3,5-dimethylmorpholino)-5-(2-((2,2-dioxido-2-thiaspiro[3.3]heptan-6-yl)amino)pyrimidin-4-yl)thiazol-4-yl)-2-fluorophenyl)-2-fluoro-6-(trifluoromethyl)benzenesulfonamide;
N-(3-(2-(2,2-dimethylazetidin-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-((3S,5S)-3,5-dimethylmorpholino)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2,6-difluorobenzenesulfonamide;
N-(3-(2-((3S,5S)-3,5-dimethylmorpholino)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;

-continued

N-(3-(2-(2,2-dimethylazetidin-1-yl)-5-(2-(((1R,5S,6s)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(2-(2,2-dimethylazetidin-1-yl)-5-(2-(((1R,5S,6r)-3,3-dioxido-3-thiabicyclo[3.1.0]hexan-6-yl)amino)pyrimidin-4-yl)thiazol-4-yl)-2-fluorophenyl)-2-fluoro-6-(trifluoromethyl)benzenesulfonamide;
N-(3-(5-(2-(((1R,5S,6r)-3,3-dioxido-3-thiabicyclo[3.1.0]hexan-6-yl)amino)pyrimidin-4-yl)-2-((2S,6S)-2,4,6-trimethylpiperazin-1-yl)thiazol-4-yl)-2-fluorophenyl)-2-fluoro-6-(trifluoromethyl)benzenesulfonamide; and
N-(3-(5-(2-((2,2-dioxido-2-thiaspiro[3.3]heptan-6-yl)amino)-pyrimidin-4-yl)thiazol-4-yl)-2-(2,2,4-trimethylpiperazin-1-yl)thiazol-4-yl)-2-fluorophenyl)-2,6-difluorobenzenesulfonamide;
N-(3-(2-(2,2-dimethylpyrrolidin-1-yl)-5-(2-((2,2-dioxido-2-thiaspiro[3.3]heptan-6-yl)amino)pyrimidin-4-yl)thiazol-4-yl)-2-fluorophenyl)-2,6-difluorobenzenesulfonamide;

or a pharmaceutically acceptable salt thereof.

22. A pharmaceutical composition comprising a compound of claim 1, or a pharmaceutically acceptable salt thereof, and a pharmaceutically acceptable excipient.

23. A method of treating cancer in a patient in recognized need thereof which method comprises administering to the patient in recognized need thereof, a therapeutically effective amount of a compound of formula (I), or a pharmaceutically acceptable salt thereof, in a pharmaceutical composition of claim 22.

24. The method of claim 23, wherein the compound of formula (I), or a pharmaceutically acceptable salt thereof, in a pharmaceutical composition is administered in combination with at least one other anticancer agent.

25. The method of claim 23, wherein the cancer is lung cancer, skin cancer, bladder cancer, breast cancer, cervical cancer, colorectal cancer, cancer of the small intestine, colon cancer, rectal cancer, cancer of the anus, endometrial cancer, gastric cancer, head and neck cancer, liver cancer, ovarian cancer, prostate cancer, testicular cancer, uterine cancer, esophageal cancer, gall bladder cancer, pancreatic cancer, stomach cancer, thyroid cancer, and/or parathyroid cancer.

26. The compound of claim 1 having the following structure:

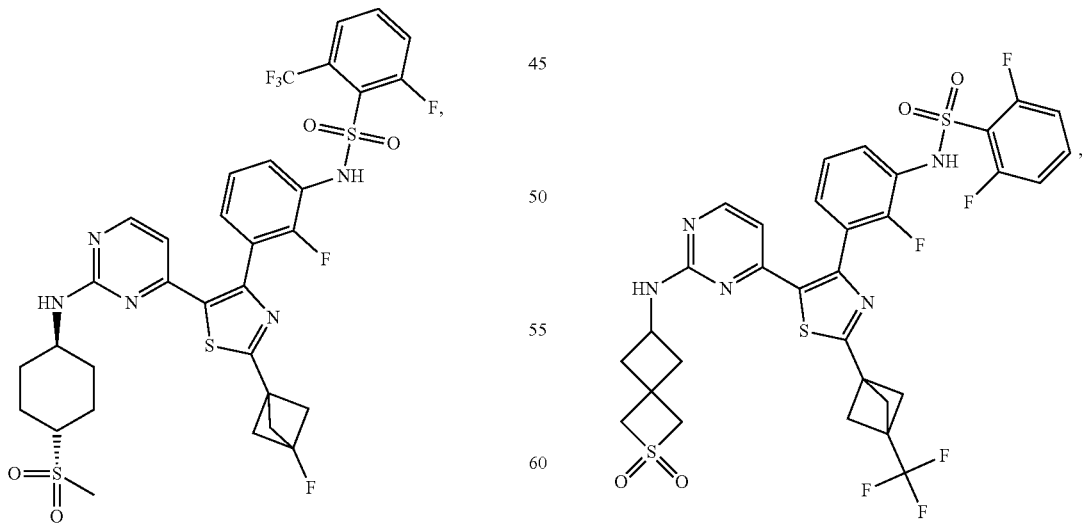

or a pharmaceutically acceptable salt thereof.

27. The compound of claim 1 having the following structure:

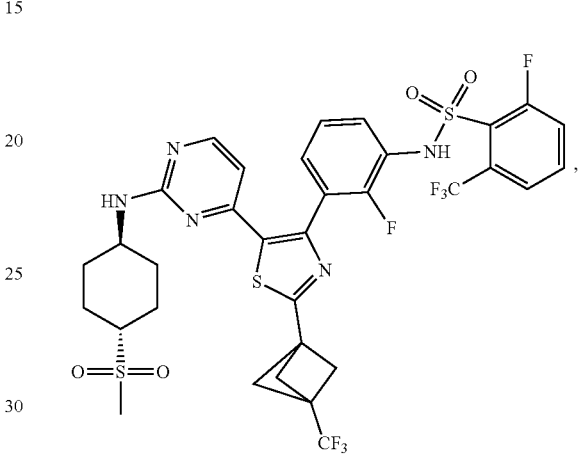

or a pharmaceutically acceptable salt thereof.

28. The compound of claim 1 having the following structure:

or a pharmaceutically acceptable salt thereof.

29. The compound of claim 1 having the following structure:

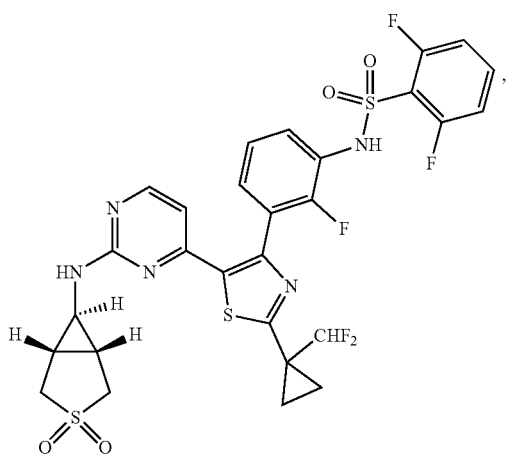 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3F)c2F)n1]

or a pharmaceutically acceptable salt thereof.

30. The compound of claim 1 having the following structure:

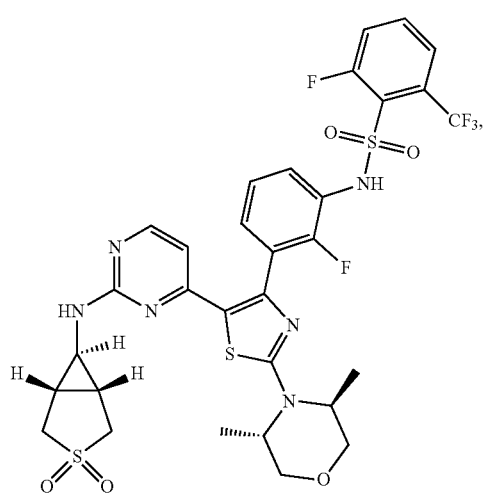 [SMILES: C[C@H]1COC[C@H](C)N1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1]

or a pharmaceutically acceptable salt thereof.

31. The compound of claim 1 having the following structure:

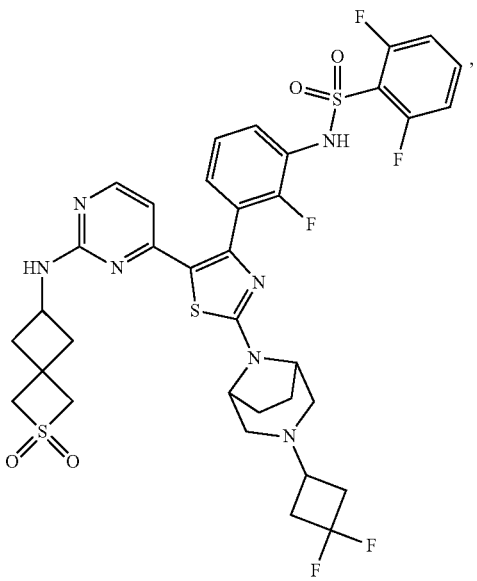 [SMILES: O=S1(=O)CC2(CC(Nc3nccc(-c4sc(N5C6CCC5CN(C5CC(F)(F)C5)C6)nc4-c4cccc(NS(=O)(=O)c5c(F)cccc5F)c4F)n3)C2)C1]

or a pharmaceutically acceptable salt thereof.

32. The compound of claim 26 having the following structure:

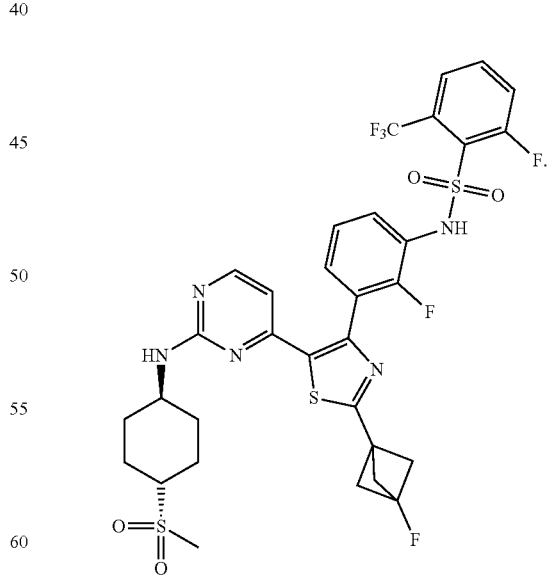

33. The compound of claim 27 having the following structure:

34. The compound of claim 28 having the following structure:
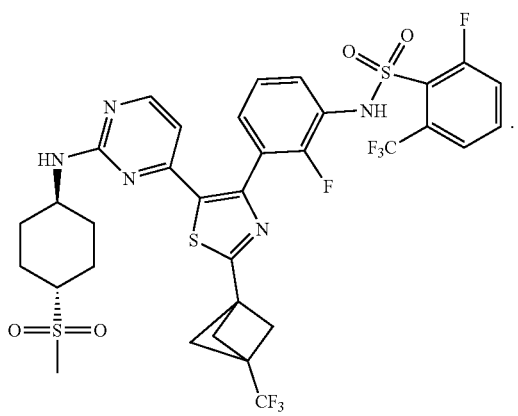 [SMILES: CS(=O)(=O)[C@H]1CC[C@H](Nc2nccc(-c3sc(C45CC(C(F)(F)F)(C4)C5)nc3-c3cccc(NS(=O)(=O)c4c(F)cccc4C(F)(F)F)c3F)n2)CC1]
35. The compound of claim 29 having the following structure:
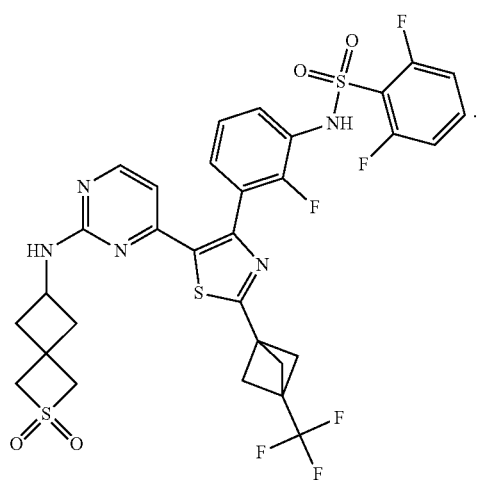 [SMILES: O=S1(=O)CC2(CC(Nc3nccc(-c4sc(C56CC(C(F)(F)F)(C5)C6)nc4-c4cccc(NS(=O)(=O)c5c(F)cccc5F)c4F)n3)C2)C1]
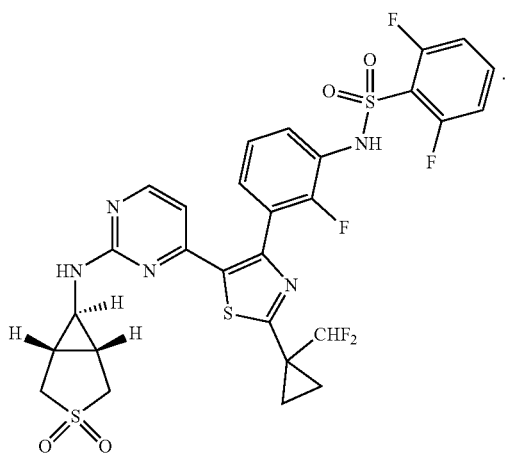 [SMILES: O=S1(=O)C[C@@H]2[C@H](C1)[C@H]2Nc1nccc(-c2sc(C3(C(F)F)CC3)nc2-c2cccc(NS(=O)(=O)c3c(F)cccc3F)c2F)n1]
36. The compound of claim 30 having the following structure:
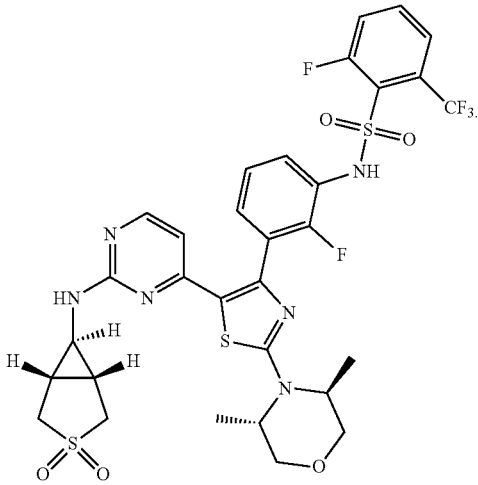 [SMILES: C[C@H]1COC[C@H](C)N1c1nc(-c2cccc(NS(=O)(=O)c3c(F)cccc3C(F)(F)F)c2F)c(-c2ccnc(N[C@H]3[C@@H]4CS(=O)(=O)C[C@@H]43)n2)s1]
37. The compound of claim 31 having the following structure:
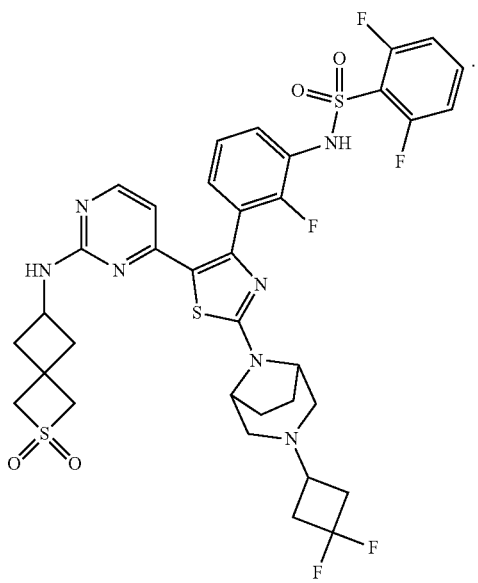 [SMILES: O=S1(=O)CC2(CC(Nc3nccc(-c4sc(N5C6CCC5CN(C5CC(F)(F)C5)C6)nc4-c4cccc(NS(=O)(=O)c5c(F)cccc5F)c4F)n3)C2)C1]
* * * * *